United States Patent
Aggarwal et al.

(10) Patent No.: US 9,242,954 B2
(45) Date of Patent: Jan. 26, 2016

(54) LACTOL AND ACETAL INTERMEDIATES FOR MAKING PROSTAGLANDINS

(71) Applicant: University of Bristol

(72) Inventors: Varinder Kumar Aggarwal, Bristol (GB); Mark Graeme Coulthard, Bristol (GB); William Erb, Bristol (GB)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 14/407,367

(22) PCT Filed: Jun. 11, 2013

(86) PCT No.: PCT/GB2013/051532
§ 371 (c)(1),
(2) Date: Dec. 11, 2014

(87) PCT Pub. No.: WO2013/186550
PCT Pub. Date: Dec. 19, 2013

(65) Prior Publication Data
US 2015/0158837 A1      Jun. 11, 2015

(30) Foreign Application Priority Data

Jun. 11, 2012  (GB) .................................. 1210235.6

(51) Int. Cl.
*C07D 307/935*  (2006.01)
*C07C 405/00*   (2006.01)

(52) U.S. Cl.
CPC .......... *C07D 307/935* (2013.01); *C07C 405/00* (2013.01); *C07C 2101/08* (2013.01)

(58) Field of Classification Search
CPC ............. C07C 2101/08; C07C 405/00; C07D 307/935
See application file for complete search history.

(56) References Cited

U.S. PATENT DOCUMENTS

| 3,816,462 A | 6/1974 | Kelly |
| 4,213,907 A | 7/1980 | Bindra |
| 5,451,689 A | 9/1995 | Matsumoto et al. |
| 2009/0163596 A1 | 6/2009 | Gutman et al. |

FOREIGN PATENT DOCUMENTS

| EP | 1211241 A1 | 6/2002 |
| GB | 1384646 A | 2/1975 |
| WO | 93/23387 A1 | 11/1993 |
| WO | 96/12713 A1 | 5/1996 |
| WO | 2011/055377 A1 | 5/2011 |

OTHER PUBLICATIONS

Bahmanyar, S., et al., "Quantum Mechanical Predictions of the Stereoselectivities of Proline-Catalyzed Asymmetric Intermolecular Aldol Reactions." Journal of the American Chemical Society, 2003, vol. 125, pp. 2475-2479.

Bui, Tommy, et al., "A Proline-Catalyzed Asymmetric Robinson Annulation Reaction." Tetrahedron Letters, 2000, vol. 41, pp. 6951-6954.

Chen, Xiao-Hua, et al., "The Role of Double Hydrogen Bonds in Asymmetric Direct Aldol Reactions Catalyzed by Amino Amide Derivatives." Chemical Communications, 2010, vol. 46, pp. 6437-6448.

Chowdari, Naidu S., et al., "Proline-Catalyzed Asymmetric Assembly Reactions: Enzyme-Like Assembly of Carbohydrates and Polyketides From Three Aldehyde Substrates." Tetrahedron Letters, 2002, vol. 43, pp. 9591-9595.

Corey, E.J., et al., "Stereo-Controlled Synthesis of Prostaglandins F2-alpha and E2 (dl)." Journal of the American Chemical Society, Sep. 24, 1969, vol. 91, No. 20, pp. 5675-5677.

Coulthard, Graeme, "Stereocontrolled Organocatalytic Synthesis of Prostaglandin PGF2-alpha in Seven Steps." Nature, Sep. 2012, vol. 489, pp. 278-281.

Fakstorp, Jorgen, et al., "Preparation and Reactions of Dialkoxytetrahydrofurans." Journal of the American Chemical Society, 1950, vol. 72, No. 2, pp. 869-874.

(Continued)

*Primary Examiner* — Valerie Rodriguez-Garcia
(74) *Attorney, Agent, or Firm* — Fitch, Even, Tabin & Flannery LLP

(57) ABSTRACT

A compound of formula (I): (I) wherein Y is, Z is $OR^{10}$, $NR^{11}R^{11}$ $SR^{11}$, $S(O)R^{11}$ $SO_2R^{11}$, $R^{10}$ is H, optionally substituted alkyl, optionally substituted cycloalkyl, optionally substituted alkenyl, optionally substituted alkynyl, optionally substituted aryl, optionally substituted heteroaryl, optionally substituted heterocyclyl, $CO-R^{11}$, or a protecting group, and $R^{11}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl; a process for making a compound of formula (I); and a process for making a prostaglandin or a prostaglandin analog using a compound of formula (I).

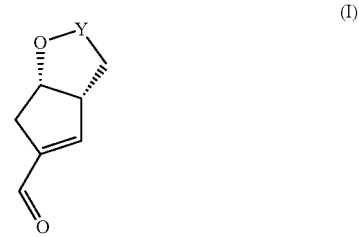

wherein
Y is

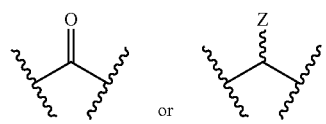

15 Claims, 8 Drawing Sheets

(56) References Cited

OTHER PUBLICATIONS

Gourley, Brendon S., et al., "A New and High Yielding Synthesis of Unstable Pyrroles Via a Modified Clauson-Kaas Reaction." Tetrahedron Letters, 2006, vol. 47, pp. 799-801.

Gu, Liuqun, et al., "4,4'-Disubstituted L-Prolines as Highly Enantioselective Catalysts for Direct Aldol Reactions." Advanced Synthesis & Catalysis, 2006, vol. 348, pp. 2223-2228.

Hajos, Zoltan G., et al., "Asymmetric Synthesis of Bicyclic Intermediates of Natural Product Chemistry." Journal of Organic Chemistry, 1974, vol. 39, No. 12, pp. 1615-1621.

Hardy, P.M., et al., "The Hydration and Polymerisation of Succinaldehyde, Glutaraldehyde, and Adipaldehyde." Journal of the Chemical Society, 1972, vol. 15, pp. 2270-2278.

He, Zhao-Quan, et al., "Enantioselective Construction of Lactone [2,3-b]piperidine Skeletons Via Organocatalytic Tandem Reactions." Organic & Biomolecular Chemistry, 2010, vol. 8, pp. 755-757.

Hoang, Linh, et al., "Kinetic and Stereochemical Evidence for the Involvement of Only One Proline Molecule in the Transition States of Proline-Catalyzed Intra- and Intermolecular Aldol Reactions." Journal of the American Chemical Society, 2003, vol. 125, pp. 16-17.

House, Herbert O., et al., "A Study of the Intramolecular Diels-Alder Reaction." Journal of Organic Chemistry, Apr. 1965, vol. 30, No. 3, pp. 1061-1070.

List, Benjamin, et al., "Proline-Catalyzed Direct Asymmetric Aldol Reactions." Journal of the American Chemical Society, 2000, vol. 122, pp. 2395-2396.

Liu, Chunjian, et al., "Synthetic Studies Toward the Kempane Diterpenes: Preparation of the Ring System." Journal of the American Chemical Society, 1997, vol. 119, pp. 9584-9585.

Mukherjee, Santanu, et al., "Asymmetric Enamine Catalysis." Chemical Reviews, 2007, vol. 107, pp. 5471-5569.

Northrup, Alan B., et al., "The First Direct and Enantioselective Cross-Aldol Reaction of Aldehydes." Journal of the American Chemical Society, 2002, vol. 124, pp. 6798-6799.

Salame, Rim, et al., "Biomimetically Relevant Self-Condensations of C5 Units Derived From Lysine." Organic & Biomolecular Chemistry, Jun. 7, 2010, vol. 8, No. 11, pp. 2522-2528.

Salame, Rim, et al., "Biomimetic Synthesis of Tangutorine Following New Biogenetic Proposals." Organic Letters, 2009, vol. 11, No. 9, pp. 1891-1894.

Sorensen, Erik J., "A Biochemical Messenger Made Easily." Nature, Sep. 2012, vol. 489, pp. 214-215.

Tashima, Toshio, et al., "Structure of a New Oligomer of Glutaraldehyde Produced by Aldol Condensation Reaction." Journal of Organic Chemistry, 1991, vol. 56, pp. 694-697.

International Search Report, International Application No. PCT/GB2013/051532, completion date Aug. 29, 2013, 4 pages.

International Preliminary Report on Patentability and Written Opinion, International Application No. PCT/GB2013/051532, dated Dec. 16, 2014, 6 pages.

British Search Report, British Patent Application No. GB1210235.6, dated Sep. 25, 2012, 2 pages.

Black, Phillip J., et al., "Borrowing Hydrogen: Indirect "Wittig" Olefination for the Formation of C-C Bonds from Alcohols." European Journal Organic Chemistry, 2006, pp. 4367-4378.

Trost, Barry M., et al., "Sequential Ru-Pd Catalysis: A Two-Catalyst One-Pot Protocol for the Synthesis of N- and O-Heterocycles." Journal of the American Chemical Society, 2006, vol. 128, pp. 6745-6754.

Murphy, John A., et al., "Direct Conversion of N-Methoxy-N-Methylamides (Weinreb Amides) to Ketones Via A Nonclassical Wittig Reaction." Organic Letters, 2005, vol. 7, No. 7, pp. 1427-1429.

Kiyotsuka, Yohei, et al., "Picolinoxy Group, a New Leaving Group for Anti SN2' Selective Allylic Substitution With Aryl Anions Based on Grignard Reagents." Organic Letters, 2008, vol. 10, No. 9, pp. 1719-1722.

Lotz, Bruce T., et al., "Diastereoselective Synthesis of the Carbacephem Framework." Journal of Organic Chemistry, 1993, vol. 58, pp. 618-625.

Schwartz, Chris, et al., "Fragmentation of Carbonyl Oxides by N-Oxides: An Improved Approach to Alkene Ozonolysis." Organic Letters, 2006, vol. 8, No. 15, pp. 3199-3201.

Sedelmeier, Jorg, et al., "KMnO4-Mediated Oxidation As a Continuous Flow Process." Organic Letters, 2010, vol. 12, No. 16, pp. 3618-3621.

Gannett, Peter M. et al., "The Capsaicinoids: Their Separation, Synthesis, and Mutagenicity." Journal of Organic Chemisty, 1988, vol. 53, pp. 1064-1071.

Corey, E. J., et al., "A Simple Route to a Key Intermediate for the Synthesis of 11-Desoxyprostaglandins." Tetrahedron Letters, 1971, No. 49, pp. 4753-4755.

Robertson, Jeremy, et al., "Synthesis and Claisen Rearrangement of Bridged Bicyclic Enol Ethers of Relevance to the Course of Ketene s-cis-diene Cycloaddition." Organic & Biomolecular Chemistry, 2006, vol. 4, pp. 4307-4318.

Kertesz, Denis J., et al., "Application of Bakers' Yeast Mediated Reductions of Bicyclo[4.2.0]oct-2-en-7-ones to the Enantioselective Synthesis of Prostacyclin Analogues." Journal of Organic Chemistry, 1988, vol. 53, pp. 4962-4968.

Powers, David C., et al., "Thermal Chemistry of Bicyclo[4.2.0]oct-2-enes." Journal of Organic Chemistry, 2007, vol. 72, pp. 187-194.

Cotterill, Ian C. et al., "Resolution of Bicyclo [3.2.0]hept-2-en-6-ols and Bicyclo [4.2.0]oct-2-en-endo-7-ol using Lipases." Journal of Chemical Society Perkin Transactions 1, 1988, pp. 3387-3389.

Selander, Nicklas, et al., "Synthesis of Stereodefined Substituted Cycloalkenes by a One-Pot Catalytic BoronationAllylation-Metathesis Sequence." Advanced Synthesis & Catalysis, 2008, vol. 350, pp. 2045-2051.

Bhandal, Harcharan, et al., "Cobalt-Mediated Radical Reactions in Organic Synthesis. Oxidative Cyclisations of Aryl and Alkyl Halides Leading to Functionalised Reduced Heterocycles and Butyrolactones." Journal of Chemisty Society Perkin Transactions 1, 1990, pp. 2691-2701.

Pangborn, Amy B., et al., "Safe and Convenient Procedure for Solvent Purification." Organometallics, 1996, vol. 15, pp. 1518-1520.

Burchat, Andrew F., et al., "Titration of Alkyllithiums With a Simple Reagent to a Blue Endpoint." Journal of Organometallic Chemistry, 1997, vol. 542, pp. 281-283.

Sakthivel, Kandasamy, et al., "Amino Acid Catalyzed Direct Asymmetric Aldol Reactions: A Bioorganic Approach to Catalytic Asymmetric Carbon-Carbon Bond-Forming Reactions." Journal of the American Chemical Society, 2001, vol. 123, pp. 5260-5267.

Hartikka, Antti, et al., "Rational Design of Asymmetric Organocatalysts-Increased Reactivity and Solvent Scope With a Tetrazolic Acid." Tetrahedron: Asymmetry, 2004, vol. 15, pp. 1831-1834.

Cobb, Alexander J. A., et al., "5-Pyrrolidin-2-yltetrazole: A New, Catalytic, More Soluble Alternative to Proline in an Organocatalytic Asymmetric Mannich-type Reaction." Synlett, 2004, No. 3 pp. 558-560.

Torii, Hiromi et al., "Asymmetric Direct Aldol Reaction Assisted by Water and a Proline-Derived Tetrazole Catalyst." Angewandte Chemie International Edition, 2004, vol. 43, pp. 1983-1986.

Cobb, Alexander J. A., et al., "Organocatalysis With Proline Derivatives: Improved Catalysts for the Asymmetric Mannich, Nitro-Michael and Aldol Reactions." Organic Biomolecular Chemistry, 2005, vol. 3, pp. 84-96.

Bellis, Evagelos, et al., "4-Substituted Prolyl Sulfonamides as Enantioselective Organocatalysts for Aldol Reactions." Synthesis, 2005, No. 14, pp. 2407-2413.

Gryko, Dorota, et al., "L-Prolinethioamides-Efficient Organocatalysts for the Direct Asymmetric Aldol Reaction." Advanced Synthesis & Catalysis, 2005, vol. 347, pp. 1948-1952.

Guillena, Gabriela, et al., "N-Tosyl-(Sa)-binam-L-prolinamide as Highly Efficient Bifunctional Organocatalyst for the General Enantioselective Solvent-Free Aldol Reaction." Synlett, 2008, No. 19, pp. 3031-3035.

Bradshaw, Ben, et al., "Efficient Solvent-Free Robinson Annulation Protocols for the Highly Enantioselective Synthesis of the Wieland-Miescher Ketone and Analogues." Advanced Synthesis & Catalysis, 2009, vol. 351, pp. 2482-2490.

(56) References Cited

OTHER PUBLICATIONS

Hayashi, Yujiro, et al., "A Diarylprolinol in an Asymmetric, Catalytic, and Direct Crossed-Aldol Reaction of Acetaldehyde." Angewandte Chemie International Edition, 2008, vol. 47, pp. 2082-2084.
Urushima, Tatsuya, et al., "Polymeric Ethyl Glyoxylate in an Asymmetric Aldol Reaction Catalyzed by Diarylprolinol." Organic Letters, vol. 12, No. 13, pp. 2966-2969.
Corey, E. J. et al., "Stereospecific Total Synthesis of Gibberellic Acid. A Key Tricyclic Intermediate." Journal of the American Chemical Society, 1978, vol. 100, pp. 8031-8034.
Zumbansen, Kristina, et al., "Morpholinium Trifluoroacetate-Catalyzed Aldol Condensation of Acetone with Both Aromatic and Aliphatic Aldehydes." Advanced Synthesis & Catalysis, 2010, vol. 352, pp. 1135-1138.
Penhoat, Mael, et al., "Direct Asymmetric Aldol Reaction Co-Catalyzed by L-proline and Group 12 Elements Lewis Acids in the Presence of Water." Tetrahedron Letters, 2011, vol. 52, pp. 159-162.
Akagawa, Kengo, et al., "Resin-Supported Acid- and Based Catalyzed One-Pot Sequential Reaction Including an Enantioselective Step." Tetrahedron Letters, 2007, vol. 48, pp. 985-987.
Naka, Hiroaki, et al., "Crossed Aldol Condensation Using Anion Exchange Resin As Solid Base Catalyst." Journal of Oleo Science, 2001, vol. 50, No. 10, pp. 813-821.
Loh, Teck-Peng, et al., "Clay Montmorillonite K10 Catalyzed Aldol-type Reaction of Aldehydes with Silyl Enol Ethers in Water." Tetrahedron, 1999, vol. 55, pp. 10789-10802.
Vogl, Erasmus M., et al., "Towards Perfect Asymmetric Catalysis: Additives and Cocatalysts." Angewandte Chemie International Edition, 1999, vol. 38, pp. 1570-1577.
Reis, Omer, et al., "Direct Enantioselective Aldol Reactions Catalyzed by a Proline-Thiorea Host-Guest Complex." Chemical Communications, 2009, pp. 1088-1090.
Zhou, Yan, et al., "Chiral Diols: A New Class of Additives for Direct Aldol Reaction Catalyzed by L-Proline." Journal of Organic Chemisty, 2006, vol. 71, pp. 9510-9512.
Chandrasekhar, S., et al., "L-Proline Catalysed Asymmetric Aldol Reactions in PEG-400 as Recyclable Medium and Transfer Aldol Reactions." Tetrahedron, 2006, vol. 62, pp. 338-345.
Chandrasekhar, S., et al., "Asymmetric Aldol Reactions in Poly(ethylene Glycol) Catalyzed by L-Proline." Tetrahedron Letters, 2004, vol. 45, pp. 4581-4582.
Nyberg, Annika I., et al., "Proline-Catalyzed Ketone-Aldehyde Aldol Reactions Are Accelerated by Water." Synlett, 2004, No. 11, pp. 1891-1896.
Pihko, Petri M., et al., "Effect of Additives on the Proline-Catalyzed Ketone-Aldehyde Aldol Reactions." Tetrahedron, 2006, vol. 62, pp. 317-328.
Zotova, Natalia, et al., "Clarification of the Role of Water in Proline-Mediated Aldol Reactions." Journal of the American Chemical Society, 2007, vol. 129, pp. 15100-15101.
Schmid, Markus B., et al., "The Elusive Enamine Intermediate in Proline-Catalyzed Aldol Reactions: NMR Detection, Formation Pathway, and Stabilization Trends." Angewandte Chemie International Edition, 2010, vol. 49, pp. 4997-5003.
Sheddan, Neil A., et al., "Cross Metathesis as a General Strategy for the Synthesis of Prostacyclin and Prostaglandin Analogues." Organic Letters, 2006, vol. 8, No. 14, pp. 3101-3104.
Nicolaou, K. C., et al., "Stereocontrolled Total Synthesis of Lipoxins A." Journal of the American Chemical Society, 1985, vol. 107, pp. 7515-7518.
Cmrecki, Vesna, et al., "Microwave Assisted Synthesis of Enantiomerically Pure Allylboronates." Tetrahedron, 2010, vol. 66, pp. 6550-6564.
Suzuki, Masaaki, et al., "Rational Design of Antitumor Prostaglandins with High Biological Stability." Journal of Medical Chemistry, 1998, vol. 41, pp. 3084-3090.
Luo, Fen Tair, et al., "A Selective Synthesis of a Mixture of 15-Epimers of -11-Deoxyprostaglandin E2 Methyl Ester." Journal of Organic Chemistry, 1985, vol. 50, No. 24, pp. 4762-4766.
de los Angeles Rey, Maria, et al., "New Synthetic Strategies to Vitamin D Analogues Modified at the Side Chain and D Ring. Synthesis of 1-alpha,25-Dihydroxy-16-ene-vitamin D3 and C-20 Analogues." Journal of Organic Chemistry, 1999, vol. 64, pp. 3196-3206.
Parve, Omar, et al., "Lipase-Catalysed Acylation of Prostanoids." Bioorganic & Medicinal Chemistry Letters, 1999, vol. 9, pp. 1853-1858.
Corey, E.J., et al., "Total Synthesis of Prostaglandin F2-alpha and E2 as the Naturally Occurring Forms." Journal of the American Chemical Society, 1970, vol. 92, pp. 397-398.
Bernier, David, et al., "Improved Procedure for the Synthesis of Enamine N-Oxides." The Journal of Organic Chemistry, 2008, vol. 73, pp. 4229-4232.
Mitchell, Judith M., et al., "New Molybdenum Catalysts for Alkyl Olefin Epoxidation. Their Implications for the Mechanism of Oxygen Atom Transfer." Journal of the American Chemical Society, 2001, vol. 123, pp. 862-869.
Elings, Jacob A., et al., "Cyclialkylation of Arylalkyl Epoxides with Solid Acid Catalysts." European Journal of Organic Chemistry, 1999, 837-846.
Schaus, Scott E., et al., "Highly Selective Hydrolytic Kinetic Resolution of Terminal Epoxides Catalyzed by Chiral (salen)Co Complexes. Practical Synthesis of Enantioenriched Terminal Epoxides and 1,2-Diols." Journal of the American Chemical Society, 2002, vol. 124, No. 7, pp. 1307-1315.
Martynow, Jacek G., et al., "A New Synthetic Approach to High-Purity (15R)-Latanoprost." European Journal of Organic Chemistry, 2007, pp. 689-703.
Molander, Gary A., et al., "Scope of the Suzuki-Miyaura Cross-Coupling Reaction of Potassium Trifluoroboratoketohomoenolates." The Journal of Organic Chemistry, 2009, vol. 74, pp. 1297-1303.
Kim, Jung Won, et al., "Synthetic Scope of Ru(OH)x/Al2O3-Catalyzed Hydrogen-Transfer Reactions: An Application to Reduction of Allylic Alcohols by a Sequential Process of Isomerization/Meerwein-Ponndorf-Verley-Type Reduction." Chemistry—A European Journal, 2008, vol. 14, pp. 4104-4109.
Alcaraz, L., et al., "Novel Conversion of Epoxides to One Carbon Homologated Allylic Alcohols by Dimethylsulfonium Methylide." Tetrahedron Letters, 1994, vol. 35, No. 30, pp. 5449-5452.
Kanbayashi, Naoya, et al., "Ruthenium-Catalyzed Regio-and Enantioselective Allylic Substitution with Water: Direct Synthesis of Chiral Allylic Alcohols." Angewandte Chemie International Edition, 2011, vol. 50, pp. 5197-5199.
Uenishi, Jun'ichi, et al., "Pd-Catalyzed Cascade Reaction with 1,3-Chirality Transfer; Stereoselective Synthesis of Chiral Nonracemic 2,2'-THF-THF Ring Units." Organic Letters, 2011, vol. 13, No. 9, pp. 2350-2353.
Denmark, Scott E., et al., "Intramolecular [4+2] Cycloaddition of Nitroalkenes for Construction of Vicinal Quaternary Stereocenters." Organic Letters, 2005, vol. 7, No. 25, pp. 5617-5620.
Dalgard, Jackline E., et al., "Memory of Chirality in the Transannular Cyclization of Cyclodecenyl Radicals." Organic Letters, 2004, vol. 6, No. 16, pp. 2713-2716.
Zanoni, Giuseppe, et al., "The Meyer-Schuster Rearrangement: A New Synthetic Strategy Leading to Prostaglandins and Their Drug Analogs, Bimatoprost and Latanoprost." Tetrahedron, 2010, vol. 66, pp. 7472-7478.
Matsuda, Fuyuhiko, et al., "Hydroxyl-Directed Intermolecular Ketone—Olefin Couplings Promoted by SmI2." Chemistry European Journal, 1999, vol. 5, No. 11, pp. 3252-3259.

LACTOL AND ACETAL INTERMEDIATES FOR MAKING PROSTAGLANDINS

FIELD OF THE INVENTION

The present invention relates to a compound of formula (I) as defined below, a process for making a compound of formula (I), and a process for making a prostaglandin or a prostaglandin analogue using a compound of formula (I).

BACKGROUND TO THE INVENTION

Prostaglandins are hormone-like chemical messengers that regulate a host of physiological activities essential to life, such as the contraction and relaxation of smooth muscle tissue, the dilation and constriction of blood vessels, control of blood pressure, and modulation of inflammation. In nature, prostaglandins are derived from arachidonic acid (AA) and transformed by prostaglandin synthetase into a number of structurally related carbocyclic molecules. These sensitive and labile molecules are not stored in the body but are synthesized in response to stimuli. They were first discovered in the early 1930s by von Euler and by the mid 1960s the structures of the first family of prostaglandins was uncovered by Bergström et al.

The breadth of biological activity, coupled with their challenging molecular architecture has made prostaglandins popular targets in synthesis for over 40 years. Furthermore, prostaglandin analogues are widely used as pharmaceuticals and some have become billion dollar drugs, such as latanoprost, an analogue of the prostaglandin $PGF_{2\alpha}$, which is used in the treatment of glaucoma.

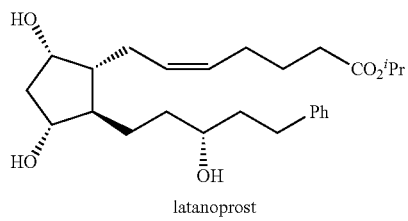

latanoprost

However, the currently available ways of manufacturing prostaglandins still require lengthy syntheses. A synthesis strategy developed by E. J. Corey in 1969, as described in Corey et al., *Journal of the American Chemical Society*, 1969, 91, 5675, involves formation of a key intermediate, the Corey lactone, synthesised in 9 steps from cyclopentadiene. The other members of the family of prostaglandins can be assembled from this lactone; prostaglandin $PGF_{2\alpha}$, for example, can be assembled from the Corey lactone in 8 further steps, i.e. in 17 steps from cyclopentadiene.

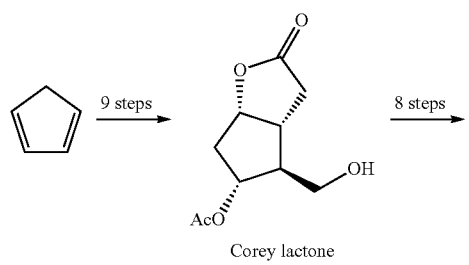

Corey lactone

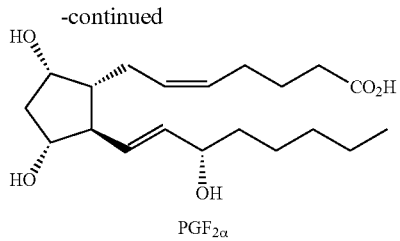

$PGF_{2\alpha}$

The manufacture of latanoprost requires 20 steps and utilizes the original 1969 synthesis developed by E. J. Corey, including the use of the Corey lactone.

Both the naturally occurring prostaglandins and their synthetic analogues such as latanoprost contain a number of chiral centres. It is well known that enantiomerically pure drugs are usually more biologically active than their racemic counterparts. In some cases the redundant enantiomer even has undesired side effects. It is highly desirable, therefore, to synthesize prostaglandins in enantiomerically pure form.

Despite the enantioselective tools available to modern synthetic chemists, a more efficient synthesis for manufacturing prostaglandins has remained elusive. Most if not all of the currently available ways of manufacturing prostaglandins require lengthy syntheses where every step costs time and money, generates waste, and is invariably accompanied by material losses. A need remains for new methods of synthesizing prostaglandins which are more efficient and less expensive than the existing syntheses.

It is an aim of the invention to provide a significantly shorter synthesis for manufacturing prostaglandins, including both the naturally occurring prostaglandins, such as $PGF_{2\alpha}$, and their synthetic analogues, such as latanoprost.

STATEMENTS OF THE INVENTION

According to a first aspect of the invention there is provided a compound of formula (I):

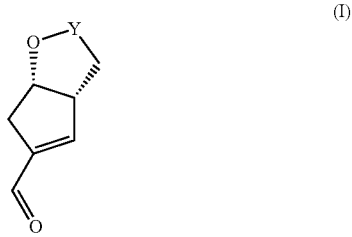

(I)

wherein
Y is

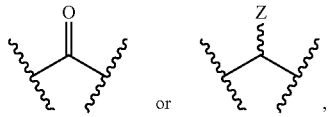

Z is $OR^{10}$, $NR^{11}R^{11}$, $SR^{11}$, $S(O)R^{11}$, $SO_2R^{11}$, $R^{10}$ is H, optionally substituted alkyl, optionally substituted cycloalkyl, optionally substituted alkenyl, optionally substituted alkynyl, optionally substituted aryl, optionally substituted heteroaryl, optionally substituted heterocyclyl, $CO-R^{11}$, or a protecting group, and $R^{11}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl.

When the compound of formula (I) contains more than one group $R^{11}$, the groups $R^{11}$ may be the same or different from each other.

Formula (I) encompasses a new key intermediate, lactol (Ia), wherein Z is $OR^{10}$ and $R^{10}$ is H, and its functionalized and/or protected forms. This new key intermediate allows significantly shorter synthetic routes to a range of naturally occurring prostaglandins, such as $PGF_{2\alpha}$, and to their synthetic analogues, such as latanoprost. Furthermore, the new key intermediate can be synthesized in only one reaction from succinaldehyde with very high enantioselectivity. The successful outcome of this reaction was highly surprising, in view of the very large number of alternative reaction pathways available to highly reactive succinaldehyde (which has two reactive aldehyde groups on each molecule), as discussed in more detail under the second aspect of the invention below.

Throughout this specification, unless expressly stated otherwise:

- An "optionally substituted" group may be unsubstituted, or substituted with one or more, for example one or two, substituents. These substituents may for example be selected from alkyl, cycloalkyl, alkenyl, alkynyl, aryl, heteroaryl and heterocyclyl groups; carboxylic acids and carboxylate ions; carboxylate esters; carbamates; alkoxyl groups; ketone and aldehyde groups; amine and amide groups; —OH; —CN; —$NO_2$; and halogens.
- An alkyl group may be a straight or branched chain alkyl group. The alkyl group may contain up to 20 carbon atoms. The alkyl group may be C1 to C6 alkyl, or C1 to C4 alkyl, or C1 to C3 alkyl, or C1 to C2 alkyl.
- A cycloalkyl group may contain up to 8 carbon atoms.
- An alkenyl group may be a straight or branched chain alkenyl group. The alkenyl group may contain up to 20 carbon atoms. The alkenyl group may be C2 to C6 alkenyl, or C2 to C4 alkenyl.
- An alkynyl group may be a straight or branched chain alkynyl group. The alkynyl group may contain up to 20 carbon atoms. The alkynyl group may be C2 to C6 alkynyl, or C2 to C4 alkynyl.
- An aryl group may be a monocyclic or bicyclic aromatic group. The aryl group may contain from 5 to 12 carbon atoms.
- A heteroaryl group may be a monocyclic or bicyclic group. The heteroaryl group may contain from 1 to 12 carbon atoms and one or more N, O or S atoms. The heteroaryl group may be a 5 or 6-membered ring containing one or more N atoms.
- A heterocyclyl group may be a monocyclic or bicyclic group. The heterocyclyl group may contain from 1 to 12 carbon atoms and one or more N, O or S atoms.
- The term "protecting group" means a group capable of protecting an oxygen atom, which protecting group may, subsequent to the reaction for which protection is employed, be removed without disturbing the remainder of the molecule. Protecting groups are well known and listed in standard texts such as Kocienski P. J., Protecting Groups, 3rd ed., Georg Thieme Verlag, New York, 2005; and Greene T. W., Wuts P. G. M., Protective Groups In Organic Synthesis, 3rd ed., John Wiley & Sons, New York, 1998. In an embodiment, the protecting group can make the chemical moiety, which consists of an oxygen atom and the protecting group, unavailable for a reaction with an organometallic reagent.

In an embodiment, Y is

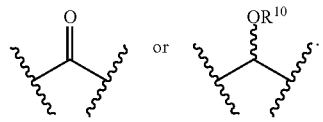

In an embodiment, $R^{10}$ is C1 to C6 alkyl. In an embodiment, $R^{10}$ is methyl, ethyl or t-butyl.

In an embodiment, $R^{10}$ is methyl or t-butyl. In an embodiment, $R^{10}$ is methyl substituted with a phenyl group, i.e. $R^{10}$ is benzyl. In an embodiment, $R^{10}$ is optionally substituted benzyl.

In an embodiment, $R^{10}$ is cyclohexyl or cyclopentyl. In an embodiment, $R^{10}$ is cyclohexyl or cyclohexyl substituted with one or more alkyl groups, such as for example one or more C1-C6 alkyl groups. In an embodiment, $R^{10}$ is menthyl (2-isopropyl-5-methylcyclohexyl).

In an embodiment, $R^{10}$ is phenyl. In an embodiment, $R^{10}$ is phenyl substituted with one or more substituents including phenyl. In an embodiment, $R^{10}$ is phenyl substituted with phenyl. In an embodiment, $R^{10}$ is a monocyclic or bicyclic aromatic group containing from 5 to 12 carbon atoms.

In an embodiment, $R^{10}$ is CO—$R^{11}$ and $R^{11}$ is phenyl, i.e. $R^{10}$ is benzoyl. In an embodiment, $R^{10}$ is optionally substituted benzoyl.

In an embodiment, $R^{10}$ is a protecting group selected from benzyl, benzoyl, methoxymethyl (MOM), methoxyethoxymethyl ether (MEM), tetrahydropyranyl (THP), and silicon protecting groups such as, for example, trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

In an embodiment, Y is

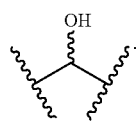

In an embodiment, Y is

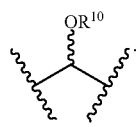

In an embodiment, Y is

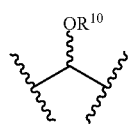

and $R^{10}$ is optionally substituted alkyl.

In an embodiment, $R^{10}$ is methyl.

According to a second aspect of the invention there is provided a process for making a compound of formula (I) as defined above, which comprises at least a key step of: treating succinaldehyde (II) with (i) a chiral secondary amine catalyst and (ii) an acidic co-catalyst, in a suitable solvent system, to form lactol (Ia), in accordance with the following reaction scheme:

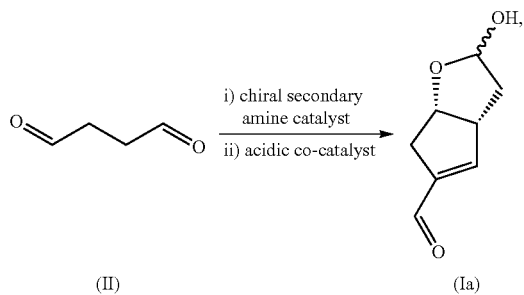

wherein the acidic co-catalyst is added to the reaction mixture after or simultaneously with the chiral secondary amine catalyst;

the chiral secondary amine catalyst has the following structure:

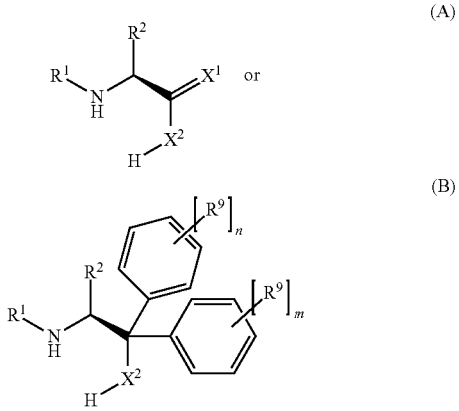

wherein
$R^1$ and $R^2$ are optionally substituted alkyl groups, or $R^1$ and $R^2$ are linked to form part of an optionally substituted 4-, 5- or 6-membered heterocycle;
$X^1$ is O, S or $NR^3$, wherein $R^3$ is an alkyl group, or $R^3$ is linked with $R^4$ to form part of a 5- or 6-membered ring which may contain one or more further N atoms;
$X^2$ is O or $NR^4$, wherein $R^4$ is haloalkyl (preferably $CF_3$), aryl substituted with one or more halogens or haloalkyl groups (preferably $CF_3$), $SO_2R^5$, or $R^4$ is linked with $R^3$ to form part of a 5- or 6-membered ring which may contain one or more further N atoms, and $R^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;
n is an integer from 1 to 5;
m is an integer from 1 to 5; and
each $R^9$ is independently selected from an electron-withdrawing group (such as for example a halogen, a haloalkyl (preferably $CF_3$), $NO_2$ or CN) and an optionally substituted alkyl, and at least one $R^9$ on each phenyl ring is an electron-withdrawing group (such as for example a halogen, a haloalkyl (preferably $CF_3$), $NO_2$ or CN);

and
the acidic co-catalyst is selected from $[Bn_2NH_2][OCOCF_3]$, $[Bn_2NH_2][BF_4]$, $[Bn_2NH_2][OCOCHCl_2]$, $[Bn_2NH_2][O—C_6H_3-2,4-(NO_2)_2]$, $[Bn_2NH_2][Cl]$, 2,6-piperidinedione, morpholinium trifluoroacetate, thiomorpholinium trifluoroacetate, pyridinium trifluoroacetate, benzylammonium trifluoroacetate, quinine trifluoroacetate, 2,2'-bipyridinium monotrifluoroacetate, 2,2':6',2''-terpyridinium monotrifluoroacetate, pyridinium p-toluenesulfonate (PPTS), trifluoroacetic acid (TFA), trifluoromethanesulfonic acid, camphorsulfonic acid (CSA) (in particular (±)-CSA, (+)-CSA or (−)-CSA), tartaric acid (in particular (+)-tartaric acid, (−)-tartaric acid or (±)-tartaric acid), 2,4-dinitrophenol, tetrafluoroboric acid, $ZnCl_2$, $Zn(OTf)_2$, $Sc(OTf)_3$, Amberlite 120, Montmorillonite K10, 1,3-bis(3,5-bis(trifluoromethyl)phenyl)thiourea, magnesium sulfate, and combinations thereof.

When $R^3$ and $R^4$ are linked to form part of a 5- or 6-membered ring, it is possible for $R^3$ and/or $R^4$ to be a nitrogen atom.

The process of the invention gives access to a new key intermediate, lactol (Ia), which allows significantly shorter synthetic routes to a range of naturally occurring prostaglandins, such as $PGF_{2a}$, and to their synthetic analogues, such as latanoprost. Furthermore, the new key intermediate can be synthesized in only one reaction from succinaldehyde with very high enantioselectivity. The term "very high enantioselectivity" means that the desired enantiomer is formed in at least 80:20 e.r. (60% ee), at least 85:15 e.r. (70% ee), at least 90:10 e.r. (80% ee), at least 91:9 e.r. (82% ee), at least 92:8 e.r. (84% ee), at least 93:7 e.r. (86% ee), at least 94:6 e.r. (88% ee), at least 95:5 e.r. (90% ee), at least 96:4 e.r. (92% ee), at least 97:3 e.r. (94% ee), at least 98:2 e.r. (96% ee) or at least 99:1 e.r. (98% ee).

The successful outcome of the single-flask conversion of two molecules of succinaldehyde to the lactol (Ia) was highly surprising, in view of the number of alternative reaction pathways available to the highly reactive succinaldehyde with its two reactive aldehyde groups on each molecule (including polymerization). The process of the present invention surprisingly provides lactol (Ia) from succinaldehyde with very high enantioselectivity while circumventing other possible reaction pathways available. Some of these possible pathways are shown in the overview below, with the desired pathway from succinaldehyde (II) to lactol (Ia) shown in the centre:

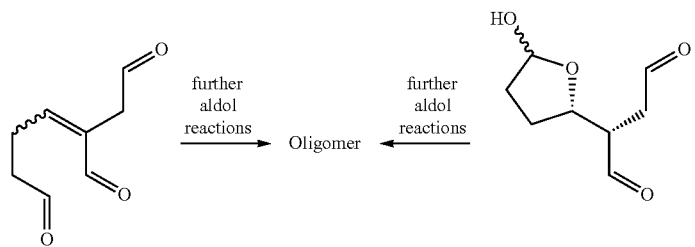

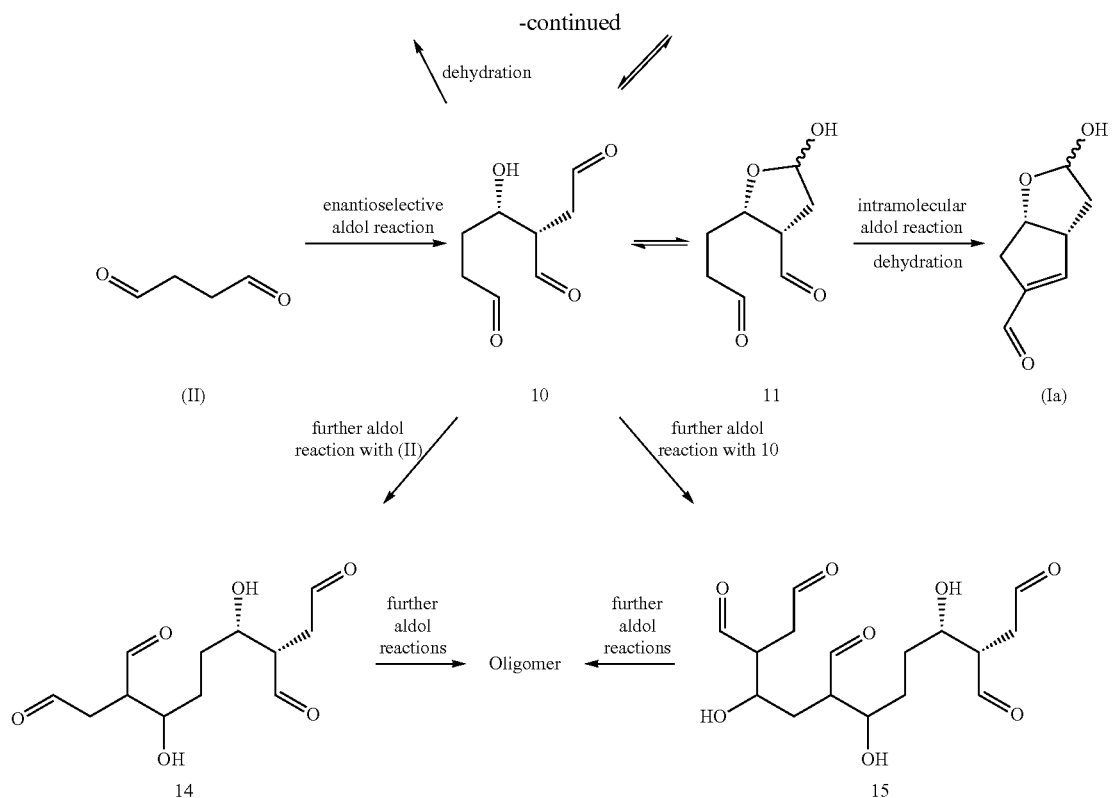

As shown in this overview, after an initial enantioselective aldol reaction between two molecules of succinaldehyde (II), aldol product 10 is required to form the less favoured hemiacetal 11 rather than hemiacetal 12. Hemiacetal 11 is required to undergo an intramolecular second aldol reaction and eliminate to give (Ia), but aldol 10 itself should not eliminate to give 13. In addition to this aldol 10 is a reactive trialdehyde which will be prone to undergo further aldol reactions with succinaldehyde (II) or with itself, leading to 14 and 15 and ultimately oligomers.

Treatment of succinaldehyde (II) with proline in a range of solvents and under a variety of conditions did not deliver any of the desired lactol (Ia) but instead gave oligomeric material. However, the inventors surprisingly found that it was possible to arrive at the desired lactol (Ia) by using the process according to the second aspect of the invention, which uses a combination of two catalysts as defined above.

Without wishing to be bound by theory, it is postulated that the chiral secondary amine catalyst catalyses the enantioselective conversion of succinaldehyde (II) to trialdehyde product 10. Product 10 may equilibrate to form a small amount of dialdehyde 11, and it is postulated that the acidic co-catalyst catalyses the conversion of any dialdehyde 11 to the desired lactol (Ia).

In an embodiment, the acidic co-catalyst is added to the reaction mixture after the chiral secondary amine catalyst has been added. Significant improvements in yield were observed using a staggered addition of the catalysts.

In particular, when the acidic co-catalyst is $ZnCl_2$, $Zn(OTf)_2$, Amberlite 120, or Montmorillonite K10, then the acidic co-catalyst is preferably added to the reaction mixture after the chiral secondary amine catalyst has been added.

The optimum delay to add the acidic co-catalyst, after the chiral secondary amine catalyst has been added to the reaction mixture, was found to be dependent on the amount of chiral secondary amine catalyst employed, the temperature and the concentration, and can readily be established by routine experimentation.

In an embodiment, the acidic co-catalyst is added to the reaction mixture at least 2 hours after the chiral secondary amine catalyst has been added.

In an embodiment, the acidic co-catalyst is added to the reaction mixture at least 8 hours after the chiral secondary amine catalyst has been added.

The chiral secondary amine catalyst has structure (A) or (B) as set out above.

In an embodiment, $R^1$ and $R^2$ are linked to form part of an optionally substituted 4-, 5- or 6-membered heterocycle.

In the definition of the optionally substituted 4-, 5- or 6-membered heterocycle, in addition to the substituents listed under the definition of an optionally substituted group above, the substituents may also be joined with the 4-, 5- or 6-membered heterocycle to form fused rings.

In an embodiment, the optionally substituted 4-, 5- or 6-membered heterocycle comprises, in addition to the N atom, at least one further heteroatom selected from N, S and/or O.

In an embodiment, $R^1$ and $R^2$ are linked to form part of an optionally substituted 4- or 5-membered heterocycle. In an embodiment, the 4- or 5-membered heterocycle is selected from pyrrolidine, thiazolidine, oxazolidine and azetidine.

In an embodiment, $R^1$ and $R^2$ are linked to form part of an optionally substituted 5-membered heterocycle. In an embodiment, the 5-membered heterocycle is selected from pyrrolidine, thiazolidine and oxazolidine. In an embodiment, the 5-membered heterocycle is pyrrolidine.

In an embodiment, the chiral secondary amine catalyst has structure (A):

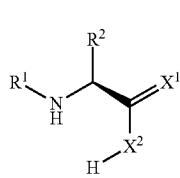
(A)

wherein $R^1$, $R^2$, $X^1$ and $X^2$ are as defined above.

In an embodiment, the chiral secondary amine catalyst comprises any one of the following compounds:

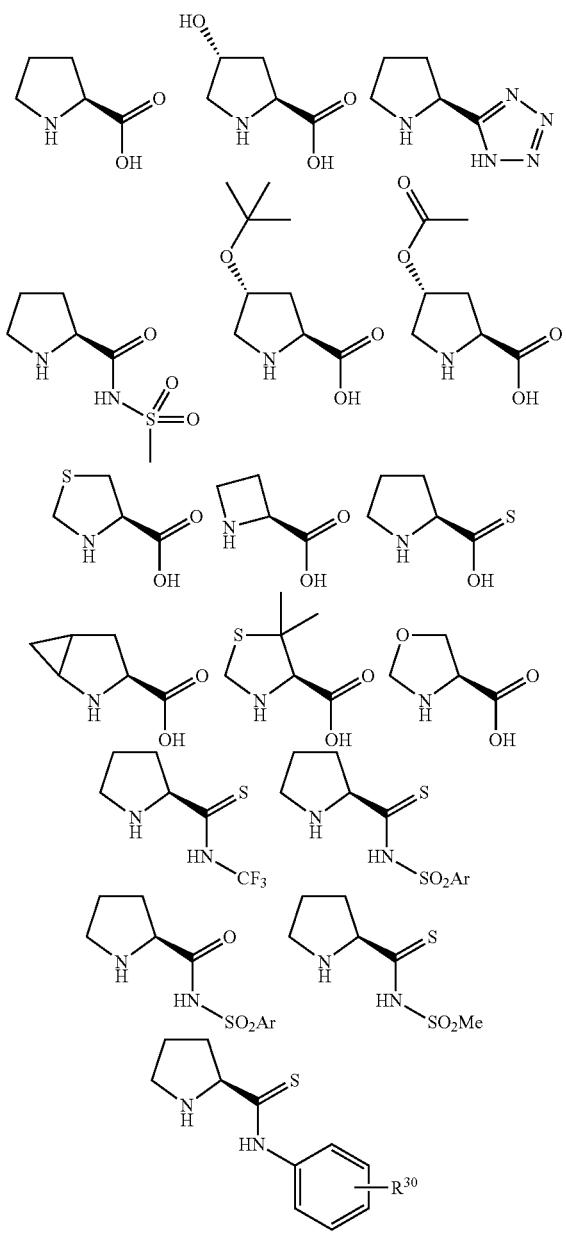

wherein $R^{30}$ is F, Cl, Br, I or $CF_3$ or any combination thereof.

In an embodiment, the chiral secondary amine catalyst comprises the compound:

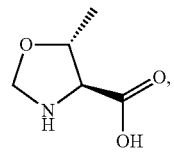

optionally in combination with any of the compounds listed as options for the chiral secondary amine catalyst above.

In an embodiment, $X^1$ is O or $NR^3$, wherein $R^3$ is as defined above.

In an embodiment, the chiral secondary amine catalyst has the following structure:

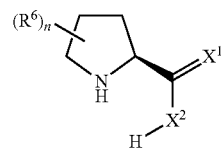

wherein $X^1$ is O or $NR^3$, wherein $R^3$ is an alkyl group, or $R^3$ is linked with $R^4$ to form part of a 5- or 6-membered ring which may contain one or more further N atoms;

$X^2$ is O or $NR^4$, wherein $R^4$ is $SO_2R^5$, or $R^4$ is linked with $R^3$ to form part of a 5- or 6-membered ring which may contain one or more further N atoms, and $R^5$ is an alkyl group or an aryl group;

n is an integer from 0 to 7;

each $R^6$ is independently selected from $-OR^7$, optionally substituted alkyl, optionally substituted cycloalkyl, optionally substituted alkenyl, optionally substituted alkynyl, optionally substituted aryl, optionally substituted heteroaryl, optionally substituted heterocyclyl, or $-CO-R^8$, $R^7$ is H, optionally substituted alkyl, optionally substituted cycloalkyl, optionally substituted alkenyl, optionally substituted alkynyl, optionally substituted aryl, optionally substituted heteroaryl, optionally substituted heterocyclyl, $CO-R^8$, or a protecting group, and $R^8$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl.

In the definition of $R^6$, two groups $R^6$ may also be joined together to form fused rings.

In an embodiment, n is 0, 1, 2, 3, 4, 5, 6 or 7. In an embodiment, n is 0 or 1.

In an embodiment, $X^1$ is O.

In an embodiment, $X^2$ is O.

In an embodiment, $X^1$ is O and $X^2$ is O.

In an embodiment, $R^6$ is $-OR^7$, wherein $R^7$ is H, an alkyl group, $-CO-R^8$, or a protecting group, and $R^8$ is an alkyl group.

In an embodiment, $R^7$ is a protecting group selected from methoxymethyl (MOM), trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

In an embodiment, $R^6$ is a hydroxyl group, —O-t-butyl or acetyl.

In an embodiment, the chiral secondary amine catalyst comprises any one of the following compounds:

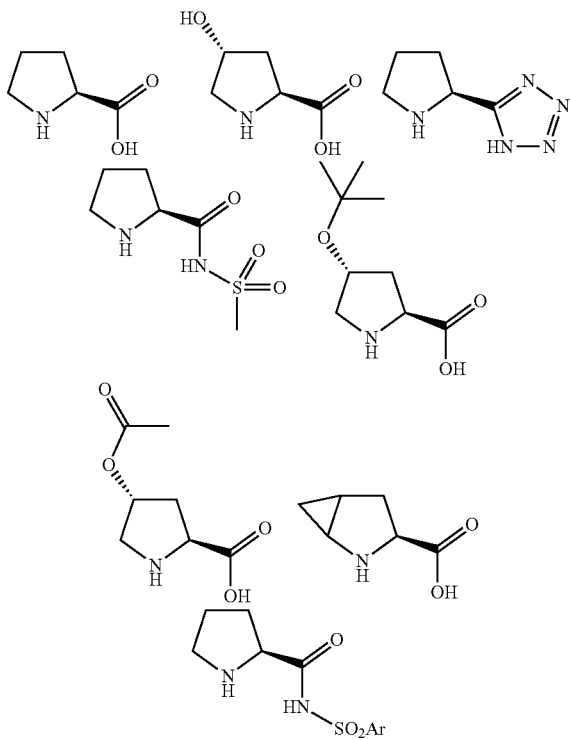

or any combination thereof.

In an embodiment, the chiral secondary amine catalyst comprises any one of the following compounds:

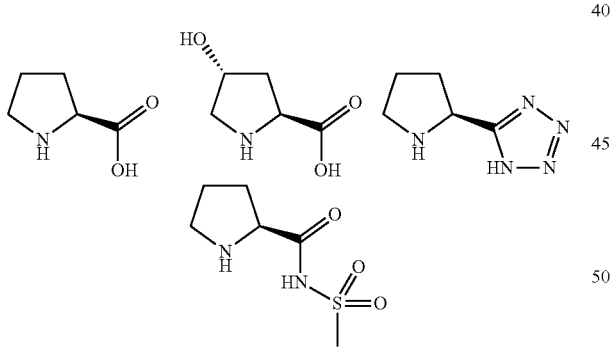

or any combination thereof.

In an embodiment, the chiral secondary amine catalyst comprises any one of the following compounds:

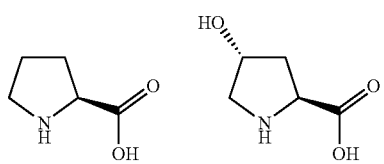 [SMILES: O=C(O)[C@@H]1CCCN1 ; O=C(O)[C@@H]1C[C@@H](O)CN1]

or a combination thereof.

In an embodiment, the chiral secondary amine catalyst comprises (S)-proline, which has the structure:

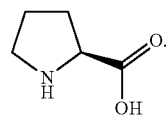

As can be seen from the Examples (see Example 2, Procedure 2), (S)-proline was found to be the most effective of the chiral secondary amine catalysts tested, resulting in the highest yield of lactol (Ia).

In an embodiment, the chiral secondary amine catalyst has structure (B):

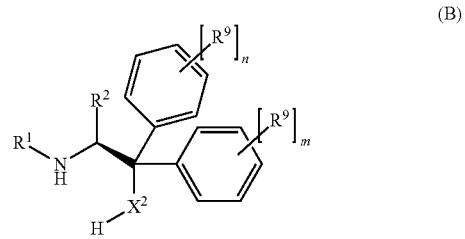

(B)

wherein $R^1$, $R^2$, $X^2$, n, m and $R^9$ are as defined above. In this case, $X^2$ may be O.

In an embodiment, the chiral secondary amine catalyst comprises any one of the following compounds:

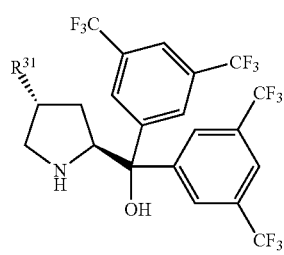

wherein
$R^{31}$ is H, OH, OTBDMS or OBn

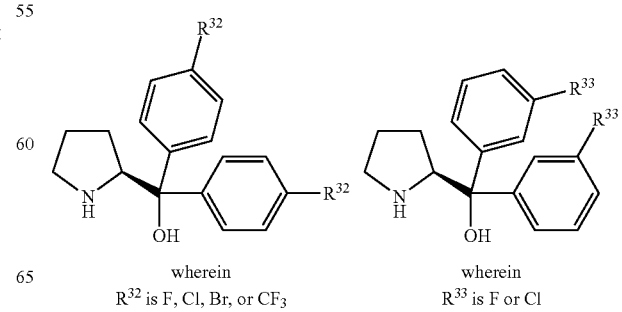

wherein
$R^{32}$ is F, Cl, Br, or $CF_3$ wherein
$R^{33}$ is F or Cl

-continued

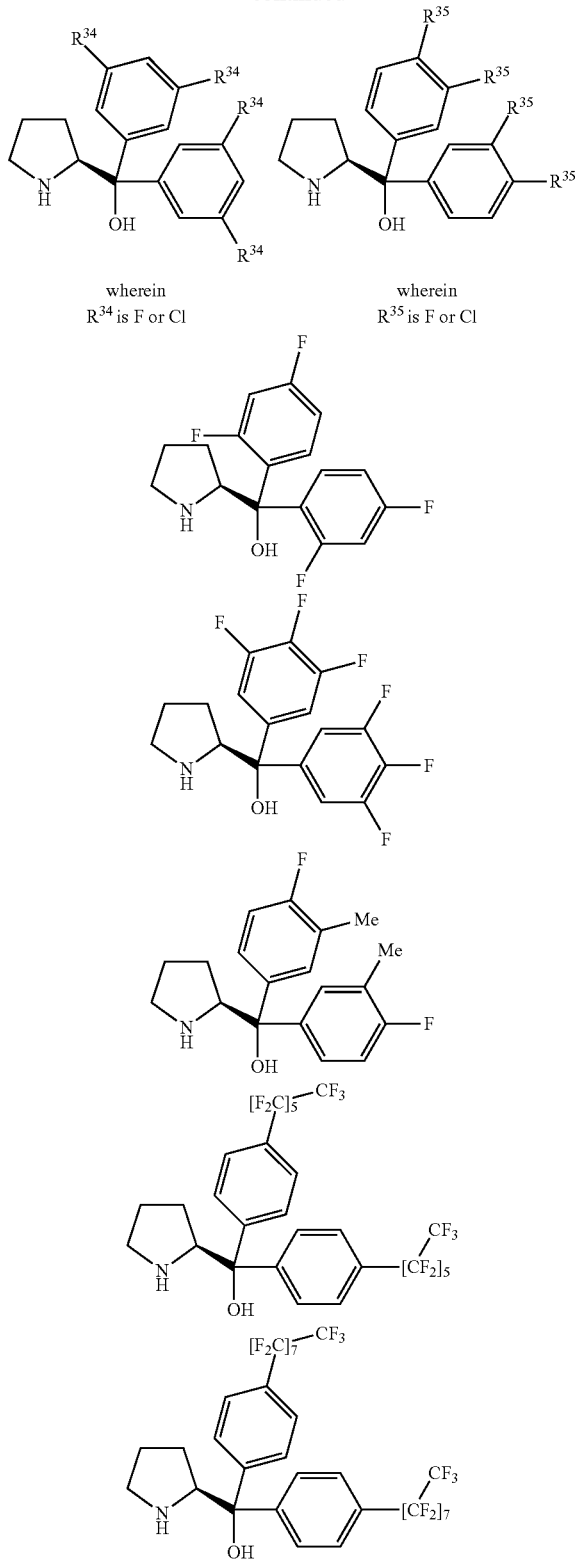

wherein
R^34 is F or Cl wherein
R^35 is F or Cl or any combination thereof.

In an embodiment, the acidic co-catalyst has the structure $[\alpha][\beta]$ wherein $[\alpha]$ is a cation selected from $[Bn_2NH_2]^+$, $[BnNH_3]^+$, $[pyridinium]^+$, $[2,2'$-bipyridinium$]^+$, $[2,2'$:$6',2''$-terpyridinium$]^+$, $[morpholinium]^+$ and $[thiomorpholinium]^+$, and $[\beta]$ is an anion selected from $[F]^-$, $[Cl]^-$, $[Br]^-$, $[I]^-$, $[OCOCF_3]^-$, $[BF_4]^-$, $[OCOCHCl_2]^-$, and $[O—C_6H_3$-$2,4$-$(NO_2)_2]^-$.

In an embodiment, the acidic co-catalyst comprises a cation selected from $[(Bn)_2NH_2]^+$, $[BnNH_3]^+$ and $[pyridinium]^+$.

In an embodiment, the acidic co-catalyst comprises a cation of the formula $[(Bn)_2NH_2]^+$.

In an embodiment, the acidic co-catalyst comprises a cation of the formula $[BnNH_3]^+$.

In an embodiment, the acidic co-catalyst comprises a cation which is $[pyridinium]^+$.

In an embodiment, the acidic co-catalyst comprises an anion of the formula $[OCOCF_3]^-$.

In an embodiment, the acidic co-catalyst comprises $[Bn_2NH_2][OCOCF_3]$. As can be seen from the Examples (see Example 2, Procedures 4, 4a and 5), $[Bn_2NH_2][OCOCF_3]$ was found to be the most effective of the co-catalysts tested, resulting in the highest yield of lactol (Ia).

In an embodiment, the acidic co-catalyst comprises a Brønsted acid.

In an embodiment, the catalyst loading of the chiral secondary amine catalyst is from 1 mol % to 20 mol % with respect to succinaldehyde (II). In an embodiment, the catalyst loading of the chiral secondary amine catalyst is from 1 mol % to 15 mol %, from 1 mol % to 10 mol %, from 1 mol % to 5 mol %, from 2 mol % to 20 mol %, from 2 mol % to 15 mol %, from 2 mol % to 10 mol %, from 2 mol % to 5 mol %, or around 2 mol % with respect to succinaldehyde (II).

In an embodiment, the catalyst loading of the acidic co-catalyst is from 0.05 mol % to 20 mol % with respect to succinaldehyde (II). In an embodiment, the catalyst loading of the acidic co-catalyst is from 0.05 mol % to 15 mol %, from 0.05 mol % to 10 mol %, from 0.05 mol % to 5 mol %, from 1 mol % to 20 mol %, from 1 mol % to 15 mol %, from 1 mol % to 10 mol %, from 1 mol % to 5 mol %, from 2 mol % to 20 mol %, from 2 mol % to 15 mol %, from 2 mol % to 10 mol %, from 2 mol % to 5 mol %, or around 2 mol % with respect to succinaldehyde (II).

As can be seen from the Examples (see Example 2, Procedures 3 and 9), the key step of forming lactol (Ia) from succinaldehyde (II) can be conducted at (unusually) low loadings of both catalysts.

In an embodiment, the key step of forming lactol (Ia) from succinaldehyde (II) is performed at a concentration of from 0.2 M to 4 M. These concentrations are calculated based on the amount of succinaldehyde present at the start of the reaction.

In an embodiment, where the acidic co-catalyst is added to the reaction mixture after the chiral secondary amine catalyst has been added, at the stage before the acidic co-catalyst has been added the reaction is performed at a concentration of around 2 M, and at the stage after the acidic co-catalyst has been added the reaction is performed at a concentration of around 1 M. As before, these concentrations are calculated based on the amount of succinaldehyde present at the start of the reaction.

The key step in the process according to the second aspect of the invention is conducted in a suitable solvent system. In the context of this application, a suitable solvent system is a solvent system which is capable of dissolving succinaldehyde (II), the chiral amine catalyst and the acidic co-catalyst at least to the extent which allows the key step to proceed to form lactol (Ia). A suitable solvent system can readily be established by routine experimentation.

In an embodiment, the solvent system comprises an organic solvent other than an alcohol.

In an embodiment, the solvent system comprises an aprotic organic solvent.

In an embodiment, the solvent system comprises tetrahydrofuran (THF), 2-methyltetrahydrofuran, dimethylsulfoxide (DMSO), acetonitrile, ethers such as tert-butyl methyl ether and dimethyl ether (DME), dioxane, toluene, dichloromethane (DCM), dimethoxyethane (DME), formamide, dimethylformamide (DMF), dimethylacetamide, N-methyl-2-pyrrolidone (NMP), sulfolane, esters such as methyl acetate, ethyl acetate, propyl acetate (n-propyl acetate or i-propyl acetate) and butyl acetate (n-butyl acetate, i-butyl acetate, t-butyl acetate or sec-butyl acetate), or a combination thereof.

In an embodiment, the solvent system comprises tetrahydrofuran (THF) or 2-methyltetrahydrofuran, or a combination thereof.

In an embodiment, the solvent system comprises tetrahydrofuran (THF).

In an embodiment, the solvent system comprises less than 50 mol % water with respect to succinaldehyde (II).

In an embodiment, the solvent system comprises less than 25 mol % water with respect to succinaldehyde (II). As can be seen from the Examples (see Example 2, Procedure 7), the key step of forming lactol (Ia) from succinaldehyde (II) was found to tolerate this amount of water without a decrease in yield. This reaction therefore does not require anhydrous conditions; the use of reagent grade THF gives the same yield as the use of anhydrous THF.

In an embodiment, the solvent system comprises water in the presence of 20 mol % or more of triethanolamine relative to succinaldehyde (II).

In an embodiment, the key step is conducted at a temperature of from −10° C. to 40° C. In an embodiment, the key step is conducted at a temperature of from −10° C. to 30° C., from −10° C. to 25° C., from 0° C. to 40° C., from 0° C. to 30° C., from 0° C. to 25° C., from 10° C. to 40° C., from 10° C. to 30° C., from 10° C. to 25° C., or around room temperature.

"Room temperature" is defined as from 16 to 22 or 25° C., or from 18 to 22 or 25° C., for example about 20° C. or about 25° C.

In an embodiment, in particular where the acidic co-catalyst is added to the reaction mixture simultaneously with the chiral secondary amine catalyst, the reaction is performed for a time period between 15 minutes and 48 hours.

In an embodiment, in particular where the acidic co-catalyst is added to the reaction mixture after the chiral secondary amine catalyst has been added, at the stage before the acidic co-catalyst has been added the reaction is performed for a time period between 15 minutes and 48 hours, and at the stage after the acidic co-catalyst has been added the reaction is performed for a time period between 15 minutes and 48 hours.

In an embodiment, the acidic co-catalyst is added to the reaction mixture after the chiral secondary amine catalyst has been added, the chiral secondary amine catalyst is (S)-proline, and the acidic co-catalyst is $[Bn_2NH_2][OCOCF_3]$. In an embodiment, the solvent system comprises tetrahydrofuran (THF) or 2-methyltetrahydrofuran, or a combination thereof. In an embodiment, the catalyst loading of the chiral secondary amine catalyst is around 2 mol % with respect to succinaldehyde (II), and the catalyst loading of the acidic co-catalyst is around 2 mol % with respect to succinaldehyde (II). In an embodiment, the acidic co-catalyst is added to the reaction mixture around 8 hours after the chiral secondary amine catalyst has been added. As can be seen from the Examples (see Example 2), these conditions were found to be the most effective of those tested, resulting in the highest yield of lactol (Ia) if the reaction is performed around the scale used in the Examples. From this starting point, for different reaction scales the optimum catalyst loadings and the optimum delay to add the acidic co-catalyst can readily be established by routine experimentation.

In an embodiment, before the key step, the process further comprises a preceding step of heating 2,5-disubstituted tetrahydrofuran (III) in water to form succinaldehyde (II), in accordance with the following reaction scheme:

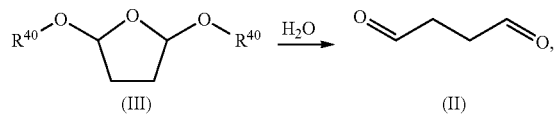

wherein $R^{40}$ is optionally substituted alkyl, optionally substituted alkenyl, optionally substituted aryl, or —$COR^{41}$, where $R^{41}$ is alkyl.

In an embodiment, $R^{40}$ is $C_1$-$C_4$ alkyl. In an embodiment, $R^{40}$ is methyl or ethyl. In an embodiment, $R^{40}$ is methyl.

In an embodiment, the preceding step is conducted in the absence of acid. A hydrolysis of 2,5-dimethoxytetrahydrofuran is known, but acid is generally required, which can interfere with the subsequent aldol reaction, and purification can be difficult. The material obtained by the known method requires purification by distillation, often more than once, unlike the material obtained in the preceding step described above.

As well as forming succinaldehyde (II), the preceding step results in the formation of an alcohol $R^{40}$—OH. In an embodiment, the preceding step comprises evaporating the formed alcohol $R^{40}$—OH.

In an embodiment, the preceding step comprises a change of the solvent system from water to a new solvent system suitable for the key step, as described above, resulting in the formation of a solution of succinaldehyde (II) in the new solvent system. With an appropriate change of the solvent system the preceding step may be carried out in situ, which can result in a one-pot conversion of the 2,5-disubstituted tetrahydrofuran (III) to the lactol (Ia) (as shown for 2,5-dimethoxytetrahydrofuran in Examples 3D, 3E, 3F and 3H).

In an embodiment, the solvent system is changed from water to a solvent system comprising an organic solvent selected from tetrahydrofuran (THF), 2-methyltetrahydrofuran, toluene, ethyl acetate, methyl acetate, and combinations thereof.

In an embodiment, the change of solvent system is achieved by using a Dean-Stark apparatus.

In an embodiment, after the key step, the process further comprises a subsequent step of functionalising lactol (Ia) to give a compound of formula (Ib):

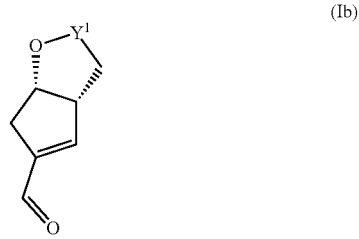

(Ib)

wherein
Y¹ is

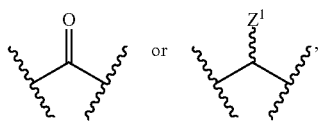

Z¹ is OR²⁰, NR¹¹R¹¹, SR¹¹, S(O)R¹¹, SO₂R¹¹,

R²⁰ is optionally substituted alkyl, optionally substituted cycloalkyl, optionally substituted alkenyl, optionally substituted alkynyl, optionally substituted aryl, optionally substituted heteroaryl, optionally substituted heterocyclyl, CO—R¹¹, or a protecting group, and R¹¹ is as defined above for the first aspect of the invention.

When the compound of formula (Ib) contains more than one group R¹¹, the groups R¹¹ may be the same or different from each other.

In an embodiment, R²⁰ is C1 to C6 alkyl. In an embodiment, R²⁰ is methyl, ethyl or t-butyl. In an embodiment, R²⁰ is methyl or t-butyl. In an embodiment, R²⁰ is methyl substituted with a phenyl group, i.e. R²⁰ is benzyl.

In an embodiment, R²⁰ is cyclohexyl or cyclopentyl. In an embodiment, R²⁰ is cyclohexyl or cyclohexyl substituted with one or more alkyl groups, such as for example one or more C1-C6 alkyl groups. In an embodiment, R²⁰ is menthyl (2-isopropyl-5-methylcyclohexyl).

In an embodiment, R²⁰ is phenyl. In an embodiment, R²⁰ is phenyl substituted with one or more substituents including phenyl. In an embodiment, R²⁰ is phenyl substituted with phenyl. In an embodiment, R²⁰ is a monocyclic or bicyclic aromatic group containing from 5 to 12 carbon atoms.

In an embodiment, R²⁰ is CO—R¹¹ and R¹¹ phenyl, i.e. R²⁰ is benzoyl.

In an embodiment, R²⁰ is a protecting group selected from benzyl, benzoyl, methoxymethyl (MOM), methoxyethoxymethyl ether (MEM), tetrahydropyranyl (THP), and silicon protecting groups such as, for example, trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

In an embodiment, the compound of formula (Ib) can be purified using purification techniques known in the art, such as, for example, column chromatography.

In an embodiment, the compound of formula (Ib) can advantageously be purified by a purification with sodium bisulfite. Purification of aldehydes with sodium bisulfite allows aldehydes in a solution to precipitate as the bisulfite adduct, which can be isolated by filtration. The bisulfite adduct can be reconverted to the aldehyde as required. Purification of the compound of formula (Ib) with sodium bisulfite may allow the compound of formula (Ib) to be purified in the absence of column chromatography, which may assist the scale up of the process. In addition, the resulting bisulfite adduct may have improved storage properties.

According to a third aspect of the invention there is provided a process for making a prostaglandin or a prostaglandin analogue, which uses a compound of formula (I) as defined above as a reactant.

The term "prostaglandin analogue" means a molecule which binds to a prostaglandin receptor, and which therefore shares a number of features with naturally occurring prostaglandins. Such molecules include, for example, latanoprost, bimatoprost, travoprost, unoprostone, cloprostenol, sulprostone, enprostil, misoprostil, nocloprost, arbaprostil, rioprostil, mexiprostil, ornoprostol, rosaprostol, limaprost, gemeprost, beraprost, enisoprost, tiprostanide, remiprostol, meteneprost, viprostol, dimoxaprost, trimoprostil, taprostene and GR-63779X.

In an embodiment, the process according to the third aspect of the invention uses an acetal of formula (Ic):

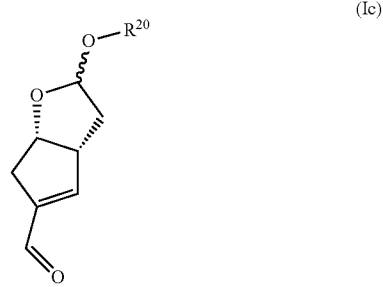

wherein R²⁰ is as defined above for the second aspect of the invention, as a reactant.

In an embodiment, the acetal of formula (Ic) is formed by protecting lactol (Ia), in accordance with the following reaction scheme:

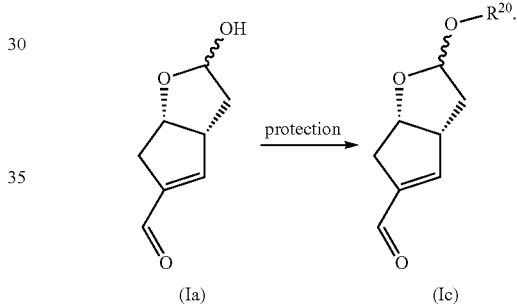

The resulting acetal of formula (Ic) is a protected form of lactol (Ia).

In an embodiment, the acetal of formula (Ic) can be purified using purification techniques known in the art, such as, for example, column chromatography. In an embodiment, the acetal of formula (Ic) can advantageously be purified by a purification with sodium bisulfite, as discussed above.

In an embodiment, the lactol (Ia) is formed by treating succinaldehyde (II), in accordance with the key step in the process of the second aspect of the invention, with (i) a chiral secondary amine catalyst and (ii) an acidic co-catalyst, in accordance with the following reaction scheme:

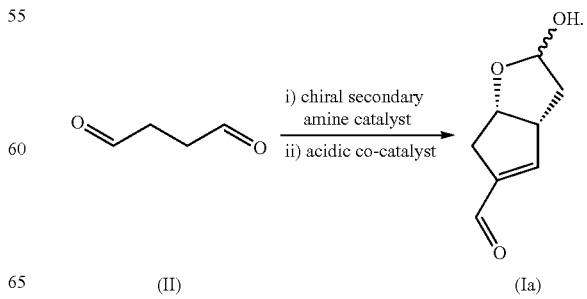

In an embodiment, the process of the third aspect of the invention comprises the steps of:

(a) optionally treating succinaldehyde (II) with (i) a chiral secondary amine catalyst and (ii) an acidic co-catalyst to form lactol (Ia) as described above;

(b) optionally protecting lactol (Ia) by converting it to an acetal of formula (Ic) as described above;

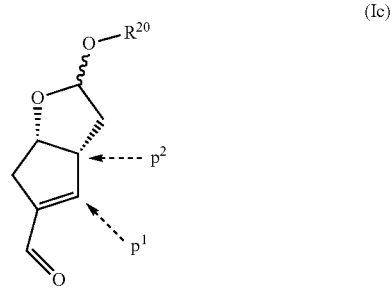

(c) reacting the acetal of formula (Ic) with a soft nucleophile to give a desired side chain at position $p^1$, and protecting the resulting enol ether;

(d) subjecting the compound formed in step (c) to oxidative cleavage, followed by reduction;

(e) deprotecting the compound formed in step (d); and (f) reacting the compound formed in step (e) with an olefination reagent to give a desired side chain at position $p^2$, to form a prostaglandin or a prostaglandin analogue.

In an embodiment, this process includes optional step (b).

In an embodiment, this process includes optional steps (a) and (b).

In an embodiment, the olefination reagent in step (f) is a Wittig reagent.

In an embodiment, the process of the third aspect of the invention is a process for making $PGF_{2\alpha}$, which comprises the steps of:

(a) optionally treating succinaldehyde (II) with (i) a chiral secondary amine catalyst and (ii) an acidic co-catalyst to form lactol (Ia) as described above;

(b) optionally protecting lactol (Ia) by converting it to an acetal of formula (Ic) as described above;

(c) reacting the acetal of formula (Ic) with a soft nucleophile of formula (IV) which is arranged to react via a Michael addition, and protecting the resulting enol ether to form a compound of formula (V);

(d) subjecting the compound of formula (V) to oxidative cleavage, followed by reduction to form a compound of formula (VI);

(e) deprotecting the compound of formula (VI) to give a compound of formula (VII); and (f) reacting the compound of formula (VII) with a phosphonium halide of formula (VIII) via a Wittig reaction to form $PGF_{2\alpha}$;

in accordance with the following reaction scheme:

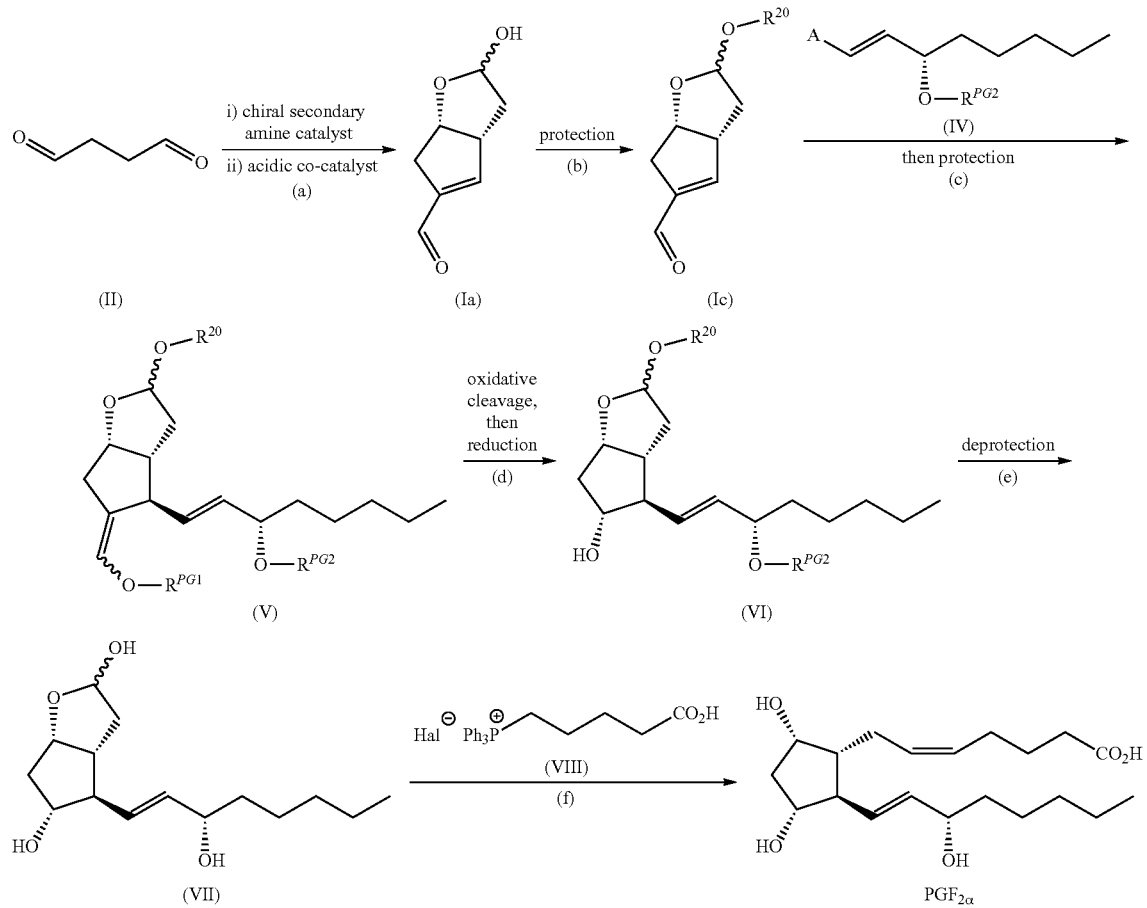

wherein
R$^{PG1}$ and R$^{PG2}$ are protecting groups;
A is a group which allows the compound of formula (IV) to react as a soft nucleophile via a Michael addition; and
Hal$^-$ is a halide group selected from iodide, bromide, chloride and fluoride.

In an embodiment, this process includes optional step (b).

In an embodiment, this process includes optional steps (a) and (b).

The protection in step (b) results in an acetal of formula (Ic), which is a protected form of lactol (Ia).

In an embodiment, R$^{PG1}$ is selected from silicon protecting groups such as, for example, trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

In an embodiment, R$^{PG2}$ is selected from optionally substituted benzyl, optionally substituted benzoyl (for example substituted with phenyl), tetrahydropyranyl (THP), acetate, methoxymethyl (MOM), methoxyethoxymethyl (MEM), ethoxyethyl ether (EE), and silicon protecting groups such as, for example, trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS), (dimethyl)thexylsilyl, and 2-(trimethylsilyl)ethoxymethyl (SEM).

In an embodiment, group A comprises a metal centre with one or more ligands. In an embodiment, group A comprises a Cu centre with one or more ligands.

In an embodiment, the soft nucleophile of formula (IV) is a cuprate reagent. In an embodiment, the cuprate reagent is selected from a mixed higher order cuprate reagent, a heterocuprate reagent and a mixed homocuprate reagent.

In an embodiment, group A is

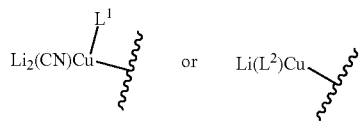

wherein
L$^1$ is a ligand selected from thiophene, pyrrole, imidazole, optionally substituted phenyl, substituted acetylene, (alkylsulfinyl)alkyl and (alkylsulfonyl)alkyl; and
L$^2$ is a ligand selected from CN, PhS, t-BuO, Ph$_2$P, (C$_6$H$_{11}$)$_2$N, t-Bu$_2$P, thiophene, pyrrole, imidazole, optionally substituted phenyl, substituted acetylene, (alkylsulfinyl)alkyl and (alkylsulfonyl)alkyl.

In an embodiment, the soft nucleophile of formula (IV) is a mixed higher order cuprate reagent and group A is

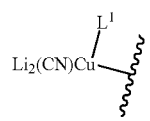

wherein L$^1$ is a ligand selected from thiophene, pyrrole, imidazole, optionally substituted phenyl, substituted acetylene, (alkylsulfinyl)alkyl and (alkylsulfonyl)alkyl.

In an embodiment, group A is selected from the following structures:

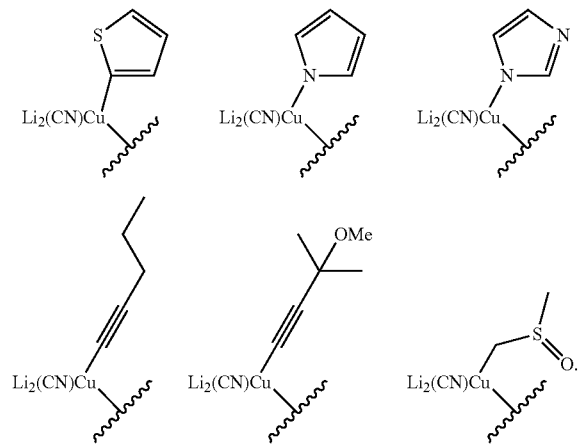

In an embodiment, group A has the following structure:

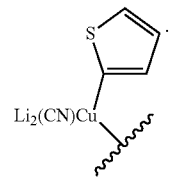

In an embodiment, the soft nucleophile of formula (IV) is a heterocuprate reagent and group A is

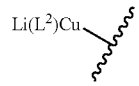

wherein L$^2$ is a ligand selected from CN, PhS, t-BuO, Ph$_2$P, (C$_6$H$_{11}$)$_2$N, and t-Bu$_2$P.

In an embodiment, the soft nucleophile of formula (IV) is a mixed homocuprate reagent and group A is

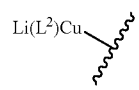

wherein L$^2$ is a ligand selected from thiophene, pyrrole, imidazole, optionally substituted phenyl, substituted acetylene, (alkylsulfinyl)alkyl and (alkylsulfonyl)alkyl.

In an embodiment, group A is

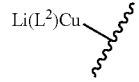

wherein L² is selected from the following structures:

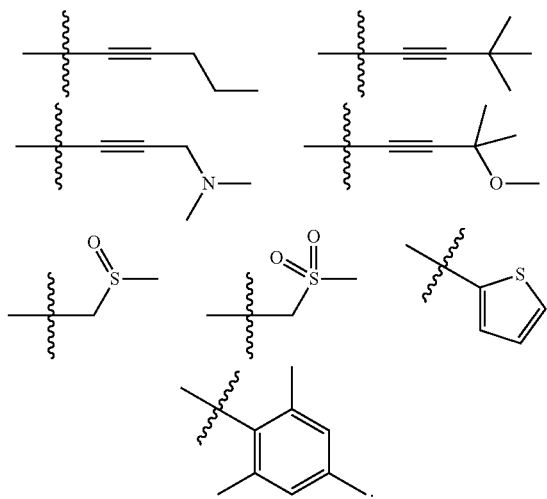

In an embodiment, the oxidative cleavage in step (d) is ozonolysis.

Protection, deprotection and reduction can be carried out in the usual ways known to the skilled person; these are routine steps in chemical synthesis.

In an embodiment, in step (f) Hal⁻ in formula (VIII) is selected from iodide, bromide and chloride. In an embodiment, in step (f) the phosphonium halide of formula (VIII) is a phosphonium bromide, i.e. Hal⁻ in formula (VIII) is bromide.

In an embodiment, the process of the third aspect of the invention is a process for making latanoprost, which comprises the steps of:

(a) optionally treating succinaldehyde (II) with (i) a chiral secondary amine catalyst and (ii) an acidic co-catalyst to form lactol (Ia) as described above;

(b) optionally protecting lactol (Ia) by converting it to an acetal of formula (Ic) as described above;

(c) reacting the acetal of formula (Ic) with a soft nucleophile of formula (IV') which is arranged to react via a Michael addition, and protecting the resulting enol ether to form a compound of formula (V');

(d) subjecting the compound of formula (V') to oxidative cleavage, followed by reduction to form a compound of formula (VI');

(e) deprotecting the compound of formula (VI') to give a compound of formula (VII');

(f) reacting the compound of formula (VII') with a phosphonium halide of formula (VIII) via a Wittig reaction to form a compound of formula (IX); and (g) alkylating the compound of formula (IX) to form latanoprost;

in accordance with the following reaction scheme:

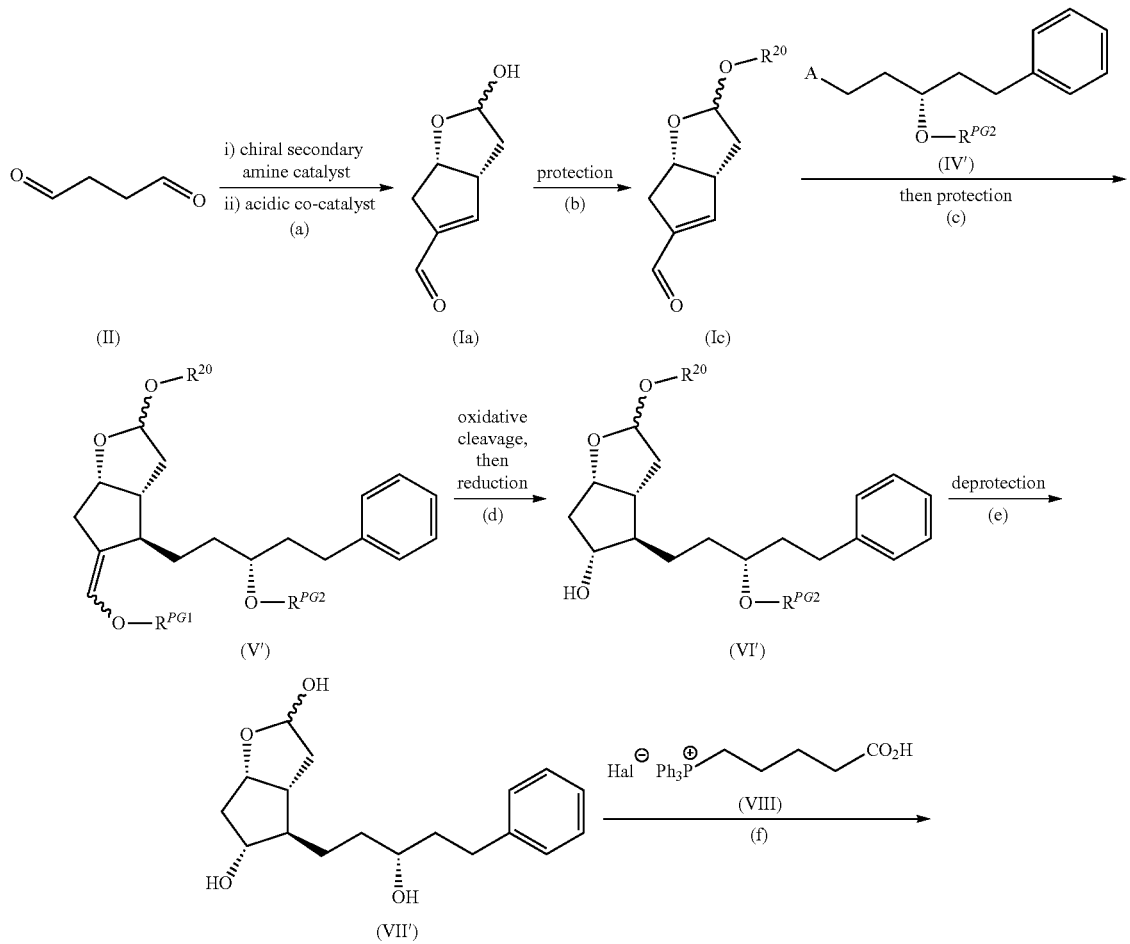

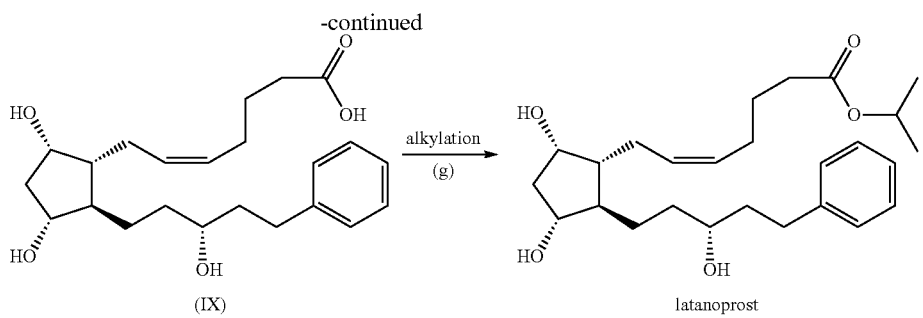

wherein
$R^{PG1}$ and $R^{PG2}$ are as defined above;
A is a group which allows the compound of formula (IV') to react as a soft nucleophile via a Michael addition; and
Hal⁻ is as defined above.

In an embodiment, this process includes optional step (b).

In an embodiment, this process includes optional steps (a) and (b).

The protection in step (b) results in an acetal of formula (Ic), which is a protected form of lactol (Ia).

In an embodiment, the soft nucleophile of formula (IV') is a cuprate reagent. In an embodiment, the cuprate reagent is selected from a mixed higher order cuprate reagent, a heterocuprate reagent and a mixed homocuprate reagent.

Group A is as defined above.

In an embodiment, the oxidative cleavage in step (d) is ozonolysis.

In an embodiment, the alkylation in step (g) comprises reacting the compound of formula (IX) with a propyl halide.

Protection, deprotection and reduction can be carried out in the usual ways known to the skilled person; these are routine steps in chemical synthesis.

In an embodiment, the process of the third aspect of the invention is a process for making bimatoprost, which comprises the steps of:

(a) optionally treating succinaldehyde (II) with (i) a chiral secondary amine catalyst and (ii) an acidic co-catalyst to form lactol (Ia) as described above;

(b) optionally protecting lactol (Ia) by converting it to an acetal of formula (Ic) as described above;

(c) reacting the acetal of formula (Ic) with a soft nucleophile of formula (IV''') which is arranged to react via a Michael addition, and protecting the resulting enol ether to form a compound of formula (V''');

(d) subjecting the compound of formula (V''') to oxidative cleavage, followed by reduction to form a compound of formula (VI''');

(e) deprotecting the compound of formula (VI''') to give a compound of formula (VII'''); and (f) reacting the compound of formula (VII''') with a phosphonium halide of formula (VIII''') via a Wittig reaction to form bimatoprost;

in accordance with the following reaction scheme:

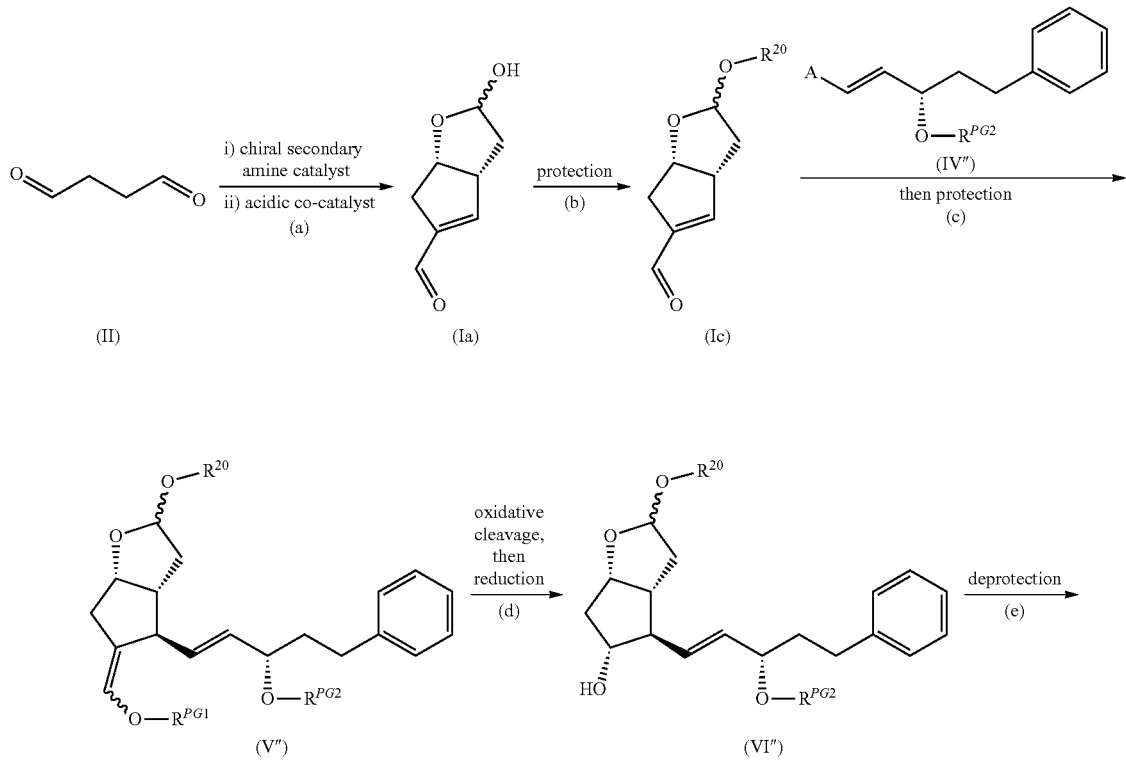

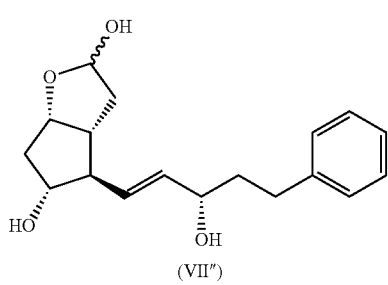
(VII″)

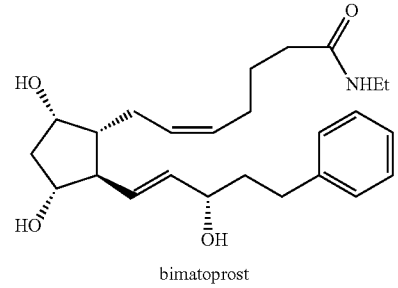
bimatoprost wherein
$R^{PG1}$ and $R^{PG2}$ are as defined above;
A is a group which allows the compound of formula (IV″) to react as a soft nucleophile via a Michael addition; and
Hal⁻ is as defined above.

In an embodiment, this process includes optional step (b).
In an embodiment, this process includes optional steps (a) and (b).

The protection in step (b) results in an acetal of formula (Ic), which is a protected form of lactol (Ia).

In an embodiment, the soft nucleophile of formula (IV″) is a cuprate reagent. In an embodiment, the cuprate reagent is selected from a mixed higher order cuprate reagent, a heterocuprate reagent and a mixed homocuprate reagent.

Group A is as defined above.

In an embodiment, the oxidative cleavage in step (d) is ozonolysis.

Protection, deprotection and reduction can be carried out in the usual ways known to the skilled person; these are routine steps in chemical synthesis.

According to a fourth aspect of the invention there is provided the use of the compound of formula (I) as defined above as a reactant in making a prostaglandin or a prostaglandin analogue.

According to a fifth aspect of the invention there is provided the use of succinaldehyde (II) as a starting material in the preparation of a compound of formula (I) as defined above via the process according to the second aspect of the invention.

According to a sixth aspect of the invention there is provided the use of succinaldehyde (II) as a starting material in the preparation of a prostaglandin or a prostaglandin analogue via the process according to the third aspect of the invention.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to compound properties such as optical rotations are—unless stated otherwise—to properties measured under ambient conditions, i.e. at atmospheric pressure and at a temperature of from 16 to 22 or 25° C., or from 18 to 22 or 25° C., for example about 20° C. or about 25° C.

The present invention will now be further described with reference to the following non-limiting examples, and the accompanying illustrative drawings, of which:

Figure 6:
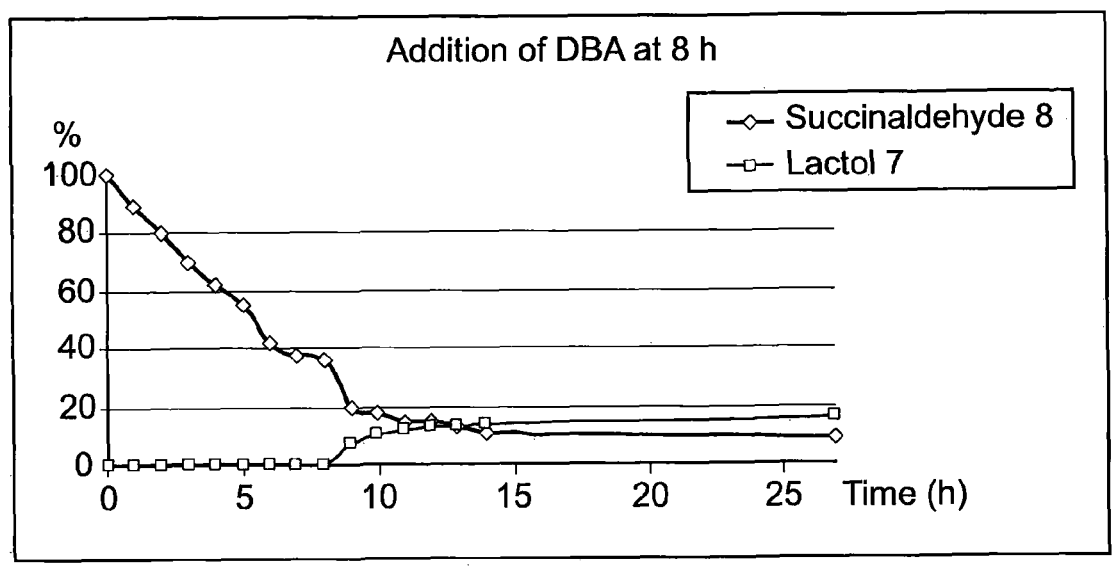

FIG. 6 is a graph showing the consumption of succinaldehyde 8 and formation of lactol 7 in a reaction with 2 mol % (S)-proline and 2 mol % [Bn$_2$NH$_2$][OCOCF$_3$] which was added at 8 h, after dilution to 1 M.

Figure 7:
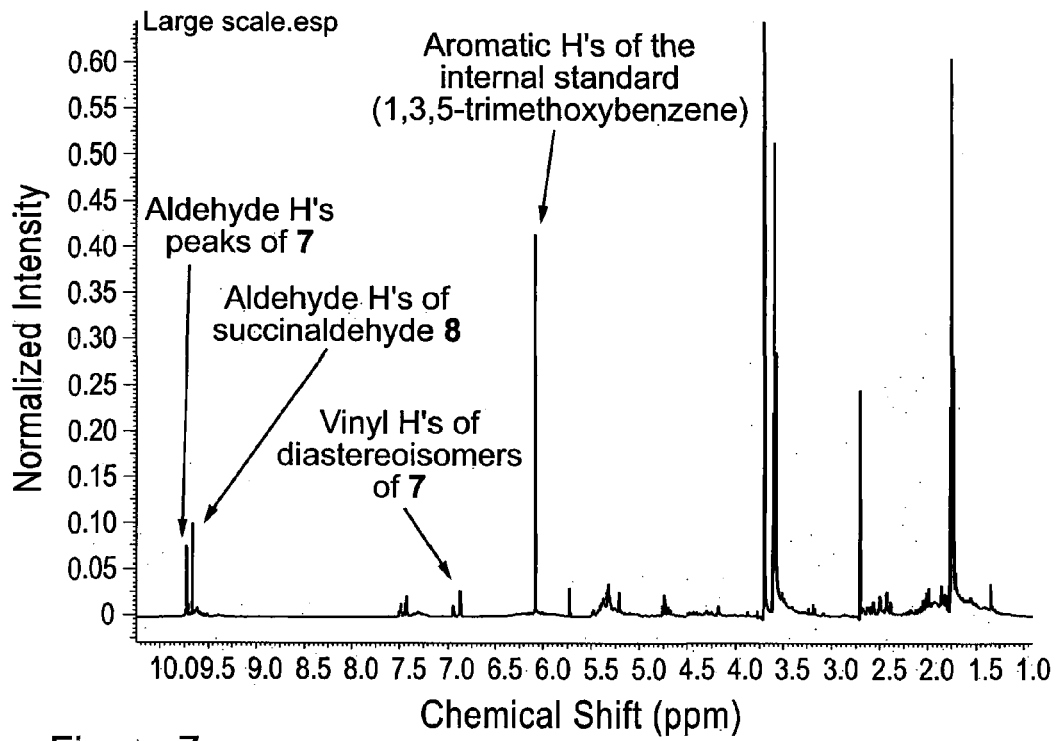

FIG. 7 is a $^1$H NMR of the crude reaction mixture from the 57.5 g scale reaction in Example 3A.

Figure 8:
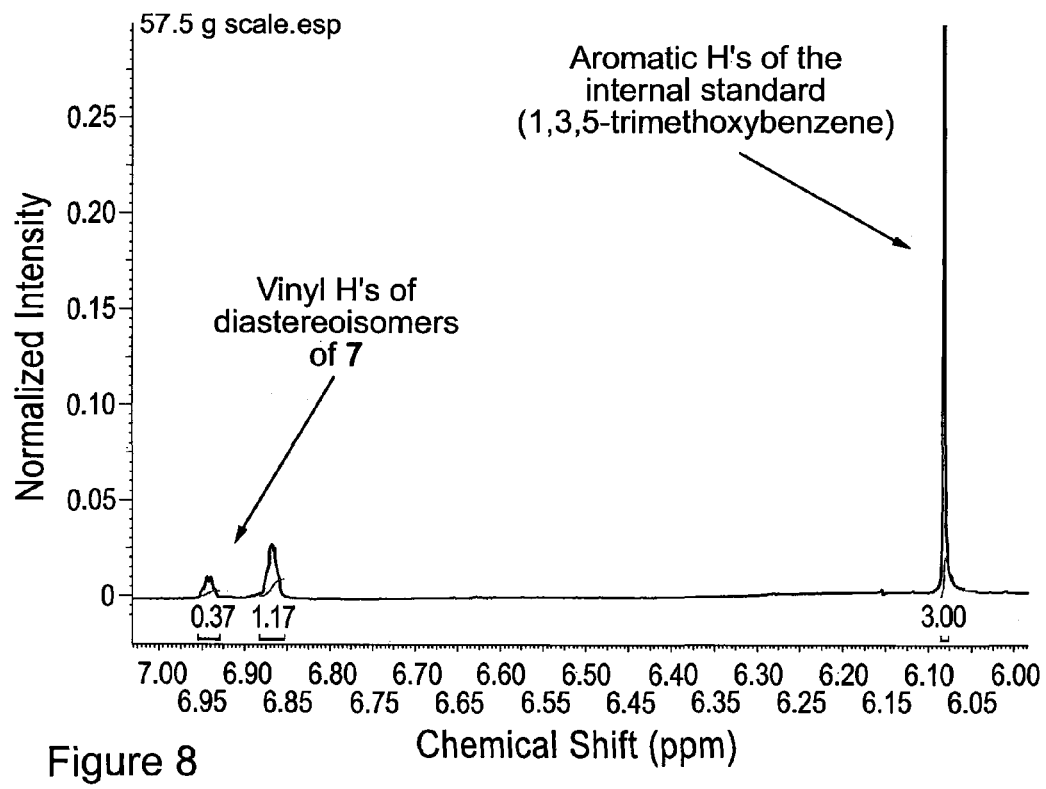

FIG. 8 shows a zoomed-in region of FIG. 7 showing peaks used for yield calculation.

Figure 9A:
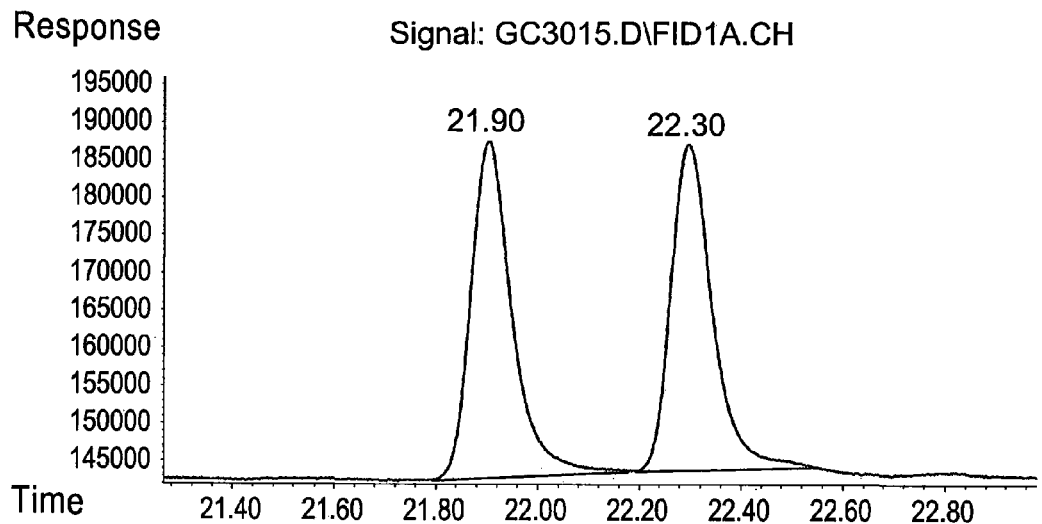

FIG. 9a shown a chiral GC trace corresponding to racemic material (±)-7, minor diastereomer.

Figure 9B:
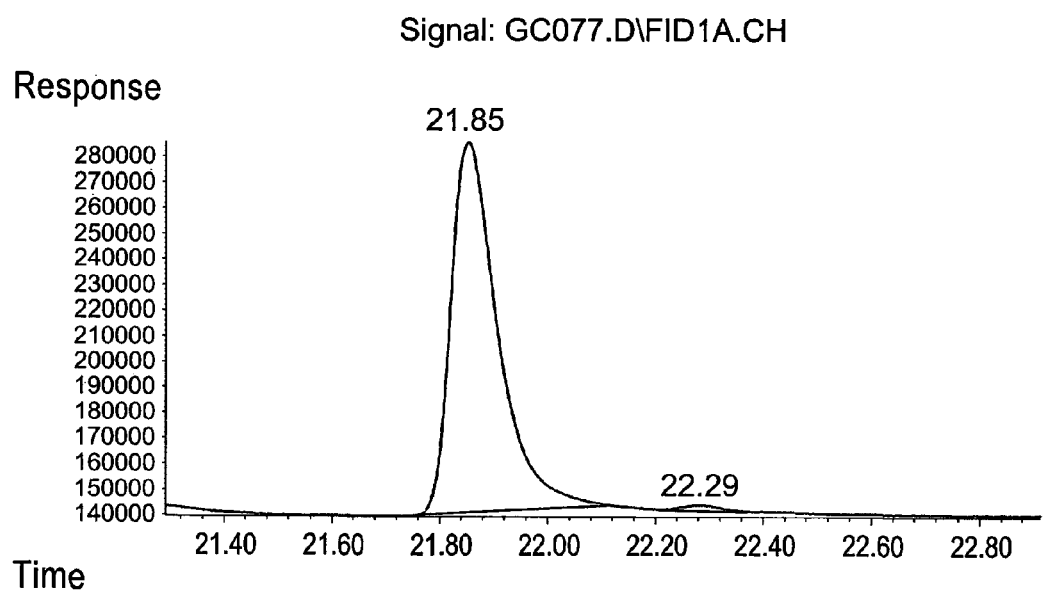

FIG. 9b shown a chiral GC trace corresponding to enantioenriched 7 from organocatalytic reaction, minor diastereoisomer.

Figure 10:
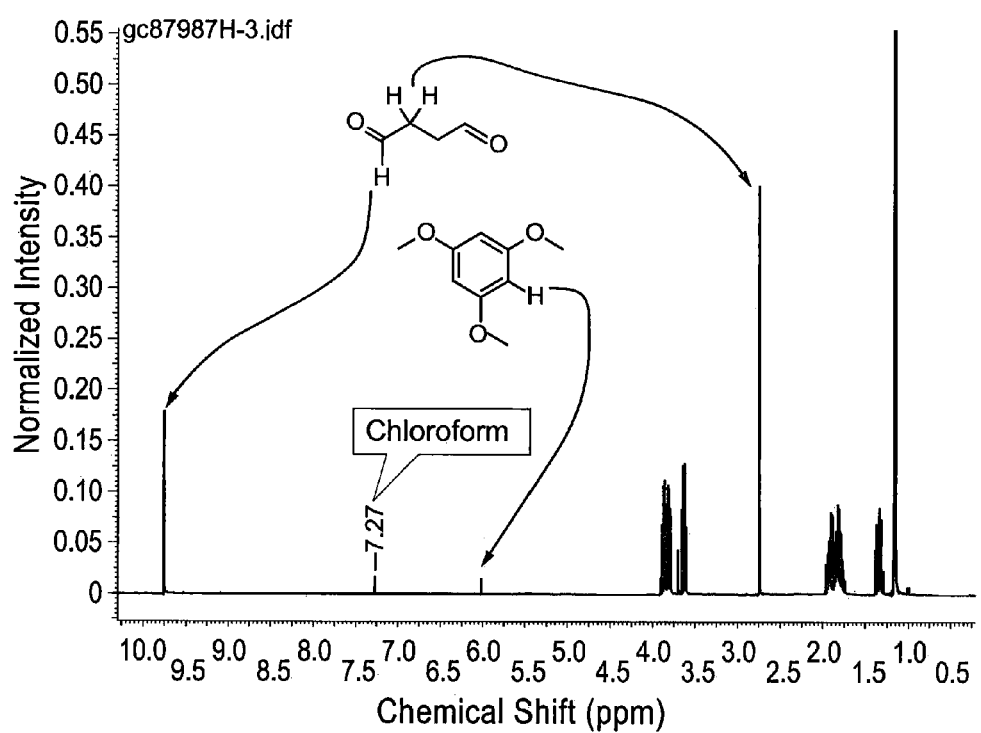

FIG. 10 is a $^1$H NMR spectrum of succinaldehyde 8 in 2-MeTHF with internal standard.

Figure 11:
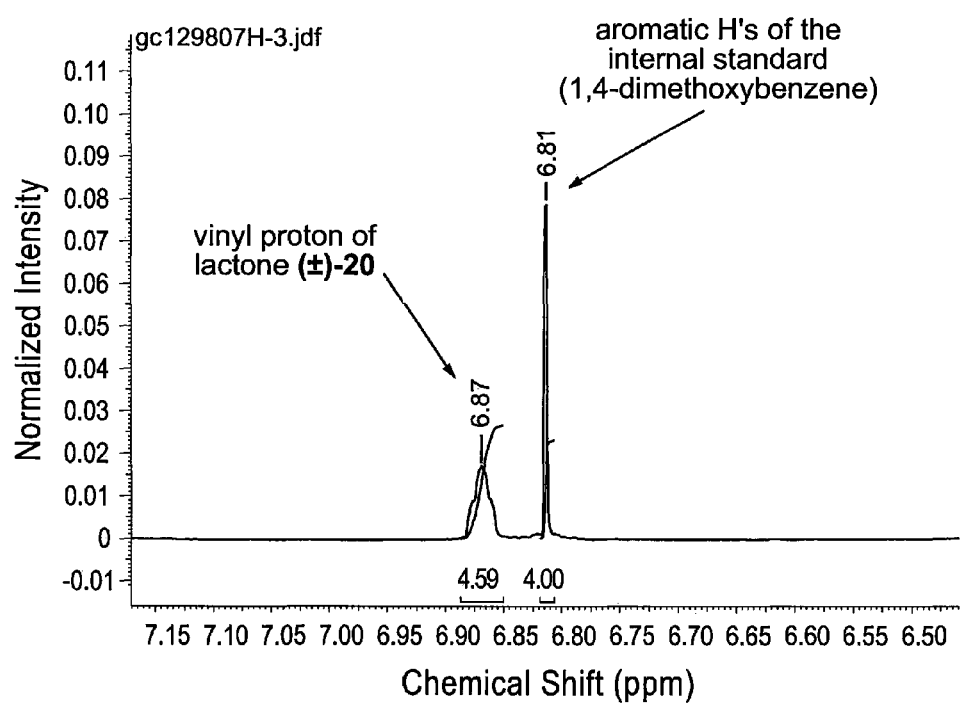

FIG. 11 is a zoomed-in region of the $^1$H NMR of a reaction mixture corresponding to Table 11, entry 2, in Example 8B(e), showing the aromatic H's of the internal standard (1,4-dimethoxybenzene) and the vinyl H of (±)-20 used to determine the yield.

EXPERIMENTAL METHODS

All reactions were carried out using reagent grade solvents and without air excluded except in the case of the preparation of the following compounds: vinyl iodide SI-9, silyl enol ether 26, PGF$_{2\alpha}$, allylic alcohols 64 and 66, alcohol 68, iodide 69, silyl enol ether 70, acid 75, latanoprost 77, alcohol 81, amide 83, ketone 84, alcohol 87, iodide 89, silyl enol ether 92, and bimatoprost 97. In these cases diethyl ether, tetrahydrofuran and dichloromethane were obtained from a purification column composed of activated alumina (Pangborn et al., *Organometallics* 15, 1518-1520 (1996)) and reactions carried out under nitrogen using standard manifold techniques (the use of anhydrous solvents is explicitly stated in the experimental for these compounds). All chemicals were purchased from Acros, Aldrich, Alfa Aesar, Fluka, Lancaster or Merck and used without further purification unless otherwise stated. Triethylamine and trimethylsilyl chloride were distilled over CaH$_2$ under reduced pressure prior to use. Solutions of t-BuLi and n-BuLi were titrated against N-benzylbenzamide using the procedure described in Chong et al., *J. Organomet. Chem.* 542, 281-283 (1997)). Molecular sieves were activated before use by microwave irradiation in a reaction microwave for 5 min at 150° C. Flash chromatography was performed on silica gel (Aldrich or Merck Kieselgel 60 F$_{254}$ 230-400 mesh). All thin layer chromatography was performed on aluminium backed plates pre-coated with silica gel (Merck, Silica Gel 60 F254). Petrol refers to 40/60 petroleum ether. Compounds were visualised by exposure to UV light and/or by dipping the plates in solutions of phosphomolybdic acid or potassium permanganate followed by heating. Details of chromatographic conditions are indicated under each compound. Chiral GC separations were performed on an Agilent 6890N. $^1$H and $^{13}$C NMR spectra were recorded on Varian 500 MHz, Varian 400 MHz, JEOL 400 MHz spectrometers and signals are reported relative to the residual signal of the undeuturated solvent. Mass spectra were recorded using electron impact (EI), electrospray (ESI), or chemical (CI) ionization techniques. Low resolution mass spectra (m/z) were recorded with only major peaks being reported with intensities quoted as percentages of the base peak. IR data was obtained on a PerkinElmer Spectrum One FT-IR-spectrometer with only selected peaks being reported. Optical rotations were obtained on a Bellingham and Stanley Ltd. ADP 220 polarimeter. Melting points were determined using a Kofler hot stage apparatus and are uncorrected.

EXAMPLES

Example 1

Synthesis of Succinaldehyde 8

1A. The Following Procedure was Used to Produce Succinaldehyde 8 (Corresponding to Compound (II) Described Above) on 5-20 g Scale

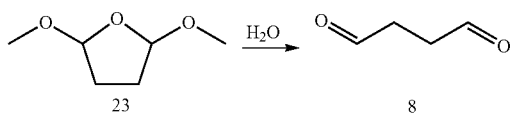

Figure 1:
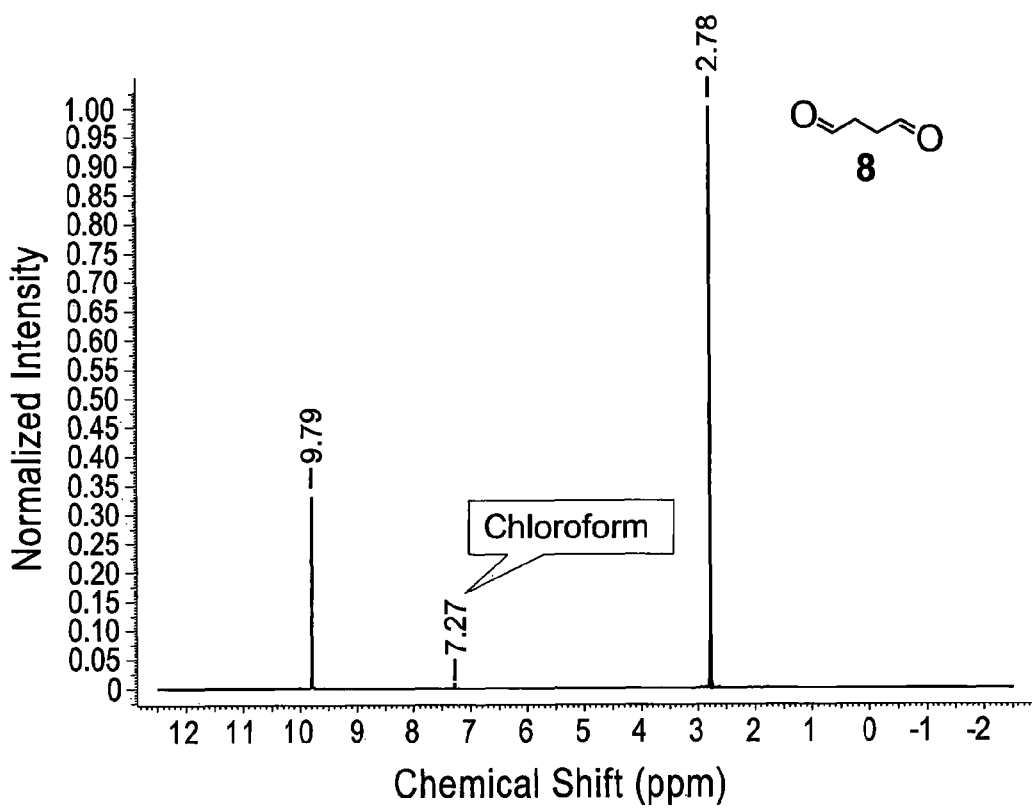
FIG. 1 is a $^1$H NMR spectrum of succinaldehyde 8.
Figure 2:
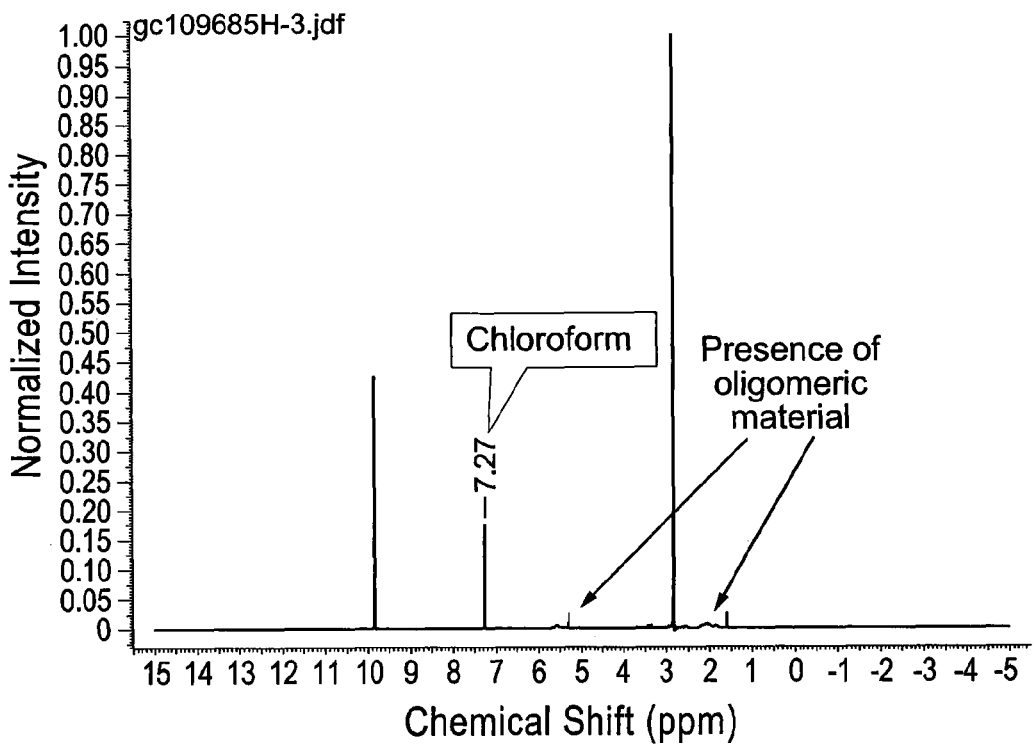
FIG. 2 is a $^1$H NMR spectrum of succinaldehyde 8 showing signs of oligomer formation.

A solution of 2,5-dimethoxytetrahydrofuran 23 (40.8 g, 40.0 ml, 309 mmol) in water (100 ml) was stirred at 75° C. (oil bath temperature) for 4 h. The temperature was then increased to 120° C. (oil bath temperature) and 100 ml of distillate collected (over a period of 3.5-4 h). The reaction mixture was allowed to cool before being extracted with CH$_2$Cl$_2$ (20×25 ml). The combined organic phases were dried (MgSO$_4$), filtered, and concentrated to give succinaldehyde 8 (18.3 g, 69%) as a yellow liquid. Note: During concentration of the CH$_2$Cl$_2$ extracts, for the purposes of this example it is important not to heat the water bath of the rotary evaporator. Doing so can lead to the acceleration of oligomer formation (see FIG. 2). The material could be further purified by distillation under vacuum (0.3 mbar, 45° C.) to give a clear, colourless oil. However, it was found that distillation was not advantageous; $^1$H NMR before distillation was very clean (see FIG. 1) and whether the succinaldehyde had been distilled or not made no difference to the yield of the proline-catalysed reaction. The reaction mixture after distillation of MeOH and water could be stored at −20° C. for over 2 weeks and extracted when required without detriment to the purity of the succinaldehyde. Alternatively, the CH$_2$Cl$_2$ extracts could be stored at −20° C. for 2 or 3 days before concentration without detriment to the purity of the succinaldehyde. The analytical data was consistent with the literature (House, H. O. et al., *J. Org. Chem.* 30, 1061-1070 (1965); Fakstorp, J. et al., *J. Am. Chem. Soc.* 72, 869-874 (1950); Hardy, P. M. et al., *J. Chem. Soc., Perkin Trans.* 2, 2270-2278 (1972)).

R$_f$=0.36 (petrol:EtOAc, 1:1)

$v_{max}$ (CHCl$_3$)/cm$^{-1}$ 2909, 2835, 2732, 1731, 1722, 1411, 1387, 1356

$^1$H NMR (400 MHz; CDCl$_3$) $\delta_H$=2.78 (4H, s, CH$_2$), 9.79 (2H, s, HC=O)

$^{13}$C NMR (100 MHz; CDCl$_3$) $\delta_C$=35.9 (2×CH$_2$), 199.7 (2×HC=O)

1B. The Following Procedure was Used to Produce Succinaldehyde 8 on >50 g Scale

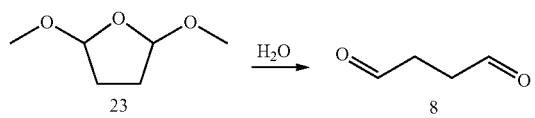

A solution of 2,5-dimethoxytetrahydrofuran 23 (142.8 g, 140 ml, 1.08 mol) in water (420 ml) was stirred at 75° C. (oil bath temperature) for 4 h. The temperature was then increased to 120° C. (oil bath temperature) and 400 ml of distillate collected. The reaction mixture was allowed to cool before being extracted with CH$_2$Cl$_2$ (70×25 ml). The combined organic phases were dried (MgSO$_4$), filtered, and concentrated in seven different batches of 250 ml each (to minimise oligomer formation). For each separate batch, after CH$_2$Cl$_2$ had been removed under vacuum and the mass noted, the appropriate amount of THF was added to make a 2 M solution of succinaldehyde 8. These solutions were combined to give a 2 M solution for subsequent aldol reaction (containing 57.5 g, 62% of succinaldehyde), see Example 3A.

Figure 3:
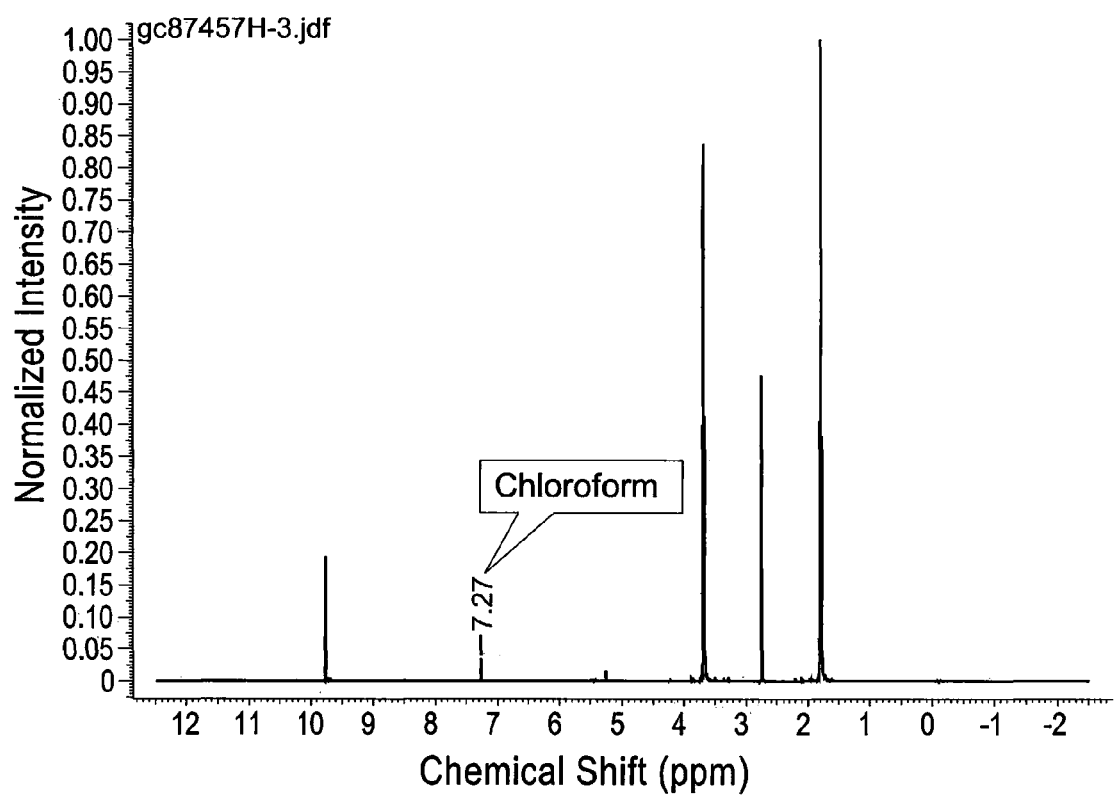
FIG. 3 is a $^1$H NMR spectrum of >50 g preparation of succinaldehyde 8 in THF.

The $^1$H NMR spectrum in FIG. 3 shows a 2 M solution of succinaldehyde 8 in THF prepared as described in the experimental above.

Example 2

General Experimental Procedures for Investigations of Proline-Catalysed Aldol Reaction of Succinaldehyde 8

A number of parameters were investigated for this reaction including solvent, different chiral secondary amine catalysts, different co-catalysts, stoichiometry of catalysts, timing, the effect of water and the effect of concentration, and these are described below.

Solvent Screen (Procedure 1)

Figure 4:
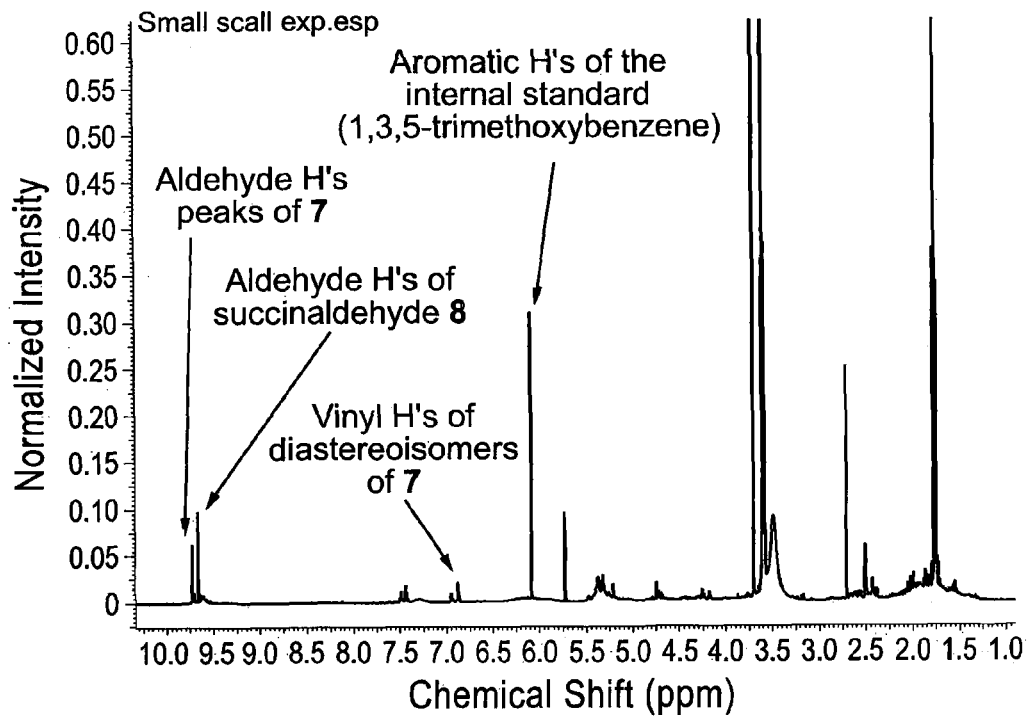
FIG. 4 is a $^1$H NMR spectrum of a 200 mg screening reaction of succinaldehyde 8 with (S)-proline and [Bn$_2$NH$_2$][OCOCF$_3$].
Figure 5:
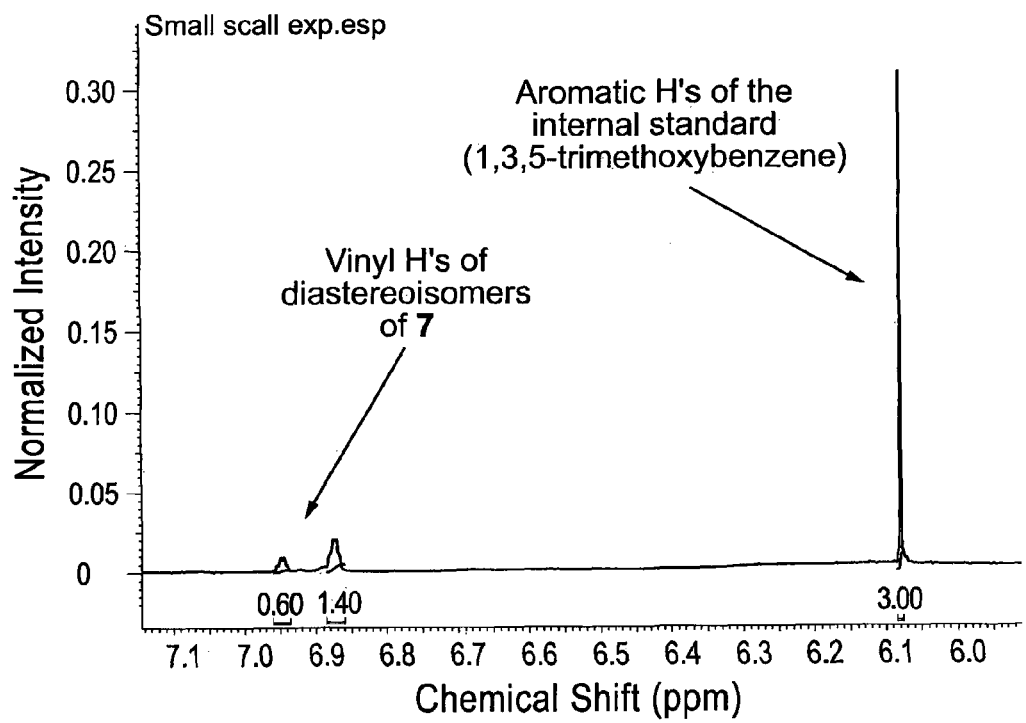
FIG. 5 shows a zoomed-in region of FIG. 4, showing the aromatic H's of the internal standard (1,3,5-trimethoxybenzene) and the vinyl H's of lactol 7 used to determine the yield.

Freshly extracted and concentrated succinaldehyde 8 (200 mg, 2.32 mmol) was dissolved in a solvent (1.16 ml) as set out in Table 1 below and (S)-proline (26.7 mg, 0.23 mmol, 10 mol % w.r.t. 8) was added. The reaction mixture was stirred at r.t. for 4 h before being diluted with the solvent (10.5 ml, taking the reaction to 0.2 M w.r.t. succinaldehyde 8) and [Bn$_2$NH$_2$][OCOCF$_3$] (145 mg, 0.46 mmol, 20 mol % w.r.t. 8) added. The reaction was stirred for 14 h before 1,3,5-trimethoxybenzene (19.5 mg, 0.116 mmol) was added. The reaction was stirred for a further 15 min before an aliquot was taken, DMSO-d6 added, the solvent removed under high vacuum, and the sample analysed by $^1$H NMR (see FIGS. 4 and 5). The amount of lactol 7 present was calculated by comparison of the signals arising from the vinyl protons of the diastereoisomers of 7 with the signals of the internal standard, 1,3,5-trimethoxybenzene.

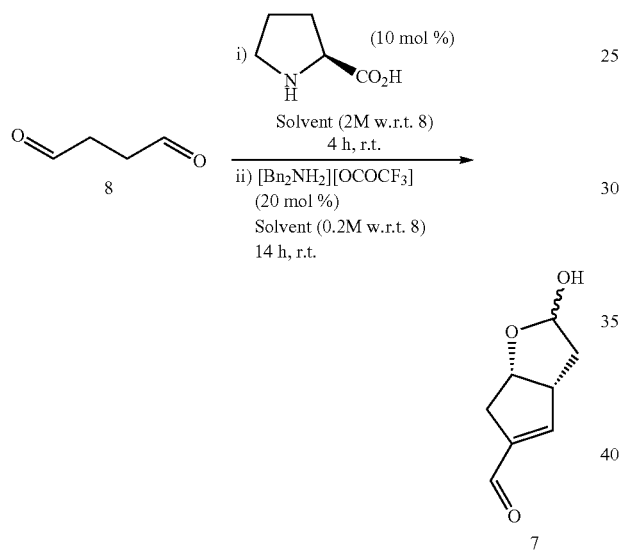

As shown in Table 1 below, the intermolecular aldol reaction of succinaldehyde and its subsequent intramolecular aldol reaction and dehydration could be performed in a wide variety of solvents.

TABLE 1

Solvent screen

| Entry | Solvent | $^1$H NMR Yield (%) |
|---|---|---|
| 1 | CH$_2$Cl$_2$ | 16 |
| 2 | EtOAc | 16.5 |
| 3 | THF | 16 |
| 4 | CH$_3$CN | 17 |
| 5 | DMSO | 11 |
| 6 | DMF | 16.5 |
| 7 | MeOH | 0 |

A wide variety of aprotic solvents, from low dielectric media such as CH$_2$Cl$_2$ (entry 1) to high polarized solvents such as DMF (entry 6) resulted in very similar yields. However, in this particular experiment, use of methanol was not suitable (entry 7). Because of the greater diastereoselectivity observed in our model system when using THF in place of DMF, we decided to carry out subsequent investigations in THF.

Proline and Proline Analogues (Procedure 2)

As for Procedure 1, but with replacement of (S)-proline with the appropriate catalyst from Table 2.

TABLE 2

Catalyst screen-proline and proline analogues

| Entry | Catalyst | $^1$H NMR Yield (%) |
|---|---|---|
| 1 | A | 17 |
| 2 | B | 4 |
| 3 | C | 3 |
| 4 | D | 2.5 |
| 5$^{a,b}$ | E | Traces |
| 6$^{a,b}$ | F | 0 |
| 7$^{a,b}$ | G | 1.5 |
| 8$^{a,b}$ | H | Traces |
| 9$^{a,b}$ | I | Traces |
| 10$^b$ | J | 0 |

$^a$Reaction performed with a 2 h stirring time before addition of 2 mol % [Bn$_2$NH$_2$][OCOCF$_3$]
$^b$Comparative example

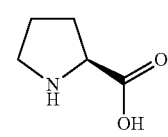

A

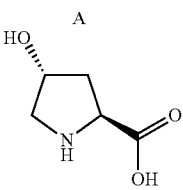

B

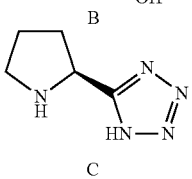

C

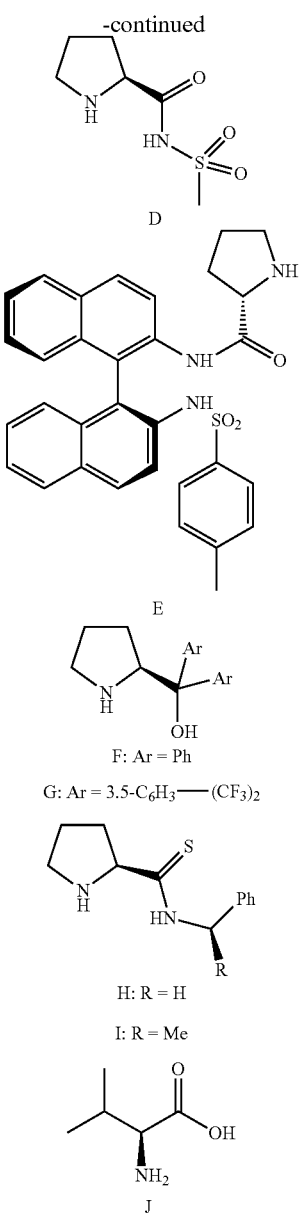

F: Ar = Ph

G: Ar = 3.5-C$_6$H$_3$──(CF$_3$)$_2$

H: R = H

I: R = Me

Substituting (S)-proline for a range of catalysts led to no improvement in conversion (Table 2). (S)-proline (A) catalysed the transformation to an appreciable extent. The use of trans-4-hydroxy-L-proline (B) (Sakthivel, K. et al., *J. Am. Chem. Soc.* 123, 5260-5267 (2001)) led to a decrease in yield. Due to the poor solubility of proline in various organic solvents, tetrazole derivative C has been developed to bypass this problem (Hartikka, A. et al., *Tetrahedron: Asymmetry* 15, 1831-1834 (2004); Cobb, A. J. A. et al., *Synlett* 558-560 (2004); Torii, H. et al., *Angew. Chem. Int. Ed.* 43, 1983-1986 (2004)). However in our case, it gave only a small amount of lactol 7. Various catalysts, including the sulfonamide derivative D (Cobb, A. J. A. et al., *Org. Biomol. Chem.* 3, 84-96 (2005); Bellis, E. et al., *Synthesis* 2407-2413 (2005)) and the prolinethioamides (H and I) (Gryko, D. et al., *Adv. Synth. Cat.* 347, 1948-1952 (2005)), have been developed which possess an NH functionality acidic enough to function in the same way as the OH group of (S)-proline. Use of catalysts H and I in our reaction was not successful, with only traces of product being detected. Use of the Binam-L-prolinamide-derived catalyst E introduced by Guillena and Nájera (Guillena, G. et al., *Synlett* 3031-3035 (2008); Bradshaw, B. et al., *Adv. Synth. Cat.* 351, 2482-2490 (2009)) and prolinol catalysts (F and G) (Hayashi, Y. et al., *Angew. Chem. Int. Ed.* 47, 2082-2084 (2008); Urushima, T. et al., *Org. Lett.* 12, 2966-2969 (2010)) only led to formation of traces of product or no product at all and primary amino acid valine J was also unsuccessful.

During our investigations we found it was possible to increase the concentration, from 0.2 M to 1 M (w.r.t. succinaldehyde 8), at the point of addition of [Bn$_2$NH$_2$][OCOCF$_3$] without detriment to the conversion (see Table 9 for further discussion) as could changing the stirring period from 4 h to 2 h before addition of [Bn$_2$NH$_2$][OCOCF$_3$]. Using these new conditions we investigated the effect of the [Bn$_2$NH$_2$][OCOCF$_3$] loading.

[Bn$_2$NH$_2$][OCOCF$_3$] Loading (Procedure 3)

Freshly extracted and concentrated succinaldehyde 8 (200 mg, 2.32 mmol) was dissolved in THF (1.16 ml) and (S)-proline (26.7 mg, 0.23 mmol) was added. The reaction mixture was stirred at r.t. for 2 h before being diluted with THF (1.16 ml, taking the reaction to 1 M w.r.t. succinaldehyde 8) and [Bn$_2$NH$_2$][OCOCF$_3$] (see Table 3 for mol %) added. The reaction was stirred for 14 h before 1,3,5-trimethoxybenzene (19.5 mg, 0.116 mmol) was added. The amount of lactol 7 present was determined as outlined in Procedure 1.

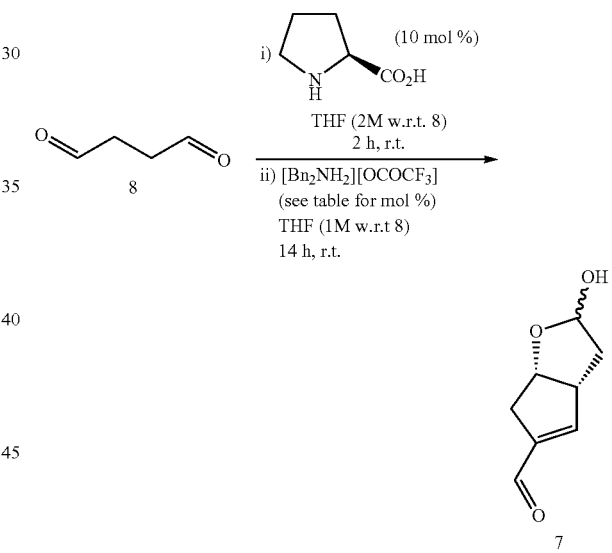

TABLE 3

| | [Bn$_2$NH$_2$][OCOCF$_3$] loading | |
|---|---|---|
| Entry | [Bn$_2$NH$_2$][OCOCF$_3$] (mol %) | $^1$H NMR Yield (%) |
| 1 | 20 | 15 |
| 2 | 2 | 18 |
| 3 | 1 | 18 |
| 4 | 0.5 | 14 |
| 5 | 0.25 | 11.5 |
| 6 | 0.1 | 6 |
| 7 | 0.05 | 4.5 |

Our initial experiments with succinaldehyde employed loadings of 20 mol % of [Bn$_2$NH$_2$][OCOCF$_3$] as described by Corey (Corey, E. J. et al., *J. Am. Chem. Soc.* 100, 8031-8034 (1978)). It was possible to reduce this loading to 1% (w.r.t.

succinaldehyde 8) without any drop in the conversion. Loadings of less than 1% gave lower conversions. On a larger scale we found 2% of [Bn$_2$NH$_2$][OCOCF$_3$] gave more consistent results than 1%. We also investigated the use of a number of alternative co-catalysts in place of [Bn$_2$NH$_2$][OCOCF$_3$]. Alternatives to [Bn$_2$NH$_2$][OCOCF$_3$] (Procedure 4)

Freshly extracted and concentrated succinaldehyde 8 (200 mg, 2.32 mmol) was dissolved in THF (1.16 ml) and (S)-proline (26.7 mg, 0.23 mmol) was added. The reaction mixture was stirred at r.t. for 2 h before being diluted with THF (10.5 ml, taking the reaction to 0.2 M w.r.t. succinaldehyde 8). The appropriate acid catalyst (0.05 mmol) was added. The reaction was stirred for 14 h before 1,3,5-trimethoxybenzene (19.5 mg, 0.116 mmol) was added. The amount of lactol 7 present was determined as outlined in Procedure 1.

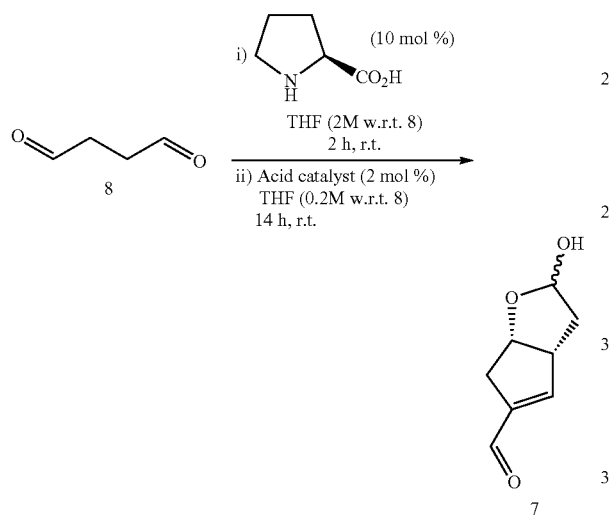

TABLE 4

Alternatives to [Bn$_2$NH$_2$][OCOCF$_3$]

| Entry | Acid | $^1$H NMR Yield (%) |
|---|---|---|
| 1 | [Bn$_2$NH$_2$][OCOCF$_3$] | 15 |
| 2[a] | PPTS | 5.5 |
| 3 | TFA | 15 |
| 4 | CF$_3$SO$_3$H | 5 |
| 5 | (±)-(CSA) | 10 |
| 6 | Morpholinium trifluoroacetate | 13 |
| 7 | (+)-Tartaric acid | 3 |
| 8[b] | Yb(OTf)$_3$ | Traces |
| 9 | ZnCl$_2$ | 7 |
| 10 | Zn(OTf)$_2$ | 3 |
| 11 | Amberlite 120 | 1.5 |
| 12 | Montmorillonite K10 | 1.5 |
| 13 | MgSO$_4$ (2 eq.) | 2.5 |

[a]Dilution to 0.5M before addition of acid catalyst
[b]Comparative example

It appears that for Brønsted acids, no correlation between the pK$_a$ of the acid and the conversion could be made as strong acids like TFA (Table 4, entry 3) and salts such as [Bn$_2$NH$_2$][OCOCF$_3$] (entry 1) gave similar results. The use of a stronger acid, methanesulfonic acid, led to a lower conversion (entry 4). Neither tartaric acid (entry 7) nor camphor sulfonic acid (entry 5) were better that [Bn$_2$NH$_2$][OCOCF$_3$]. Morpholinium trifluoroacetate (entry 6) has been used by List to catalyse the aldol condensation of acetone with aldehydes (Zumbansen, K. et al., Adv. Synth. Cat. 351, 2482-2490 (2010)). Its use in our case led to no improvement in yield.

Penhoat reported a study of the effect of Lewis acids in the asymmetric aldol reaction, postulating aldehyde activation by the metal salt (Penhoat, M. et al., Tetrahedr. Lett. 52, 159-162 (2011)). Among various Lewis acids screened in our conditions, only zinc chloride (entry 9) gave significant amounts of lactol 7.

Others have reported the use of solid basic or acidic catalysts in aldol and aldol-type reactions, with or without proline or proline derivatives (Akagawa, K. et al., Tetrahedr. Lett. 48, 985-987 (2007); Naka, H. et al., J. Oleo. Sci. 50, 813-821 (2001); Loh, T.-P. et al., Tetrahedron. 55, 10789-10802 (1999)). The use of Amberlite 120 and Montmorillonite K10 (entries 11 and 12) resulted in small amounts of product being detected.

Further Alternatives to [Bn$_2$NH$_2$][OCOCF$_3$] (Procedure 4a)

Procedure 4 was repeated with a number of other co-catalysts in place of [Bn$_2$NH$_2$][OCOCF$_3$], as shown in Table 5 below.

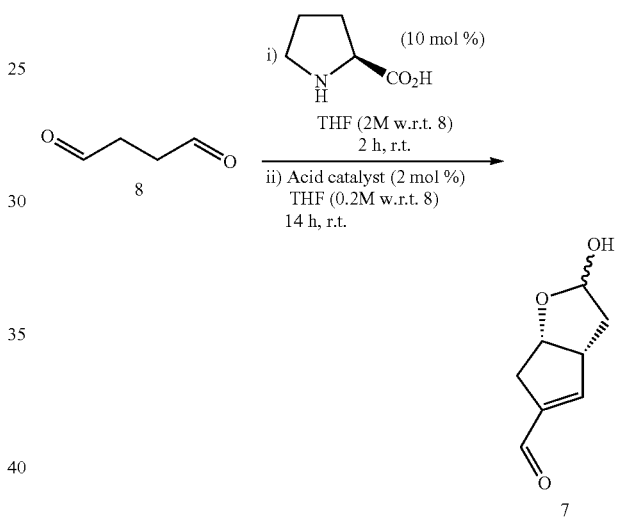

TABLE 5

Alternatives to [Bn$_2$NH$_2$][OCOCF$_3$]

| Entry | Acid | $^1$H NMR Yield (%) |
|---|---|---|
| 1 | [Bn$_2$NH$_2$][OCOCF$_3$] | 15 |
| 2[a] | [Bn$_2$NH$_2$][BF$_4$] | 6.5 |
| 3[a,d] | [Bn$_2$NH$_2$][CF$_3$SO$_3$] | 0 |
| 4[a,d] | [Bn$_2$NH$_2$][OCOCH$_3$] | <1 |
| 5[a,d] | [Bn$_2$NH$_2$][OCOCH$_2$Cl] | 1 |
| 6[a] | [Bn$_2$NH$_2$][OCOCHCl$_2$] | 13 |
| 7[a,d] | [Bn$_2$NH$_2$][OCOCBr$_3$] | 1 |
| 8[a] | [Bn$_2$NH$_2$][O—C$_6$H$_3$-2,4—(NO$_2$)$_2$] | 4 |
| 9[a,d] | [Bn$_2$NH$_2$][OCOCMe$_3$] | 1 |
| 10[a] | [Bn$_2$NH$_2$][Cl] | 4 |
| 11[a,d] | [Bn$_2$NH$_2$][OCOC$_6$H$_5$] | 1 |
| 12[a,d] | [Bn$_2$NH$_2$][OCOC$_6$H$_2$-2,4,6—(iPr)$_3$] | 1 |
| 13[a,d] | N-Ethyldiisopropylammonium trifluoroacetate | 1 |
| 14[a,d] | N,N-Diisopropylammonium trifluoroacetate | <1 |
| 15[b] | 2,6-Piperidinedione | 4 |
| 16 | Morpholinium trifluoroacetate | 13 |
| 17 | Thiomorpholinium trifluoroacetate | 12 |
| 18[c] | Pyridinium trifluoroacetate | 14 |

TABLE 5-continued

Alternatives to [Bn₂NH₂][OCOCF₃]

| Entry | Acid | ¹H NMR Yield (%) |
|---|---|---|
| 19[c] | Benzylammonium trifluoroacetate | 14 |
| 20 | Quinine trifluoroacetate | 2.5 |
| 21 | 2,2'-Bipyridinium monotrifluoroacetate | 12.5 |
| 22 | 2,2': 6',2''-Terpyridinium monotrifluoroacetate | 11 |
| 23 | Pyridinium p-toluenesulfonate | 5.5 |
| 24 | Trifluoroacetic acid | 15 |
| 25 | Trifluoromethanesulfonic acid | 5 |
| 26 | (±)-Camphorsulfonic acid | 10 |
| 27 | (+)-Tartaric acid | 3 |
| 28[a] | 2,4-Dinitrophenol | 2 |
| 29[a] | Tetrafluoroboric acid | 3 |
| 30[b,d] | Yb(OTf)₃ | Traces |
| 31[b] | ZnCl₂ | 7 |
| 32[b] | Zn(OTf)₂ | 3 |
| 33[b] | Sc(OTf)₃ | 2.5 |
| 34[b,d] | MgBr₂ | 1 |
| 35 | Amberlite 120 | 1.5 |
| 36 | Montmorillonite K10 | 1.5 |

[a]Reaction performed with 2 mol % of (S)-proline, a 10 h stirring time before dilution to 1M and addition of 2 mol % acid catalyst
[b]Reaction performed with a 2 h stirring time before 10 mol % of acid catalyst
[c]Reaction performed with 10 mol % of (S)-proline, a 4 h stirring time before dilution to 1M and addition of 20 mol % of acid catalyst
[d]Comparative example As the low yield of the reaction is a consequence of oligomerization of the intermediate trialdehyde, which is prone to undergo further aldol reactions with succinaldehyde, we investigated the presence of various acid catalysts (with additives), in combination with (S)-proline, from the start of the reaction.

Use of (S)-Proline and an Acid Catalyst (with Additive) in Combination at the Start of the Reaction (Procedure 5)

Freshly extracted and concentrated succinaldehyde 8 (200 mg, 2.32 mmol) was dissolved in THF (1.16 ml). (S)-proline (26.7 mg, 0.23 mmol) and the appropriate acid catalyst or additive (0.05 mmol, 2 mol %) was added. The reaction mixture was stirred at r.t. for 14 h. 1,3,5-Trimethoxybenzene (19.5 mg, 0.116 mmol) was added and the amount of lactol 7 present was determined as outlined in Procedure 1.

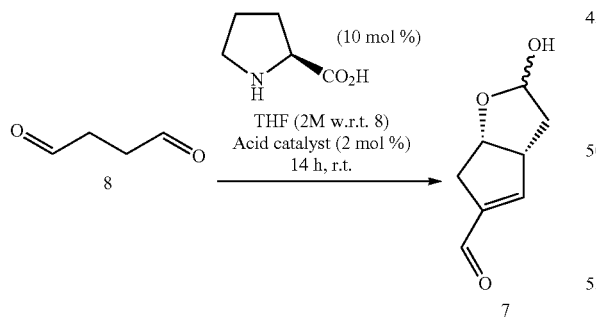

TABLE 6

(S)-Proline and an acid catalyst added together

| Entry | Acid | ¹H NMR Yield (%) |
|---|---|---|
| 1 | [Bn₂NH₂][OCOCF₃] | 7 |
| 2 | PPTS | 3 |
| 3 | TFA | 6 |
| 4 | CF₃SO₃H | 2 |
| 5 | (±)-(CSA) | 3 |
| 6 | Morpholinium trifluoroacetate | 2.5 |
| 7 | (+)-Tartaric acid | 4 |
| 8a | Yb(OTf)₃ | Traces |
| 9 | ZnCl₂ | 0 |
| 10 | Zn(OTf)₂ | 0 |
| 11 | Amberlite 120 | 0 |
| 12 | Montmorillonite K10 | 0 |
| 13 | 36 (10 mol %) | 2 |
| 14 | [Bn₂NH₂][OCOCF₃] + 4Å MS | 0 |

[a]Comparative example

Acid 36 is described in Procedure 6 below.

In all cases the use of an acid catalyst (with additive) in combination with (S)-proline from the beginning of the reaction led to a decrease in yield. Under various conditions investigated (solvent, proline loading, and [Bn₂NH₂][OCOCF₃] loading) we always observed a decrease in yield when [Bn₂NH₂][OCOCF₃] was added at the start of the reaction, compared to addition after 2 hours.

It is known that additives can improve the enantioselectivity and/or accelerate the rate of asymmetric reactions (Vogl, E. M. et al., *Angew. Chem. Int. Ed.* 38, 1570-1577 (1999)) and over the last few years the effect of various additives on the course of the aldol reaction has been studied. We carried out a number of reactions in which we used [Bn₂NH₂][OCOCF₃] in combination with various additives (or replaced it).

[Bn₂NH₂][OCOCF₃] with Additive (Procedure 6)

As for Procedure 4, but using [Bn₂NH₂][OCOCF₃] in combination with various additives (or replacing it) (Table 7).

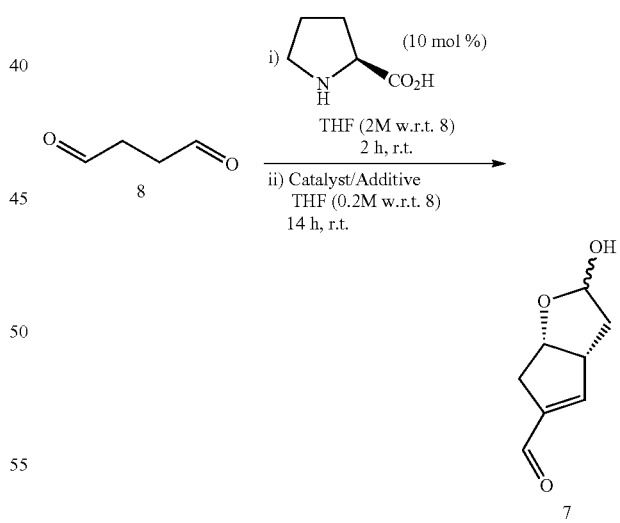

TABLE 7

Additives screen

| Entry | Catalyst/Additive Combination | ¹H NMR Yield (%) |
|---|---|---|
| 1[c] | (S)-Proline only, no further catalyst or additive | Trace |
| 2 | [Bn₂NH₂][OCOCF₃] (2 mol %) | 15 |

TABLE 7-continued

Additives screen

| Entry | Catalyst/Additive Combination | 1H NMR Yield (%) |
|---|---|---|
| 3 | [Bn$_2$NH$_2$][OCOCF$_3$] (2 mol %) + 36 (10 mol %) | 14 |
| 4 | 36 (10 mol %) | 7 |
| 5 | [Bn$_2$NH$_2$][OCOCF$_3$] (2 mol %) + MgSO$_4$ (2 eq.) | 13 |
| 6 | [Bn$_2$NH$_2$][OCOCF$_3$] (2 mol %) + 4Å MS | 5 |
| 7[a] | [Bn$_2$NH$_2$][OCOCF$_3$] (2 mol %) + (S)-BINOL (1 mol %) | 16 |
| 8[b] | PEG 400 (20 mol %) + [Bn$_2$NH$_2$][OCOCF$_3$] (2 mol %) | 5 |
| 9[b,c,e] | PEG 400 (20 mol %) + [Bn$_2$NH$_2$][OCOCF$_3$] (2 mol %) | 0 |
| 10[b,d] | PEG 400 (20 mol %) + [Bn$_2$NH$_2$][OCOCF$_3$] (2 mol %) | 3.5 |

[a]Dilution to 0.5M before addition of acid catalyst
[b]Dilution to 1M before addition of acid catalyst
[c]Reaction performed in water instead of THF
[d]Reaction performed in DMSO instead of THF
[e]Comparative example

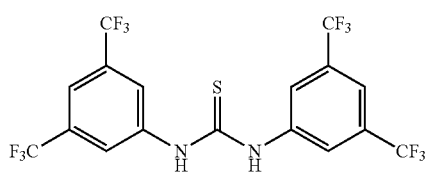

36

We established that the presence of [Bn$_2$NH$_2$][OCOCF$_3$] was necessary to obtain the product with a yield of ~15% (Table 7, entries 1 and 2). Recently, Demir et al. introduced the use of thiourea 36 (1,3-bis(3,5-bis(trifluoromethyl)phenyl)thiourea) as an additive in proline-catalysed aldol reactions to improve both yields and selectivity (Reis, O. et al., *Chem. Commun.* 1088-1090 (2009)). In our case, the addition of 36 to the reaction along with [Bn$_2$NH$_2$][OCOCF$_3$] at the 2 h point did not lead to an increase in conversion (entry 3). Use of 36 in place of [Bn$_2$NH$_2$][OCOCF$_3$] led to a decrease in yield (entry 4).

During the course of the reaction, conversion of trialdehyde 10 to lactol 7 requires a dehydration. In an attempt to promote this step we added magnesium sulfate (entry 5) and 4 Å molecular sieves (entry 6) to the reaction at the same time as the [Bn$_2$NH$_2$][OCOCF$_3$]. Neither of these additives improved conversion, and the use of molecular sieves actually led to a significant decrease in conversion.

The use of chiral diols as additives in aldol reactions has been studied by Shan and co-workers (Zhou, Y. et al., *J. Org. Chem.* 71, 9510-9512 (2006)). However, addition of (S)-BINOL to our reaction did not lead to an increase in yield (entry 7).

Finally we tried to perform the reaction in various solvents with poly(ethylene glycol) as a surfactant (Chandrasekhar, S. et al., *Tetrahedron.* 62, 338-345 (2006); Chandrasekhar, S. et al., *Tetrahedr. Lett.* 45, 4581-4582 (2004)). However, the use of this additive led to a decrease in yield (entries 8-10).

In 2004, Pihko and co-workers reported higher yields with the addition of water to intermolecular aldol reactions. It was postulated that water could decrease the amount of oxazolidinones formed, a proposed non-productive pathway leading to proline deactivation (Nyberg, A. I. et al., *Synlett.* 1891-1896 (2004); Pihko, P. M. et al., *Tetrahedron* 62, 317-328 (2006)). The role of water in proline-catalysed aldol reactions is a complex issue which has been further studied by Blackmond (Zotova, N. et al., *J. Am. Chem. Soc.* 129, 15100-15101 (2007)) and Gschwind (Schmid, M. B. et al., *Angew. Chem. Int. Ed.* 49, 4997-5003 (2010)). We investigated the effect of water on the proline-catalysed condensation of succinaldehyde.

Effect of Water (Procedure 7)

Freshly extracted and concentrated succinaldehyde 8 (200 mg, 2.32 mmol) was dissolved in anhydrous THF (1.16 ml) and the appropriate amount of H$_2$O added via syringe. (S)-Proline (26.7 mg, 0.23 mmol) was added. The reaction mixture was stirred at r.t. for 2 h before being diluted with anhydrous THF (1.16 ml, taking the reaction to 1 M w.r.t. succinaldehyde 8) and [Bn$_2$NH$_2$][OCOCF$_3$] (14.5 mg, 0.05 mmol, 2% w.r.t. succinaldehyde 8) was added. The reaction was stirred for 14 h before 1,3,5-trimethoxybenzene (19.5 mg, 0.116 mmol) was added. The amount of lactol 7 present was determined as outlined in Procedure 1.

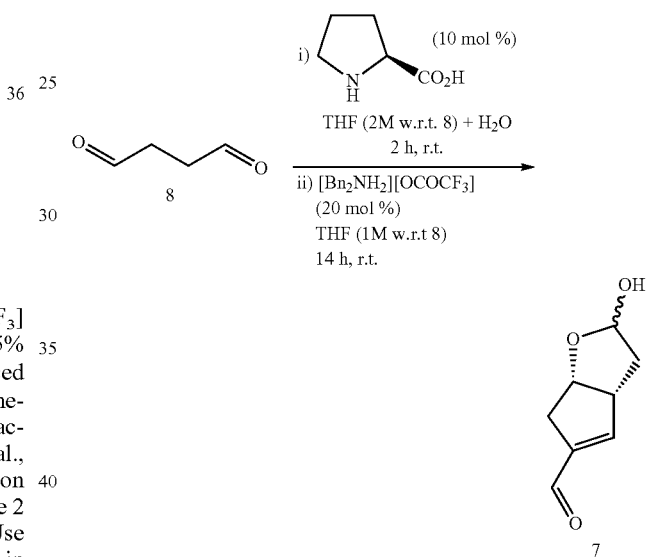

TABLE 8

Effect of water

| Entry | Water Added (% mol) | 1H NMR Yield (%) |
|---|---|---|
| 1 | 200 | 2 |
| 2 | 100 | 6 |
| 3 | 75 | 8 |
| 4 | 50 | 11 |
| 5 | 25 | 15 |
| 6 | 10 | 13 |
| 7 | 5 | 15 |
| 8 | 1 | 16 |
| 9 | 0.5 | 16 |
| 10 | 0.25 | 15 |
| 11 | 0.1 | 15 |
| 12 | 0.05 | 14 |
| 13 | 0 | 14 |
| 14 | THF from bottle | 15 |

It was found that the reaction tolerates up to 25 mol % of water (w.r.t. to succinaldehyde 8), giving the product in ~15% yield (entries 5-13). Increased amounts of water decreased the yield (entries 1-4). It was established that the reaction does not require anhydrous conditions and that the use of reagent grade THF (entry 14) gave the same yield as the use of anhydrous THF.

In view of developing reaction conditions applicable to larger scale reactions (up to 50-110 g of succinaldehyde), we investigated the possibility of carrying out the second step of our transformation at higher concentration.

Effect of Concentration (Procedure 8)

Freshly extracted and concentrated succinaldehyde 8 (200 mg, 2.32 mmol) was dissolved in THF (1.16 ml) and (S)-proline (26.7 mg, 0.23 mmol, 10 mol % w.r.t. 8) was added. The reaction mixture was stirred at r.t. for 2 h before being diluted with the appropriate amount of THF (see Table 9 for concentrations, which are calculated based on the amount of succinaldehyde 8 present at the start of the reaction) and [$Bn_2NH_2$][$OCOCF_3$] (14.5 mg, 0.05 mmol, 2 mol % w.r.t. succinaldehyde 8) added. The reaction was stirred for 14 h before 1,3,5-trimethoxybenzene (19.5 mg, 0.116 mmol) was added. The amount of lactol 7 present was determined as outlined in Procedure 1.

tion to 0.2 M or dilution to 1.4 M (entry 5). It was found that dilution to 1 M gave reproducible results on both small and larger scales. Since we had been able to reduce the amount of [$Bn_2NH_2$][$OCOCF_3$] used and also increase the concentration at which the second stage of the reaction was carried out, we investigated varying the proline loading.

Effect of Proline Stoichiometry and Initial Stirring Period (Procedure 9)

Freshly extracted and concentrated succinaldehyde 8 (200 mg, 2.32 mmol) was dissolved in THF (1.16 ml) and the appropriate amount (S)-proline added (see Table 10). The reaction mixture was stirred at r.t. for the appropriate amount of time (see Table 10) before being diluted with THF (1.16 ml, taking the reaction to 1 M w.r.t. succinaldehyde 8) and [$Bn_2NH_2$][$OCOCF_3$] (14.5 mg, 0.05 mmol) added. The reaction was stirred for 14 h before 1,3,5-trimethoxybenzene (19.5 mg, 0.116 mmol) was added. The amount of lactol 7 present was determined as outlined in Procedure 1.

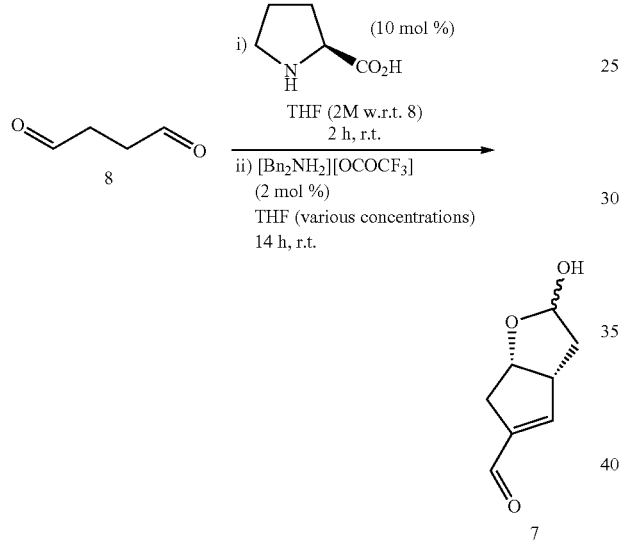

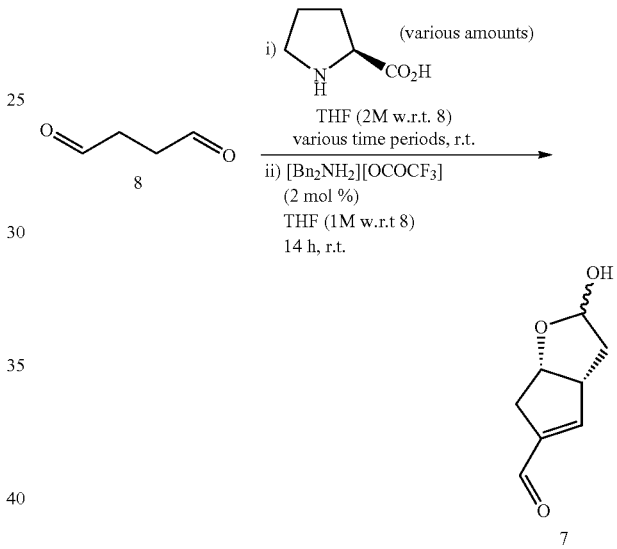

TABLE 9

Effect of concentration

| Entry | Concentration (M) | $^1$H NMR Yield (%) |
|---|---|---|
| 1 | 0.2 | 16.5 |
| 2 | 0.5 | 17.5 |
| 3 | 1.0 | 16.5 |
| 4 | 1.2 | 17 |
| 5 | 1.4 | 16 |
| 6 | 1.6 | 15 |
| 7 | 1.8 | 13.5 |
| 8 | 2.0 | 12 |

It was found that the concentration of the reaction after addition of [$Bn_2NH_2$][$OCOCF_3$] affects the yield. As mentioned above, these concentrations are calculated based on the amount of succinaldehyde 8 present at the start of the reaction. When the concentration was maintained at 2 M (i.e no THF added before the addition of [$Bn_2NH_2$][$OCOCF_3$]) a 12% yield was obtained (entry 8). Dilution to 0.2 M before addition of [$Bn_2NH_2$][$OCOCF_3$] led to an increase in yield (entry 1). There appeared to be little difference between dilu-

TABLE 10

Effect of proline loading and initial stirring period

| Entry | (S)-proline (mol %) | Time (h) | $^1$H NMR Yield (%) |
|---|---|---|---|
| 1[a] | 10 | 2 | 14.4 |
| 2[a] | 5 | 2 | 15.7 |
| 3[a] | 5 | 4 | 18.8 |
| 4[a] | 2.5 | 2 | 11.2 |
| 5[a] | 2.5 | 4 | 16.7 |
| 6[a] | 2.5 | 6 | 19.1 |
| 7[b] | 2 | 0 | ~2 |
| 8[b] | 2 | 4 | 10 |
| 9[a] | 2 | 6 | 15.8 |
| 10[a] | 2 | 10 | 19.5 |
| 11[a] | 2 | 24 | 19.7 |
| 12[a] | 1 | 24 | 18.1 |

[a]Yield is average of five reactions
[b]Yield is based on single reaction

It was found that the reaction could be carried out with lower loadings of proline. When the proline loading was reduced to 1, 2.5, or 5%, yields were lower unless the stirring time was increased before the addition of [$Bn_2NH_2$][$OCOCF_3$] (entries 4-6). The reaction could also be performed with only 1% proline, but a longer time was required before dilution and addition of [Bn$_2$NH$_2$][OCOCF$_3$] (entry 12).

Optimal conditions involved the use of 2% proline, in THF at 2 M for 10 hours, followed by dilution to 1 M and addition of 2% of [Bn$_2$NH$_2$][OCOCF$_3$] (entry 10). These conditions form the basis for the larger scale reaction described later (see Example 3).

Monitoring of Optimum Conditions by NMR (Procedure 10)

Freshly extracted and concentrated succinaldehyde 8 (2.00 g, 23.232 mmol) was dissolved in THF (11.6 ml, 2 M w.r.t. 8) and (S)-proline (53.5 mg, 0.46 mmol), and 1,3,5-trimethoxybenzene (195 mg, 1.16 mmol) were added. The reaction was stirred at r.t. for 8 h before [Bn$_2$NH$_2$][OCOCF$_3$] (145 mg, 0.46 mmol) was added. The reaction mixture was stirred at r.t. and aliquots were removed every hour. The amount of succinaldehyde 8 and lactol 7 present was determined as described in Procedure 1.

FIG. 6 is a graph resulting from the monitoring of this reaction, showing the consumption of succinaldehyde 8 and formation of lactol 7 in a reaction with 2 mol % (S)-proline and 2 mol % [Bn$_2$NH$_2$][OCOCF$_3$] which was added at 8 h, after dilution to 1 M.

FIG. 6 shows steady consumption of dialdehyde 8 during the initial phase with proline but no product formation until the addition of [Bn$_2$NH$_2$][OCOCF$_3$] at 8 h. Upon addition of [Bn$_2$NH$_2$][OCOCF$_3$], product steadily forms.

These results support earlier observations that only trace product was detected with proline alone and that a co-catalyst such as, for example, [Bn$_2$NH$_2$][OCOCF$_3$] is required to catalyse the intramolecular aldol reaction and dehydration. At the end of the reaction, product and unreacted succinaldehyde were clearly identified by NMR (see following example).

Example 3

Experimental Procedures for Large Scale Preparation of Bicyclic Lactol 7 and Bicyclic Methyl Acetal 24

3A. (3aR,6aS)-2-Hydroxy-3,3a,6,6a-tetrahydro-2H-cyclopenta[b]furan-5-carbaldehyde, 7

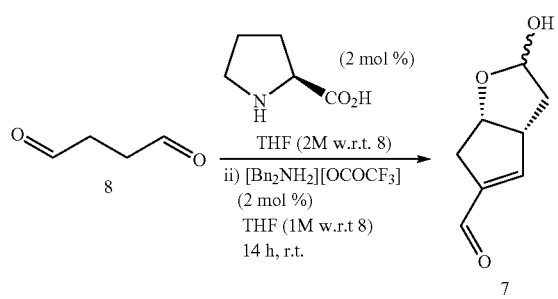

The solution of succinaldehyde 8 (57.5 g, 668 mmol) in THF (334 ml) obtained in Example 1B was stirred at r.t. (S)-Proline (1.54 g, 13.4 mmol, 0.02 eq.) was added as a solid and the reaction stirred at r.t. for 20 h. THF (334 ml) was added, followed by [Bn$_2$NH$_2$][OCOCF$_3$] (4.16 g, 13.4 mmol, 0.02 eq.). The reaction was stirred for a further 14 h. The volume of the reaction mixture was reduced by half under reduced pressure. tert-Butyl methyl ether (TBME) (334 ml) was added and the mixture stirred for 20 min before filtration of the resulting solids (through a sinter funnel). The solids were washed with TBME (3×50 ml) and the filtrate was concentrated under reduced pressure. (Note: During concentration of the filtrate, for the purposes of this example it is important not to heat the water bath of the rotary evaporator). The material was purified by column chromatography (~350 g silica), eluting with petrol/EtOAc (6:4 to 4:6), to give the lactol 7 (as an approximately 2:1 mixture of diastereoisomers, 16%), as a brown oil. This material is of sufficient purity to take forward for the next transformation (see Example 3C). While it does contain some unreacted succinaldehyde and oligomeric side-products these do not interfere with the subsequent transformation and purification.

The lactol 7 is a compound according to the first aspect of the invention, and corresponds to compound (Ia) described above.

The $^1$H NMR spectra in FIGS. 7 and 8 show a sample of the reaction mixture from 57.5 g scale reaction of succinaldehyde with (S)-proline and [Bn$_2$NH$_2$][OCOCF$_3$] prior to work up. The sample was removed from reaction mixture, dissolved in DMSO-d6, and the THF evaporated under vacuum. The amount of lactol 7 present was calculated by comparison of the signals arising from the vinyl protons of the diastereoisomers of 7 with the signals of the internal standard, 1,3,5-trimethoxybenzene.

The oil could be further purified with more rigorous column chromatography to give the lactol 7 as a light brown solid. After recrystallisation from petrol/EtOAc the lactol was obtained as pale brown needles.

Mp 88-91° C. (after recrystallisation from petrol/EtOAc)

R$_f$=0.16 (petrol:EtOAc, 1:1)

$v_{max}$ (film)/cm$^{-1}$ 3320, 2973, 2927, 2879, 1673, 1380, 1088, 1047, 880

$^1$H NMR (400 MHz; CDCl$_3$) $\delta_H$=(mixture of 2 diastereoisomers, signals of minor indicated by *) 1.96 (1H, app dt, J=13.2, 5.1 Hz, CHH), 2.12* (1H, d, J=13.2 Hz, CHI-1), 2.26 (1H, m, CHH), 2.26* (1H, m, CHH), 2.65-2.90 (3H, m, CH$_2$ and OH), 2.65-2.90* (3H, m, CH$_2$ and OH), 3.58* (1H, m, CH), 3.68 (1H, m, CH), 4.91* (1H, m, CH), 4.97 (1H, td, J=5.8, 2.0 Hz, CH), 5.54* (1H, d, J=3.9 Hz, CH), 5.58 (1H, d, J=5.1 Hz, CH), 6.66 (1H, app q, 2.0 Hz, CH), 6.80* (1H, app q, J=1.8 Hz, CH), 9.78 (1H, s, HC=O), 9.80* (1H, s, HC=O)

$^{13}$C NMR (100 MHz; CDCl$_3$) $\delta_C$=35.3 (CH$_2$), 37.9 (CH$_2$), 37.9 (CH$_2$), 38.4 (CH$_2$), 49.3 (CH), 49.9 (CH), 80.7 (CH), 82.9 (CH), 98.5 (CH), 98.9 (CH), 144.6 (C), 144.6 (C), 152.2 (CH), 153.1 (CH), 189.9 (HC=O), 189.9 (HC=O)

m/z (CI) 155 (MH$^+$, 11%), 137 (MH$^+$—H$_2$O, 100%)

HRMS (CI) calcd for C$_8$H$_{11}$O$_3$ [MH$^+$] 155.0708. found 155.0704.

Anal. Calcd for C$_8$H$_{10}$O$_3$: C, 62.33; H, 6.54. Found: C, 62.56; H, 6.36.

Chiral GC: Data for minor diastereoisomer: Supelco Beta Dex (30 m×0.25 mm×0.25 μm), 70° C. for 3 min, then 3° C./min to 200° C., hold for 5 min. t$_R$=21.9 min (major), 22.3 min (minor), e.r.=99:1

Chiral GC Traces are shown in FIG. 9a, which corresponds to racemic lactol (±)-7, minor diastereoisomer; and FIG. 9b, which corresponds to enantioenriched lactol 7 from the organocatalytic reaction in Example 3A, minor diastereoisomer.

Despite the low yield, work-up and purification of the lactol 7 was straightforward as the oligomeric side products could be largely removed by filtration, leaving a relatively pure crude material. Partial purification through a plug of silica gave the desired lactol 7 in ~16% yield and 99:1 e.r. on multigram scale. The absolute stereochemistry of the product was ultimately established through the synthesis of PGF$_{2\gamma}$ (see Example 5), and follows from the List-Houk model for this type of reaction (see the transition state structure below, which accounts for the observed enantioselectivity in the initial intermolecular enantioselective aldol reaction).

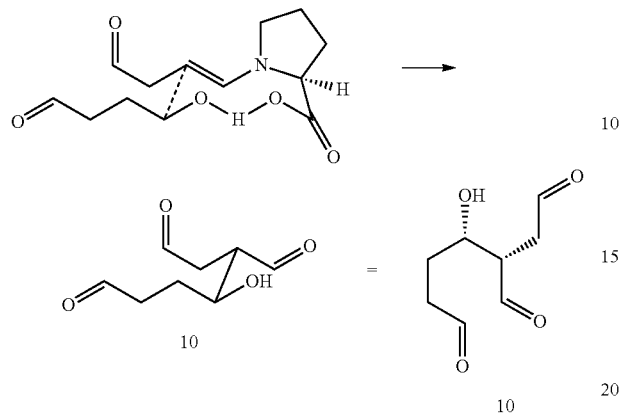

A mixture of diastereoisomers of trialdehyde 10 was expected to be formed (~3.6:1 d.r. would be expected based on results with the model compound 16, see Example 8 below) but as the minor diastereoisomer cannot give the alternative diastereomeric lactol it must be consumed by formation of oligomers.

3B. Synthesis of Lactol 7 with Modified Precipitation and Filtration Procedure

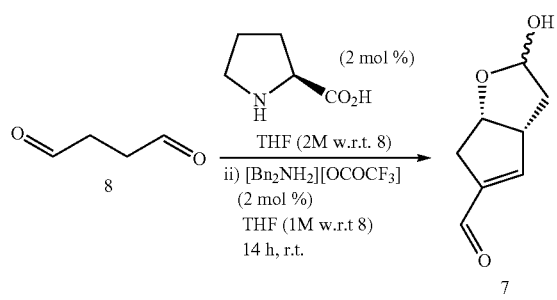

In a modified procedure, after hydrolysis of 2,5-dimethoxytetrahydrofuran (140 ml scale) as described in Example 1B above, and the subsequent aldol reaction as described in Example 3A above, Celite (30 g) was added to the reaction and the volume of the reaction mixture was reduced by ¾ under reduced pressure. tert-Butyl methyl ether (TBME) (an equal volume to the volume of THF/2-MeTHF removed) was added slowly (over ~10 mins) and with vigorous stirring of the mixture. The mixture was stirred for 20 min before filtration of the resulting solids (through a sinter funnel). The solids were washed with TBME (3×100 ml) and the filtrate was concentrated under reduced pressure. This material was partially purified by chromatography (as described in Example 3A above) and the resultant material was then used for acetal formation.

It was found that the addition of celite to the reaction mixture before removal of 2-MeTHF and/or THF allows ¾ of this solvent to be removed rather than ½ while ensuring the resultant solids are very easy to filter (previous attempts to remove ¾ of the solvent led to 'gluey' material when adding TBME). This modified procedure appears to lead to more oligomers being 'crashed out'/precipitated, allows even easier filtration of the oligomers, and leads to a cleaner product after chromatography.

3C. (3aR,6aS)-2-Methoxy-3,3a,6,6a-tetrahydro-2H-cyclopenta[b]furan-5-carbaldehyde, 24

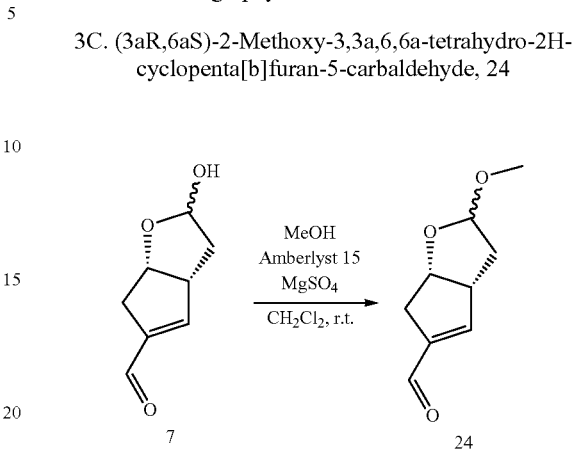

The residue from Example 3A, containing 7, was dissolved in $CH_2Cl_2$ (120 ml) and stirred at r.t. MeOH (3.42 g, 4.33 ml, 107 mmol, 2.0 eq. based on ~16% of 7 detected by internal standard in Example 3A) was added via syringe. Amberlyst 15 (765 mg) and $MgSO_4$ (15.8 g) were added as solids in one portion and the reaction mixture was stirred at r.t. for 14 h. The reaction mixture was filtered through a sinter funnel and the solids washed with $CH_2Cl_2$ (2×30 ml). The filtrate was concentrated under reduced pressure and purified by column chromatography (~150 g silica), eluting with petrol/EtOAc (10:1 to 4:1), to give the methyl acetal 24, (as an approximately 2:1 mixture of diastereoisomers, 7.85 g, 14% over 2 steps from succinaldehyde) as a yellow oil (this solidifies in the freezer, but the physical state and appearance differs depending on the exact ratio of diastereoisomers formed, one is a solid, the other an oil).

The methyl acetal 24 is a compound according to the first aspect of the invention, and corresponds to compound (Ic) (and compound (Ib)) described above.

$v_{max}$ ($CHCl_3$)/cm$^{-1}$ 2926, 2829, 1676, 1617, 1099, 1052, 1031, 978 m/z (CI) MH$^+$ not seen, 137 (MH$^+$-MeOH, 100%)

HRMS (ESI) calcd for $C_9H_{12}O_3Na$ [MNa$^+$] 191.0679. found 191.0687.

It was possible to partially separate the diastereoisomers by column chromatography for further characterisation purposes (although this was not necessary for the synthesis of $PGF_{2\alpha}$).

Major Diastereoisomer:

Mp 67-69° C. (after recrystallisation from 40/60 petroleum ether)

$R_f$=0.6 (petrol:EtOAc, 1:1)

$^1$H NMR (400 MHz; CDCl$_3$) $\delta_H$=1.89 (1H, dt, J=13.3, 5.3 Hz, CHH), 2.24 (1H, ddd, 13.3, 10.1, 1.1 Hz, CHH), 2.72 (2H, m, CH$_2$), 3.32 (3H, s, OCH$_3$), 3.61 (1H, m, CH), 4.77 (1H, m, CH), 5.02 (1H, d, J=5.3 Hz, CH), 6.64 (1H, app q, 1.7 Hz, CH), 9.77 (1H, s, HC=O)

$^{13}$C NMR (100 MHz; CDCl$_3$) $\delta_C$=35.1 (CH$_2$), 37.2 (CH$_2$), 49.2 (CH), 54.4 (OCH$_3$), 80.3 (CH), 104.8 (CH), 144.5 (C), 152.4 (CH), 189.9 (C=O)

Anal. Calcd for $C_9H_{12}O_3$: C, 64.27; H, 7.19. Found: C, 64.24; H, 7.11.

$[\alpha]_D^{26}$ −213 (c. 1, CHCl$_3$)

Minor Diasteroisomer:

R$_f$=0.45 (petrol:EtOAc, 1:1)

$^1$H NMR (400 MHz; CDCl$_3$) δ$_H$=2.08 (1H, d, J=13.4 Hz, CHH), 2.20 (1H, ddd, J=13.4, 9.9, 5.0 Hz, CHH), 2.72-2.87 (2H, m, CH$_2$), 3.22 (3H, s, OCH$_3$), 3.55 (1H, m, CH), 4.95 (1H, td, J=6.5, 1.7 Hz, CH), 5.03 (1H, d, J=5.0 Hz, CH), 6.74 (1H, app q, J=2.0 Hz, CH), 9.78 (1H, s, HC=O)

$^{13}$C NMR (100 MHz; CDCl$_3$) δ$_C$=37.2 (CH$_2$), 37.7 (CH$_2$), 49.6 (CH), 54.6 (OCH$_3$), 82.6 (CH), 105.2 (CH), 144.5 (C), 153.0 (CH), 190.0 (C=O)

[α]D$^{25}$ −7.5 (c. 1, CHCl$_3$)

3D. Synthesis of Lactol 7-One Pot Conversion of 2,5-dimethoxytetrahydrofuran 23 to Lactol 7 (50 mL Scale)

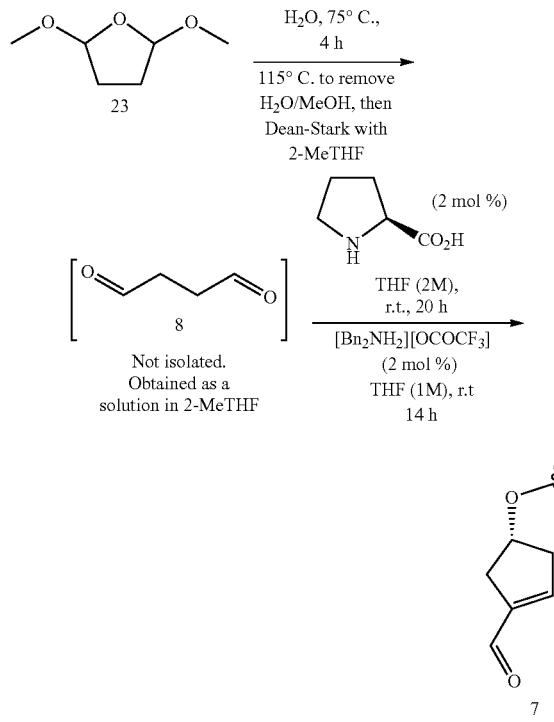

First Step—2,5-dimethoxytetrahydrofuran 23 to Succinaldehyde 8

A solution of 2,5-dimethoxytetrahydrofuran 23 (51.0 g, 50.0 ml, 386 mmol) in water (100 ml) was stirred at 75° C. (oil bath temperature) for 4 h. The temperature was then increased to 115° C. (oil bath temperature) and 100 ml of distillate collected (a short path distillation apparatus with condenser was used). The temperature was allowed to cool to 95° C. (oil bath temperature) and a Dean-Stark apparatus fitted to the flask. 2-Methyltetrahydrofuran (175 ml (and 200 ml extra to fill the Dean-Stark trap) was added and heating at 95° C. continued until water ceased to be collected in the Dean-Stark trap (~6 h). After cooling, 1,4-dimethoxybenzene (2.67 g, 19.3 mmol, 0.05 eq.) was added as an internal standard. A sample (a few drops) of the reaction mixture was taken and diluted with CDCl$_3$. $^1$H NMR analysis showed 70% of succinaldehyde 8 (23.3 g, 270 mmol) present in the solution.

Second Step—Succinaldehyde 8 to Lactol 7

The reaction mixture was concentrated to the appropriate volume such that the concentration of the solution was 2 M (w.r.t. succinaldehyde 8, 135 ml for this example). (S)-Proline (622 mg, 5.40 mmol, 0.02 eq. w.r.t. succinaldehyde) was added and the reaction stirred at room temperature for 20 h. 2-Methyltetrahydrofuran (135 ml) was added to the reaction mixture followed by [Bn$_2$NH$_2$][OCOCF$_3$] (1.68 g, 5.40 mmol) and the reaction stirred for a further 14 h at room temperature. After this time a sample of the reaction (~5 drops) was taken, concentrated with a flow of N$_2$, and dissolved in d6-DMSO. $^1$H NMR analysis showed ~18% of lactol 7 present in the reaction mixture. This could be partially purified for subsequent transformation.

3E. Synthesis of Lactol 7-One Pot Conversion of 2,5-dimethoxytetrahydrofuran 23 to Lactol 7 (140 mL Scale)

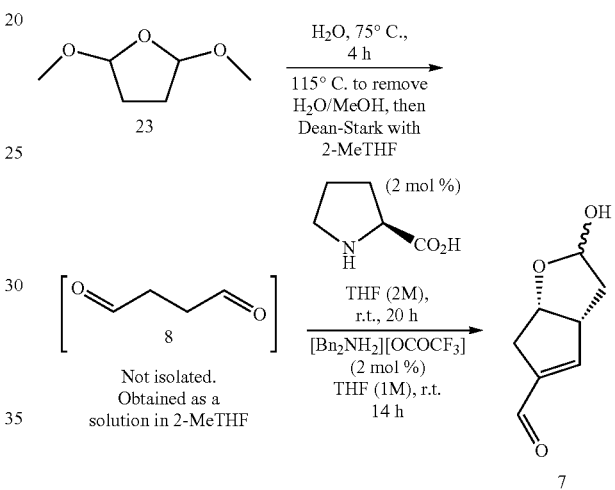

First Step—2,5-dimethoxytetrahydrofuran 23 to Succinaldehyde 8

A solution of 2,5-dimethoxytetrahydrofuran 23 (142.8 g, 140 ml, 1.08 mol) in water (280 ml) was stirred at 75° C. (oil bath temperature) for 4 h. The temperature was then increased to 115° C. (oil bath temperature) and 280 ml of distillate collected (a short path distillation apparatus with condenser was used). Note: On this scale this process takes 4-4.5 h and the material can be allowed to cool and be stored in the freezer prior to the Dean-Stark if required. The temperature was allowed to cool to 95° C. (oil bath temperature) and a Dean Stark apparatus fitted to the flask. 2-Methyltetrahydrofuran (378 ml (and 200 ml extra to fill the Dean-Stark trap) was added and heating at 95° C. continued until water ceased to be collected in the Dean-Stark trap (~8 h) Note: For the purposes of this example, it is important an appropriately large and wide Dean-Stark trap is used to ensure efficient removal of water. After cooling, 1,3,5-trimethoxybenzene (4.54 g, 27.0 mmol, 0.025 eq. w.r.t. s.m.) was added as an internal standard. A sample (a few drops) of the reaction mixture was taken and diluted with CDCl$_3$. $^1$H NMR analysis showed 66% of succinaldehyde 8 (61.4 g, 713 mmol) present in the solution (Yields typically range between 60-70% for this reaction). Note: FIG. 10 shows the $^1$H NMR spectrum of the sample used to determine the yield.

Second Step-Succinaldehyde 8 to Lactol 7

The solution can then be adjusted in concentration to the required 2 M (w.r.t. succinaldehyde 8) and (S)-proline added directly to carry out the aldol reaction in accordance with the procedure in Example 3D.

3F. Synthesis of Lactol 7-One Pot Conversion of 2,5-dimethoxytetrahydrofuran 23 to Lactol 7 (280 mL Scale)

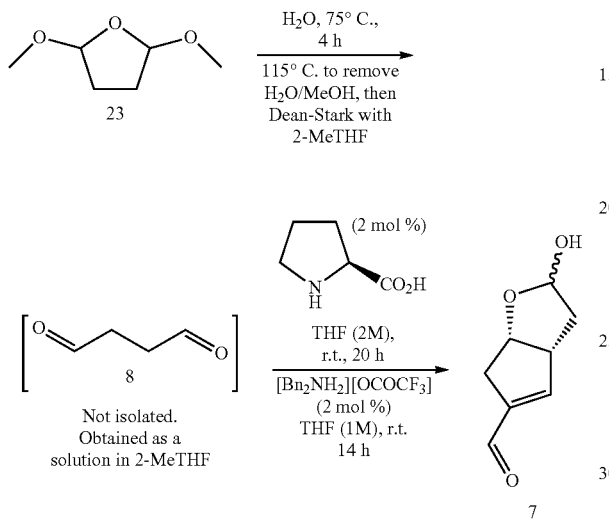

First Step—2,5-dimethoxytetrahydrofuran 23 to Succinaldehyde 8

A solution of 2,5-dimethoxytetrahydrofuran 23 (285.6 g, 280 ml, 2.16 mol) in water (560 ml) was stirred at 75° C. (oil bath temperature) for 4 h. The temperature was then increased to 115° C. (oil bath temperature) and 560 ml of distillate collected (a short path distillation apparatus with condenser was used). The temperature was allowed to cool to 95° C. (oil bath temperature) and a Dean-Stark apparatus fitted to the flask. 2-Methyltetrahydrofuran (650 ml (and 200 ml extra to fill the Dean-Stark trap)) was added and heating at 95° C. continued until water ceased to be collected in the Dean-Stark trap (~14 h) Note: For the purposes of this example, it is important an appropriately large and wide Dean-Stark trap is used to ensure efficient removal of water. After cooling, 1,3,5-trimethoxybenzene (9.08 g, 27.0 mmol, 0.025 eq. w.r.t. s.m.) was added as an internal standard. A sample (a few drops) of the reaction mixture was taken and diluted with CDCl$_3$. $^1$H NMR analysis showed 58.8% of succinaldehyde 8 (109.5 g, 1.272 mol) present in the solution. This solution can then be adjusted in concentration to the required 2 M (w.r.t. succinaldehyde 8) and (S)-proline added directly to carry out the aldol reaction.

Second Step—Succinaldehyde 8 to Lactol 7

The solution of succinaldehyde 8 from the first step (109.5 g, 1.272 mol) in 2-MeTHF was stirred at r.t. (S)-Proline (2.93 g, 25.4 mmol, 0.02 eq.) was added as a solid and the reaction stirred at r.t. for 20 h. THF (650 ml) was added, followed by [Bn$_2$NH$_2$][OCOCF$_3$] (8.43 g, 25.4 mmol, 0.02 eq.). The reaction was stirred for a further 14 h. Celite (60 g) was added to the reaction and the volume of the reaction mixture was reduced by ¾ under reduced pressure. tert-Butyl methyl ether (TBME) (an equal volume to the volume of THF/2-MeTHF removed) was added slowly (over ~15 mins) and with vigorous stirring of the mixture. The mixture was stirred for 20 min before filtration of the resulting solids (through a sinter funnel). The solids were washed with TBME (3×150 ml) and the filtrate was concentrated under reduced pressure. The material was purified by column chromatography (~600 g silica), eluting with petrol/EtOAc (6:4 to 5:5), to give the lactol 7 (as an approximately 2:1 mixture of diastereoisomers), as a brown oil.

3G. Synthesis of Methyl Acetal 24

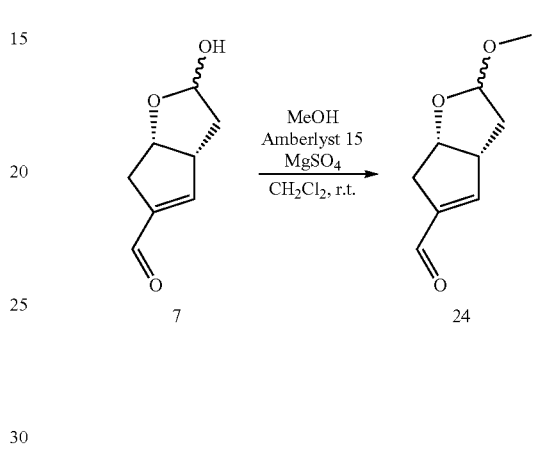

The residue from Example 3F, containing 7, was dissolved in CH$_2$Cl$_2$ (190 ml) and stirred at r.t. MeOH (5.47 g, 6.90 ml, 170.6 mmol, 2.0 eq. based on ~13.4% of 7 detected by internal standard in the previous reaction) was added via syringe. Amberlyst 15 (1.22 g) and MgSO$_4$ (25.2 g) were added as solids in one portion and the reaction mixture was stirred at r.t. for 14 h. The reaction mixture was filtered through a sinter funnel and the solids washed with CH$_2$Cl$_2$ (3×60 ml). The filtrate was concentrated under reduced pressure and purified by column chromatography (~300 g silica), eluting with petrol/EtOAc (9:1 to 4:1), to give the methyl acetal 24, (as an approximately 2:1 mixture of diastereoisomers, 14.98 g, 14.0% (over 2 steps from succinaldehyde)) as a yellow oil (this solidifies in the freezer, but the physical state and appearance differs depending on the exact ratio of diastereoisomers formed, the major diastereoisomer is a solid, the minor an oil).

3H. Modified Procedure for the Synthesis of Lactol 7-One Pot Conversion of 2,5-dimethoxytetrahydrofuran 23 to Lactol 7

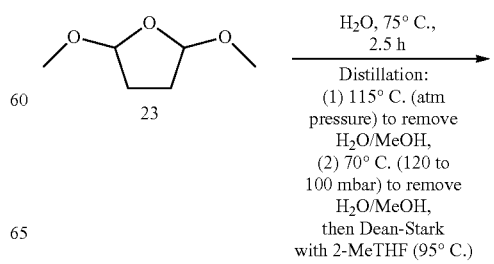

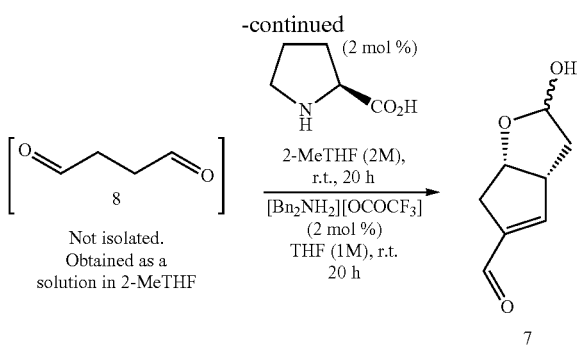

First Step—2,5-dimethoxytetrahydrofuran 23 to Succinaldehyde 8

A solution of 2,5-dimethoxytetrahydrofuran 23 (102.3 g, 100 ml, 0.774 mol) in water (200 ml) was stirred at 75° C. (oil bath temperature) for 2.5 h. The temperature was then increased to 115° C. (oil bath temperature) and 100 ml of distillate collected over 1 h (a short path distillation apparatus with condenser was used). The temperature was allowed to cool to 70° C. (oil bath temperature), then distilled under reduced pressure (120 mbar for 1 h, then the pressure was dropped down to 100 mbar for 30 min to collect ~120 mL of distillate). Note: For the purposes of this example, it is important to ensure vigorous stirring during distillation, while controlling the speed of the stirring to avoid splashing of the reaction mixture onto the side of the round bottom flask to minimize formation of oligomers. Typical combined volumes of the distillate ranges from 120-130 ml. For the purposes of this example, not exceeding this volume helps to avoid the formation of oligomers. A Dean Stark apparatus fitted to the flask. 2-Methyltetrahydrofuran (232 ml and 60 ml extra to fill the Dean-Stark trap) was added and heating at 95° C. continued until water ceased to be collected in the Dean-Stark trap (~3 h) Note: For the purposes of this example, it is important an appropriately large and wide Dean-Stark trap is used to ensure efficient removal of water. After cooling, 1,3,5-trimethoxybenzene (3.25 g, 19.4 mmol, 0.025 eq. w.r.t. s.m.) was added as an internal standard. A sample (a few drops) of the reaction mixture was taken and diluted with CDCl$_3$. $^1$H NMR analysis showed 76% of succinaldehyde 8 (50.6 g, 0.588 mol) present in the solution (Yields typically range between 61-87% for this reaction). This solution can then be adjusted in concentration to the required 2 M (w.r.t. succinaldehyde 8) and (S)-proline added directly to carry out the aldol reaction. Note: FIG. 10 shows the $^1$H NMR spectrum of the sample used to determine the yield. The success of the subsequent aldol cascade transformation is improved by good quality dialdehyde (with minimal amounts of oligomers present); the use of poor quality dialdehyde typically results in lower yields of lactol 7.

Advantages of Modified Procedure for the First Step:

Compared to the procedure for the first step in Examples 3E and 3F, the modified procedure for this scale (102.3 g) reduces the overall process time of the reaction (reduction of 1.5 h reaction time, 2-2.5 h for the distillation process and 1 h for the Dean-Stark process; total process time reduction: 4.5-5 h). Furthermore, high quality of dialdehyde (with minimum formation of oligomers) could be obtained when the distillation is performed at lower heating temperature (70° C.) under reduced pressure.

Second Step—Succinaldehyde 8 to Lactol 7

The solution of succinaldehyde 8 from the first step (50.6 g, 0.588 mol) in 2-MeTHF was stirred at r.t. (S)-Proline (1.35 g, 11.8 mmol, 0.02 eq.) was added as a solid (Note: The reaction turns from a colourless suspension to a pink suspension over 10 min) and the reaction stirred at r.t. for 20 h. THF (294 ml) was added, followed by [Bn$_2$NH$_2$][OCOCF$_3$] (3.67 g, 11.8 mmol, 0.02 eq.). The reaction was stirred for a further 20 h. Note: The reaction turns to a dark maroon suspension over 20 h. Activated charcoal (100 g) was added to the reaction and the volume of the reaction mixture was reduced by ½ under reduced pressure (~300 mL). tert-Butyl methyl ether (TBME) (an equal volume to the volume of THF/2-MeTHF removed; 300 mL) was added slowly (over ~15 mins) and with vigorous stirring of the mixture. Note: For the purposes of this example, slow addition of TBME helps to avoid the formation of oligomer aggregates. The mixture was stirred for 60 min before filtration of the resulting solids (through a sinter funnel; diameter: ~10 cm). The solids were washed with 2-MeTHF (3×120 ml or until the product was not observed in the filtrate by TLC, 1:1 petroleum ether/EtOAc) and the filtrate was concentrated under reduced pressure. Note: For the purposes of this example, the filtrate should not be concentrated to complete dryness to help avoid solidifying the oligomers on the column, thereby clogging the column during the purification process. The material was purified by column chromatography (~400 g silica), eluting with petroleum ether/EtOAc (8:2 to 5:5), to give the lactol 7 (as an approximately 2:1 mixture of diastereoisomers), as a brown oil.

Advantages of Modified Work-Up Procedure for the Second Step:

Compared to the procedure for the second step in Example 3F, the use of activated charcoal for the work-up procedure has removed a significant amount of discolouration from the reaction mixture, as well as oligomers. Furthermore, the use of 2-MeTHF as the optimal solvent for the filtration washing has led to reduced losses of the desired product resulting in increased yields (17%, rather than 14%, of the acetal 24 over 2 steps from succinaldehyde).

3I. Synthesis of Methyl Acetal 24

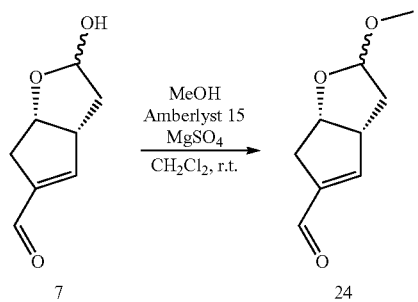

The residue from Example 3H, containing partially pure 7 (12.7 g, 82.3 mmol, 1 eq.) was dissolved in CH$_2$Cl$_2$ (187 ml) and stirred at r.t. MeOH (10.6 g, 2.2 ml, 333 mmol, 4.0 eq.) was added via syringe. Amberlyst 15 (2.02 g) and MgSO$_4$ (41.0 g) were added as solids in one portion and the reaction mixture was stirred at r.t. for 15 h. The reaction mixture was filtered through a sinter funnel and the solids washed with CH$_2$Cl$_2$ (3×60 ml). The filtrate was concentrated under reduced pressure and purified by column chromatography (~400 g silica), eluting with petroleum ether/EtOAc (10:1 to 4:1), to give the methyl acetal 24, (as an approximately 2:1 mixture of diastereoisomers, 8.22 g, 17% (over 2 steps from succinaldehyde)) as a brown oil (this solidifies in the freezer, but the physical state and appearance differs depending on the exact ratio of diastereoisomers formed, the major diastereoisomer is a solid, the minor an oil. Yields typically range from 14-17%).

3J. Synthesis of Methyl Acetal 24

Conversion of Distilled Succinaldehyde 8 to Methyl Acetal 24 without Isolation of Lactol 7 (35 g Scale)

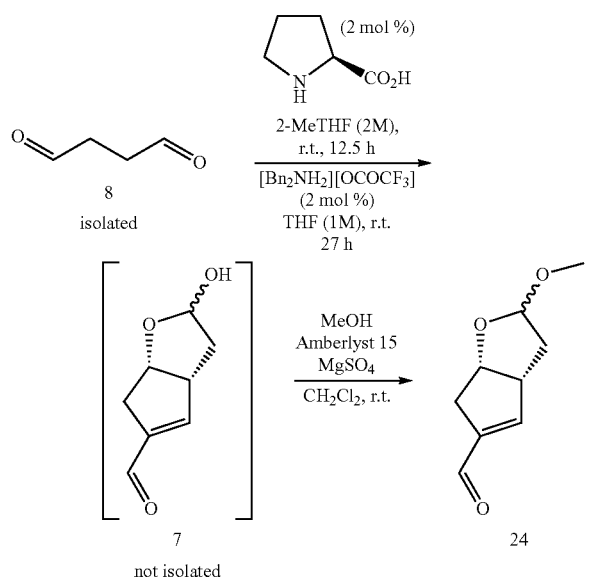

First Step—Succinaldehyde 8 to Lactol 7

Freshly prepared and distilled (4 mbar, 60° C.) succinaldehyde 8 (35.0 g, 407 mmol) was immediately dissolved in 2-MeTHF (203 mL, 2 M) and (S)-proline (937 mg, 8.14 mmol, 0.02 eq.) as well as 1,3,5-trimethoxybenzene (1.37 g, 8.14 mmol, 0.02 eq.) were added as solids directly to carry out the aldol reaction at r.t. for 12.5 h. THF (203 ml) was added, followed by [Bn$_2$NH$_2$][OCOCF$_3$] (2.53 g, 8.14 mmol, 0.02 eq.). The reaction was stirred at r.t. for 27 h. Activated charcoal (80 g) was added to the reaction and the volume of the reaction mixture was reduced by ½ under reduced pressure (~200 mL). tert-Butyl methyl ether (TBME) (an equal volume to the volume of THF/2-MeTHF removed; 200 mL) was added slowly (over ~20 mins) and with vigorous stirring of the mixture. Note: For the purposes of this example, slow addition of TBME helps to avoid the formation of oligomer aggregates. The mixture was stirred for 120 min before filtration of the resulting solids (through a sinter funnel; diameter: ~10 cm). The solids were washed with 2-MeTHF (4×150 ml, or until the product was not observed in the filtrate by TLC, 1:1 petroleum ether/EtOAc) and the filtrate was concentrated under reduced pressure. The crude lactol 7 (~40.7 mmol, as an approximately 2:1 mixture of diastereoisomers) was directly used in the second step.

Advantages of Modified Work-Up Procedure for the First Step:

Compared to the procedure for the second step in Example 3F, the use of activated charcoal for the work procedure has removed a significant amount of discolouration from the reaction mixture, as well as oligomers. Furthermore, the use of 2-MeTHF as the optimal solvent for the filtration washing has led to minimum loss of the desired product through this modified work-up procedure. Compared to the procedure for the second step in Examples 3F and 3H, the omitted column chromatography of the hemi-acetal product saves time, solvent, as well as silica gel.

Second Step—Lactol 7 to Methyl Acetal 24

The residue from the first step containing 7 (~40.7 mmol, 1.0 eq.) was dissolved in CH$_2$Cl$_2$ (92.5 ml) and stirred at r.t. MeOH (39.1 g, 49.0 ml, 12.2 mol, 30 eq.) was added via syringe. Amberlyst 15 (1.17 g) and MgSO$_4$ (24.2 g) were added as solids in one portion and the reaction mixture was stirred at r.t. for 15 h. The reaction mixture was filtered through a sinter funnel and the solids washed with CH$_2$Cl$_2$ (3×60 ml). The filtrate was concentrated under reduced pressure and purified by column chromatography (~400 g silica), eluting with petrol/EtOAc (10:1 to 4:1), to give the methyl acetal 24, (as an approximately 2:1 mixture of diastereoisomers, 6.29 g, 18.0% over 2 steps from succinaldehyde) as a yellow oil.

Advantages of Modified Procedure:

Compared to the procedures for the preparation of methyl acetal 24 in Examples 3F, 3G and 3I, omission of the isolation of the lactol 7 led to higher overall yield of the methyl acetal 24. Without wishing to be bound by theory, it appears that the lactol 7 may decompose on silica gel. It has, therefore, been shown that a purification of the lactol 7 is not crucial for the process. However, purification of the methyl acetal 24 is more difficult due to a higher amount of oligomers present in the crude mixture.

3K. Synthesis of Methyl Acetal 24

Conversion of Distilled Succinaldehyde 8 to Methyl Acetal 24 (30.8 g Scale)

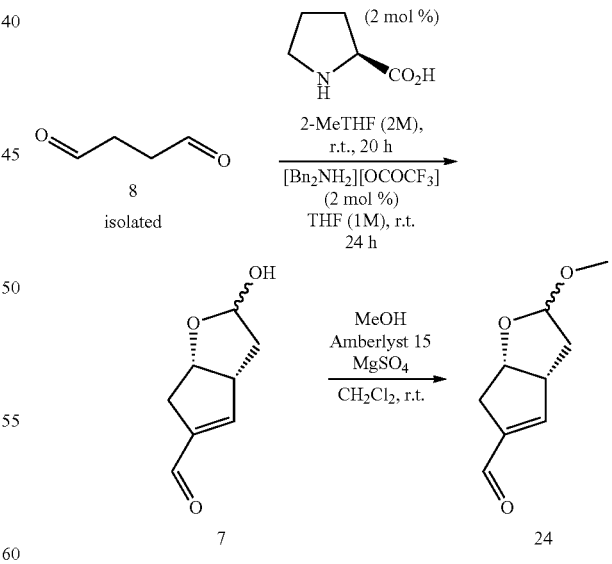

First Step—Succinaldehyde 8 to Lactol 7

Freshly prepared and distilled (4 mbar, 60° C.) succinaldehyde 8 (30.8 g, 358 mmol) was immediately dissolved in 2-MeTHF (180 mL, 2 M) and (S)-proline (825 mg, 7.16 mmol, 0.02 eq.) was added as solid directly to carry out the aldol reaction at r.t. for 20 h (Note: the reaction turned from a colourless suspension to a pink suspension after ~3 h). THF (180 ml) was added, followed by [Bn$_2$NH$_2$][OCOCF$_3$] (2.23 g, 7.16 mmol, 0.02 eq.). The reaction was stirred at r.t. for 24 h. Activated charcoal (70 g) was added to the reaction and the volume of the reaction mixture was reduced by ½ under reduced pressure (~180 mL). tert-Butyl methyl ether (TBME) (an equal volume to the volume of THF/2-MeTHF removed; 180 mL) was added slowly (over ~15 mins) and with vigorous stirring of the mixture. Note: For the purposes of this example, slow addition of TBME helps to avoid the formation of oligomer aggregates. The mixture was stirred for 60 min before filtration of the resulting solids (through a sinter funnel; diameter: ~10 cm). The solids were washed with 2-MeTHF (3×120 ml or until the product was not observed in the filtrate by TLC, 1:1 petroleum ether/EtOAc) and the filtrate was concentrated under reduced pressure. Note: For the purposes of this example, the filtrate should not be concentrated to complete dryness, to help avoid solidifying the oligomers on the column, thereby clogging the column during the purification process. The solvent was removed and the residue was dissolved in CH$_2$Cl$_2$ (50 mL) and purified by column chromatography (~400 g silica), eluting with petroleum ether/EtOAc (6:4 to 4:6), to give the lactol 7 (as an approximately 2:1 mixture of diastereoisomers), as an orange oily solid.

Advantages of Modified Work-Up Procedure for the First Step:

Compared to the procedure for the second step in Example 3F, the use of activated charcoal for the work procedure has removed a significant amount of discolouration from the reaction mixture, as well as oligomers. Furthermore, the use of 2-MeTHF as the optimal solvent for the filtration washing has led to minimum loss of the desired product through this modified work-up procedure. The column chromatography removes the oligomers avoiding the consumption of the reagents in the following reaction and simplifies the purification process of the acetal product 24.

Second Step—Lactol 7 to Methyl Acetal 24

The residue from the first step containing 7 (4.65 g, 30.2 mmol, 1.0 eq.) was dissolved in CH$_2$Cl$_2$ (69.0 ml) and stirred at r.t. MeOH (1.94 g, 2.4 ml, 60.4 mmol, 2.0 eq.) was added via syringe. Amberlyst 15 (967 mg) and MgSO$_4$ (17.9 g) were added as solids in one portion and the reaction mixture was stirred at r.t. for 15 h. The reaction mixture was filtered through a sinter funnel and the solids washed with CH$_2$Cl$_2$ (3×60 ml). The filtrate was concentrated under reduced pressure and purified by column chromatography (~400 g silica), eluting with petroleum ether/EtOAc (10:1 to 4:1), to give the methyl acetal 24, (as an approximately 2:1 mixture of diastereoisomers, 4.86 g, 28.9 mmol, 16% (over 2 steps from succinaldehyde) as a yellow oil (this solidifies in the freezer, but the physical state and appearance differs depending on the exact ratio of diastereoisomers formed, the major diastereoisomer is a solid, the minor an oil, yields typically range between 16-18% for this reaction).

Advantages of Modified Procedure:

Compared to Example 3J, isolation of the lactol 7 leads to the use of less drying agent and MeOH. The purification of the lactol 7 simplifies the column chromatography after the methyl acetal formation.

Example 4

Experimental Procedures for Preparation of Further Acetals 4A. (3aR,6aS)-2-(Cyclohexyloxy)-3,3a,6,6a-tetrahydro-2H-cyclopenta[b]furan-5-carbaldehyde, 50

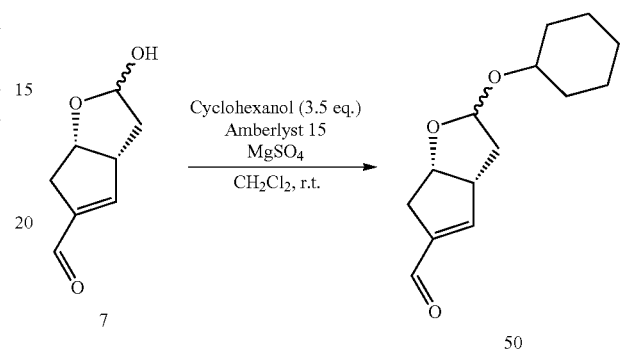

Partially purified residue containing lactol 7 from a procedure in accordance with Example 3E (6.24 g, 12.5% detected by NMR, 40.5 mmol, 1 eq.) was dissolved in CH$_2$Cl$_2$ (90 ml) and stirred at room temperature. Cyclohexanol (14.2 g, 14.9 ml, 3.5 eq.) was added via syringe and Amberlyst 15 (825 mg) and MgSO$_4$ (16.83 g) were added as solids. The reaction mixture was stirred at r.t. for 36 h. The reaction mixture was filtered through a sinter funnel and the solids washed with CH$_2$Cl$_2$ (2×30 ml). The filtrate was concentrated under reduced pressure and the excess cyclohexanol was removed by distillation at 65° C. under high vacuum. The residue was purified by column chromatography (silica), eluting with petrol/EtOAc (10:1), to give the cyclohexyl acetal 50, (as an approximately 1.5:1 mixture of diastereoisomers, 6.10 g, 64% from lactol 7) as a yellow solid.

The cyclohexyl acetal 50 is a compound according to the first aspect of the invention, and corresponds to compound (Ic) (and compound (Ib)) described above.

$v_{max}$ (film)/cm$^{-1}$ 2940, 2912, 1680, 1667, 1614, 1365, 1338, 1194, 1157, 1094, 1053, 1026, 983, 965, 894, 866

$^1$H NMR (400 MHz; CDCl$_3$) $\delta_H$=(mixture of 2 diastereoisomers, signals of minor diastereoisomer indicated by *) 1.00-1.31 (10H, m, CH$_2$), 1.40-1.72 (m, 7H, CH$_2$), 1.78-1.91 (m, 4H, CH$_2$), 2.00 (m, 1H, CH$_2$), 2.12* (m, 1H, CH$_2$), 2.19 (dd, J=10.0, 1.2 Hz, 1H, CH$_2$), 2.68 (m, 2H, CH$_2$), 2.74* (m, 2H, CH$_2$), 3.43* (m, 1H, CH), 3.52 (m, 1H, CH), 3.52* (m, 1H, CH), 3.60 (m, 1H, CH), 4.78 (td, J=6.1, 1.9 Hz, 1H, CH), 4.86* (m, 1H, CH), 5.24* (d, J=4.9 Hz, 1H, CH), 5.27 (d, J=4.9 Hz, 1H, CH), 6.63 (app q, J=1.9 Hz, 1H; CH), 6.74* (app q, J=1.9 Hz, 1H, CH), 9.73* (1H, s, HC=O), 9.74 (1H, s, CH=O)

$^{13}$C NMR (100 MHz; CDCl$_3$) $\delta_C$=(mixture of 2 diastereoisomers, signals of minor diastereoisomer indicated by *) 24.0 (CH$_2$), 24.1 (CH$_2$), 24.2 (CH$_2$), 24.3 (CH$_2$), 25.5 (CH$_2$), 25.6 (CH$_2$), 31.2 (CH$_2$), 31.7 (CH$_2$), 33.1 (CH$_2$), 33.8 (CH$_2$), 35.0 (CH$_2$), 37.1 (CH$_2$), 37.4 (CH$_2$), 37.7 (CH$_2$), 49.3 (CH), 49.8* (CH), 73.7* (CH), 74.4 (CH), 80.0 (CH), 82.1* (CH), 101.0* (CH), 101.5 (CH), 144.4* (C), 144.5 (C), 152.7 (CH), 153.6* (CH), 189.8 (HC=O)

m/z (EI$^+$) 236.1 (Mt), 137.1, 108.0, 95.1, 91.0, 81.1 HRMS (Er) calcd for $C_{14}H_{20}O_3$ [M$^+$] 236.1412. found 236.1414.

4B. Purification by Crystallization

Partially purified residue containing lactol 7 from a procedure in accordance with Example 3D (2.7 g, 11.3% detected by NMR, 17.5 mmol, 1 eq.) was dissolved in $CH_2Cl_2$ (39 ml) and stirred at room temperature. Cyclohexanol (6.13 g, 6.5 ml, 3.5 eq.) was added via syringe and Amberlyst 15 (250 mg) and $MgSO_4$ (5.14 g) were added as solids. The reaction mixture was stirred at r.t. for 36 h. The reaction mixture was filtered through a sinter funnel and the solids washed with $CH_2Cl_2$ (2×30 ml). The filtrate was concentrated under reduced pressure and the excess cyclohexanol was removed by distillation at 65° C. under high vacuum. The residue was dissolved in hot pentane (20 ml), cooled to r.t. and filtered over celite. The filtrate was concentrated under reduced pressure, hexane (2 ml) and diethyl ether (4 ml) were added, followed by a crystal of pure acetal 50. The mixture was taken at −20° C. for 14 hours during which crystallization occurs. Solids were filtered over a cold (−20° C.) sintered glass funnel, washed with a cold (−20° C.) mixture of hexane/$Et_2O$ (3:1) and dried under vacuum. Cyclohexyl acetal 50 (one diastereoisomer, 927.7 mg, 22% from lactol 7) was obtained as slightly brown crystals. The filtrate was concentrated under reduced pressure and dissolved in a hexane/$Et_2O$ mixture (5:1). $HBF_4.OEt_2$ (0.1 ml) is added via syringe and the mixture is kept at −20° C. for 14 hours. Solids were filtered over a cold (−20° C.) sintered glass funnel, washed with a cold (−20° C.) mixture of hexane/$Et_2O$ (3:1) and dried under vacuum to give the cyclohexyl acetal 50, (as an approximately 1:2 mixture of diastereoisomers, 676.2 mg, 16% from lactol 7) as a black solid.

4C. (3aR,6aS)-2-((2,3-Dimethylbutan-2-yl)dimethylsilyloxy)-3,3a,6,6a-tetrahydro-2H-cyclopenta[b]furan-5-carbaldehyde, 51

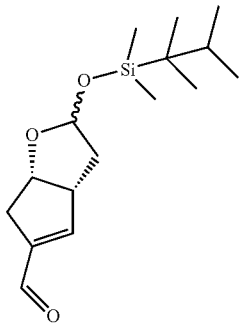

51

Partially purified residue containing lactol 7 from a procedure in accordance with Example 3D (2.3 g, 9% detected by NMR, 14.9 mmol, 1 eq.) was dissolved in $CH_2Cl_2$ (50 ml) and stirred at room temperature. Imidazole (2.03 g, 29.8 mmol, 2 eq.) and 4-dimethylaminopyridine (91 mg, 7.4 mmol, 0.05 eq.) were added as solids and chloro(dimethyl)thexylsilane (5.85 ml, 5.33 g, 29.8 mmol, 2 eq.) via syringe. The reaction mixture was stirred at r.t. for 14 h. The reaction mixture was filtered over a pad a silica, washed with petrol/EtOAc (10:1), and concentrated under vacuum. The excess of chloro(dimethyl)thexylsilane was removed by distillation at 50-55° C. under high vacuum. The residue was purified by column chromatography ($SiO_2$), eluting with petrol/$Et_2O$ (25:2) to give the silyl protected acetal 51 (as an approximately 1.3:1 mixture of diastereoisomers, 3.68 g, 77%) as a yellowish oil.

The silyl protected acetal 51 is a compound according to the first aspect of the invention, and corresponds to compound (Ic) (and compound (Ib)) described above.

$v_{max}$ (film)/cm$^{-1}$ 3336 (road), 2954, 1682, 1250 1098, 1044, 1006, 833, 778

$^1$H NMR (400 MHz; CDCl$_3$) $\delta_H$=(mixture of 2 diastereoisomers, signals of minor diastereoisomer indicated by *) −0.02* (s, 3H, $CH_3$), 0.04* (s, 3H, $CH_3$), 0.10 (s, 3H, $CH_3$), 0.11 (s, 3H, $CH_3$), 0.68* (s, 3H, $CH_3$), 0.69* (s, 3H, $CH_3$), 0.76* (d, J=6.8 Hz, 6H, $CH_3$), 0.80 (s, 6H, $CH_3$), 0.83 (d, J=6.8 Hz, 3H, $CH_3$), 0.84 (d, J=6.8 Hz, 3H, $CH_3$), 1.47* (sept, J=6.8, 1H, CH), 1.57 (sept, J=6.8 Hz, 1H, CH), 1.79 (ddd, J=5.8, 4.8, 1.0 Hz, 1H, $CH_2$), 1.97* (app d, J=12.7 Hz, 1H, $CH_2$), 2.05-2.20 (m, 2H, $CH_2$), 2.05-2.20* (m, 2H, $CH_2$), 2.68 (m, 2H, $CH_2$), 2.68* (m, 2H, $CH_2$), 3.50* (m, 1H, CH), 3.59 (m, 1H, CH), 4.82 (m, 1H, CH), 4.82* (m, 1H, CH), 5.42* (app d, J=4.4 Hz, 1H, CH), 5.46 (app d, J=4.6 Hz, 1H, CH), 6.63 (app q, J=1.7 Hz, 1H, CH), 6.69* (app d, J=1.6 Hz, 1H, CH), 9.71* (s, 1H, HC=O), 9.72 (s, 1H, HC=O)

$^{13}$C NMR (100 MHz; CDCl$_3$) $\delta_C$=(mixture of 2 diastereoisomers, signals of minor diastereoisomer indicated by *) −3.8* (CH$_3$), −3.6 (CH$_3$), −2.3 (CH$_3$), −2.2* (CH$_3$), 18.3 (CH$_3$), 18.4* (CH$_3$), 18.5 (CH$_3$), 19.8 (CH$_3$), 19.9* (CH$_3$), 20.1 (CH$_3$), 24.4* (C), 24.6 (C), 33.9* (CH), 34.1 (CH), 35.1* (CH$_2$), 37.7 (CH$_2$), 39.4* (CH$_2$), 39.9 (CH$_2$), 49.1 (CH), 49.8* (CH), 80.3 (CH), 82.5* (CH), 98.5* (CH), 98.6 (CH), 144.5 (C), 144.5* (C), 152.6 (CH), 153.7* (CH), 189.6* (HC=O), 189.8 (HC=O)

HRMS (ESI) calcd for $C_{16}H_{28}O_3SiNa$ [MNa$^+$] 319.1699. found 319.1701.

4D. (3aR,6aS)-2-(tert-Butoxy)-3,3a,6,6a-tetra hydro-2H-cyclopenta[b]furan-5-carbaldehyde, 52

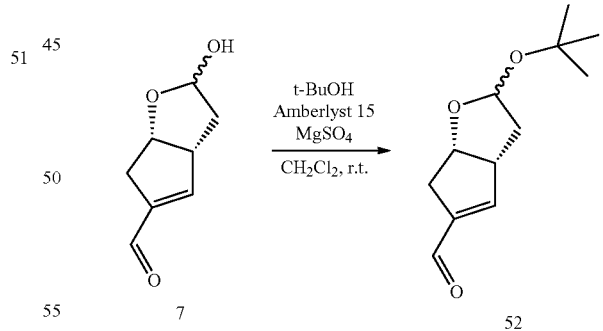

Partially purified residue containing lactol 7, was dissolved in $CH_2Cl_2$ (40 ml) and stirred at r.t. t-BuOH (2.58 g, 3.33 ml, 34.8 mmol, 2.0 eq. based on ~14% of 7 detected by internal standard in the previous reaction) was added via syringe. Amberlyst 15 (249 mg) and $MgSO_4$ (5.15 g) were added as solids in one portion and the reaction mixture was stirred at r.t. for 14 h. The reaction was charged with further portions of t-BuOH (2.58 g, 3.33 ml, 34.8 mmol, 2.0 eq.), Amberlyst 15 (249 mg) and $MgSO_4$ (5.15 g) and stirred for a further 24 h. The reaction mixture was filtered through a sinter funnel and the solids washed with $CH_2Cl_2$ (2×15 ml). The filtrate was concentrated under reduced pressure and purified by column chromatography (~50 g silica), eluting with petrol/EtOAc (4:1), to give the t-butyl acetal 52, (as an approximately 2:1 mixture of diastereoisomers (635 mg, 2% (over 2 steps from succinaldehyde, 17% from lactol 7))) as a yellow oil.

The t-butyl acetal 52 is a compound according to the first aspect of the invention, and corresponds to compound (Ic) (and compound (Ib)) described above.

Major Diastereoisomer:

$R_f$=0.39 (petrol:EtOAc, 4:1)

$v_{max}$ (neat)/cm$^{-1}$ 2974, 2926, 2807, 2714, 1682, 1617, 1388, 1361, 1179, 1161, 1095, 1046, 1026, 1008, 981, 869, 703

$^1$H NMR (400 MHz; CDCl$_3$) $\delta_H$=1.25 (9H, s, C(CH$_3$)$_3$), 1.93 (1H, app dt, J=13.2, 5.3 Hz, CHH), 2.16 (1H, ddd, J=13.2, 10.0, 1.8 Hz, CHH), 2.64-2.78 (2H, m, CH$_2$), 3.63 (1H, m, CH), 4.86 (1H, td, J=5.9, 1.8 Hz, CH), 5.45 (1H, dd, J=5.3, 1.8 Hz, CH), 6.66 (1H, app q, J=1.8 Hz, C=CH), 9.78 (1H, s, HC=O)

$^{13}$C NMR (100 MHz; CDCl$_3$) $\delta_C$=28.8 (C(CH$_3$)$_3$), 35.4 (CH$_2$), 38.3 (CH$_2$), 49.5 (CH), 74.3 (C(CH$_3$)$_3$), 79.8 (CH), 98.8 (CH), 144.8 (C=CH), 152.9 (C=CH), 189.9 (C=O)

HRMS (ESI) calcd for $C_{12}H_{18}O_3$Na [MNa$^+$] 233.1148. found 233.1158.

$[\alpha]_D^{26}$ −127 (c. 1, acetone)

Minor Diastereoisomer:

$R_f$=0.31 (petrol:EtOAc, 4:1)

$^1$H NMR (400 MHz; CDCl$_3$) $\delta_H$=1.13 (9H, s, C(CH$_3$)$_3$), 1.93 (1H, br. d, J=13.0 Hz, CHH), 2.17 (1H, ddd, J=13.0, 9.8, 5.2 Hz, CHH), 2.70-2.90 (2H, m, CH$_2$), 3.51 (1H, m, CH), 4.82 (1H, t, J=6.0 Hz, CH), 5.38 (1H, dd, J=5.2, 0.7 Hz, CH), 6.77 (1H, app q, J=2.0 Hz, C=CH), 9.78 (1H, s, HC=O)

$^{13}$C NMR (100 MHz; CDCl$_3$) $\delta_C$=28.8 (C(CH$_3$)$_3$), 37.6 (CH$_2$), 37.9 (CH$_2$), 50.0 (CH), 73.8 (C(CH$_3$)$_3$), 81.8 (CH), 98.5 (CH), 144.6 (C=CH), 153.9 (C=CH), 190.0 (C=O)

4E. (3aR,6aS)-5-formyl-3,3a,6,6a-tetrahydro-2H-cyclopenta[b]furan-2-yl[1,1'-biphenyl]-4-carboxylate, 53

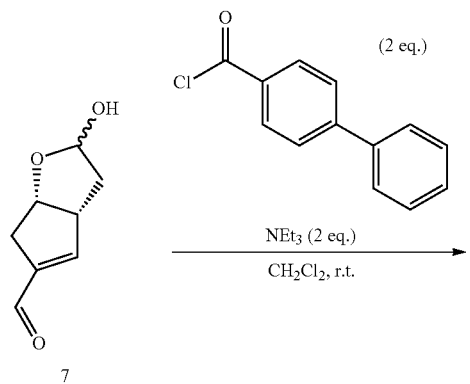

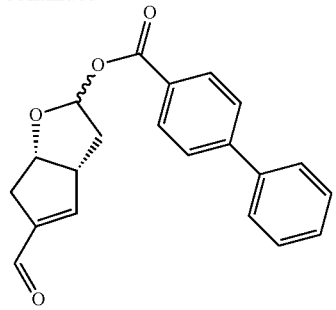

53

Purified lactol 7 (500 mg, 3.24 mmol), was dissolved in $CH_2Cl_2$ (10 ml) and stirred at r.t. Biphenyl-4-carbonyl chloride (1.41 g, 6.49 mmol) was added as a solid and triethylamine (904 µl, 6.49 mmol) was added via syringe. The reaction was stirred at r.t. for 14 h. The reaction mixture was washed with water (2×10 ml) and the organic phase was dried (MgSO$_4$), filtered, and concentrated to give the crude material as yellow solids. The material was purified by column chromatography eluting with petrol/EtOAc (3:1), to give the biphenyl acetal 53, (as an approximately 2:1 mixture of diasteroisomers, 236 mg, 54%) as pale yellow solids.

The biphenyl acetal 53 is a compound according to the first aspect of the invention, and corresponds to compound (Ic) (and compound (Ib)) described above.

It was possible to partially separate the diastereoisomers for full characterisation purposes using column chromatography eluting with petrol/EtOAc (3:1).

Major Diastereoisomer:
Physical State Very Fine White Needles

Mp 134-139° C. (after recrystallisation from 40/60 petroleum ether/EtOAc)

$R_f$=0.65 (petrol:EtOAc, 1:1)

$v_{max}$ (neat)/cm$^{-1}$ 2997, 2951, 2927, 1713, 1671, 1605, 1403, 1269, 1174, 1158, 1105, 1083, 1069, 1038, 976, 862, 745, 693

$^1$H NMR (400 MHz; CDCl$_3$) $\delta_H$=2.26 (1H, app dt, J=14.0, 5.4 Hz, CHH), 2.60 (1H, ddd, J=14.0, 10.0, 0.8 Hz, CHH), 2.75-2.92 (2H, m, CH$_2$), 3.80 (1H, m, CH), 5.09 (1H, app t, J=6.0 Hz, HCO), 6.60 (1H, d, J=5.4 Hz, OCHO), 6.71 (1H, br. d, J=2.0 Hz, =CH), 7.38-7.53 (3H, m, ArCH's), 7.60-7.72 (4H, m, ArCH's), 8.07-8.14 (2H, m, ArCH's), 9.83 (1H, s, HC=O)

HRMS (ESI) calcd for $C_{21}H_{18}O_4$Na [MNa$^+$] 357.1097. found 357.1114.

Anal. Calcd for $C_{21}H_{18}O_4$: C, 75.43; H, 5.43. Found: C, 75.47; H, 5.50.

Minor Diastereoisomer:
Physical State White Plates

Mp 130-132° C. (after recrystallisation from 40/60 petroleum ether/EtOAc)

$R_f$=0.47 (petrol:EtOAc, 1:1)

$v_{max}$ (CHCl$_3$)/cm$^{-1}$ 2978, 2811, 2714, 1714, 1670, 1609, 1265, 1085, 1057, 1001, 915, 889, 825, 747, 696

$^1$H NMR (400 MHz; CDCl$_3$) $\delta_H$=2.39 (1H, d, J=14.0 Hz, CHH), 2.50 (1H, ddd, J=14.0, 9.9, 4.7 Hz, CHH), 2.93 (2H, m, CH$_2$), 3.76 (1H, m, CH), 5.13 (1H, m, HCO), 6.62 (1H, d, J=4.7 Hz, OCHO), 6.84 (1H, app q, J=1.8 Hz, =CH), 7.40 (1H, m, ArCH), 7.47 (2H, m, ArCH's), 7.61 (4H, m, ArCH's), 7.87 (2H, m, ArCH's), 9.89 (1H, s, HC=O)

HRMS (ESI) calcd for $C_{21}H_{18}O_4$Na [MNa$^+$] 357.1097. found 357.1110.

Anal. Calcd for $C_{21}H_{18}O_4$: C, 75.43; H, 5.43. Found: C, 75.41; H, 5.49.

4F. (3aR,6aS)-2-Oxo-3,3a,6,6a-tetrahydro-2H-cyclopenta[b]furan-5-carbaldehyde, 54

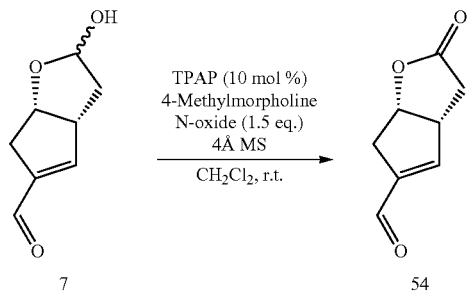

Purified lactol 7 (800 mg, 4.15 mmol), was dissolved in $CH_2Cl_2$ (52 ml) and stirred at r.t. 4-Methylmorpholine N-oxide (729 mg, 6.23 mmol) and 4 Å molecular sieve (2.8 g) were added as solids and the reaction mixture was stirred at r.t. for 10 min. Tetrapropylammonium perruthenate (146 mg, 0.415 mmol) was added as a solid and the reaction was stirred at r.t. for 14 hours. The reaction mixture was filtered over Celite® and the solids were washed with $CH_2Cl_2$ (3×10 ml). The organic phase was concentrated to give the crude material as a black oil. The material was purified by column chromatography eluting with $CH_2Cl_2$/EtOAc (9:1), to give the lactone 54, (439 mg, 70%) as a white solid.

The lactone 54 is a compound according to the first aspect of the invention, and corresponds to compound (Ib) described above.

Mp 78-80° C.
$R_f$=0.44 (EtOAc)
$v_{max}$ (neat)/cm$^{-1}$ 2935, 2832, 1766, 1676, 1170, 1157
$^1$H NMR (400 MHz; CDCl$_3$) $\delta_H$=2.58 (1H, dd, J=18.3, 2.0 Hz, CHH), 2.85-2.90 (1H, m, CHH), 2.91 (1H, dd, J=18.3, 10.3 Hz, CHH), 2.98 (1H, d, J=18.3, CHH), 3.80 (1H, m, CH), 5.23 (1H, app t, J=5.8, CH), 6.63 (1H, d, J=1.7 Hz, CH), 9.83 (1H, s, CH)
$^{13}$C NMR (100 MHz; CDCl$_3$) $\delta_C$=32.1 (CH$_2$), 36.0 (CH$_2$), 46.4 (CH), 82.3 (CH), 145.2 (C), 148.4 (CH), 175.1 (C=O), 188.9 (C=O)
m/z (CI) 153 (MH$^+$, 100%), 107 (25%)
HRMS (CI) calcd for $C_8H_9O_3$ [MH$^+$] 153.0552. found 153.0555.

4G. (3aR,6aS)-5-Formyl-3,3a,6,6a-tetrahydro-2H-cyclopenta[b]furan-2-yl benzoate, 55

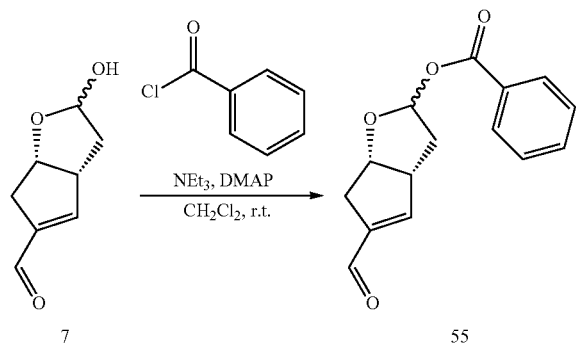

Purified lactol 7 (591.5 mg, 3.84 mmol, 1 eq.), was dissolved in $CH_2Cl_2$ (7 ml) and stirred at r.t. Dimethylaminopyridine (23.5 mg, 0.19 mmol, 5 mol %) was added as a solid. Triethylamine (647.5 µl, 4.61 mmol, 1.2 eq.) and benzoyl chloride (534.5 µL, 4.61 mmol, 1.2 eq.) were added via syringe. The reaction mixture was stirred at r.t. for 36 h, filtered over basic alumina and the organic phase was concentrated to give the crude material. The material was purified by column chromatography eluting with petrol/EtOAc (3:1) to give the benzoyl acetal 55 (as an approximately 1.3:1 mixture of diastereoisomers, 706.7 mg, 71%) as pale yellow solid.

$v_{max}$ (film)/cm$^{-1}$ 2943, 2817, 1717, 1675, 1451, 1360, 1267, 1160, 1088, 1063, 1026, 971, 921, 871, 832, 706, 686
$^1$H NMR (400 MHz; CDCl$_3$; observed signals; mixture of 2 diastereoisomers, signals of minor indicated by *) $\delta_H$=2.25 (m, 1H, CHH), 2.37* (app d, J=13.6 Hz, 1H, CHH), 2.48* (m, 1H, CHH), 2.58 (ddd, J=13.2, 10.0, 1.0 Hz, 1H, CHH), 2.79-2.93* (m, 2H, CH$_2$), 2.79-2.93 (m, 2H, CH$_2$), 3.77* (m, 1H, CH), 3.77 (m, 1H, CH), 5.07 (app t, J=5.6 Hz, 1H, HCO), 5.11* (m, 1H, HCO), 6.59* (m, 1H, OCHO), 6.59 (m, 1H, OCHO), 6.71 (app q, J=1.9 Hz, 1H, =CH), 6.83* (app q, J=1.9 Hz, 1H, =CH), 7.35-7.85* (m, 3H, ArCH's), 7.35-7.85 (m, 3H, ArCH's), 7.81* (dd, J=8.5, 1.2 Hz, 2H, ArCH's), 8.04 (dd, J=8.3, 1.2 Hz, 2H, ArCH's), 9.82 (s, 1H, CHO), 9.86* (s, 1H, CHO)
$^{13}$C NMR (100 MHz; CDCl$_3$; observed signals; mixture of 2 diastereoisomers, signals of minor indicated by *) $\delta_C$=35.3 (CH$_2$), 37.2 (CH$_2$), 37.4* (CH$_2$), 38.0* (CH$_2$), 48.9 (CH), 493* (CH), 83.1 (CH), 84.3* (CH), 99.7 (OCHO), 99.8* (OCHO), 128.4* (2×ArCH), 128.5 (2×ArCH), 129.6* (2×ArCH), 129.8 (2×ArCH), 130.1* (ArC), 130.2 (ArC), 133.3* (ArCH), 133.4 (ArCH), 144.9 (C=CH), 145.5* (C=CH), 151.3 (C=CH), 152.1* (C=CH), 165.5* (COO), 165.8 (COO), 189.5* (CHO), 189.9 (CHO)

(3aR,6aS)-2-(Benzyloxy)-3,3a,6,6a-tetrahydro-2H-cyclopenta[b]furan-5-carbaldehyde, 56

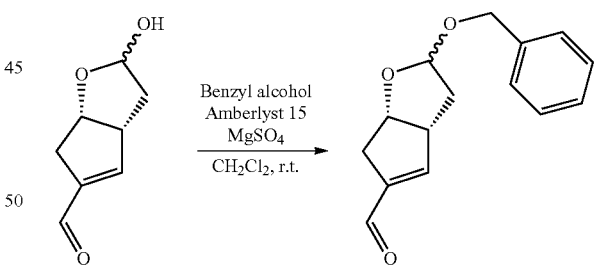

Purified lactol 7 (591.5 mg, 3.84 mmol, 1 eq.), was dissolved in $CH_2Cl_2$ (7 ml) and stirred at r.t. Benzyl alcohol (794.1 µL, 7.68 mmol, 2 eq.) was added via syringe and amberlyst 15 (56.5 mg) and MgSO$_4$ (1.16 g) were added as solids. The reaction mixture was stirred at r.t. for 36 h. The reaction mixture was filtered through a sinter funnel and the solids washed with $CH_2Cl_2$ (2×10 ml). The filtrate was concentrated under reduced pressure to give the crude material which was purified by column chromatography eluting with petrol/EtOAc (9:1) to give the benzyl acetal 56 (as an approximately 1.5:1 mixture of diastereoisomers, 657.8 mg, 70%) as pale yellow oil.

$v_{max}$ (film)/cm$^{-1}$ 2943, 1676, 1454, 1358, 1269, 1159, 1093, 1074, 1022, 977, 948, 869, 735, 696

$^1$H NMR (400 MHz; CDCl$_3$; observed signals; mixture of 2 diastereoisomers, signals of minor indicated by *) $\delta_H$=1.94 (app dt, J=13.4, 5.1 Hz, 1H, CHH), 2.22* (m, 2H, CH$_2$), 2.36 (ddd, J=13.4, 10.1, 1.0 Hz, 1H, CHH), 2.78 (m, 2H, CH$_2$), 2.84* (m, 2H, CH$_2$), 3.59* (m, 1H, CH), 3.67 (m, 1H, CH), 4.35* (d, J=11.5 Hz, 1H, CHH), 4.49 (d, J=11.7 Hz, 1H, CHH), 4.62* (d, J=11.5 Hz, 1H, CHH), 4.75 (d, J=11.7 Hz, 1H, CHH), 4.88 (m, 1H, CH), 4.98* (app td, J=5.7, 2.8 Hz, 1H, CH), 5.24* (app d, J=4.6 Hz, 1H, OCHO), 5.26 (app d, J=5.1 Hz, 1H, OCHO), 6.67 (app q, J=1.7 Hz, 1H, =CH), 6.77* (app q, J=1.8 Hz, 1H, =CH), 7.19* (m, 1H, ArCH), 7.19 (m, 1H, ArCH), 7.20-7.40* (m, 4H, ArCH's), 7.20-7.40 (m, 4H, ArCH's), 9.78* (s, 1H, CHO), 9.80 (s, 1H, CHO)

$^{13}$C NMR (100 MHz; CDCl$_3$; observed signals; mixture of 2 diastereoisomers, signals of minor indicated by *) $\delta_C$=35.3 (CH$_2$), 37.3* (CH$_2$), 37.4 (CH$_2$), 37.9* (CH$_2$), 49.4 (CH), 49.9* (CH), 68.9 (CH$_2$), 69.1* (CH$_2$), 80.7 (CH), 82.9* (CH), 103.1 (OCHO), 103.3* (OCHO), 127.7* (ArCH), 127.8 (ArCH), 128.0* (2×ArCH), 128.1 (2×ArCH), 128.5* (2×ArCH), 128.6 (2×ArCH), 137.9* (ArC), 138.0 (ArC), 144.6* (C=CH), 144.7 (C=CH), 152.6 (C=CH), 153.4* (C=CH), 190.1* (CHO), 190.1 (CHO)

Example 5

Experimental Procedures for the Synthesis of PGF$_{2\alpha}$

A complete synthesis of PGF$_{2\alpha}$ from commercially available materials is shown below.

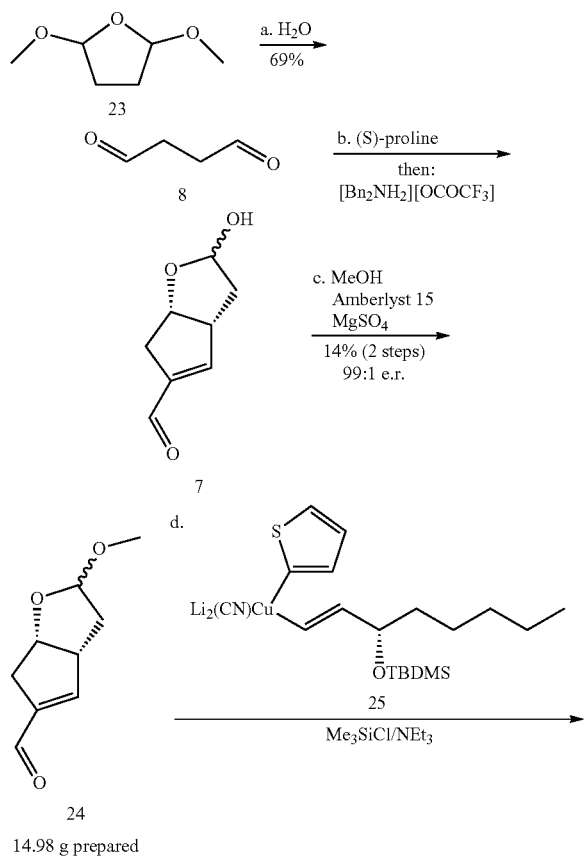

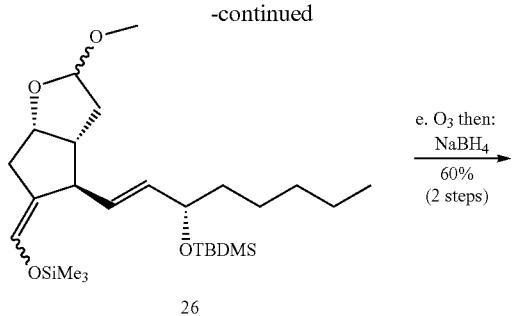

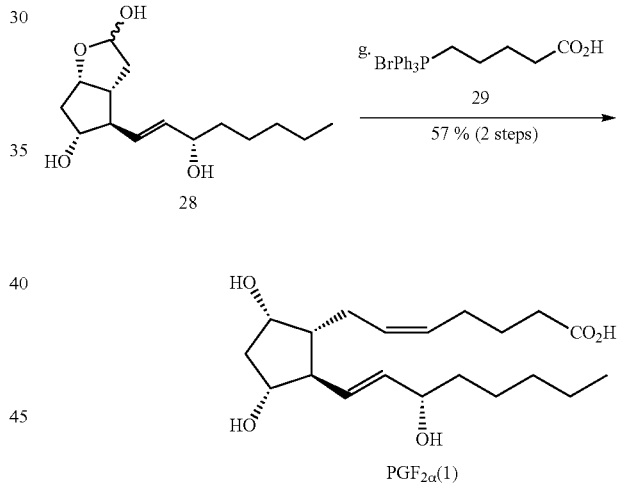

As described in Example 1B, heating 2,5-dimethoxytetrahydrofuran 23 in water followed by evaporation and extraction gave crude dialdehyde 8. This was directly subjected to the aldol reaction, described in Example 3A. The lactol 7 was converted into a 2:1 diastereoisomeric mixture of methoxy acetals 24, described in Example 3C, which were carried through the subsequent reaction sequence. From 57.5 g of succinaldehyde we were able to obtain 7.85 g of pure methoxy acetal 24 in 14% yield over 2 steps.

Conjugate addition of the mixed vinyl cuprate 25 followed by trapping with TMSCl furnished the silyl enol ether 26. Controlled ozonolysis followed by treatment with NaBH$_4$ gave the alcohol 27. As planned, these two steps occurred with complete stereocontrol at the newly created stereogenic centres. Finally, simultaneous deprotection of the acetal and silyl ether with aqueous HCl followed by Wittig reaction with the phosphonium salt 29 gave the target molecule PGF$_{2\alpha}$, which was identical in all respects to the natural product (Sheddan, N. A. et al., *Org. Lett.* 8, 3101-3104 (2006)).

5A. (S)-tert-Butyldimethyl(oct-1-yn-3-yloxy)silane, SI-7

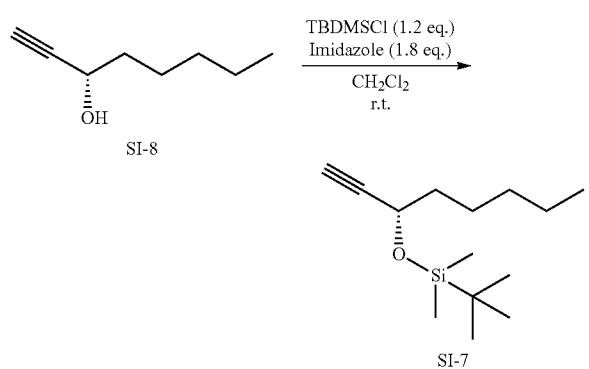

The procedure of Noyori (Suzuki, M., et al., *J. Med. Chem.* 41, 3084-3090 (1998)) was used. Imidazole (971 mg, 14.3 mmol) and t-butylchlorodimethylsilane (1.43 g, 9.51 mmol) were added to a solution of (S)-1-octyn-3-ol SI-8 (1.00 g, 1.16 ml, 7.92 mmol) in CH$_2$Cl$_2$ (18 ml), cooled to 0° C. The reaction mixture was then stirred at room temperature for 24 h before being poured into 1 M HCl (50 ml). The mixture was extracted with 40/60 petroleum ether (3×50 ml). The combined organic phases were washed with brine (50 ml) before being dried (MgSO$_4$), filtered, and concentrated to give the title compound SI-7 (1.89 g, 99%) as a clear, colourless oil. Analytical data consistent with the literature (Nicolaou, K. C. et al., A. *J. Am. Chem. Soc.* 107, 7515-7518 (1985); Cmrecki, V. et al., *Tetrahedron* 66, 6550-6564 (2010)).

R$_f$=0.31 (petrol)

$\nu_{max}$ (film)/cm$^{-1}$ 3313, 2955, 2930, 2858, 1472, 1464, 1251, 1119, 1089, 836, 777

$^1$H NMR (400 MHz; CDCl$_3$) $\delta_H$=0.12 (3H, s, CH$_3$), 0.14 (3H, s, CH$_3$), 0.90 (3H, t, J=6.9 Hz, CH$_3$), 0.91 (9H, s, 3×CH$_3$), 1.24-1.38 (4H, m, 2×CH$_2$), 1.38-1.48 (2H, m, CH$_2$), 1.64-1.72 (2H, m, CH$_2$), 2.38 (1H, d, =2.0 Hz, CH), 4.34 (1H, td, J=6.5, 2.0 Hz, CH)

$^{13}$C NMR (100 MHz; CDCl$_3$) $\delta_C$=−5.1 (CH$_3$), −4.6 (CH$_3$), 14.0 (CH$_3$), 18.2 (C), 22.6 (CH$_2$), 24.8 (CH$_2$), 25.8 (3×CH$_3$), 31.4 (CH$_2$), 38.5 (CH$_2$), 62.8 (CH), 71.8 (CH) 85.8 (C)

m/z (CI) 241 (MH$^+$, 62%), 225 (88%), 133 ($^+$H$_2$OSi (CH$_3$)$_2$C(CH$_3$)$_3$, 93%), 109 (MH$^+$—HOSi(CH$_3$)$_2$C(CH$_3$)$_3$, 100%).

$[\alpha]_D^{21}$ −55.0 (c. 1.0, CHCl$_3$) (lit., $^{44}[\alpha]_D^{23}$ −41.7 (c. 1.0, CHCl$_3$))

5B. (S,E)-tert-Butyl(1-iodooct-1-en-3-yloxy)dimethylsilane, SI-9

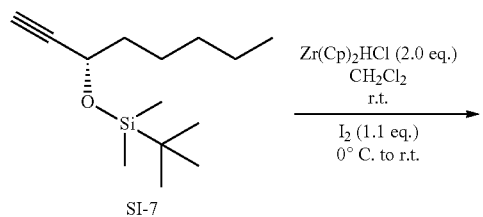

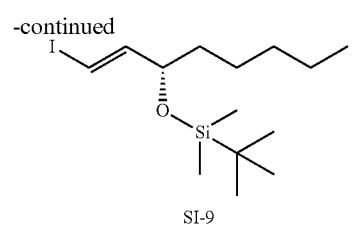

A modified procedure of Noyori (Suzuki, M. et al., *J. Med. Chem.* 41, 3084-3090 (1998)) was used. A flame dried schlenk flask, evacuated and purged with nitrogen, was charged with alkyne SI-7 (1.89 g, 7.86 mmol). Anhydrous CH$_2$Cl$_2$ (50 ml) was added and the reaction stirred at r.t. Zr(Cp)$_2$HCl (4.05 g, 15.7 mmol) was added as a solid, in portions. The yellow suspension was stirred at r.t. for 1 h. The resulting yellow solution was cooled to 0° C. and iodine (2.19 g, 8.65 mmol) added as a solid, in one portion. The cooling bath was removed and the reaction mixture stirred at room temperature for 15 min. The reaction mixture was poured into water (100 ml) and extracted with 40/60 petroleum ether. This organic phase was washed with saturated Na$_2$S$_2$O$_3$ solution (2×100 ml) and brine (100 ml) before being dried (MgSO$_4$), filtered, and concentrated to give the crude material as a yellow oil. This was purified by flash chromatography, eluting with hexane or 40/60 petroleum ether. The fractions containing product were combined and washed with saturated Na$_2$S$_2$O$_3$ solution (100 ml), dried (MgSO$_4$), filtered, and concentrated to give the title compound SI-9 (2.67 g, 92%) as a clear, colourless oil. Analytical data consistent with the literature (Luo, F. T. et al., *J. Org. Chem.* 50, 4762-4766 (1985)).

R$_f$=0.51 (hexane)

$\nu_{max}$ (film)/cm$^{-1}$ 2955, 2928, 2857, 1607, 1463, 1361, 1254, 1087, 942, 835, 775

$^1$H NMR (400 MHz; CDCl$_3$) $\delta_H$=0.04 (3H, s, CH$_3$), 0.05 (3H, s, CH$_3$), 0.89 (3H, m, CH$_3$), 0.90 (9H, s, 3×CH$_3$), 1.20-1.38 (6H, m, 3×CH$_2$), 1.40-1.53 (2H, m, CH$_2$), 4.07 (1H, m, CH), 6.19 (1H, dd, J=14.4, 1.3 Hz, CH), 6.52 (1H, dd, J=14.4, 6.0 Hz, CH)

$^{13}$C NMR (100 MHz; CDCl$_3$) $\delta_C$=−4.9 (CH$_3$), −4.5 (CH$_3$), 14.0 (CH$_3$), 18.2 (C), 22.6 (CH$_2$), 24.5 (CH$_2$), 25.8 (3×CH$_3$), 31.7 (CH$_2$), 37.5 (CH$_2$), 75.2 (CH), 75.4 (CH), 149.4 (CH)

m/z (CI) MH$^+$ not seen, 353 (60%), 311 (52%), 215 (100%), 109 (MH$^+$—HOSi(CH$_3$)$_2$C(CH$_3$)$_3$, 60%)

5C. [(1S,2E)-3-((3aR,4R,6aS)-2-Methoxy-5-(Z)-1-[(1,1,1-trimethylsilyl)oxy]methylideneperhydrocyclopenta[b]furan-4-yl)-1-pentyl-2-propenyl]oxy(tert-butyl)dimethylsilane, 26

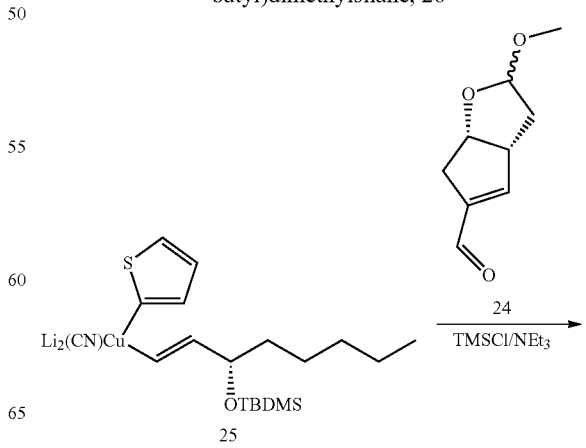

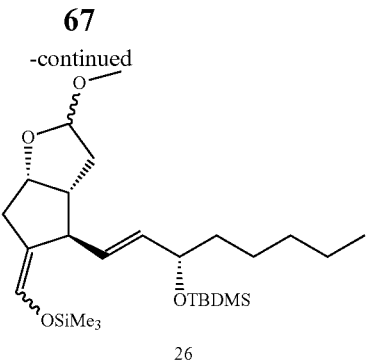

26

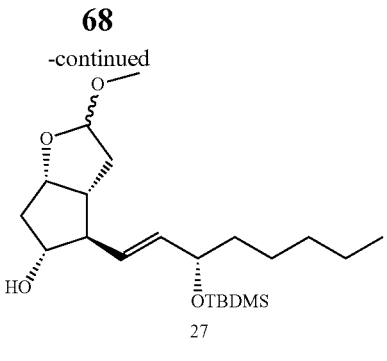

27

Vinyl iodide SI-9 (2.41 g, 6.54 mmol, 1.1 eq.) was added via syringe to a flame dried schlenk flask (evacuated and purged with nitrogen several times and allowed to cool). Anhydrous Et$_2$O (26.5 ml) was added via syringe and the resulting solution cooled to −78° C. 1.7 M t-BuLi (7.69 ml, 13.1 mmol, 2.2 eq.) was added dropwise and the reaction mixture stirred at −78° C. for 2 h and −40° C. for 2 h before being cooled back to −78° C. Meanwhile, thiophene (550 mg, 524 µl, 6.54 mmol, 1.1 eq.) was added via syringe to a flame dried schlenk flask (evacuated and purged with nitrogen several times and allowed to cool). Anhydrous THF (26.5 ml) was added via syringe and the resulting solution cooled to −30° C. 1.6 M n-BuLi (4.09 ml, 6.54 mmol, 1.1 eq.) was added dropwise and the solution stirred at −30° C. for 30 min. The solution was then cooled to −78° C. and CuCN (586 mg, 6.54 mmol, 1.1 eq.) added as a solid, in one portion. The cooling bath was removed and the suspension allowed to warm to r.t. The resulting tan/brown solution of cuprate was added dropwise via syringe to the schlenk flask containing the vinyl lithium and anhydrous THF (26.5 ml) added. The mixture was stirred at −20° C. for 1 h to allow formation of mixed cuprate 25. The cuprate 25 corresponds to compound (IV) described above.

The mixture was cooled to −78° C. and a solution of enal 24 (1.00 g, 5.95 mmol, 1.0 eq.) in anhydrous THF (26.5 ml) was added dropwise. The mixture was stirred at −78° C. for 1 h and then allowed to warm slowly to −20° C. TMSCl (3.23 g, 3.77 ml, 29.7 mmol, 5.0 eq.) was added via syringe followed by NEt$_3$ (3.61 g, 4.97 ml, 35.7 mmol, 6 eq.). The reaction was quenched by the addition of saturated NH$_4$Cl solution (100 ml) and extracted with Et$_2$O (3×100 ml). The combined organic phases were washed with saturated NH$_4$Cl solution (50 ml) before being dried (MgSO$_4$), filtered, and concentrated to give the crude material as a yellow oil. This was used directly in the next step.

Formed compound 26 corresponds to compound (V) described above.

5D. (3aR,4R5R,6aS)-4-((E,3S)-3-[1-(tert-Butyl)-1,1-dimethylsilyl]oxy-1-octenyl)-2-methoxyperhydrocyclopenta[b]furan-5-ol, 27

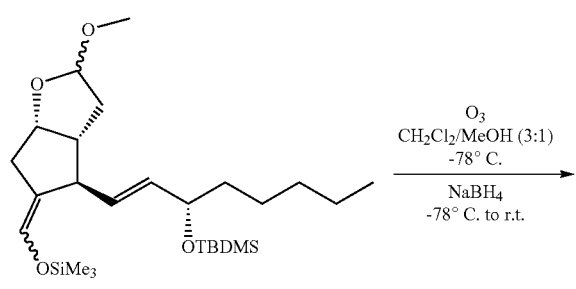

26

The crude material from the conjugate addition/trapping experiment, containing 26, was dissolved in CH$_2$Cl$_2$/MeOH (3:1) (60 ml) and cooled to −78° C. A stream of ozone was passed through the stirred solution. The reaction was monitored periodically by TLC in order to judge completion of the ozonolysis (judged by consumption of silyl enol ether). The reaction mixture was flushed with a stream of N$_2$, for 15 min, to remove any remaining O$_3$. At this point NaBH$_4$ (406 mg, 10.7 mmol) was added in one portion. The reaction mixture was stirred at −78° C. for 2 h before the cooling bath was removed and the reaction allowed to warm to r.t. The reaction was stirred at r.t. for 1 h. The reaction mixture was poured into saturated NaCl solution (25 ml) and extracted with EtOAc (3×50 ml). The combined organic phases were dried (MgSO$_4$), filtered, and concentrated to give the crude product as a pale yellow oil. This was purified by column chromatography on silica, eluting with petrol/EtOAc (6:1), giving the alcohol 27 (as an approximately 2:1 mixture of diastereoisomers) as a clear, colourless oil (1.40 g, 60% (2 steps from enal 24)).

The alcohol 27 corresponds to compound (VI) described above.

$R_f$=0.22 (petrol:EtOAc, 6:1)

$v_{max}$ (neat)/cm$^{-1}$ 3425, 2955, 2929, 2857, 1463, 1361, 1251, 1207, 1098, 1047, 835, 774

$^1$H NMR (400 MHz; CDCl$_3$) $\delta_H$=(mixture of 2 diastereoisomers, signals of minor diastereoisomer indicated by *) 0.02 (3H, s, CH$_3$), 0.03* (3H, s, CH$_3$), 0.04 (3H, s, CH$_3$), 0.05* (3H, s, CH$_3$), 0.89 (12H, s+m, C(CH$_3$)$_3$, CH$_3$), 0.89* (12H, s+m, C(CH$_3$)$_3$, CH$_3$), 1.29 (6H, m, 3×CH$_2$), 1.29* (6H, m, 3×CH$_2$), 1.44 (2H, m, CH$_2$), 1.44* (2H, m, CH$_2$), 1.80-2.50 (6H, m, 2×CH$_2$, 2×CH), 1.80-2.50* (6H, m, 2×CH$_2$, 2×CH), 3.33 (3H, s, OCH$_3$), 3.38* (3H, s, OCH$_3$), 3.79* (1H, app quin., J=7.0 Hz, CHOH), 3.92 (1H, app quin., J=6.3 Hz, CHOH), 4.05 (1H, m, CHOTBDMS), 4.05* (1H, m, CHOTBDMS), 4.51 (1H app td, J=6.7, 3.1 Hz, CH), 4.62* (1H, app td, J=7.5, 4.4 Hz, CH), 5.07* (1H, d, J=5.6 Hz, CH), 5.12 (1H, br. d, J=5.4 Hz, CH), 5.42 (1H, ddd, J=15.4, 7.7, 0.7, =CH), 5.42* (1H, ddd, J=15.4, 8.3, 0.9, =CH) 5.54 (1H, m, =CH), 5.54* (1H, m, =CH)

$^{13}$C NMR (100 MHz; CDCl$_3$) $\delta_C$=(observed signals, mixture of 2 diastereoisomers) −4.8 (SiCH$_3$), −4.3 (SiCH$_3$), −4.2 (SiCH$_3$), 14.0 (2×CH$_3$), 18.3 (2×CCH$_3$), 22.6 (CH$_2$), 25.0 (CH$_2$), 25.9 (6×CCH$_3$), 31.7 (CH$_2$), 37.9 (CH$_2$), 38.4 (CH$_2$), 38.4 (CH$_2$), 39.2 (CH$_2$), 39.5 (CH$_2$), 42.3 (CH$_2$), 45.7 (CH), 46.1 (CH), 54.5 (2×OCH$_3$), 54.9 (CH), 56.7 (CH), 57.5 (CH$_3$), 73.2 (CH), 73.3 (CH), 77.7 (CH), 78.8 (CH), 81.1 (CH), 83.3 (CH), 106.5 (OCHOCH$_3$), 107.6 (OCHOCH$_3$), 129.6 (=CH), 130.3 (=CH), 135.5 (=CH), 135.7 (=CH). One SiCH$_3$ and three CH$_2$'s could not be assigned due to overlapping signals.

HRMS (ESI) calcd for C$_{22}$H$_{42}$O$_4$SiNa [MNa$^+$] 421.2745. found 421.2754.

5E. (3aR,4R,5R,6aS)-4-[(E,3S)-3-Hydroxy-1-octenyl]perhydrocyclopenta[b]furan-2,5-diol, 28

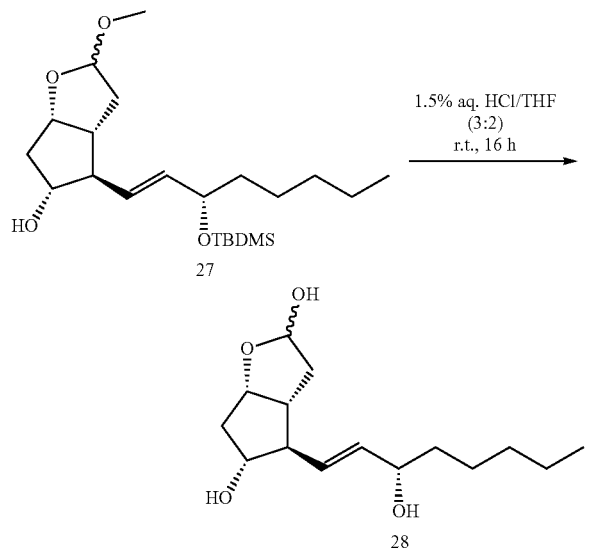

Alcohol 27 (300 mg, 0.75 mmol) was stirred with 1.5% aqueous HCl/THF (3:2) (15 ml) at r.t. for 16 h. The mixture was extracted with $CH_2Cl_2$ (5×25 ml) and the combined organic phases were dried ($MgSO_4$), filtered, and concentrated to give the triol 28 and silanol by-product as a clear, colourless oil (~300 mg). This material was taken forward for the subsequent transformation without purification.

The triol 28 corresponds to compound (VII) described above.

5F. (Z)-7-(1R,2R,3R,5S)-3,5-Dihydroxy-2-[(E,3S)-3-hydroxy-1-octenyl]cyclopentyl-5-heptenoic acid, PGF$_{2α}$ (1)

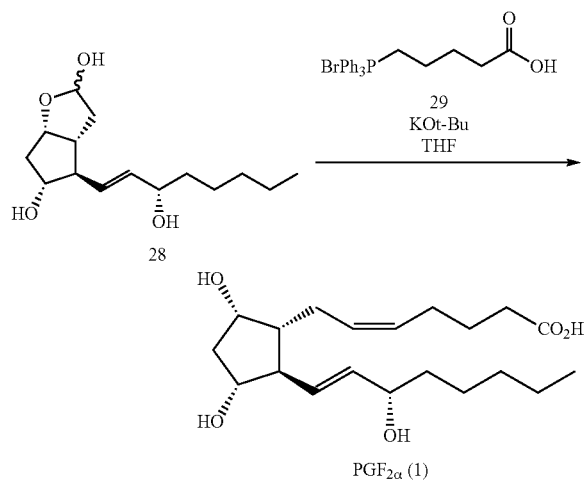

(4-Carboxybutyl)(triphenyl)phosphonium bromide 29 (de los Angeles Rey, M. et al., *J. Org. Chem.* 64, 3196-3206 (1999) Note: Material prepared as described in this reference, but using toluene in place of benzene and pentane in place of hexane during the washing of the product) (2.00 g, 4.52 mmol), which corresponds to compound (VIII) described above, was added to a flame dried schlenk flask, under $N_2$, and anhydrous THF (16.0 ml) added. The resulting suspension was cooled to 0° C. KOt-Bu (1.01 g, 9.03 mmol) was added in one portion and the resulting orange mixture stirred at 0° C. for 40 min. A solution of crude triol 28 (203 mg, 0.75 mmol) in anhydrous THF (4.0 ml) was added dropwise via syringe. After complete addition the mixture was stirred at r.t. for 1 h. The reaction was quenched with $H_2O$ (25 ml) and washed with $Et_2O$ (2×25 ml) to remove triphenylphosphine oxide. The aqueous phase was made acidic with 1 M HCl (~10 ml) and extracted with $CH_2Cl_2$ (5×25 ml). The combined organic phases were dried ($MgSO_4$), filtered, and concentrated to give the crude material. This was triturated with EtOAc/heptane and the solids filtered and washed with EtOAc (4×5 ml). The filtrate was concentrated under vacuum and purified by column chromatography on silica, eluting with EtOAc/petrol/AcOH (60:35:5) to give PGF$_{2α}$. This was dissolved in $CH_2Cl_2$ and washed with $H_2O$ (5 ml). The organic phase was then dried ($MgSO_4$), filtered, and concentrated to give PGF$_{2α}$ (152 mg, 57% over 2 steps) as a clear, colourless oil.

The $^1H$ NMR data was consistent with that reported by Mulzer (Sheddan, N. A. et al., *Org. Lett.* 8, 3101-3104 (2006)). The $^{13}C$ NMR data was in excellent agreement with that reported by Parve (Parve, O. et al., *Bioorg. Med. Chem. Lett.* 9, 1853-1858 (1999)). The IR and optical rotation data are in agreement with that reported by Mulzer (Sheddan, N. A. et al., *Org. Lett.* 8, 3101-3104 (2006)) and Corey (Corey, E. et al., *J. Am. Chem. Soc.* 92, 397-398 (1970)).

$R_f$=0.24 (EtOAc:40/60 petroleum ether:AcOH, 60:35:5)

$v_{max}$ (neat)/cm$^{-1}$ 3339, 2961, 2930, 2857, 2490, 1705, 1457, 1380, 1245, 1118, 1086, 1047, 970, 910, 878, 731

$^1H$ NMR (400 MHz; CDCl$_3$) $\delta_H$=0.89 (3H, t, J=6.8 Hz, CH$_3$), 1.24-1.41 (6H, m, 3×CH$_2$), 1.43-1.54 (2H, m,), 1.54-1.63 (1H, m), 1.63-1.73 (2H, m), 1.76 (1H, m), 2.07-2.28 (5H, m), 2.28-2.39 (3H, m), 3.96 (1H, m, CHOH), 4.11 (1H, q, J=6.8 Hz, CHOH), 4.18 (1H, m, CHOH), 4.35-5.20 (1H, br. s, CO$_2$H), 5.32-5.41 (1H, m, =CH), 5.41-5.50 (1H, m, =CH), 5.50 (1H, dd, J=15.4, 8.4 Hz, =CH), 5.58 (1H, dd, J=15.4, 6.6 Hz, =CH)

$^{13}C$ NMR (125 MHz; CDCl$_3$) $\delta_C$=14.0 (CH$_3$), 22.6 (CH$_2$), 24.5 (CH$_2$), 25.2 (CH$_2$), 25.2 (CH$_2$), 26.3 (CH$_2$), 31.7 (CH$_2$), 33.1 (CH$_2$), 36.9 (CH$_2$), 42.7 (CH$_2$), 50.0 (CH), 55.2 (CH), 72.3 (HCOH), 73.2 (HCOH), 77.4 (HCOH), 129.2 (=CH), 129.5 (=CH), 132.8 (=CH), 135.1 (=CH), 177.5 (C=O)

HRMS (ESI) calcd for $C_{20}H_{34}O_5Na$ [MNa$^+$] 377.2298. found 377.2303.

$[α]_D^{22}$ −23.5 (c. 1.0, THF) (lit., $^{49}[α]_D^{20}$ −24.9 (c. 0.57, THF)) (lit., $^{51}[α]_D^{25}$ −23.8 (synthetic material) (c. 1.0, THF)) (lit., 51$[α]_D^{25}$ −23.5 (natural material) (c. 1.0, THF))

In summary, we have developed a short (7 step) synthesis of prostaglandin PGF$_{2α}$ from inexpensive 2,5-dimethoxyfuran 23. The key step is an organocatalytic aldol dimerization reaction of succinaldehyde 8 which generates the bicyclic lactol 7 with very high enantioselectivity and fully primed with suitable functionality to directly introduce the required side chains. The aldol cascade used proline to perform the initial aldol reaction and a second catalyst ([Bn$_2$NH$_2$][OCOCF$_3$]) to induce an intramolecular aldol reaction and elimination. The enantioselectivity was very high, isolation and purification was straightforward and the reaction could be conducted on multi-gram scale. Its application in a short synthesis of the most complex of prostaglandins, PGF$_{2α}$, has been demonstrated. Indeed the bicyclic lactol 7 is an ideal building block not just for the cost-effective synthesis of the whole family of prostaglandins, but for also exploring chemical space around the ubiquitous five membered carbocyclic ring motif, where other biologically active molecules undoubtedly lie.

Example 6

Experimental Procedures for the Synthesis of Latanoprost

A synthesis of latanoprost is shown and described below.

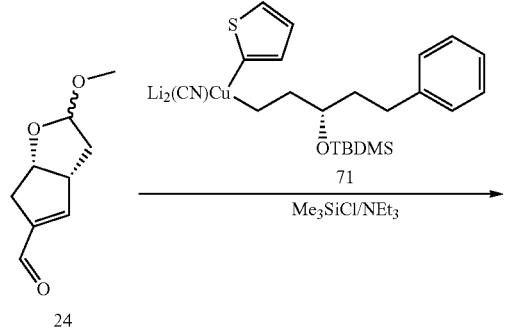

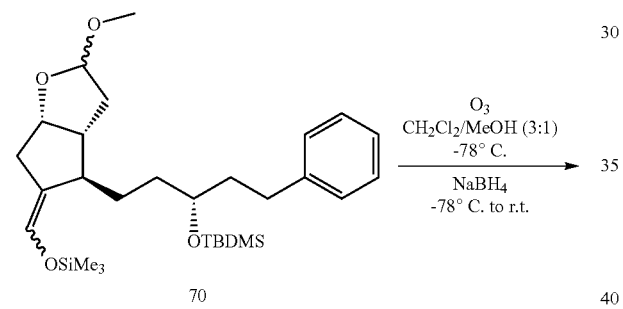

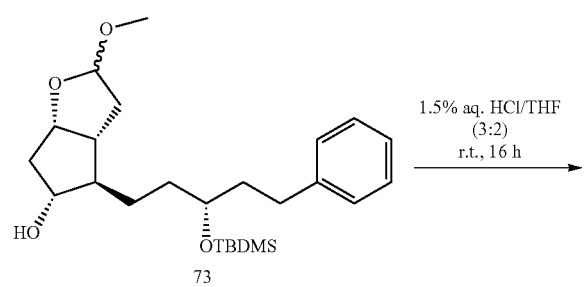

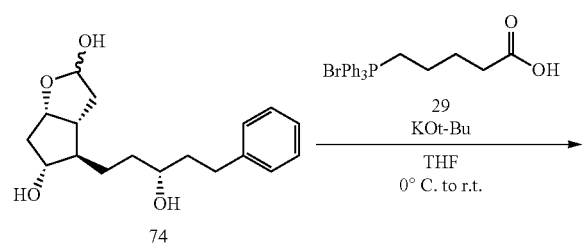

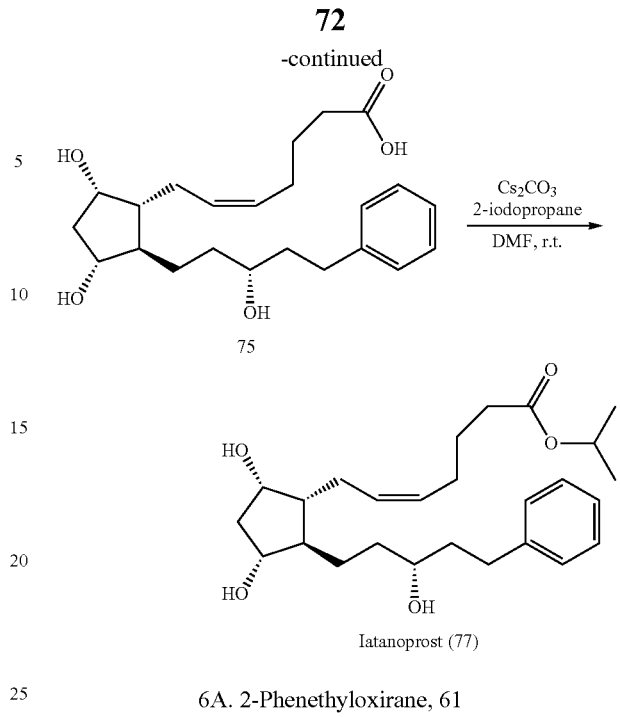

6A. 2-Phenethyloxirane, 61

A modified procedure of Woodward was used (Bernier, D. et al., *The Journal of Organic Chemistry* 2008, 73, 4229). A stirred solution of 4-phenyl-1-butene 62 (500 mg, 568 μl, 3.78 mmol) in $CH_2Cl_2$ (20 ml) was cooled to 0° C. m-CPBA (816 mg, 4.73 mmol) was added as a solid and the reaction mixture was stirred at 0° C. for 1.5 h, then r.t. for 24 h. The reaction mixture was poured into saturated $K_2CO_3$ solution (50 ml) and extracted with $CH_2Cl_2$ (2×50 ml). The combined organic phases were washed with saturated $K_2CO_3$ solution (50 ml) before being dried ($MgSO_4$), filtered and concentrated to give a clear colourless liquid. This material was purified by column chromatography, eluting with petrol/EtOAc (9:1), to give the epoxide 61 (10.2 g, 91%) as a clear colourless liquid. The $^1H$, $^{13}C$, and IR data were consistent with the literature (Mitchell, J. M. et al., *Journal of the American Chemical Society* 2001, 123, 862; Elings, J. A. et al., *European Journal of Organic Chemistry* 1999, 1999, 837).

$R_f$=0.42 (petrol:EtOAc, 9:1)

$v_{max}$ (neat)/$cm^{-1}$ 3027, 2989, 2922, 2859, 1602, 1495, 1454, 1410, 835, 750, 699

$^1H$ NMR (400 MHz; $CDCl_3$) $\delta_H$=1.83-1.99 (2H, m, $CH_2$), 2.53 (1H, dd, J=5.0, 2.7 Hz, CHH), 2.75-2.93 (2H, m, $CH_2$), 2.80 (1H, dd, J=5.0, 4.0 Hz, CHH), 3.01 (1H, dddd, J=6.5, 5.0, 4.0, 2.7 Hz, CH), 7.22-7.38 (5H, m, Ar H's)

$^{13}C$ NMR (100 MHz; $CDCl_3$) $\delta_C$=32.2 ($CH_2$), 34.2 ($CH_2$), 47.2 ($CH_2$), 51.7 (CH), 126.0 (2×ArCH), 128.3 (2×ArCH), 128.4 (ArCH), 141.2 (ArC)

m/z(EI) 148.1 ($M^+$, 10%), 130.1 (23%), 129.0 (18%), 118.1 (29%), 117.1 (83%), 115.0 (28%), 105.0 (22%), 104.0 (61%), 92.0 (22%), 91.0 (100%), 83.9 (37%), 77.0 (17%), 65.0 (31%)

6B. (2S)-2-Phenethyloxirane, 63

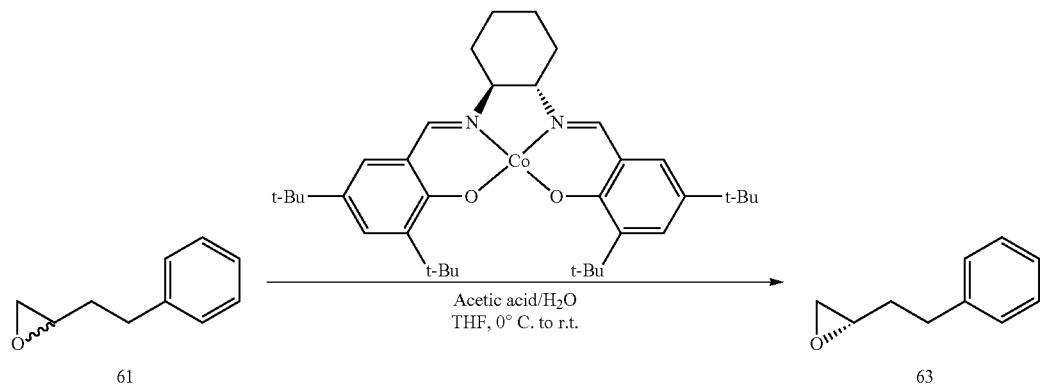

A modified procedure of Jacobsen was used (Schaus, S. E. et al., *Journal of the American Chemical Society* 2002, 124, 1307). Racemic epoxide 61 (10.0 g, 67.5 mmol) was dissolved in THF (10 ml) and stirred at r.t. (S,S)-(+)-N,N'-Bis(3,5-di-tert-butylsalicylidene)-1,2-cyclohexanediaminocobalt (II) (204 mg, 0.34 mmol) was added and the resultant dark brown solution cooled to 0° C. Acetic acid (77 µl, 1.35 mmol) and water (669 µl, 37.1 mmol) were added. The reaction was stirred at 0° C. for 1 h and then at r.t. for 23 h. The reaction mixture was concentrated under reduced pressure and purified by column chromatography (~200 g silica), eluting with petrol/EtOAc (9:1), to give the epoxide 3 as a dark red liquid. This was re-purified by column chromatography eluting with petrol/EtOAc (9.5:0.5 to 9:1), to give the epoxide 3 (4.62 g, 46%) as an orange liquid. The analytical data matched that of the racemic material described above. The enantioselectivity of the resolution was determined after subsequent conversion to the allylic alcohol 66. The optical rotation matched closely with that reported in the literature (Martynow, J. G. et al., *European Journal of Organic Chemistry* 2007, 2007, 689).

$[\alpha]_D^{21}$ −21.0 (c. 1.0, $CHCl_3$) (lit., $[\alpha]_D^{20}$ −22.5 (c. 1.0, $CHCl_3$))

6C. 5-Phenyl-1-penten-3-ol, 64

A modified procedure of Molander was used (Molander, G. A. et al., *The Journal of Organic Chemistry* 2009, 74, 1297). A stirred solution of hydrocinnamaldehyde 65 (2.50 g, 2.45 ml, 18.6 mmol) in THF (25 ml) was cooled to −78° C. Vinyl magnesium bromide solution (1 M in THF) (22.4 ml, 22.4 mmol) was added dropwise over ~5 min. The reaction mixture was stirred at −78° C. for 1.5 h, then 0° C. for 3 h. The reaction mixture was poured into saturated $NH_4Cl$ solution (50 ml) and extracted with $Et_2O$ (3×50 ml). The combined organic phases were washed with saturated NaCl solution (50 ml) before being dried ($MgSO_4$), filtered and concentrated to give a pale yellow liquid. This material was purified by column chromatography, eluting with petrol/EtOAc (9:1), to give the vinyl alcohol 64 (1.89 g, 63%) as a clear colourless liquid. The $^1H$, $^{13}C$, and IR data were consistent with the literature (Molander, G. A. et al., *The Journal of Organic Chemistry* 2009, 74, 1297; Kim, J. W. et al., *Chemistry—A European Journal* 2008, 14, 4104).

$R_f$=0.40 (petrol:EtOAc, 4:1)

$v_{max}$ ($CHCl_3$)/cm$^{-1}$ 3335, 3026, 2923, 2859, 1496, 1454, 990, 922, 747, 698

$^1H$ NMR (400 MHz; $CDCl_3$) $\delta_H$=1.55 (1H, br.s, OH), 1.84-1.99 (2H, m, $CH_2$), 2.70-2.89 (2H, m, $CH_2$), 4.19 (1H, app q, J=6.0 Hz, CHOH), 5.20 (1H, app dt, J=10.5, 1.4 Hz, HHC=C), 5.30 (1H, app dt, J=17.1, 1.4 Hz, HHC=C), 5.96 (1H, ddd, J=17.1, 10.5, 6.0 Hz, $H_2C$=CH), 7.20-7.40 (5H, m, ArCH's)

$^{13}C$ NMR (100 MHz; $CDCl_3$) $\delta_C$=31.6 ($CH_2$), 38.5 ($CH_2$), 72.4 (HCOH), 114.9 ($H_2C$=C), 125.8 (ArCH), 128.4 (2×ArCH), 128.4 (2×ArCH), 141.0 ($H_2C$=C), 141.8 (ArC)

m/z(EI) 162.1 (M$^+$, 30%), 144.1 (52%), 129.1 (72%), 105.1 (68%), 92.1 (71%), 91.0 (100%), 57.0 (61%)

6D. (3S)-5-Phenyl-1-penten-3-ol, 66

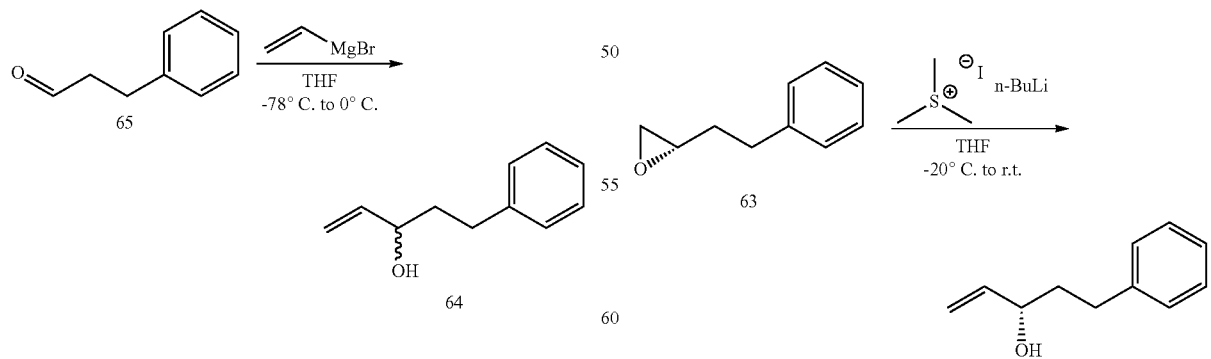

A modified procedure of Falck was used (Alcaraz, L. et al., *Tetrahedron Letters* 1994, 35, 5449). A suspension of trimethylsulfonium iodide (18.2 g, 89.1 mmol) in anhydrous THF (220 ml) was stirred and cooled to −20° C. 1.6 M n-BuLi (55.7 ml, 89.1 mmol) was added slowly and the reaction stirred at −20° C. for 1 h. A solution of epoxide 63 (4.40 g, 29.7 mmol) in anhydrous THF (50.0 ml) was added slowly. The reaction was stirred at −20° C. for 1 h and then allowed to warm to r.t. slowly. The reaction mixture was poured into water (200 ml) and extracted with Et$_2$O (1×200 ml, 1×100 ml). The combined organic phases were washed with saturated NaCl solution (100 ml) before being dried (MgSO$_4$), filtered, and concentrated to give the crude material. This was purified by column chromatography (130 g silica), eluting with petrol/EtOAc (9:1), to give partially purified material. This was re-purified by column chromatography (50 g silica), eluting with petrol/EtOAc (9:1), to give allylic alcohol 66 (3.19 g, 66%) as a pale yellow liquid. The analytical data matched that described for the racemic material above.

$[\alpha]_D^{21}$ −11.0 (c. 1.0, CHCl$_3$) (lit—Kanbayashi, N. et al., *Angewandte Chemie International Edition* 2011, 50, 5197, $[\alpha]_D^{25}$ −3.6 (for 85% ee (c. 0.4, CHCl$_3$)))

Chiral-HPLC data: er=>99:1 (Chiralcel AD-H column, 210 nm, hexane/2-propanol: 98/2, flow rate: 0.5 mL/min, room temperature; $t_R$: minor 41.0 min, major 43.7 min)

6E. tert-Butyl(dimethyl)[(1S)-1-phenethyl-2-propenyl]oxysilane, 67

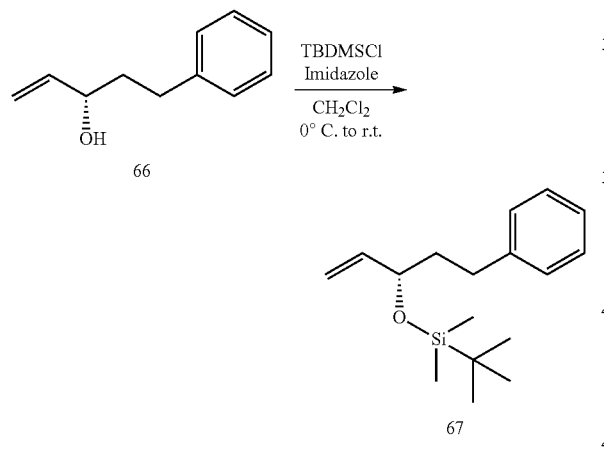

A stirred solution of allylic alcohol 66 (3.00 g, 18.5 mmol) in CH$_2$Cl$_2$ (53 ml) was cooled to 0° C. Imidazole (2.27 g, 33.3 mmol) was added in one portion followed by t-butylchlorodimethylsilane (3.34 g, 22.2 mmol). The cooling bath was removed and the reaction mixture stirred at r.t. for 16 h before being poured into 10% aq. HCl (100 ml). The mixture was extracted with 40/60 petroleum ether (2×100 ml). The combined organics were washed with saturated NaCl solution (100 ml), dried (MgSO$_4$), filtered, and concentrated to give the crude material. This was purified by column chromatography, eluting with 40/60 petroleum ether, to give the protected alcohol 67 (4.68 g, 92%) as a colourless liquid. The $^1$H NMR data and optical rotation matched that reported in the literature (Uenishi, J. i. et al., *Organic Letters* 2011, 13, 2350).

R$_f$=0.25 (40/60 petroleum ether)

$v_{max}$ (film)/cm$^{-1}$ 3064, 3027, 2952, 2929, 2886, 2856, 1497, 1472, 1462, 1455, 1361, 1251, 1122, 1083, 1030, 990, 921, 834, 774, 697

$^1$H NMR (400 MHz; CDCl$_3$) $\delta_H$=0.05 (3H, s, SiCH$_3$), 0.08 (3H, s, SiCH$_3$), 0.93 (9H, s, C(CH$_3$)$_3$), 1.82 (2H, m, CH$_2$), 2.66 (2H, m, CH$_2$), 4.17 (1H, m, OCH), 5.08 (1H, ddd, J=10.4, 1.5, 1.3 Hz, HHC=CH), 5.19 (1H, app dt, J=17.2, 1.5 Hz, HHC=CH), 5.86 (1H, ddd, J=17.2, 10.4, 6.0 Hz, H$_2$C=CH), 7.18 (3H, m, ArH's), 7.28 (2H, m, ArH's)

$^{13}$C NMR (100 MHz; CDCl$_3$) $\delta_C$=−4.8 (SiCH$_3$), −4.3 (SiCH$_3$), 18.3 (C(CH$_3$)$_3$), 25.9 (C(CH$_3$)$_3$), 31.5 (CH$_2$), 39.8 (CH$_2$), 73.3 (CHOSi), 114.0 (H$_2$C=C), 125.7 (ArCH), 128.3 (2×ArCH), 128.4 (2×ArCH), 141.4 (H$_2$C=C), 142.5 (ArC).

$[\alpha]_D^{22}$ 12.0 (c. 1.0, CHCl$_3$) (lit., $[\alpha]_D^{20}$ 14.5 (c. 1.0, CHCl$_3$))

6F. (3S)-3-[1-(tert-Butyl)-1,1-dimethylsilyl]oxy-5-phenylpentan-1-ol, 68

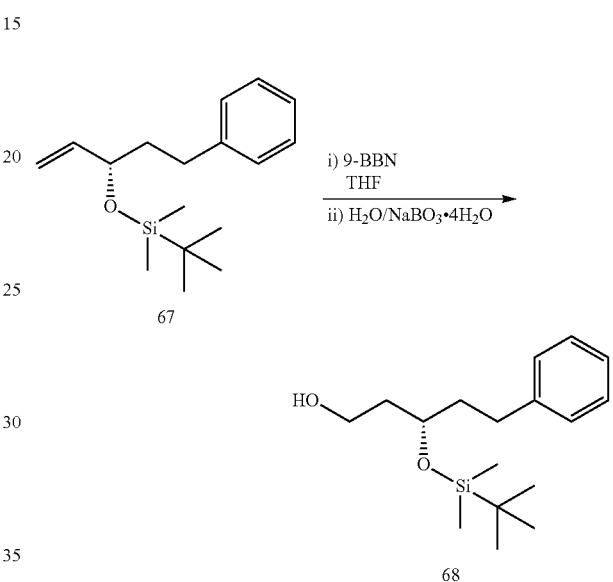

A modified procedure of Denmark was used (Denmark, S. E. et al., *Organic Letters* 2005, 7, 5617). Compound 67 (2.00 g, 7.23 mmol) was added to a flame dried schlenk flask under N$_2$. 9-BBN (0.5 M in THF) (15.9 ml, 7.96 mmol) was added via syringe and the resulting solution stirred at r.t. for 1 h. A further 1.1 eq. (15.9 ml, 7.96 mmol) of 9-BBN was added and the reaction stirred at r.t. for 2 h. Water (16.0 ml) and NaBO$_3$.4H$_2$O (5.56 g, 36.2 mmol) were added and the reaction stirred at r.t. for 2 h. The reaction mixture was poured into saturated NH$_4$Cl solution (60 ml) and extracted with Et$_2$O (3×100 ml). The combined organic phases were washed with sat. NaCl solution (100 ml), dried (MgSO$_4$), filtered, and concentrated to give the crude material. This was purified 3 times by column chromatography (twice eluting with petrol/EtOAc (6:1) and once with petrol/EtOAc/Et$_2$O (9:0.5:0.5)) to give the alcohol 68 (672 mg, 32%) as a clear colourless oil.

R$_f$=0.18 (petrol:EtOAc, 9:1)

$v_{max}$ (film)/cm$^{-1}$ 3351 (broad), 3063, 2950, 2928, 2885, 2856, 1496, 1471, 1462, 1454, 1360, 1253, 1092, 1057, 1028, 1005, 834, 773, 746, 698

$^1$H NMR (400 MHz; CDCl$_3$) $\delta_H$=0.09 (3H, s, SiCH$_3$), 0.10 (3H, s, SiCH$_3$), 0.92 (9H, s, C(CH$_3$)$_3$), 1.75 (1H, m, CHH), 1.83-1.94 (3H, m, CH$_2$, CHH), 2.32 (1H, app t, J=5.2 Hz, OH), 2.64 (2H, m, CH$_2$), 3.75 (1H, app dq, J=10.8, 5.5 Hz, OCHH), 3.87 (1H, app ddt, J=10.8, 8.1, 4.8 Hz, OCHH), 3.99 (1H, app qd, J=6.1, 4.4 Hz, HCOTBDMS), 7.16-7.23 (3H, m, ArCH's), 7.27-7.33 (2H, m, ArCH's)

$^{13}$C NMR (100 MHz; CDCl$_3$) $\delta_C$=−4.7 (SiCH$_3$), −4.4 (SiCH$_3$), 18.0 (C(CH$_3$)$_3$), 25.8 (C(CH$_3$)$_3$), 31.7 (CH$_2$), 37.8

(CH$_2$), 38.7 (CH$_2$), 60.1 (CH$_2$), 71.2 (SiOCH), 125.8 (ArCH), 128.2 (2×ArCH), 128.4 (2×ArCH), 142.1 (ArC)

HRMS (ESI) calcd for C$_{17}$H$_{30}$O$_2$SiNa [MNa$^+$] 317.1907. found 317.1906.

[α]$_D^{23}$ 23.0 (c. 1.0, CHCl$_3$)

6G. tert-Butyl[(1S)-3-iodo-1-phenethylpropyl]oxydimethylsilane, 69

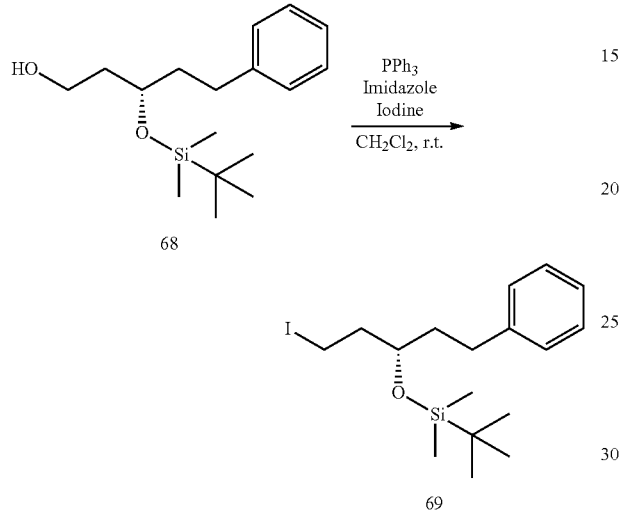

A modified procedure of Rychnovsky was used (Dalgard, J. E. et al., *Organic Letters* 2004, 6, 2713). Alcohol 68 (600 mg, 2.04 mmol) was added to a flame dried schlenk flask under N$_2$. CH$_2$Cl$_2$ (10 ml) was added via syringe and the resulting solution stirred at r.t. Triphenylphosphine (695 mg, 2.65 mmol) and imidazole (222 mg, 3.26 mmol) were added as solids in one portion. Iodine (672 mg, 2.65 mmol) was added to the resulting solution. A slight exotherm was noted and the solution changed from a light yellow colour to a brown colour with the formation of a precipitate. The reaction was stirred at r.t. for 1 h. The reaction mixture was dry loaded onto silica (2 g) and purified by column chromatography (14 g silica), eluting with petrol to petrol/EtOAc (9:1). This gave the iodide 69 (725 mg, 88%) as a clear, colourless oil.

R$_f$=0.20 (40/60 petroleum ether)

ν$_{max}$ (film)/cm$^{-1}$ 3063, 3026, 2951, 2928, 2886, 2856, 1495, 1471, 1461, 1360, 1253, 1187, 1165, 1140, 1092, 1063, 1005, 975, 931, 833, 773, 697

$^1$H NMR (400 MHz; CDCl$_3$) δ$_H$=0.09 (3H, s, SiCH$_3$), 0.10 (3H, s, SiCH$_3$), 0.92 (9H, s, (C(CH$_3$)$_3$), 1.79 (2H, m, CH$_2$), 2.05 (2H, m, CH$_2$), 2.64 (2H, m, CH$_2$), 3.24 (2H, m, CH$_2$), 3.82 (1H, quin., J=5.7 Hz, OCH), 7.16-7.23 (3H, m, ArCH's), 7.27-7.33 (2H, m, ArCH's)

$^{13}$C NMR (100 MHz; CDCl$_3$) δ$_C$=−4.3 (SiCH$_3$), −4.3 (SiCH$_3$), 3.0 (CH$_2$), 18.1 (C(CH$_3$)$_3$), 25.9 (C(CH$_3$)$_3$), 31.3 (CH$_2$), 38.7 (CH$_2$), 40.8 (CH$_2$), 71.7 (OCH), 125.8 (ArCH), 128.3 (2×ArCH), 128.4 (2×ArCH), 142.1 (ArC)

HRMS (ESI) calcd for C$_{17}$H$_{30}$OSiI [MH$^+$] 405.1108. found 405.1105.

[α]$_D^{23}$ 26.0 (c. 1.0, CHCl$_3$)

6H. [(1R)-3-((3aR,4R,6aS)-2-Methoxy-5-(E)-1-[(1,1-trimethylsilyl)oxy]methylideneperhydrocyclopenta[b]furan-4-yl)-1-phenethylpropyl]oxy(tert-butyl)dimethylsilane, 70

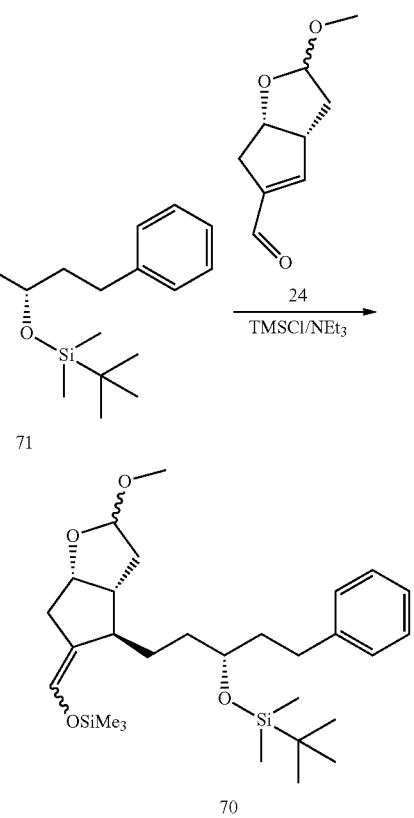

Iodide 69 (1.32 g, 3.27 mmol, 1.1 eq.) was added via syringe to a flame dried schlenk flask (evacuated and purged with nitrogen several times and allowed to cool). Anhydrous Et$_2$O (13.3 ml) was added via syringe and the resulting solution cooled to −78° C. 1.63 M t-BuLi (4.01 ml, 6.54 mmol, 2.2 eq.) was added dropwise and the reaction mixture stirred at −78° C. for 2 h and −40° C. for 2 h before being cooled back to −78° C. Meanwhile, thiophene (275 mg, 262 µl, 3.27 mmol, 1.1 eq.) was added via syringe to a flame dried schlenk flask (evacuated and purged with nitrogen several times and allowed to cool). Anhydrous THF (13.3 ml) was added via syringe and the resulting solution cooled to −30° C. 1.63 M n-BuLi (2.01 ml, 3.27 mmol, 1.1 eq.) was added dropwise and the solution stirred at −30° C. for 30 min. CuCN (293 mg, 3.27 mmol, 1.1 eq.) was added as a solid, in one portion. The cooling bath was removed and the suspension allowed to warm to r.t. The resulting tan/brown solution of cuprate was added dropwise via syringe to the schlenk flask containing the alkyl lithium and anhydrous THF (13.3 ml) added. The mixture was stirred at −20° C. for 1 h to allow formation of mixed cuprate 71. This was cooled to −78° C. and a solution of enal 24 (500 mg, 2.97 mmol, 1.0 eq.) in anhydrous THF (13.3 ml) was added dropwise. The mixture was stirred at −78° C. for 1 h and then allowed to warm slowly to −20° C. TMSCl (1.61 g, 1.89 ml, 14.9 mmol, 5.0 eq.) was added via syringe followed by NEt$_3$ (1.80 g, 2.49 ml, 17.8 mmol, 6 eq.). The reaction was quenched by the addition of saturated NH₄Cl solution (50 ml) and extracted with Et₂O (3×50 ml). The combined organic phases were washed with saturated NH₄Cl solution (50 ml) and saturated NaCl solution (50 ml) before being dried (MgSO₄), filtered, and concentrated to give the crude material as a yellow oil. This was used directly in the next step.

6I. (3aR,4R5R,6aS)-4-((3R)-3-[1-(tert-Butyl)-1,1-dimethylsilyl]oxy-5-phenylpentyl)-2-methoxyperhydrocyclopenta[b]furan-5-ol, 73

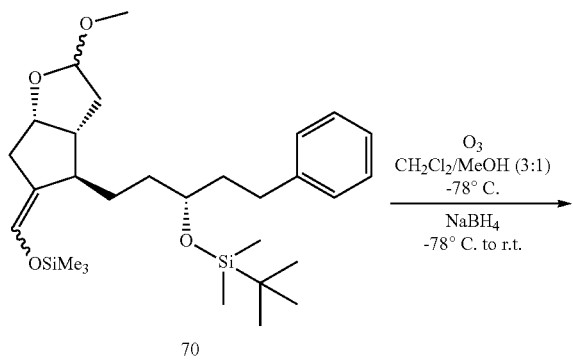

The crude material from the conjugate addition/trapping experiment, containing 70, was dissolved in CH₂Cl₂/MeOH (3:1) (30 ml) and cooled to −78° C. A stream of ozone was passed through the stirred solution. The reaction was monitored periodically by TLC in order to judge completion of the ozonolysis (judged by consumption of silyl enol ether). The reaction mixture was flushed with a stream of N₂, for 15 min, to remove excess O₃. NaBH₄ (202 mg, 5.35 mmol) was added in one portion. The reaction mixture was stirred at −78° C. for 2 h before the cooling bath was removed and the reaction allowed to warm to r.t. The reaction was stirred at r.t. for 1 h. NaBH₄ (67.4 mg, 1.78 mmol) was added and the reaction stirred at r.t. for a further 15 min. The reaction mixture was poured into saturated NaCl solution (25 ml) and extracted with EtOAc (3×25 ml). The combined organic phases were dried (MgSO₄), filtered, and concentrated to give the crude product as a pale yellow oil. This was purified by column chromatography on silica, eluting with petrol/EtOAc (4:1), giving the alcohol 73 (as an approximately 2:1 mixture of diastereoisomers) as a clear, colourless oil (800 mg, 62% (2 steps from enal 24)).

$R_f$=0.23 (petrol:EtOAc, 4:1)

$v_{max}$ (neat)/cm⁻¹ 3434 (broad), 3026, 2928, 2856, 1496, 1471, 1454, 1360, 1343, 1254, 1098, 1053, 1004, 937, 833, 773, 698

¹H NMR (400 MHz; CDCl₃) $\delta_H$=(mixture of 2 diastereoisomers, signals of minor diastereoisomer indicated by *) 0.05 (3H, s, CH₃), 0.06* (3H, 5, CH₃), 0.07 (3H, 5, CH₃), 0.07* (3H, s, CH₃), 0.91 (9H, s, C(CH₃)₃), 0.92* (9H, s, C(CH₃)₃), 1.12-1.80 (7H, m), 1.12-1.80* (7H, m), 1.90-2.38 (5H, m), 1.90-2.38* (5H, m), 2.53-2.75 (2H, m, CH₂), 2.53-2.75* (2H, m, CH₂), 3.32 (3H, s, OCH₃), 3.39* (3H, s, OCH₃), 3.72 (1H, m, CHOTBDMS), 3.72* (1H, m, CHOTBDMS), 3.79* (1H, m, CHOH), 3.89 (1H, m, CHOH), 4.55 (1H, app td, J=6.3, 2.5 Hz, CH), 4.64* (1H, app td, J=6.8, 2.7 Hz, CH), 5.06* (1H, d, J=5.5 Hz, OCHO), 5.11 (1H, d, J=4.9 Hz, OCHO), 7.19 (3H, m, ArCH's), 7.19* (3H, m, ArCH's), 7.29 (2H, ArCH's), 7.29* (2H, m, ArCH's)

¹³C NMR (100 MHz; CDCl₃) $\delta_C$=(observed signals, mixture of 2 diastereoisomers) −4.42 (SiCH₃), −4.41 (SiCH₃), −4.33 (SiCH₃), 18.1 (2×C(CH₃)₃), 25.9 (2×C(CH₃)₃), 29.3 (CH₂), 30.3 (CH₂), 31.7 (CH₂), 35.1 (CH₂), 38.8 (CH₂), 39.9 (CH₂), 40.0 (CH₂), 41.1 (CH₂), 42.7 (CH₂), 46.5, 47.2, 54.4, 55.1, 55.3, 55.7, 71.8, 71.8, 79.3, 79.7, 82.5, 85.8, 106.5 (OCHOCH₃), 108.0 (OCHOCH₃), 125.7 (ArCH), 125.7 (ArCH), 128.3 (4×ArCH), 128.3 (4×ArCH), 142.6 (ArC), 142.6 (ArC). One SiCH₃ and three CH₂'s could not be assigned due to overlapping signals.

6J. (3aR,4R,5R,6aS)-4-[(3R)-3-Hydroxy-5-phenylpentyl]perhydrocyclopenta[b]furan-2,5-diol, 74

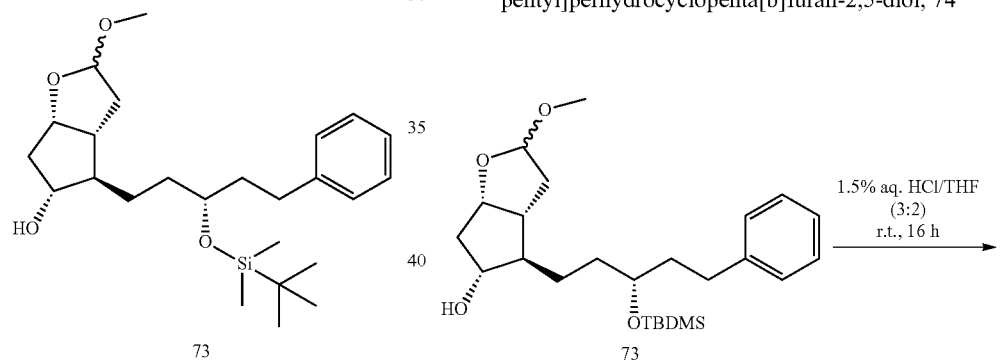

Alcohol 73 (400 mg, 0.920 mmol) was stirred with 1.5% aqueous HCl/THF (3:2) (18 ml) at r.t. for 16 h. The mixture was neutralised with 1 M NaOH and extracted with CH₂Cl₂ (5×30 ml). The combined organic phases were dried (MgSO₄), filtered, and concentrated to give the triol 74 and silanol by-product as a clear, colourless oil (˜400 mg). This material was taken forward for the subsequent transformation without purification.

6K. (Z)-7-(1R,2R,3R,5S)-3,5-Dihydroxy-2-[(3R)-3-hydroxy-5-phenylpentyl]cyclopentyl-5-heptenoic acid, 75

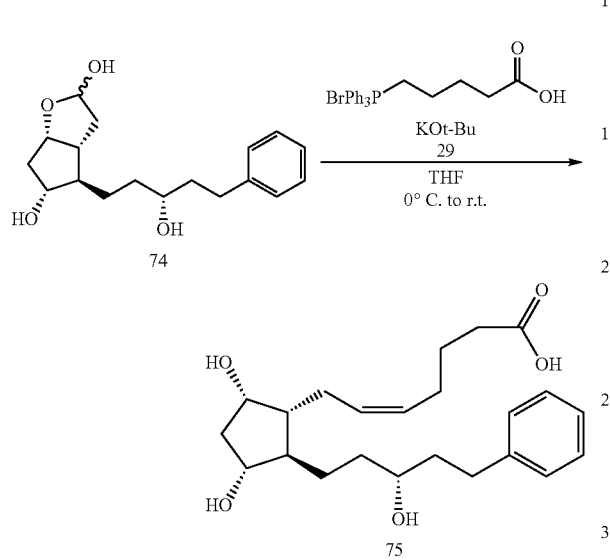

6L. Isopropyl (Z)-7-(1R,2R,3R,5S)-3,5-dihydroxy-2-[(3R)-3-hydroxy-5-phenylpentyl]cyclopentyl-5-heptenoate, latanoprost, 77

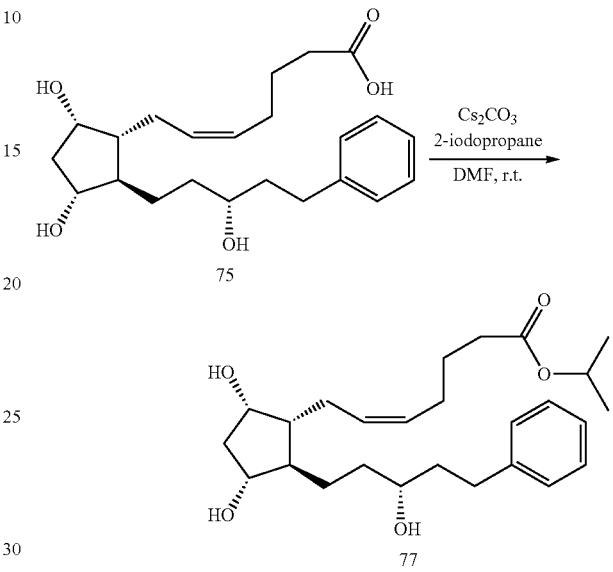

(4-Carboxybutyl)(triphenyl)phosphonium bromide 29 (2.45 g, 5.52 mmol) was added to a flame dried schlenk flask, under $N_2$, and anhydrous THF (20.0 ml) added. The resulting suspension was cooled to 0° C. KOt-Bu (1.24 g, 11.0 mmol) was added in one portion and the resulting orange mixture stirred at 0° C. for 40 min. A solution of crude triol 74 (282 mg, 0.920 mmol) in anhydrous THF (5.0 ml) was added dropwise via syringe. After complete addition the cooling bath was removed and the mixture was stirred at r.t. for 1.5 h. The reaction was quenched with $H_2O$ (30 ml) and washed with $Et_2O$ (2×30 ml) to remove triphenylphosphine oxide. The aqueous phase was made acidic with 1 M HCl (~10 ml) and extracted with $CH_2Cl_2$ (5×25 ml). The combined organic phases were dried ($MgSO_4$), filtered, and concentrated to give the crude material as solids. These were placed on a sinter funnel and washed with petrol/EtOAc (1:1) (4×20 ml) and then EtOAc (2×40 ml). The filtrate was concentrated under vacuum and purified by column chromatography on silica, eluting with $CH_2Cl_2$/MeOH (9.5:0.5 to 9:1) to give acid 75 (163 mg, 45% over 2 steps from alcohol 73) as a clear, colourless oil. The $^1$H data and optical rotation were consistent with the literature (Martynow, J. G. et al., *European Journal of Organic Chemistry* 2007, 2007, 689).

$R_f$=0.27 ($CH_2Cl_2$:MeOH, 9:1)

$v_{max}$ (neat)/cm$^{-1}$ 3338 (broad), 2930, 2857, 1704, 1452, 1407, 1254, 1028, 747, 699, 636

$^1$H NMR (400 MHz; CDCl$_3$) $\delta_H$=1.39 (2H, m, CH$_2$), 1.47-1.97 (10H, m, 4×CH$_2$, 2×CH), 2.07-2.48 (6H, m, 3×CH$_2$), 2.67 (1H, m, CHH), 2.80 (1H, m, CHH), 3.60-4.85 (6H, broad signal, 2×OCH, 3×OH, COOH), 3.72 (1H, m, OCH), 5.40 (1H, m, =CH), 5.49 (1H, m, =CH), 7.15-7.24 (3H, m, ArCH's), 7.25-7.32 (2H, m, ArCH's)

$[\alpha]_D^{24}$ 29.0 (c. 1.0, MeOH) (lit., $[\alpha]_D^{20}$ 29.7 (c. 1.0, MeOH))

A modified procedure of Zanoni and Vidari was used (Zanoni, G. et al., *Tetrahedron* 2010, 66, 7472). Carboxylic acid 75 (100 mg, 0.256 mmol) was dissolved in DMF (2.0 ml) and stirred at r.t. $Cs_2CO_3$ (125 mg, 0.384 mmol) was added in one portion followed by 2-iodopropane (51 μl, 0.512 mmol). The reaction was stirred at r.t. for 18 h. The reaction mixture was poured into 3% citric acid solution (10 ml) and extracted with TBME (4×10 ml). The combined organic phases were washed with 10% NaHCO$_3$ solution (10 ml) and saturated NaCl (2×10 ml) before being dried (MgSO$_4$), filtered, and concentrated to give the crude product as a clear, colourless oil (95 mg). This was purified by column chromatography (3 g silica), eluting with petrol/EtOAc (2:1 to 1:2), to give latanoprost 77 (71 mg, 64%) as a clear colourless oil. The IR, $^1$H, $^{13}$C, and optical rotation data were consistent with the literature (Zanoni, G. et al., *Tetrahedron* 2010, 66, 7472).

$R_f$=0.44 (EtOAc)

$v_{max}$ (neat)/cm$^{-1}$ 3360 (broad), 2980, 2931, 2857, 1712, 1495, 1454, 1374, 1311, 1247, 1180, 1106, 1030, 966, 910, 820, 731, 699

$^1$H NMR (400 MHz; CDCl$_3$) $\delta_H$=1.23 (6H, d, J=6.4 Hz, 2×CH$_3$), 1.30-1.90, (14H, m, 5×CH$_2$, 2×CH, 2×OH), 2.07-2.39 (6H, m, 3×CH$_2$), 2.45 (1H, d, J=5.5 Hz, OH), 2.63-2.86 (2H, m, CH$_2$), 3.68 (1H, br.s, CHOH), 3.95 (1H, br.s, CHOH), 4.18 (1H, br.s, CHOH), 5.01 (1H, sept., J=6.4 Hz, OCH(CH$_3$)$_2$), 5.35-5.52 (2H, m, 2×=CH), 7.16-7.24 (3H, m, ArH's), 7.25-7.32 (2H, m, ArH's)

$^{13}$C NMR (125 MHz; CDCl$_3$) $\delta_C$=21.9 (2×CH$_3$), 24.9 (CH$_2$), 26.6 (CH$_2$), 26.8 (CH$_2$), 29.6 (CH$_2$), 32.1 (CH$_2$), 34.0 (CH$_2$), 35.7 (CH$_2$), 39.0 (CH$_2$), 42.5 (CH$_2$), 51.8 (CH), 52.7 (CH), 67.6 (OCH), 71.2 (OCH), 74.5 (OCH), 78.6 (OCH), 125.7 (CH), 128.3 (2×ArCH), 128.3 (2×ArCH), 129.3 (CH), 129.5 (CH), 141.1 (ArC), 173.5 (C=O)

$[\alpha]_D^{23}$ 33.0 (c. 1.0, MeCN) (lit., $[\alpha]_D^{20}$ 32.7 (c. 1.0, MeCN))

Example 7

Experimental Procedures for the Synthesis of Bimatoprost

A synthesis of bimatoprost is shown and described below.

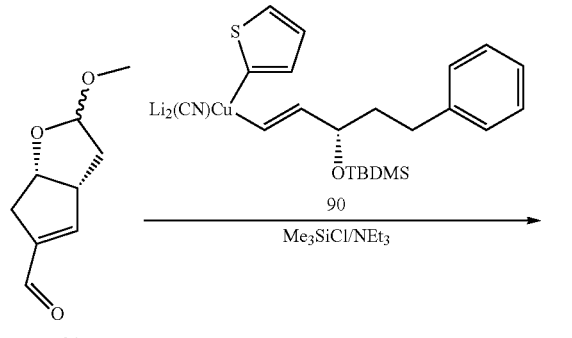

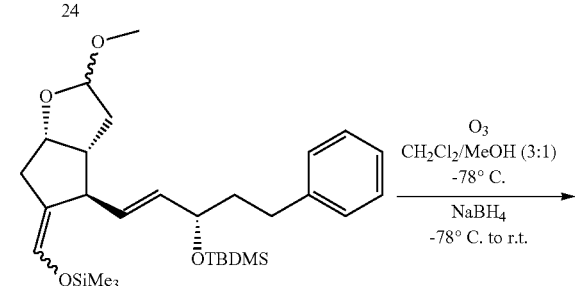

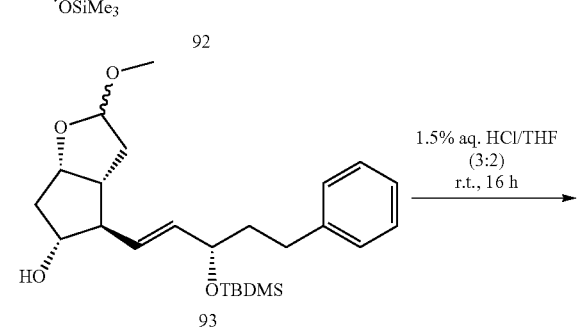

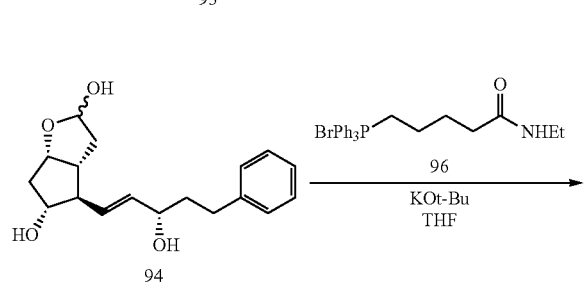

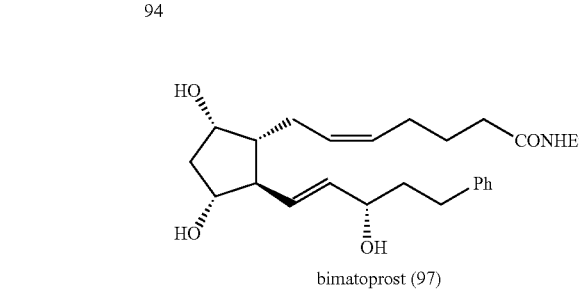

7A. (±)-5-Phenyl-1-(trimethylsilyl)pent-1-yn-3-ol, 81

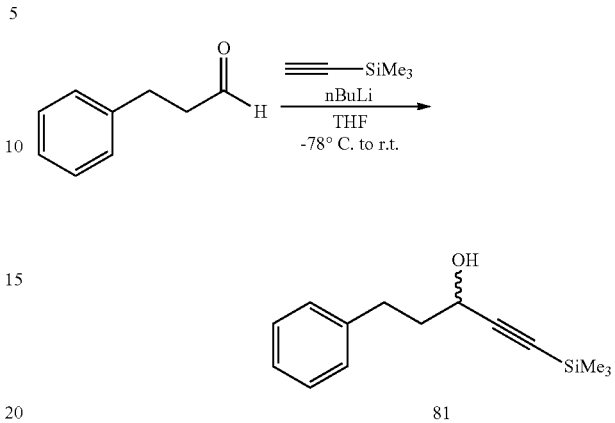

Following a modified procedure of Matsuda (Matsuda, F. Et al., *Chem. Eur. J.* 5, 3252-3259 (1999)); n-butyllithium (1.6 M in hexanes, 8.8 ml, 14.1 mmol, 1.0 eq.) was added dropwise to a solution of ethynyltrimethylsilane (2.0 ml, 14.1 mmol, 1.0 eq.) in THF (6 ml) at −78° C. After addition, the mixture was allowed to warm slowly to 0° C. and stirred for 1 h. The mixture was cooled to −78° C. and a solution of hydrocinnamaldehyde (2.2 ml, 17.0 mmol, 1.2 eq.) in THF (3 ml) was added dropwise. The mixture was then allowed to slowly warm to −10° C. and stirred for 1 h before being quenched by the addition of saturated NH$_4$Cl solution (10 ml) followed by EtOAc (10 ml). The aqueous layer was extracted with EtOAc (3×10 ml), the combined organic phases were washed with brine (15 ml) before being dried (MgSO$_4$), filtered and concentrated to give the crude product. This was purified by column chromatography on silica, eluting with petrol/EtOAc (100:5), giving the title product 81 as a clear, colourless oil (3.1 g, 94%). Analytical data consistent with the literature (Matsuda, F. Et al., *Chem. Eur. J.* 5, 3252-3259 (1999)).

$\nu_{max}$ (film)/cm$^{-1}$ 3326 (broad), 2951, 2172, 1604, 1496, 1454, 1249, 1045, 838

$^1$H NMR (400 MHz; CDCl$_3$) $\delta_H$=0.23 (s, 9H, 3×CH$_3$), 2.07 (m, 3H, CH$_2$, OH), 2.84 (t, J=7.8 Hz, 2H, CH$_2$), 4.40 (t, J=6.6 Hz, 1H, CHOH), 7.25 (m, 3H, ArCH's), 7.33 (app t, J=7.3 Hz, 2H, ArCH's)

$^{13}$C NMR (100 MHz; CDCl$_3$) $\delta_C$=0.0 (3×CH$_3$), 31.6 (CH$_2$), 39.3 (CH$_2$), 62.3 (CH), 90.0 (C), 106.7 (C), 126.1 (ArCH), 128.6 (2×ArCH), 128.7 (2×ArCH), 141.4 (ArC)

m/z (ESI$^+$) 255.1 [MNa]$^+$, 215.1

7B. Methyl 3-phenylpropanoate, 82

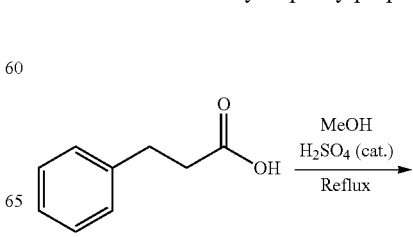

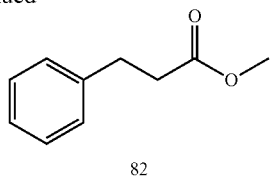

82

Hydrocinnamic acid (10.0 g, 66.6 mmol, 1 eq.) was dissolved in methanol (90 ml), conc. H₂SO₄ (1 ml) added dropwise with stirring and the reaction mixture was stirred under reflux for 5 h. The reaction mixture was cooled to room temperature and concentrated under reduced pressure. The residue was dissolved in water (100 ml) and extracted with EtOAc (3×50 ml). The combined organic phases were washed with 10% NaHCO₃ aq. (2×50 ml), brine (50 ml) before being dried (MgSO₄), filtered and concentrated to give the title compound 82 (10.8 g, 99%) as a clear, colourless oil. Analytical data consistent with the literature (Black, P. J. et al., *Eur. J. Org. Chem.* 4367-4378 (2006)).

$\nu_{max}$ (film)/cm$^{-1}$ 3028, 2952, 1734, 1436, 1194, 1160, 749, 697

¹H NMR (400 MHz; CDCl₃) $\delta_H$=2.68 (t, J=7.8 Hz, 2H, CH₂), 3.00 (t, J=7.8 Hz, 2H, CH₂), 3.71 (s, 3H, CH₃), 7.25 (m, 3H, ArCH's), 7.33 (m, 2H, ArCH's)

¹³C NMR (100 MHz; CDCl₃) $\delta_C$=31.1 (CH₂), 35.8 (CH₂), 51.7 (CH₃), 126.4 (2×ArCH), 128.4 (ArCH), 128.6 (2×ArCH), 140.6 (ArC), 173.5 (C=O)

m/z (CI⁺) 165.1 [MH]⁺ (20%), 133.1 (100%), 105.1 (55%), 93.1 (51%), 85.0 (57%)

7C. N-Methoxy-N-methyl-3-phenylpropanamide, 83

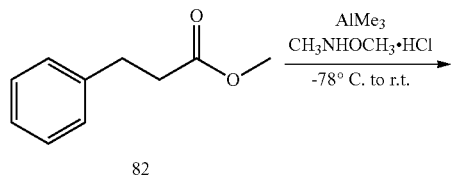

Following a procedure of Trost (Trost, B. M. et al., *J. Am. Chem. Soc.* 128, 6745-6754 (2006)); to a slurry of N,O-dimethylhydroxylamine hydrochloride (4.91 g, 50.4 mmol, 2.1 eq.) in toluene (50 ml) at −10° C. was added AlMe₃ (2 M in hexanes, 25.2 ml, 50.4 mmol, 2.1 eq.) dropwise. After addition, the mixture was allowed to warm to r.t. and stirred for 1 h. The mixture was cooled to −5° C. and a solution of methyl 3-phenylpropanoate 82 (3.94 g, 24.0 mmol, 1 eq.) in toluene (40 ml) was added dropwise. The reaction mixture was then allowed to warm slowly to r.t. and stirred for 3 h. The solution was cooled to 0° C. and quenched carefully by dropwise addition of HCl and the reaction mixture was extracted with EtOAc (4×70 ml). The combined organic phases were washed with brine (50 ml) before being dried (MgSO₄), filtered and concentrated to give the crude product. This was purified by column chromatography on silica, eluting with petrol/EtOAc (80:20 to 75:25), giving the Weinreb amide 83 as a clear, colourless oil (4.45 g, 97%). Analytical data consistent with the literature (Trost, B. M. et al., *J. Am. Chem. Soc.* 128, 6745-6754 (2006); Murphy, J. A. et al., *Org. Lett.* 7, 1427-1429 (2005)).

$\nu_{max}$ (film)/cm$^{-1}$ 3017, 2937, 1659, 1453, 1414, 1383, 1176, 988, 750

¹H NMR (400 MHz; CDCl₃) $\delta_H$=2.74 (t, J=7.8 Hz, 2H, CH₂), 2.97 (t, J=7.8 Hz, 2H, CH₂), 3.18 (s, 3H, CH₃), 3.60 (s, 3H, CH₃O), 7.25 (m, 5H, ArCH's)

¹³C NMR (100 MHz; CDCl₃) $\delta_C$=30.7 (CH₃), 32.2 (CH₂), 33.8 (CH₂), 61.2 (CH₃O), 126.1 (ArCH), 128.4 (4×ArCH), 141.3 (ArC), 173.7 (C=O)

m/z (CI⁺) 194.1 [MH]⁺ (100%), 164.1 (20%), 133.1 (12%)

7D. 5-Phenyl-1-(triisopropylsilyl)pent-1-yn-3-one, 84

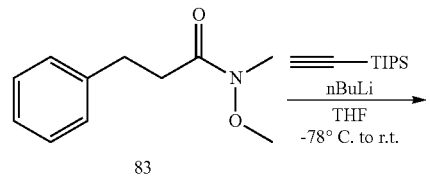

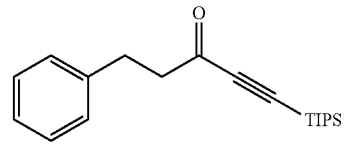

Following a procedure of Trost (Trost, B. M. et al., *J. Am. Chem. Soc.* 128, 6745-6754 (2006)); n-Butyllithium (2.5 M in hexanes, 10.4 ml, 26 mmol, 1.7 eq.) was added dropwise to a solution of triisopropylsilyl acetylene (5.8 ml, 26 mmol, 1.7 eq.) in THF (53 ml) at −78° C. After addition, the mixture was allowed to warm slowly to 0° C. and stirred for 1 h. The mixture was cooled to −78° C. and a solution of 83 (3.0 g, 15.3 mmol, 1 eq.) in THF (20 ml) was added dropwise. The mixture was then allowed to slowly warm to −10° C. and stirred for 1 h before being quenched by the addition of saturated aq. NH₄Cl (50 ml). The mixture was extracted with EtOAc (3×30 ml) and the combined organic phases were washed with brine (50 ml) before being dried (MgSO₄), filtered and concentrated to give the crude product. This was purified by column chromatography on silica, eluting with petrol/Et₂O (100:0 to 98:2), giving the title product 84 as a clear, colourless oil (4.61 g, 96%).

$\nu_{max}$ (film)/cm$^{-1}$ 2944, 2866, 1675, 1462, 1445, 1103, 881, 696

¹H NMR (400 MHz; CDCl₃) $\delta_H$=1.12 (m, 21H, 6×CH₃, 3×CH), 2.92 (m, 2H, CH₂), 3.03 (m, 2H, CH₂), 7.22 (m, 3H, ArCH's), 7.31 (m, 2H, ArCH's)

¹³C NMR (100 MHz; CDCl₃) $\delta_C$=11.1 (3×CH), 18.6 (6×CH₃), 30.2 (CH₂), 47.4 (CH₂), 96.2 (C), 104.2 (C), 126.4 (ArCH), 128.4 (2×ArCH), 128.7 (2×ArCH), 140.4 (ArC), 186.7 (C=O)

m/z (CI⁺) 315.3 [MH]⁺ (100%), 271.2 52%), 157.2 (27%)

HRMS (CI⁺) calcd for C₂₀H₃₁OSi [MH]⁺ 315.2144. found 315.2139.

7E. (S)-5-Phenyl-1-(triisopropylsilyl)pent-1-yn-3-ol, 85

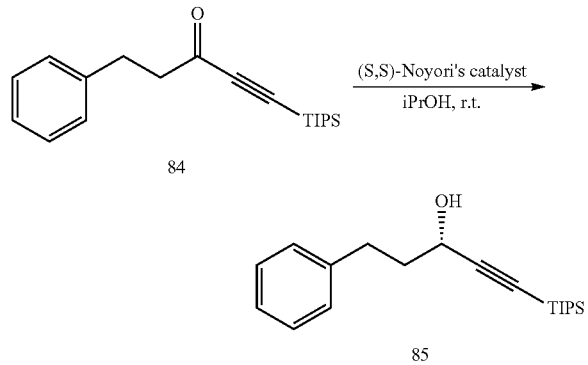

Following a modified procedure of Trost (Trost, B. M. et al., *J. Am. Chem. Soc.* 128, 6745-6754 (2006)); Potassium hydroxide (8.5 mg, 0.15 mmol, 1.2 mol %) and RuCl(p-cymene)[(S,S)-Ts-DPEN] (80.7 mg, 0.127 mmol, 1 mol %) were added to) PrOH (110 ml) and the resultant mixture was stirred for 2 min at r.t. 5-Phenyl-1-(triisopropylsilyl)pent-1-yn-3-one 84 (4.0 g, 12.7 mmol, 1 eq.) was added via syringe and the mixture was stirred at r.t. for 45 min. The mixture was concentrated in vacuo to give the crude product. This was purified by column chromatography on silica, eluting with petrol/Et$_2$O (20:1 to 10:1), giving the title product 85 as a clear, colourless oil (4.0 g, 99%). The enantiomeric excess was determined to be 99% via HPLC analysis of its derivative 87. Analytical data consistent with the literature (Trost, B. M. et al., *J. Am. Chem. Soc.* 128, 6745-6754 (2006)).

$v_{max}$ (film)/cm$^{-1}$ 3322 (broad), 2942, 2864, 1462, 1045, 1011, 996, 882, 697, 675

$^1$H NMR (300 MHz; CDCl$_3$) $\delta_H$=1.07-1.11 (m, 21H, 6×CH$_3$, 3×CH), 1.83 (d, J=5.5 Hz, 1H, OH), 2.03 (m, 2H, CH$_2$), 2.82 (t, J=7.9 Hz, 2H, CH$_2$), 4.40 (dd, J=6.4, 5.5 Hz, 1H, CHOH), 7.17-7.32 (m, 5H, ArCH's)

$^{13}$C NMR (75 MHz; CDCl$_3$) $\delta_C$=11.2 (3×CH), 18.7 (6×CH$_3$), 31.6 (CH$_2$), 39.7 (CH$_2$), 62.4 (CH), 86.1 (C), 108.5 (C), 126.1 (ArCH), 128.6 (4×ArCH), 141.5 (ArC)

m/z (ESI$^+$) 339.2 [MNa]$^+$, 299.2, 225.0

HRMS (ESI$^+$) calcd for C$_{20}$H$_{32}$OSiNa [MNa]$^+$ 339.2114. found 339.2127.

[α]$_D^{22}$ +28.5 (c. 2.0, CHCl$_3$) (lit., +27.17 (c. 2.14, CH$_2$Cl$_2$))

7F. (S)-5-Phenylpent-1-yn-3-ol, 86

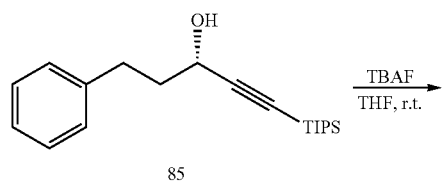

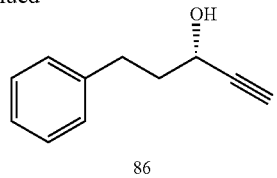

Following a modified procedure of Trost (Trost, B. M. et al., *J. Am. Chem. Soc.* 128, 6745-6754 (2006)); Tetrabutylammonium fluoride (1.0 M in THF, 25 ml, 25 mmol, 2.5 eq.) was added to a solution of (S)-5-phenyl-1-(triisopropylsilyl)pent-1-yn-3-ol 85 (3.165 g, 10 mmol, 1 eq.) in THF (95 ml). The reaction mixture was stirred for 1 h at r.t. and then quenched by addition of saturated aq. NH$_4$Cl (50 ml). The mixture was extracted with Et$_2$O (3×40 ml), the combined organic phases were washed with brine (50 ml) before being dried (MgSO$_4$), filtered and concentrated to give the crude product. This was purified by column chromatography on silica, eluting with petrol/Et$_2$O (10:1 to 9:1), giving the title product 86 as a clear, colourless oil (1.6 g, 99%).

$v_{max}$ (film)/cm$^{-1}$ 3289 (broad), 1603, 1496, 1454, 1300 (broad), 1040, 1010, 744

$^1$H NMR (400 MHz; CDCl$_3$) $\delta_H$=2.10 (m, 3H, CH$_2$, OH), 2.55 (d, J=2.2 Hz, 1H, C≡CH), 2.85 (t, J=7.8 Hz, 2H, CH$_2$), 4.40 (m, 1H, CHOH), 7.25 (m, 3H, ArCH's), 7.33 (m, 2H, ArCH's)

$^{13}$C NMR (100 MHz; CDCl$_3$) $\delta_C$=31.4 (CH$_2$), 39.2 (CH$_2$), 61.7 (CHOH), 73.5 (C≡CH), 84.8 (C≡CH), 126.2 (2×ArCH), 128.6 (3×ArCH), 141.2 (ArC)

m/z (CI$^+$) 161.1 [MH]$^+$ (15%), 155.1 (37%), 143.1 (88%), 119.1 (42%), 91.1 (100%)

HRMS (CI$^+$) calcd for C$_{11}$H$_{13}$O [MH]$^+$ 161.0966. found 161.0972.

[α]$_D^{22}$ +20.0 (c. 2.0, CHCl$_3$)

7G. (S)-5-Phenyl-1-(trimethylsilyl)pent-1-yn-3-ol, 87

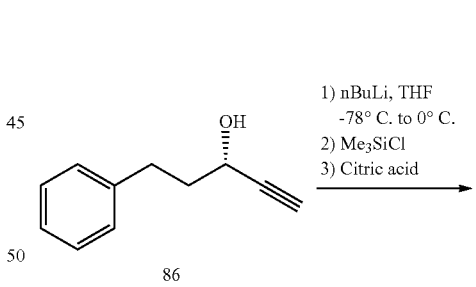

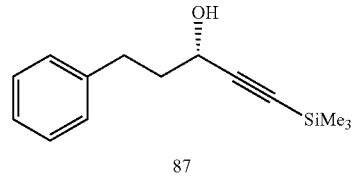

Following a procedure of Trost (Trost, B. M. et al., *J. Am. Chem. Soc.* 128, 6745-6754 (2006)); n-butyllithium (2.5 M in hexanes, 474 μL, 1.18 mmol, 3 eq.) was added dropwise to a solution of (S)-5-phenylpent-1-yn-3-ol 86 (63.3 mg, 0.39 mmol, 1 eq.) in THF (1 ml) at −78° C. The mixture was allowed to warm to 0° C. and stirred 30 min before being cooled to −78° C. TMSCl (148.2 μL, 1.18 mmol, 3 eq.) was added dropwise and the mixture was allowed to warm to r.t.

and stirred for 2 h. Citric acid (65 mg) in methanol (0.7 ml) was added and the mixture stirred for 1 h. The mixture was poured into a mixture of brine (3 ml) and Et$_2$O (5 ml). The aqueous layer was extracted with Et$_2$O (3×10 ml) and the combined organic phases were washed with brine (10 ml) before being dried (MgSO$_4$), filtered and concentrated to give the crude product. This was purified by column chromatography on silica, eluting with petrol/Et$_2$O (9:1), giving the title product 87 as a clear, colourless oil (18.5 mg, 15.5%). Analytical data consistent with the literature (Trost, B. M. et al., *J. Am. Chem. Soc.* 128, 6745-6754 (2006)).

$v_{max}$ (film)/cm$^{-1}$ 3344 (broad), 2956, 2172, 1496, 1454, 1249, 1046, 838

$^1$H NMR (400 MHz; CDCl$_3$) $\delta_H$=0.19 (s, 9H, 3×CH$_3$), 1.80 (d, J=5.6 Hz, 1H, OH), 2.02 (m, 2H, CH$_2$), 2.80 (t, J=7.8 Hz, 2H, CH$_2$), 4.36 (dd, J=6.3, 5.6 Hz, 1H, CHOH), 7.20 (m, 3H, ArCH's), 7.29 (m, 2H, ArCH's)

$^{13}$C NMR (100 MHz; CDCl$_3$) $\delta_C$=-0.1 (3×CH$_3$), 31.4 (CH$_2$), 39.2 (CH$_2$), 62.2 (CHOH), 89.9 (C), 106.4 (C), 125.9 (ArCH), 128.4 (2×ArCH), 128.5 (2×ArCH), 141.3 (ArC)

m/z (ESI$^+$) 255.1 [MNa]$^+$

HRMS (ESI$^+$) calcd for C$_{14}$H$_{20}$OSiNa [MNa]$^+$ 255.1175. found 255.1185.

$[\alpha]_D^{22}$ +28.6 (c. 0.735, CHCl$_3$) (lit., +32.91 (c. 2.37, CH$_2$Cl$_2$))

Chiral-HPLC data: ee=>99% (Chiralcel OD column, 210 nm, hexane/2-propanol: 90/10, flow rate: 0.7 mL/min, room temperature; $t_R$: minor 15.5 min, major 10.7 min)

7H. (S)-tert-Butyldimethyl(5-phenylpent-1-yn-3-yloxy)silane, 88

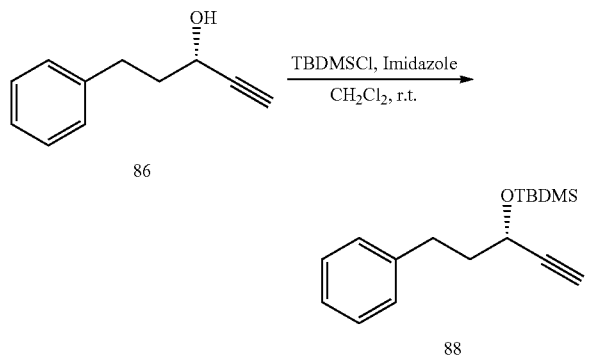

Following a procedure of Noyori (Suzuki, M. et al., *J. Med. Chem.* 41, 3084-3090 (1998)); Imidazole (919.1 mg, 13.5 mmol, 1.8 eq.) and t-butylchlorodimethylsilane (1.35 g, 9.0 mmol) were added to a solution of (S)-5-phenylpent-1-yn-3-ol 86 (1.2 g, 7.5 mmol, 1 eq.) in CH$_2$Cl$_2$ (18 ml), cooled to 0° C. The reaction mixture was then stirred at room temperature for 14 h before being poured into 1 M HCl (50 ml). The mixture was extracted with 40/60 petroleum ether (3×50 ml). The combined organic phases were washed with brine (50 ml) before being dried (MgSO$_4$), filtered and concentrated to give the crude product. This was purified by column chromatography on silica, eluting with petrol/Et$_2$O (99:1), giving the title product 88 as a clear, colourless oil (1.77 g, 86%). Analytical data consistent with the literature (Kiyotsuka, Y. et al., *Org. Lett.* 10, 1719-1722 (2008); Sato, F. et al., EP 1211241 A1, Taisho Pharmaceutical co., LTD (2002)).

$v_{max}$ (film)/cm$^{-1}$ 3309, 2954, 2929, 2886, 2857, 1251, 1091, 834, 776

$^1$H NMR (400 MHz; CDCl$_3$) $\delta_H$=0.15 (s, 3H, CH$_3$), 0.17 (s, 3H, CH$_3$), 0.95 (s, 9H, 3×CH$_3$), 2.04 (m, 2H, CH$_2$), 2.46 (d, J=2.1 Hz, C≡CH), 2.81 (m, 2H, CH$_2$), 4.41 (dt, J=6.3, 2.1 Hz, CHOTBDMS), 7.24 (m, 3H, ArCH's), 7.32 (m, 2H, ArCH's)

$^{13}$C NMR (100 MHz; CDCl$_3$) $\delta_C$=-4.9 (CH$_3$), -4.4 (CH$_3$), 18.3 (C), 25.9 (3×CH$_3$), 31.4 (CH$_2$), 40.3 (CH$_2$), 62.2 (CHOTBDMS), 72.5 (C≡CH), 85.4 (C≡CH), 125.9 (ArCH), 128.5 (2×ArCH), 128.6 (2×ArCH), 141.7 (ArC)

m/z (CI$^+$) 275.2 [MH]$^+$ (12%), 259.1 (37%), 217.1 (50%), 189.1 (38%), 143.1 (100%)

HRMS (CI$^+$) calcd for C$_{17}$H$_{27}$OSi [MH]$^+$ 275.1831. found 275.1825.

$[\alpha]_D^{22}$ -17.0 (c. 2.0, CHCl$_3$)

7I. (S,E)-tert-Butyl(1-iodo-5-phenylpent-1-en-3-yloxy)dimethylsilane, 89

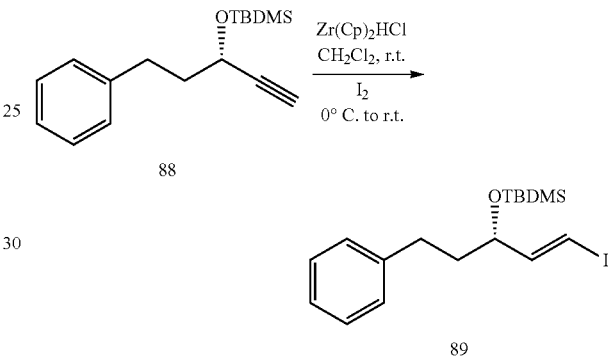

A flame dried Schlenk flask, evacuated and purged with nitrogen, was charged with alkyne 88 (1.50 g, 5.46 mmol, 1 eq.). Anhydrous CH$_2$Cl$_2$ (35 ml) was added and the reaction stirred at r.t. Zr(Cp)$_2$HCl (2.82 g, 10.9 mmol, 2 eq.) was added as a solid, in portions. The yellow suspension was stirred at r.t. for 1 h. The resulting yellow solution was cooled to 0° C. and iodine (1.52 g, 6.01 mmol, 1.1 eq.) added as a solid, in one portion. The cooling bath was removed and the reaction mixture stirred at room temperature for 1 h. The reaction mixture was poured into water (100 ml) and extracted with 40/60 petroleum ether (4×50 ml). The combined organic phases were washed with water (100 ml), saturated Na$_2$S$_2$O$_3$ solution (2×100 ml) and brine (100 ml) before being dried (MgSO$_4$), filtered, and concentrated to give the crude material. This was purified by flash chromatography, eluting with 40/60 petroleum ether. The fractions containing product were combined and washed with saturated Na$_2$S$_2$O$_3$ solution (20 ml), dried (MgSO$_4$), filtered, and concentrated to give the title compound 89 (1.98 g, 90%) as a clear, colourless oil. Analytical data consistent with the literature (Sato, F. et al., EP 1211241 A1, Taisho Pharmaceutical co., LTD (2002)).

$v_{max}$ (film)/cm$^{-1}$ 2952, 2928, 2856, 1604, 1360, 1251, 1086, 942, 833, 774

$^1$H NMR (400 MHz; CDCl$_3$) $\delta_H$=0.04 (s, 3H, CH$_3$), 0.06 (s, 3H, CH$_3$), 0.92 (s, 9H, 3×CH$_3$), 1.82 (m, 2H, CH$_2$), 2.65 (m, 2H, CH$_2$), 4.15 (dq, J=6.0, 1.2 Hz, 1H, CHOTBDMS), 6.25 (dd, J=14.3, 1.2 Hz, 1H, CH=CHI), 6.57 (dd, J=14.3, 6.0 Hz, 1H, CH=CHI), 7.18 (m, 3H, ArCH's), 7.29 (m, 2H, ArCH's)

$^{13}$C NMR (100 MHz; CDCl$_3$) $\delta_C$=-4.9 (CH$_3$), -4.5 (CH$_3$), 18.2 (C), 25.8 (3×CH$_3$), 31.0 (CH$_2$), 39.1 (CH$_2$), 74.6

(CHOTBDMS), 76.1 (CH=CHI), 125.8 (ArCH), 128.3 (2×ArCH), 128.4 (2×ArCH), 141.8 (ArC), 148.8 (CH=CHI)
m/z (ESI⁺) 425.1 [MNa]⁺

HRMS (ESI⁺) calcd for $C_{17}H_{27}IOSiNa$ [MNa]⁺ 425.0768. found 425.0754.

$[\alpha]_D^{22}$ −4.5 (c. 2.0, CHCl₃)

7J. tert-Butyl(S,1E)-1-((3aR,4R,6aS)-2-methoxy-5-((trimethylsilyloxy)methylene)hexahydro-2H-cyclopenta[b]furan-4-yl)-5-phenylpent-1-en-3-yloxy)dimethylsilane, 92

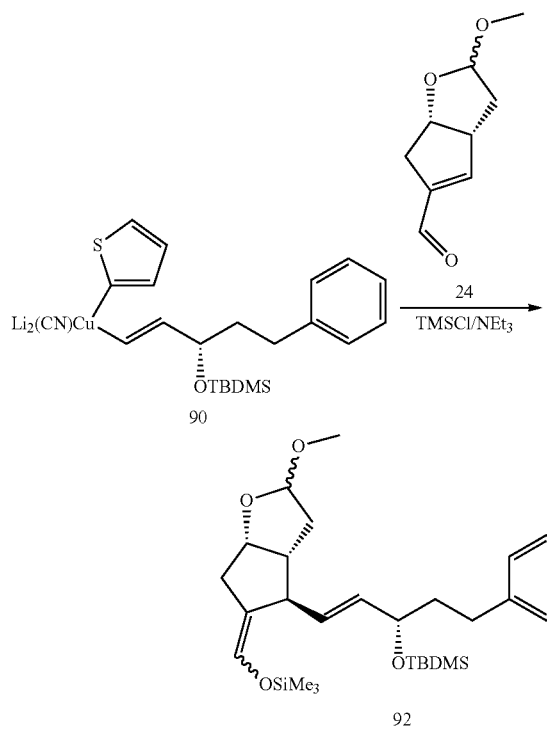

Vinyl iodide 89 (1.45 g, 3.6 mmol, 1.2 eq.) was added via syringe to a flame dried Schlenk flask (evacuated and purged with nitrogen several times and allowed to cool). Anhydrous Et₂O (14.5 ml) was added via syringe and the resulting solution cooled to −78° C. t-BuLi (1.6 M, 4.5 ml, 7.2 mmol, 2.4 eq.) was added dropwise and the reaction mixture stirred at −78° C. for 2 h and −40° C. for 2 h before being cooled back to −78° C. Meanwhile, thiophene (303 mg, 288 µl, 3.6 mmol, 1.2 eq.) was added via syringe to a flame dried Schlenk flask (evacuated and purged with nitrogen several times and allowed to cool). Anhydrous THF (14.5 ml) was added via syringe and the resulting solution cooled to −30° C. n-BuLi (1.6 M, 2.25 ml, 3.6 mmol, 1.2 eq.) was added dropwise and the solution stirred at −30° C. for 30 min. The solution was then cooled to −78° C. and CuCN (322.4 mg, 3.6 mmol, 1.2 eq.) added as a solid, in one portion. The cooling bath was removed and the suspension allowed to warm to r.t. The resulting tan/brown solution of cuprate was added dropwise via syringe to the Schlenk flask containing the vinyl lithium and anhydrous THF (14.5 ml) added. The mixture was stirred at −20° C. for 1 h to allow formation of mixed cuprate 90. This was cooled to −78° C. and a solution of enal 24 (504.6 mg, 3.0 mmol, 1.0 eq.) in anhydrous THF (14.5 ml) was added dropwise. The mixture was stirred at −78° C. for 1 h and then allowed to warm slowly to −20° C. TMSCl (2.2 ml) was added via syringe followed by NEt₃ (2.8 ml). The reaction was quenched by the addition of saturated NH₄Cl solution (80 ml) and extracted with Et₂O (3×80 ml). The combined organic phases were washed with saturated NH₄Cl solution (40 ml) before being dried (MgSO₄), filtered, and concentrated to give the crude material as a yellow oil. This was used directly in the next step.

7K. (3aR,4R5R,6aS)-4-((S,E)-3-(tert-Butyldimethylsilyloxy)-5-phenylpent-1-enyl)-2-methoxyhexahydro-2H-cyclopenta[b]furan-5-ol, 93

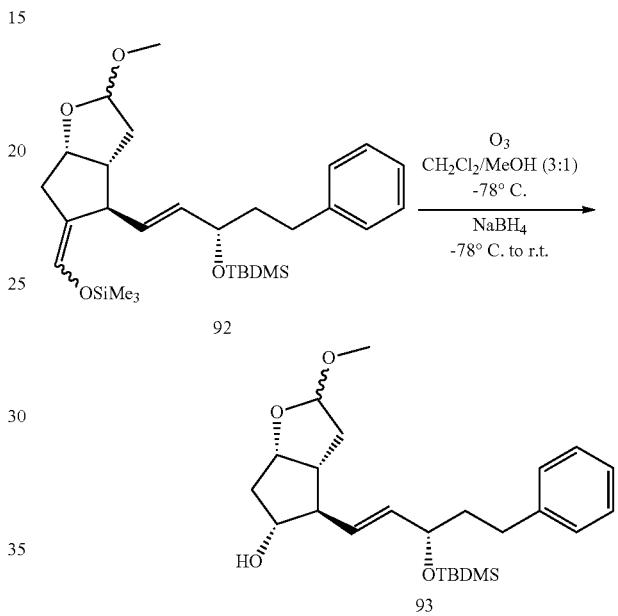

The crude material from the conjugate addition/trapping experiment, containing 92, was dissolved in CH₂Cl₂/MeOH (3:1) (32 ml) and cooled to −78° C. A stream of ozone was passed through the stirred solution. The reaction was monitored periodically by TLC in order to judge completion of the ozonolysis (judged by consumption of silyl enol ether). At this point, the flask was purged with a stream of nitrogen during 10 min and NaBH₄ (204 mg, 5.4 mmol) was added in one portion. The reaction mixture was stirred at −78° C. for 2 h before the cooling bath was removed and the reaction allowed to warm to r.t. The reaction was stirred at r.t. for 1 h. The reaction mixture was poured into saturated NaCl solution (20 ml) and extracted with EtOAc (3×40 ml). The combined organic phases were dried (MgSO₄), filtered, and concentrated to give the crude product as a pale yellow oil. This was purified by column chromatography on silica, eluting with petrol/EtOAc (9:1 to 8:2), giving the alcohol 93 (as a mixture of diastereoisomers) as a clear, colourless oil (731.0 mg, 56.0% (2 steps from enal 24)).

$v_{max}$ (film)/cm⁻¹ 3434 (broad), 2928, 1496, 1471, 1454, 1360, 1250, 1098, 1044, 1003, 970, 834, 774

¹H NMR (400 MHz; CDCl₃)

$\delta_H$=(mixture of 2 diastereoisomers, signals of minor diastereoisomer indicated by *) 0.05 (s, 3H, CH₃), 0.06* (s, 3H, CH₃), 0.07 (s, 3H, CH₃), 0.08* (s, 3H, CH₃), 0.93 (s, 9H, 3×CH₃), 0.94* (s, 9H, 3×CH₃), 1.74-2.52* (m, 8H, 3×CH₂, 2×CH), 1.74-2.52 (m, 7H, 3×CH₂, CH), 2.56-2.76* (m, 2H, CH₂), 2.56-2.76 (m, 3H, CH₂, CH), 3.35 (s, 3H, OCH₃), 3.39* (s, 3H, OCH$_3$), 3.81* (m, 1H, CHOH), 3.94 (m, 1H, CHOH), 4.15* (m, 1H, CHOTBDMS), 4.15 (m, 1H, CHOTBDMS), 4.53 (app td, J=6.6, 3.2 Hz, 1H, CH), 4.63* (app td, J=7.5, 4.6 Hz, 1H, CH), 5.09* (app d, J=5.6 Hz, 1H, CH), 5.14 (app d, J=4.4 Hz, 1H, CH), 5.48* (m, 1H, =CH), 5.48 (m, 1H, =CH), 5.60* (m, 1H, =CH), 5.60 (m, 1H, =CH), 7.20* (m, 3H, ArCH's), 7.20 (m, 3H ArCH's), 7.30* (m, 2H, ArCH's), 7.30 (m, 2H, ArCH's)

$^{13}$C NMR (100 MHz; CDCl$_3$) $\delta_C$=(mixture of 2 diastereoisomers, signals of minor diastereoisomer indicated by *) −4.6 (CH$_3$), 4.6* (CH$_3$), 4.0* (CH$_3$), −3.9 (CH$_3$), 18.4 (C), 18.4* (C), 26.0 (3×CH$_3$), 26.0* (3×CH$_3$), 31.8 (CH$_2$), 31.9 (CH$_2$), 38.0 (CH$_2$), 39.3 (CH$_2$), 39.7 (CH$_2$), 40.2 (CH$_2$), 40.3 (CH$_2$), 42.5 (CH$_2$), 45.8 (CH), 46.1* (CH), 54.6* (CH$_3$O), 55.0 (CH$_3$O), 56.7* (CH), 57.6 (CH), 72.8 (CHOTBDMS), 72.9* (CHOTBDMS), 77.9* (CHOH), 78.9 (CHOH), 81.2 (CH), 83.3* (CH), 106.6 (CH), 107.7* (CH), 125.7 (ArCH), 125.8 (ArCH), 126.0 (ArCH), 128.4 (ArCH), 128.5 (ArCH), 128.6 (ArCH), 130.3* (=CH), 131.1 (=CH), 135.1* (=CH), 135.2 (=CH), 142.2* (ArC), 142.5 (ArC)

m/z (ESI$^+$) 455.1 [MNa]$^+$

HRMS (ESI$^+$) calcd for C$_{25}$H$_{40}$O$_4$SiNa [MNa]$^+$ 455.2588. found 455.2587.

7L. (3aR,4R,5R,6aS)-4-((S,E)-3-Hydroxy-5-phenylpent-1-enyl)hexa hydro-2H-cyclopenta[b]furan-2,5-diol, 94

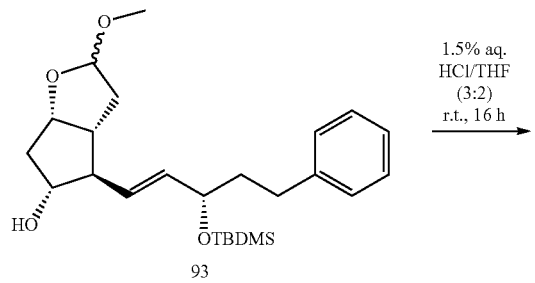

Alcohol 93 (210 mg, 0.485 mmol) was stirred with 1.5% aqueous HCl/THF (3:2) (10 ml) at r.t. for 16 h. The mixture was extracted with CH$_2$Cl$_2$ (5×15 ml) and the combined organic phases were dried (MgSO$_4$), filtered, and concentrated to give the triol 94 and silanol by-product as a clear, colourless oil. This material was taken forward for the subsequent transformation without purification.

7M. 5-Bromo-N-ethylpentanamide, 95

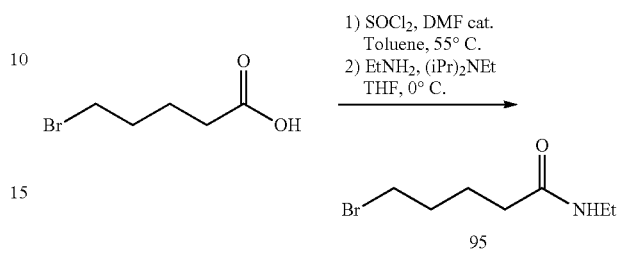

Dimethylformamide (116 μL, 1.5 mmol, 0.1 eq.) and thionyl chloride (1.63 ml, 22.5 mmol, 1.5 eq.) were added to a solution of 5-bromovaleric acid (2.71 g, 15 mmol, 1 eq.) in toluene (20 ml) and the reaction mixture was stirred at 50° C. for 4 h. The volatiles were removed under high vacuum, THF (130 ml) was added and the mixture was cooled to 0° C. N,N-Diisopropylethylamine (4.2 ml, 24 mmol, 1.6 eq.) and ethylamine (2 M solution in THF, 9.0 ml, 18 mmol, 1.2 eq.) were added dropwise. The reaction mixture was stirred for 1 h at 0° C. before being quenched by the addition of saturated aq. NH$_4$Cl (100 ml). The reaction mixture was extracted with Et$_2$O (4×75 ml) and the combined organic phases were washed with brine (100 ml) before being dried (MgSO$_4$), filtered, and concentrated to give the crude material. This was purified by flash chromatography, eluting with petrol/EtOAc (4:6), giving the title product 95 as a clear, colourless oil (2.75 g, 88%). Analytical data consistent with the literature (Halazy, S. et al., WO 9612713, Pierre Fabre Medicament (1996)).

$v_{max}$ (film)/cm$^{-1}$ 3275 (broad), 2970, 2933, 1640, 1543, 1439, 1276, 1150, 643

$^1$H NMR (400 MHz; CDCl$_3$) $\delta_H$=1.13 (t, J=7.2 Hz, 3H, CH$_3$), 1.78 (m, 2H, CH$_2$), 1.89 (m, 2H, CH$_2$), 2.19 (t, J=7.3 Hz, CH$_2$CO), 3.27 (dt, J=7.2, 5.5 Hz, 2H, NHCH$_2$), 3.41 (t, J=6.5 Hz, 2H, BrCH$_2$), 5.79 (broad s, 1H, NH)

$^{13}$C NMR (100 MHz; CDCl$_3$) $\delta_C$=15.0 (CH$_3$), 24.4 (CH$_2$), 32.2 (CH$_2$Br), 33.4 (CH$_2$), 34.4 (NHCH$_2$), 35.7 (CH$_2$C=O), 172.3 (C=O)

m/z (CI$^+$) 210.0 [M$^{81}$BrH]$^+$ (80%), 208.0 [M$^{79}$BrH]$^+$ (80%), 128.1 (100%), 107.1 (60%)

HRMS (CI$^+$) calcd for C$_7$H$_{15}^{81}$BrNO [M$^{81}$BrH]$^+$ 210.0317. found 210.0320. calcd for C$_7$H$_{15}^{79}$BrNO [M$^{79}$BrH]$^+$ 208.0337. found 208.0341.

7N. (5-(Ethylamino)-5-oxopentyl)triphenylphosphonium bromide, 96

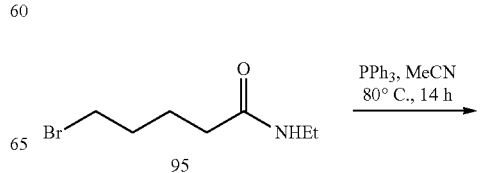

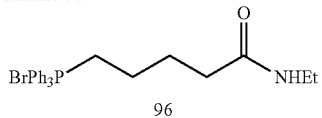

Triphenylphosphine (2.88 g, 11 mmol, 1.1 eq.) was added to a solution of 5-bromo-N-ethylpentanamide 95 (2.08 g, 10 mmol, 1 eq.) in MeCN (5 ml) and the mixture was stirred for 14 h at 80° C. The mixture was allowed to cool to r.t. and concentrated under vacuum. The residue was added dropwise into Et$_2$O (100 ml) and stirred vigorously for 10 min. The resulting solid was filtered, washed with Et$_2$O (2×10 ml) and dissolved in CH$_2$Cl$_2$ (15 ml). This solution was then added dropwise into Et$_2$O (200 ml) and stirred for 10 min. Solids were filtered, washed with Et$_2$O (2×10 ml) and dried under high vacuum to give the title product 96 as a white powder (3.87 g, 82%).

Mp 177-179° C.

$v_{max}$ (film)/cm$^{-1}$ 3275 (broad), 2970, 2933, 1640, 1543, 1439, 1276, 1150, 643

$^1$H NMR (400 MHz; CDCl$_3$) $\delta_H$=1.06 (t, J=7.3 Hz, 3H, CH$_3$), 1.63 (m, 2H, CH$_2$), 1.91 (quin., J=6.5 Hz, CH$_2$), 2.57 (t, J=6.5 Hz, 2H, CH$_2$C=O), 3.15 (q, J=7.3, 5.6 Hz, 2H, NHCH$_2$), 3.66 (m, 2H, CH$_2$P$^+$), 7.66 (m, 6H, ArCH's), 7.75-7.82 (m, 9H, ArCH's), 8.26 (t, 3=5.6 Hz, 1H, NH)

$^{13}$C NMR (100 MHz; CDCl$_3$) $\delta_C$=14.8 (s, CH$_3$), 21.1 (d, J=4.6 Hz, CH$_2$), 22.4 (d, J=49.9 Hz, CH$_2$P$^+$), 26.1 (d, J=17.7 Hz, CH$_2$), 34.1 (s, CH$_2$), 34.2 (s, CH$_2$NH), 118.2 (d, J=86.1 Hz, 3×ArC), 130.6 (d, J=12.3 Hz, 6×ArCH), 133.8 (d, J=10.0 Hz, 6×ArCH), 135.1 (d, J=3.1 Hz, 3×ArCH), 172.7 (C=O)

m/z (ESI$^+$) 390.2 [M-Br]$^+$

HRMS (ESI$^+$) calcd for C$_{25}$H$_{29}$NOP [M-Br]$^+$ 390.1981. found 390.1971.

7O. (Z)-7-((1R,2R,3R,5S)-3,5-Dihydroxy-2-((S,E)-3-hydroxy-5-phenylpent-1-enyl)cyclopentyl)-N-ethylhept-5-enamide, bimatoprost, 97

(5-(Ethylamino)-5-oxopentyl)triphenylphosphonium bromide 96 (1.37 g, 2.91 mmol, 6 eq.) was added to a flame dried Schlenk flask, under N$_2$, and anhydrous THF (10 ml) added. The resulting suspension was cooled to 0° C. KOt-Bu (653.0 mg, 5.82 mmol, 12 eq.) was added in one portion and the resulting orange mixture stirred at 0° C. for 40 min. A solution of crude triol 94 (0.485 mmol, 1 eq.) in anhydrous THF (2.5 ml) was added dropwise via syringe. After complete addition the mixture was stirred at r.t. for 1 h. The reaction was quenched with saturated aq. NH$_4$Cl (10 ml) and extracted with EtOAc (5×10 ml). The combined organic phases were dried (MgSO$_4$), filtered, and concentrated to give the crude material as solids. These were triturated with EtOAc (10 ml) and the solids filtered and washed with EtOAc (4×10 ml). The filtrate was concentrated under vacuum and purified by column chromatography on silica, eluting with EtOAc/MeOH (97.5:2.5 to 95:5) to give 97 (99.2 mg) as a yellowish oil which was further purified by preparative TLC (EtOAc/MeOH 5%) to give 97 (82.6 mg, 41% over 2 steps) as a clear, colourless oil. Analytical data consistent with the literature (Zanoni, G. et al., *Tetrahedron* 66, 7472-7478 (2010); Gutman, A. et al., US 20090163596 (2009)).

$v_{max}$ (film)/cm$^{-1}$ 3300 (broad), 2930, 1643, 1550, 1453, 1332, 1293, 1048, 1029, 968, 729, 698

$^1$H NMR (400 MHz; CDCl$_3$) $\delta_H$=1.09 (t, J=7.1 Hz, 3H, CH$_3$), 1.42-2.40 (m, 14H, 6×CH$_2$, 2×CH), 2.67 (m, 2H, CH$_2$), 3.22 (dq, J=7.1, 6.3 Hz, 2H, CH$_2$NH), 3.41 (broad s, 3H, 3×OH), 3.80-4.30 (broad m, 3H, 3×CHOH), 5.37 (m, 2H, 2×=CH), 5.47 (dd, J=15.2, 7.9 Hz, 1H, =CH), 5.59 (dd, J=15.2, 7.9 Hz, 1H, =CH), 5.90 (broad s, 1H, NH), 7.17 (m, 3H, ArCH's), 7.26 (m, 2H, ArCH's)

$^{13}$C NMR (100 MHz; CDCl$_3$) $\delta_C$=14.8 (CH$_3$), 25.4 (CH$_2$), 25.6 (CH$_2$), 26.7 (CH$_2$), 31.9 (CH$_2$), 34.4 (CH$_2$NH), 35.8 (CH$_2$C=O), 38.8 (CH$_2$), 42.9 (CH$_2$), 50.2 (CH), 55.5 (CH), 72.3 (CHOH), 72.4 (CHOH), 77.7 (CHOH), 125.8 (ArCH), 128.4 (2×ArCH), 128.5 (2×ArCH), 129.1 (=CH), 129.7 (=CH), 133.7 (=CH), 135.1 (=CH), 142.0 (ArC), 173.4 (C=O)

m/z (ESI$^+$) 438.2 [MNa]$^+$

HRMS (ESI$^+$) calcd for C$_{25}$H$_{37}$NO$_4$Na [MNa]$^+$ 438.2614. found 438.2615.

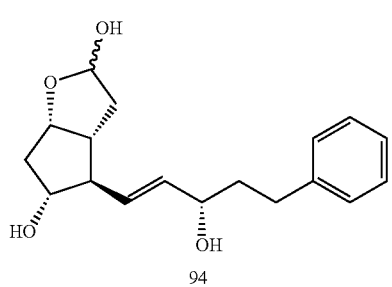

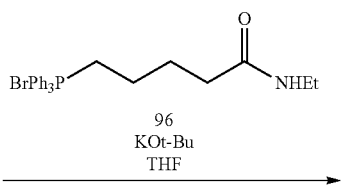

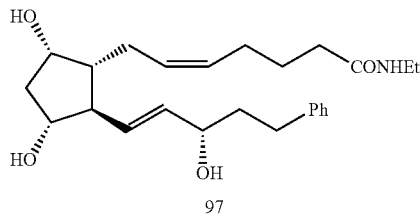

$[\alpha]_D^{22}$ +41.1 (c. 0.35, CH$_2$Cl$_2$) (lit.—Zanoni, G. et al., *Tetrahedron* 66, 7472-7478 (2010), +32.7 (c. 0.33, CH$_2$O$_2$)) (lit.—Gutman, A. et al., US 20090163596 (2009), +36 (c. 1, MeOH))

Example 8

Model Studies

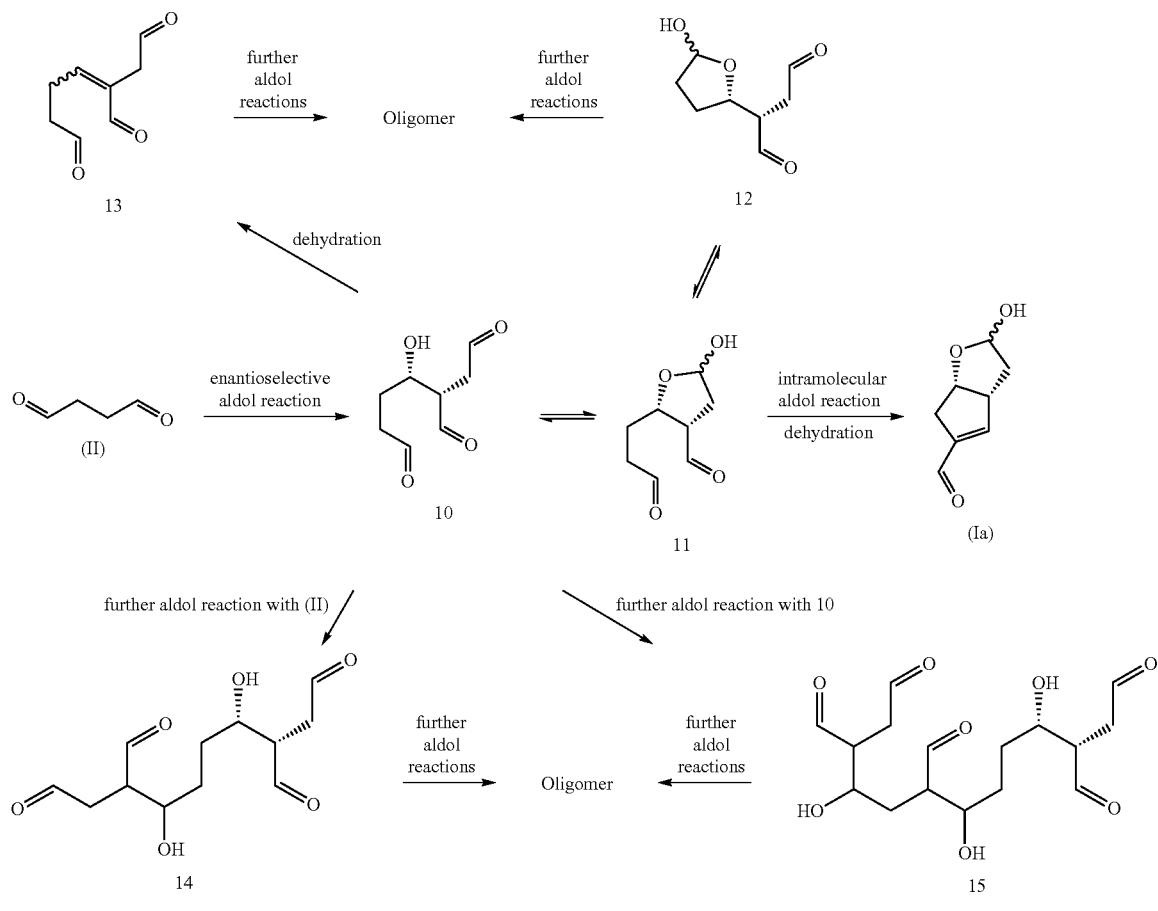

As discussed above, the process of the present invention surprisingly provides lactol (Ia) from succinaldehyde (II) with very high enantioselectivity while largely circumventing the other possible reaction pathways available. Some of these possible pathways are shown in the overview above, with the desired pathway from succinaldehyde (II) to lactol (Ia) shown in the centre.

Model studies were conducted in which the reaction cascade was deconstructed into the initial intermolecular enantioselective aldol reaction and the subsequent intramolecular aldol reaction and dehydration.

To investigate the intermolecular enantioselective aldol reaction of aldehydes bearing an ester at the 4-position, model aldehyde 16 was treated with proline. Aldol product 17 was obtained as a 3.6:1 mixture of diastereoisomers in moderate yield. This confirmed that aldol reactions of aldehydes bearing a carbonyl group in the 4-position were suitable substrates for the proline catalysed aldol reaction.

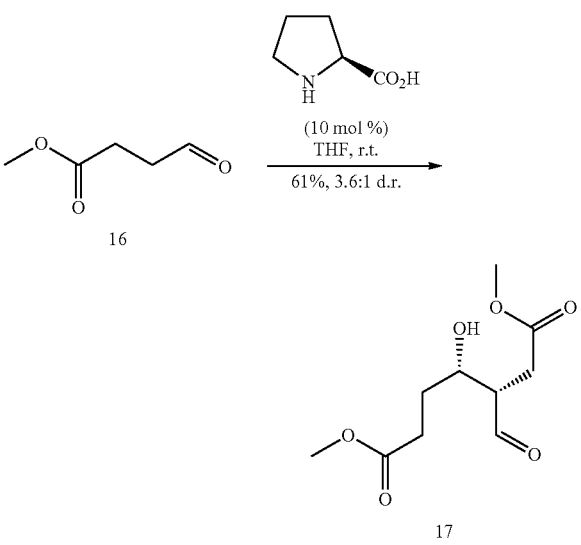

In order to test the subsequent intramolecular aldol reaction and dehydration, model dialdehyde (±)-18 was prepared by ozonolysis of known lactone (±)-19. Treatment of this dialdehyde with proline provided only low conversion to the expected enal (±)-20. [Bn$_2$NH$_2$][OCOCF$_3$] was found to be a much more effective catalyst, giving enal (±)-20 in 51% isolated yield (from (±)-19).

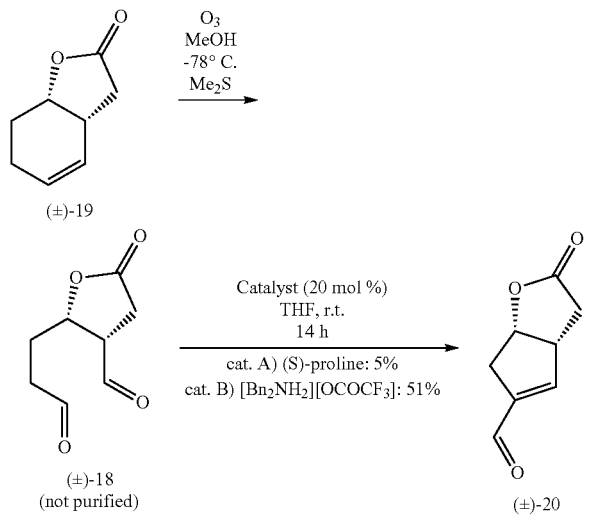

(±)-19

(±)-18
(not purified)

Catalyst (20 mol %)
THF, r.t.
14 h
cat. A) (S)-proline: 5%
cat. B) [Bn$_2$NH$_2$][OCOCF$_3$]: 51%

(±)-20

8A. Experimental Procedures for the Model Studies into the Intermolecular Enantioselective Aldol Reaction

8A(a) Methyl 4-pentenoate, SI-1

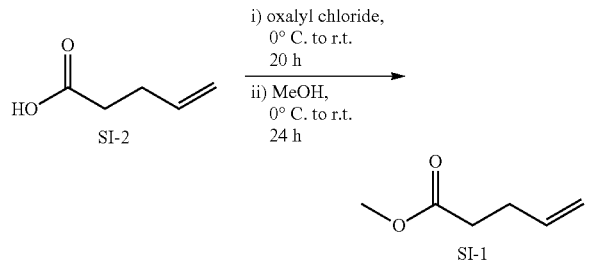

SI-2 i) oxalyl chloride,
0° C. to r.t.
20 h
ii) MeOH,
0° C. to r.t.
24 h

SI-1

A modified procedure of Miller was used (Lotz, B. T. et al., *J. Org. Chem.* 58, 618-625 (1993)). Oxalyl chloride (6.97 g, 4.65 ml, 54.9 mmol) was added dropwise, over 10 min, to 4-pentenoic acid SI-2 (5.00 g, 5.10 ml, 49.9 mmol) cooled to 0° C. The reaction mixture was stirred at 0° C. for 20 min before being allowed to warm to room temperature (vigorous gas evolution was noted). Stirring was continued for 20 h. The reaction mixture was re-cooled to 0° C. and anhydrous MeOH (8.09 ml, 200 mmol) was added dropwise over 10 min. The solution was then stirred at 0° C. for 1.5 h before the ice bath was removed and stirring continued at r.t. for 24 h. The reaction mixture was poured into water (25 ml) and the top layer carefully isolated providing the methyl ester SI-1 (4.70 g, 83%) as pale yellow oil. The IR, $^1$H, and $^{13}$C NMR data were consistent with the literature.

R$_f$=0.39 (heptane/EtOAc, 9:1)

v$_{max}$ (film)/cm$^{-1}$ 3081, 2981, 2954, 1736, 1642, 1437, 1359, 1253, 1193, 1169, 989, 914

$^1$H NMR (400 MHz; CDCl$_3$) δ$_H$=2.30-2.45 (4H, m, 2×CH$_2$), 3.67 (3H, s, CH$_3$), 4.97-5.02 (1H, app dq, J=10.3, 1.2 Hz, =CHH), 5.02-5.09 (1H, app dq, J=17.1, 1.6 Hz, HC=CHH), 5.75-5.90 (1H, m, HC=CH$_2$)

$^{13}$C NMR (100 MHz; CDCl$_3$) δ$_C$=28.8 (CH$_2$), 33.3 (CH$_2$), 51.5 (CH$_3$), 115.4 (=CH$_2$), 136.6 (=CH), 173.4 (C=O)

8A(b) Methyl 4-oxobutanoate, 16

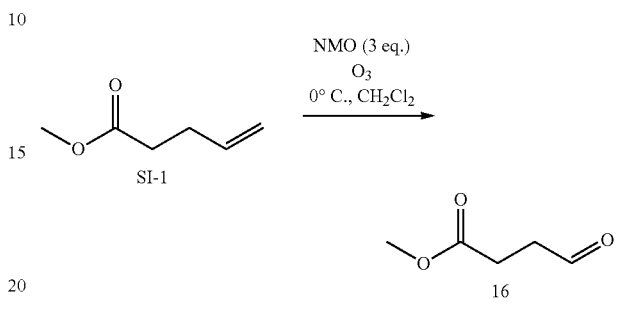

SI-1

NMO (3 eq.)
O$_3$
0° C., CH$_2$Cl$_2$

16

A modified procedure of Dussault was used (Schwartz, C. et al., *Org. Lett.* 8, 3199-3201 (2006)). A stirred solution of methyl pent-4-enoate SI-1 (1.00 g, 8.76 mmol) and N-methylmorpholine-N-oxide (NMO) (3.08 g, 26.3 mmol) in CH$_2$Cl$_2$ (50 ml) was cooled to 0° C. A stream of ozone was passed through the reaction mixture for 50 min. The reaction mixture was washed successively with 1 M HCl (30 ml), water (30 ml), saturated Na$_2$CO$_3$ solution (30 ml), and brine (30 ml) before being dried (MgSO$_4$), filtered, and concentrated to give the aldehyde 16 (854 mg, 83%) as a clear, colourless oil. The $^1$H and $^{13}$C spectra matched data reported by Ley (Sedelmeier, J. et al., *Org. Lett.* 12, 3618-3621 (2010)) and IR data was consistent with that reported by both Miller (Lotz, B. T. et al., *J. Org. Chem.* 58, 618-625 (1993)) and Gannett (Gannett, P. M. et al., *J. Org. Chem.* 53, 1064-1071 (1988)).

R$_f$=0.29 (heptane/EtOAc, 1:1)

v$_{max}$ (film)/cm$^{-1}$ 2956, 2845, 2735, 1732 (br.), 1438, 1367, 1205, 1172

$^1$H NMR (400 MHz; CDCl$_3$) δ$_H$=2.61 (2H, t, J=6.6 Hz, CH$_2$), 2.79 (2H, t, J=6.6 Hz, CH$_2$), 3.67 (3H, s, CH$_3$), 9.79 (1H, t, J=0.6 Hz, CH)

$^{13}$C NMR (100 MHz; CDCl$_3$) δ$_C$=26.2 (CH$_2$), 38.4 (CH$_2$), 51.8 (CH$_3$), 172.6 (C=O), 199.9 (C=O)

8A(c) Dimethyl 3-formyl-4-hydroxyheptanedioate, 17+SI-3 (model study into the intermolecular enantioselective aldol reaction)

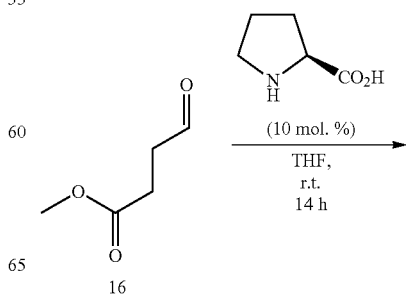

16

(10 mol. %)
THF,
r.t.
14 h

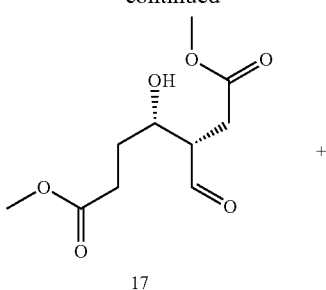

17

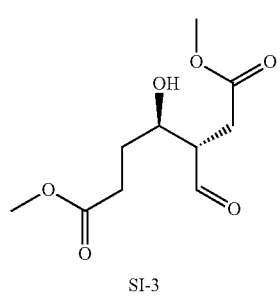

SI-3

(S)-Proline (14.9 mg, 0.13 mmol) was added to a stirred solution of 16 (150 mg, 1.29 mmol) in THF (650 μl). The reaction mixture was stirred at r.t. for 14 h. The reaction mixture was purified directly by column chromatography, eluting with petrol/EtOAc (2:1), to give the aldehydes 17 and SI-3 (as a 3.6:1 mixture of anti:syn diastereoisomers, 91 mg, 61%) as a clear colourless oil. The reaction was also conducted on a 244 mg scale of aldehyde 16 in DMF which gave a 2:1 ratio of anti:syn diastereoisomers (100 mg, 41%).

$R_f$=0.28 (petrol/EtOAc, 1:1)

$v_{max}$ (film)/cm$^{-1}$ 3616, 3443, 2955, 1731 (br.)

$^1$H NMR (400 MHz; CDCl$_3$) $\delta_H$=(mixture of diastereoisomers, signals of minor diastereoisomer indicated by *) 1.82* (2H, m, CH$_2$), 1.90 (2H, m, CH$_2$), 2.54 (2H, app t, J=7.0 Hz, CH$_2$), 2.54* (2H, app t, J=7.0 Hz, CH$_2$), 2.63 (1H, m, CHH), 2.63* (1H, m, CHH), 2.82 (1H, m, CHH), 2.82* (1H, m, CHH), 2.96 (1H, m, CH), 2.96* (1H, m, CH), 3.06* (1H, br. s, OH), 3.23 (1H, br. s, OH), 3.68 (3H, s, CH$_3$), 3.68* (3H, s, CH$_3$), 3.69 (3H, s, CH$_3$), 3.70* (3H, s, CH$_3$), 3.99 (1H, m, CHOH), 4.19* (1H, m, CHOH), 9.79* (1H, br.s, HC=O), 9.85 (1H, d, J=0.9 Hz HC=O)

$^{13}$C NMR (100 MHz; CDCl$_3$) $\delta_C$=(observed signals, mixture of 2 diastereoisomers) 28.4 (CH$_2$), 29.7 (CH$_2$), 29.8 (CH$_2$), 30.6 (CH$_2$), 30.6 (CH$_2$), 30.7 (CH$_2$), 51.8 (CH$_3$), 51.8 (CH), 52.1 (CH$_3$), 52.1 (CH), 53.2 (CH$_3$), 53.5 (CH$_3$), 69.1 (CH), 70.1 (CH), 172.6 (C=O), 173.1 (C=O), 174.2 (C=O), 202.1 (C=O), 202.5 (C=O). One C=O signal is not observed.

HRMS (ESI) calcd for C$_{10}$H$_{16}$O$_6$Na [MNa$^+$] 255.0845. found 255.0839.

8B. Experimental Procedures for the Model Studies into the Intramolecular Aldol Reaction and Dehydration 8B(a) (±)-8,8-Dichlorobicyclo[4.2.0]oct-2-en-7-one, (±)-SI-4

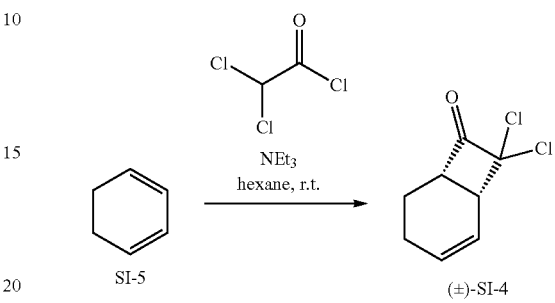

A modified procedure of Corey was used (Corey, E. J. et al., *Tetrahedr. Lett.* 12, 4753-4755 (1971)). Dichloroacetylchloride (19.3 g, 12.6 ml, 131 mmol) in hexane (100 ml) and triethylamine (12.6 g, 17.4 ml, 125 mmol) in hexane (100 ml) were added simultaneously, from separate dropping funnels, to a stirred solution of 1,3-cyclohexadiene SI-5 (5.00 g, 5.95 ml, 62.4 mmol) in hexane (50 ml) over 4 h. After complete addition, the reaction mixture was allowed to stir at r.t. for 2 h. The resultant solids were removed by filtration and washed with hexane. The organic phase (the filtrate) was washed with a Na$_2$CO$_3$ solution (200 ml of a 1:1 sat. Na$_2$CO$_3$:water mixture), 0.5 M HCl (200 ml), and brine (200 ml) before being dried (MgSO$_4$), filtered, and the solvent removed under vacuum to give crude material. This was distilled under vacuum (0.3 mbar, 75° C.) to give the title compound (±)-SI-4 (8.46 g, 71%) as a pale yellow liquid. The IR, $^1$H and $^{13}$C NMR data were consistent with that reported in the literature (Robertson, J. et al., *Org. Biomol. Chem.* 4, 4307-4318 (2006)).

$R_f$=0.19 (petrol)

$v_{max}$ (film)/cm$^{-1}$ 3035, 2930, 2848, 1798, 1649, 1435, 1284, 905, 807, 740

$^1$H NMR (400 MHz; CDCl$_3$) $\delta_H$=1.65 (1H, m, CHH), 2.02 (2H, m, CH$_2$), 2.14 (1H, m, CHH), 3.46 (1H, ddd, J=9.8, 3.7, 2.2 Hz, CH), 4.13 (1H, ddd, J=9.8, 6.0, 3.4 Hz, CH), 5.89 (1H, m, =CH), 6.10 (1H, m, =CH)

$^{13}$C NMR (100 MHz; CDCl$_3$) $\delta_C$=18.7 (CH$_2$), 20.8 (CH$_2$), 44.2 (CH), 53.3 (CH), 86.6 (CO$_2$), 123.0 (=CH), 132.4 (=CH), 196.7 (C=O)

8B(b) (±)-Bicyclo[4.2.0]oct-2-en-7-one, (±)-SI-6

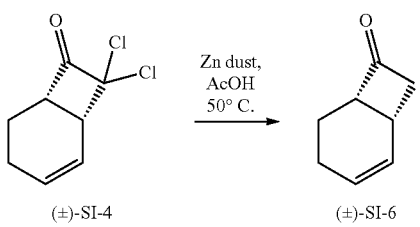 [SMILES: O=C1[C@H]2CCC=C[C@H]2C1(Cl)Cl ; O=C1C[C@@H]2C=CCC[C@H]12]

Following a modified procedure of Corey (Corey, E. J. et al., *Tetrahedr. Lett.* 12, 4753-4755 (1971)), zinc dust (2.74 g, 41.9 mmol) was added in portions over 30 min to a stirred solution of (±)-SI-4 (2.00 g, 10.5 mmol) in acetic acid (15 ml), keeping the temperature below 60° C. After complete addition the reaction mixture was stirred at 50° C. for 2 h. After being allowed to cool the reaction mixture was filtered through celite and the filter cake washed with acetic acid. The filtrate was diluted with water and extracted with CH₂Cl₂ (3×30 ml). The combined organic phases were washed with a Na₂CO₃ solution (60 ml of a 1:1 sat. Na₂CO₃:water mixture), and water (100 ml) before being dried (MgSO₄), filtered, and the solvent removed under vacuum to give the title compound (±)-SI-6 (933 mg, 73%) as a pale yellow oil. $^1$H NMR of this material showed it to be of sufficient purity for subsequent reactions. A small quantity was subjected to flash chromatography, eluting with 9:1 petrol:EtOAc, to provide an analytical sample for which the IR, $^1$H and $^{13}$C NMR data were consistent with that reported in the literature (Corey, E. J. et al., *Tetrahedr. Lett.* 12, 4753-4755 (1971); Kertesz, D. J. et al., *J. Org. Chem.* 53, 4962-4968 (1988); Powers, D. C. et al., *J. Org. Chem.* 72, 187-194. (2006)).

$R_f$=0.87 (petrol/EtOAc 1:1)

$\nu_{max}$ (film)/cm$^{-1}$ 3022, 2923, 2848, 1774, 1645, 1066

$^1$H NMR (400 MHz; CDCl₃) $\delta_H$=1.54 (1H, m, CHH), 1.98 (3H, m, CHH+CH₂), 2.57 (1H, ddd, J=17.0, 3.8, 2.5 Hz, CHH), 2.90 (1H, m, CH), 3.26 (1H, ddd, J=17.0, 9.4, 2.8 Hz, CHH), 3.55 (1H, m, CH), 5.85 (1H, m, =CH), 5.93 (1H, m, =CH)

$^{13}$C NMR (100 MHz; CDCl₃) $\delta_C$=19.4 (CH₂), 21.2 (CH₂), 22.9 (CH), 52.0 (CH₂), 57.3 (CH), 128.4 (=CH), 128.8 (=CH), 211.9 (C=O)

8B(c) (±)-3,3a,7,7a-Tetrahydrobenzofuran-2(6H)-one, (±)-19

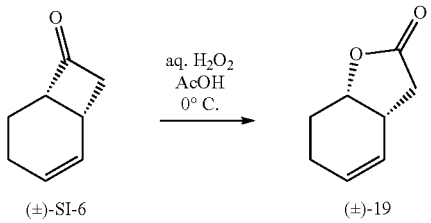 [SMILES: O=C1C[C@@H]2C=CCC[C@H]12 ; O=C1C[C@@H]2C=CCC[C@@H]2O1]

Following a modified procedure of Roberts (Cotterill, I. C. et al., *J. Chem. Soc., Perkin Trans.* 1, 3387-3389 (1988)), an ice cold 1:1 mixture of H₂O₂ (30% in water) and acetic acid (21.6 ml total) was added dropwise to a stirred solution of (±)-SI-6 (1.37 g, 11.2 mmol) in acetic acid (21.6 ml) cooled to 0° C. After complete addition the reaction mixture was stirred at 0° C. for 2 h until the reaction was complete, as judged by TLC. CH₂Cl₂ (45 ml) and water (45 ml) were added to the reaction mixture. The organics were isolated and washed with water (3×45 ml). The combined aqueous phases were extracted with CH₂Cl₂ (45 ml). The combined organic phases were dried (MgSO₄), filtered, and concentrated to give the title compound (±)-19 (1.41 g, 91%) as a pale orange oil. $^1$H NMR of this material showed it to be of sufficient purity for subsequent reactions. A small quantity was subjected to flash chromatography, eluting with 1:1 petrol:EtOAc, to provide an analytical sample for which the $^1$H and $^{13}$C NMR data was consistent with that reported in the literature (Selander, N. et al., *Adv. Syn. Cat.* 350, 2045-2051 (2008); Bhandal, H. et al., *J. Chem. Soc., Perkin Trans.* 1, 2691-2701 (1990)).

$R_f$=0.55 (petrol:EtOAc, 1:1)

$^1$H NMR (400 MHz; CDCl₃) $\delta_H$=1.77 (1H, m), 2.00 (1H, m), 2.15 (2H, m), 2.29 (1H, dd, J=17.2, 3.3 Hz, CHH), 2.76 (1H, dd, J=17.2, 8.6 Hz, CHH), 3.00 (1H, m, CH), 4.76 (1H, app td, J=5.6, 2.8 Hz, CH), 5.47 (1H, m, =CH), 5.87 (1H, m, =CH)

$^{13}$C NMR (100 MHz; CDCl₃) $\delta_C$=19.1 (CH₂), 24.5 (CH₂), 34.4 (CH), 35.8 (CH₂), 78.0 (CH), 125.6 (=CH), 128.7 (=CH), 176.8 (C=O)

8B(d) 2-Oxo-3,3a,6,6a-tetrahydro-2H-cyclopenta[b]furan-5-carbaldehyde, (±)-20 (model study into intramolecular aldol reaction and dehydration)

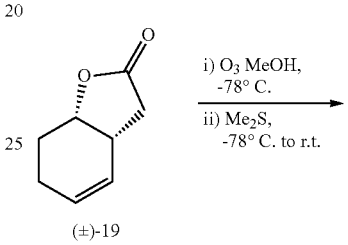

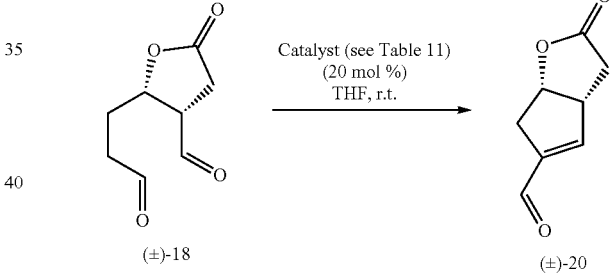

A solution of (±)-19 (100 mg, 0.724 mmol) in MeOH (5 ml) was cooled to −78° C. and a stream of ozone passed through until a blue colour persisted. N₂ was then passed through the solution until the blue colour faded and excess ozone was removed. Me₂S (450 mg, 532 µl, 7.24 mmol) was added and stirring continued at −78° C. for 10 min before the cooling bath was removed and the reaction mixture stirred at r.t. overnight. The reaction mixture was then concentrated under reduced pressure to give crude dialdehyde (±)-18 (NOTE: A blast shield was put in place around the rotary evaporator during this operation). The residue was dissolved in THF (0.8 ml), the appropriate catalyst (0.145 mmol, 0.2 eq.) added, and the reaction stirred at room temperature for 14 h. 1,4-dimethoxybenzene (10.0 mg, 0.072 mmol) was added and the reaction stirred for 15 min. An aliquot of the reaction mixture was removed, concentrated with an N₂ stream, and analysed by $^1$H NMR (DMSO-d6). The amount of 5,5-bicyclic lactone (±)-20 present was calculated by comparison of the signals arising from the vinyl proton of (±)-20 with the signals of the internal standard, 1,4-dimethoxybenzene (see FIG. 11).

TABLE 11

Model study catalyst screen

| Entry | Catalyst | ¹H NMR Yield (%) |
|---|---|---|
| 1 | (S)-Proline | 5 |
| 2 | [Bn₂NH₂][OCOCF₃] | 46 |
| 3 | PPTS | 0 |
| 4 | Trifluoroacetic acid | 0 |

The results show that (S)-proline is a poor catalyst, even at a 20 mol % loading, for this intramolecular aldol reaction/dehydration. In contrast, [Bn$_2$NH$_2$][OCOCF$_3$] was far superior.

8B(e) 2-oxo-3,3a,6,6a-Tetrahydro-2H-cyclopenta[b]furan-5-carbaldehyde, (±)-20 (preparative scale)

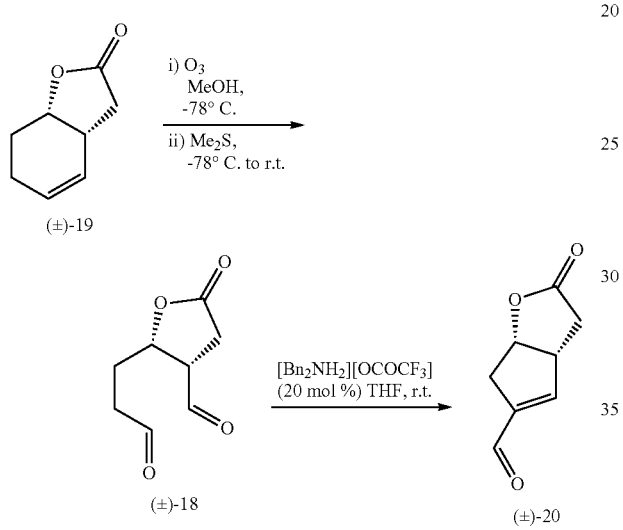

A solution of (±)-19 (250 mg, 1.81 mmol) in MeOH (2 ml) was cooled to −78° C. and a stream of ozone passed through until a blue colour persisted. N$_2$ was then passed through the solution until the blue colour faded and excess ozone was removed. Me$_2$S (1.12 g, 1.33 ml, 18.1 mmol) was added and stirring continued at −78° C. for 10 min before the cooling bath was removed and the reaction mixture stirred for 50 min. An N$_2$ stream was then used to concentrate the reaction mixture. The residue was dissolved in THF (2 ml) and dibenzylammonium trifluoroacetate (113 mg, 0.36 mmol) added and the resulting solution stirred at room temperature for 22 h. An N$_2$ stream was then used to concentrate the reaction mixture and the residue purified by column chromatography, eluting with 2:1 EtOAc:petrol, to afford the aldehyde (±)-20 (141 mg, 51%) as an orange oil. ¹H NMR of this material showed it to be of sufficient purity for further reaction. A sample was re-columned to provide an analytical sample as a white solid.

Mp 78-80° C.
R$_f$=0.44 (EtOAc)
ν$_{max}$ (film)/cm$^{-1}$ 2935, 2832, 1766, 1676, 1170, 1157
¹H NMR (400 MHz; CDCl$_3$) δ$_H$=2.58 (1H, dd, J=18.3, 2.0 Hz, O=CCHH), 2.85-2.90 (1H, m, HHCC=CH), 2.91 (1H, dd, J=18.3, 10.3 Hz, O=CCHH), 2.98 (1H, d, J=18.3, HHCC=CH), 3.80 (1H, m, C=CHCH), 5.23 (1H, app t, J=5.8, CHOC=O), 6.63 (1H, d, J=1.7 Hz, C=CH), 9.83 (1H, s, HC=O)

¹³C NMR (100 MHz; CDCl$_3$) δ$_C$=32.1 (CH$_2$), 36.0 (CH$_2$), 46.4 (CH), 82.3 (CH), 145.2 (C), 148.4 (=CH), 175.1 (OC=O), 188.9 (HC=O)
m/z (CI) 153 (MH$^+$, 100%), 107 (25%)
HRMS (CI) calcd for C$_8$H$_9$O$_3$ [MH$^+$] 153.0552. found 153.0555.

The invention claimed is:

1. A compound of formula (I):

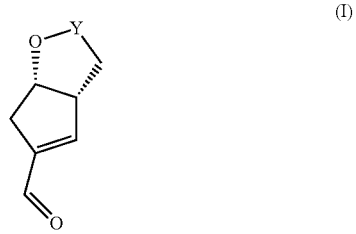

wherein
Y is

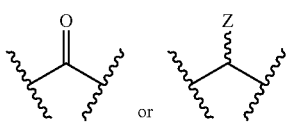

Z is OR$^{10}$, NR$^{11}$R$^{11}$, SR$^{11}$, S(O)R$^{11}$, SO$_2$R$^{11}$,
R$^{10}$ is H, optionally substituted alkyl, optionally substituted cycloalkyl, optionally substituted alkenyl, optionally substituted alkynyl, optionally substituted aryl, optionally substituted heteroaryl, optionally substituted heterocyclyl, CO—R$^{11}$, or a protecting group, and
R$^{11}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl.

2. A compound according to claim 1, wherein Y is

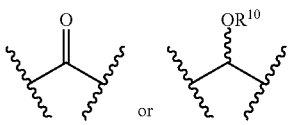

3. A compound according to claim 2, wherein Y is

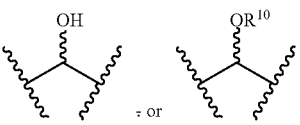

and R$^{10}$ is optionally substituted alkyl.

4. A process for making a compound of formula (Ia), which comprises a key step of:
treating succinaldehyde (II) with (i) a chiral secondary amine catalyst and (ii) an acidic co-catalyst, in a solvent system, to form lactol (Ia), in accordance with the following reaction scheme:

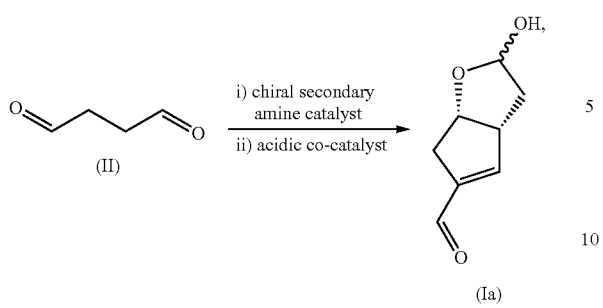

wherein the acidic co-catalyst is added to the reaction mixture after or simultaneously with the chiral secondary amine catalyst;

the chiral secondary amine catalyst has the following structure:

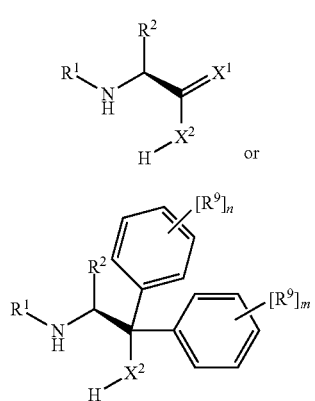

wherein
- $R^1$ and $R^2$ are optionally substituted alkyl groups, or $R^1$ and $R^2$ are linked to form part of an optionally substituted 4-, 5- or 6-membered heterocycle;
- $X^1$ is O, S or $NR^3$, wherein $R^3$ is an alkyl group, or $R^3$ is linked with $R^4$ to form part of a 5- or 6-membered ring which may contain one or more further N atoms;
- $X^2$ is O or $NR^4$, wherein $R^4$ is haloalkyl, aryl substituted with one or more halogens or haloalkyl groups, $SO_2R^5$, or $R^4$ is linked with $R^3$ to form part of a 5- or 6-membered ring which may contain one or more further N atoms, and $R^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;
- n is an integer from 1 to 5;
- m is an integer from 1 to 5; and
- each $R^9$ is independently selected from an electron-withdrawing group and an optionally substituted alkyl, and at least one $R^9$ on each phenyl ring is an electron-withdrawing group;

and the acidic co-catalyst is selected from $[Bn_2NH_2][OCOCF_3]$, $[Bn_2NH_2][BF_4]$, $[Bn_2NH_2][OCOCHCl_2]$, $[Bn_2NH_2][O-C_6H_3-2,4-(NO_2)_2]$, $[Bn_2NH_2][Cl]$, 2,6-piperidinedione, morpholinium trifluoroacetate, thio-morpholinium trifluoroacetate, pyridinium trifluoroacetate, benzylammonium trifluoroacetate, quinine trifluoroacetate, 2,2'-bipyridinium monotrifluoroacetate, 2,2':6',2''-terpyridinium monotrifluoroacetate, pyridinium p-toluenesulfonate (PPTS), trifluoroacetic acid (TFA), trifluoromethanesulfonic acid, camphorsulfonic acid (CSA), tartaric acid, 2,4-dinitrophenol, tetrafluoroboric acid, $ZnCl_2$, $Zn(OTf)_2$, $Sc(OTf)_3$, Amberlite 120, Montmorillonite K10, 1,3-bis(3,5-bis(trifluoromethyl)phenyl)thiourea, magnesium sulfate, and combinations thereof.

5. The process according to claim 4, wherein the acidic co-catalyst is added to the reaction mixture after the chiral secondary amine catalyst has been added.

6. The process according to claim 4, wherein the chiral secondary amine catalyst has the following structure:

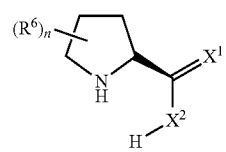

wherein
- $X^1$ is O or $NR^3$, wherein $R^3$ is an alkyl group, or $R^3$ is linked with $R^4$ to form part of a 5- or 6-membered ring which may contain one or more further N atoms;
- $X^2$ is O or $NR^4$, wherein $R^4$ is $SO_2R^5$, or $R^4$ is linked with $R^3$ to form part of a 5- or 6-membered ring which may contain one or more further N atoms, and $R^5$ is an alkyl group or an aryl group;
- n is an integer from 0 to 7;
- each $R^6$ is independently selected from —$OR^7$, optionally substituted alkyl, optionally substituted cycloalkyl, optionally substituted alkenyl, optionally substituted alkynyl, optionally substituted aryl, optionally substituted heteroaryl, optionally substituted heterocyclyl, or —CO—$R^8$,
- $R^7$ is H, optionally substituted alkyl, optionally substituted cycloalkyl, optionally substituted alkenyl, optionally substituted alkynyl, optionally substituted aryl, optionally substituted heteroaryl, optionally substituted heterocyclyl, CO—$R^8$, or a protecting group, and
- $R^8$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl.

7. The process according to claim 6, wherein the chiral secondary amine catalyst comprises any one of the following compounds:

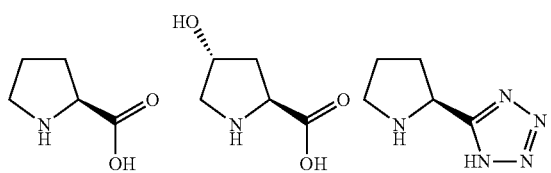

-continued

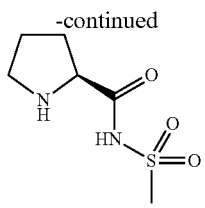

or any combination thereof.

8. The process according to claim 7, wherein the chiral secondary amine catalyst comprises (S)-proline, which has the structure:

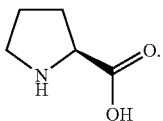

9. The process according to claim 4, wherein the acidic co-catalyst has the structure [α][β] wherein [α] is a cation selected from [Bn$_2$NH$_2$]$^+$, [BnNH$_3$]$^+$, [pyridinium]$^+$, [2,2'-bipyridinium]$^+$, [2,2':6',2"-terpyridinium]$^+$, [morpholinium]$^+$ and [thiomorpholinium]$^+$, and [β] is an anion selected from [F]$^-$, [Cl]$^-$, [Br]$^-$, [I]$^-$, [OCOCF$_3$]$^-$, [BF$_4$]$^-$, [OCOCHCl$_2$]$^-$, and [O—C$_6$H$_3$-2,4-(NO$_2$)$_2$]$^-$.

10. The process according to claim 9, wherein the acidic co-catalyst comprises [Bn$_2$NH$_2$][OCOCF$_3$].

11. The process according to claim 4 which, before the key step, further comprises a preceding step of heating 2,5-disubstituted tetrahydrofuran (III) in water to form succinaldehyde (II), in accordance with the following reaction scheme:

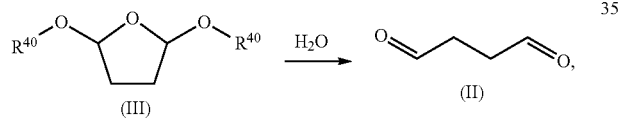

wherein R$^{40}$ is optionally substituted alkyl, optionally substituted alkenyl, optionally substituted aryl, or —COR$^{41}$, where R$^{41}$ is alkyl, and wherein the preceding step comprises a change of the solvent system from water to a different solvent system for the key step, resulting in the formation of a solution of succinaldehyde (II) in the different solvent system.

12. A process for making a compound of formula (Ib), the process comprising: treating succinaldehyde (II) with (i) a chiral secondary amine catalyst and (ii) an acidic co-catalyst, in a solvent system, to form lactol (Ia), in accordance with the following reaction scheme:

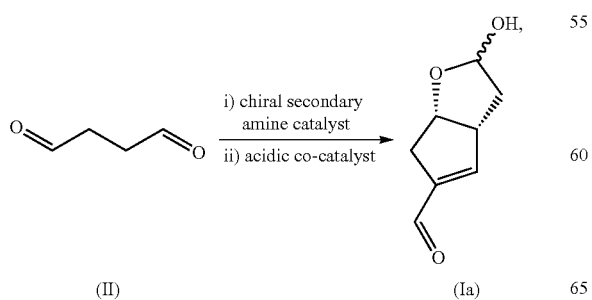

wherein the acidic co-catalyst is added to the reaction mixture after or simultaneously with the chiral secondary amine catalyst;

the chiral secondary amine catalyst has the following structure:

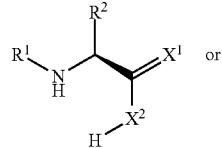

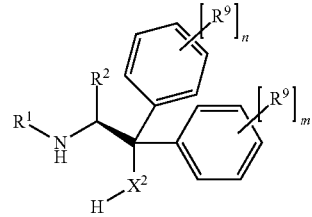

wherein

R$^1$ and R$^2$ are optionally substituted alkyl groups, or R$^1$ and R$^2$ are linked to form part of an optionally substituted 4-, 5- or 6-membered heterocycle;

X$^1$ is O, S or NR$^3$, wherein R$^3$ is an alkyl group, or R$^3$ is linked with R$^4$ to form part of a 5- or 6-membered ring which may contain one or more further N atoms;

X$^2$ is O or NR$^4$, wherein R$^4$ is haloalkyl, aryl substituted with one or more halogens or haloalkyl groups, SO$_2$R$^5$, or R$^4$ is linked with R$^3$ to form part of a 5- or 6-membered ring which may contain one or more further N atoms, and R$^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;

n is an integer from 1 to 5;

m is an integer from 1 to 5; and each R$^9$ is independently selected from an electron-withdrawing group and an optionally substituted alkyl, and at least one R$^9$ on each phenyl ring is an electron-withdrawing group;

and the acidic co-catalyst is selected from [Bn$_2$NH$_2$][OCOCF$_3$], [Bn$_2$NH$_2$][BF$_4$], [Bn$_2$NH$_2$][OCOCHCl$_2$], [Bn$_2$NH$_2$][O—C$_6$H$_3$-2,4-(NO$_2$)$_2$], [Bn$_2$NH$_2$][Cl], 2,6-piperidinedione, morpholinium trifluoroacetate, thiomorpholinium trifluoroacetate, pyridinium trifluoroacetate, benzylammonium trifluoroacetate, quinine trifluoroacetate, 2,2'-bipyridinium monotrifluoroacetate, 2,2':6',2"-terpyridinium monotrifluoroacetate, pyridinium p-toluenesulfonate (PPTS), trifluoroacetic acid (TFA), trifluoromethanesulfonic acid, camphorsulfonic acid (CSA), tartaric acid, 2,4-dinitrophenol, tetrafluoroboric acid, ZnCl$_2$, Zn(OTf)$_2$, Sc(OTf)$_3$, Amberlite 120, Montmorillonite K10, 1,3-bis(3,5-bis(trifluoromethyl)phenyl)thiourea, magnesium sulfate, and combinations thereof; and converting lactol (Ia) to give a compound of formula (Ib):

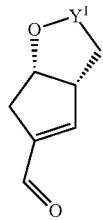

(Ib)

wherein $Y^1$ is

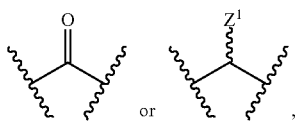

$Z^1$ is $OR^{20}$, $NR^{11}R^{11}$, $SR^{11}$, $S(O)R^{11}$, $SO_2R^{11}$ $R^{20}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, CO—$R^{11}$, or a protecting group, and $R^{11}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl.

13. A process for making $PGF_{2\alpha}$, which comprises the steps of:

(a) optionally treating succinaldehyde (II) with (i) a chiral secondary amine catalyst and (ii) an acidic co-catalyst, in a solvent system, to form lactol (Ia), in accordance with the following reaction scheme:

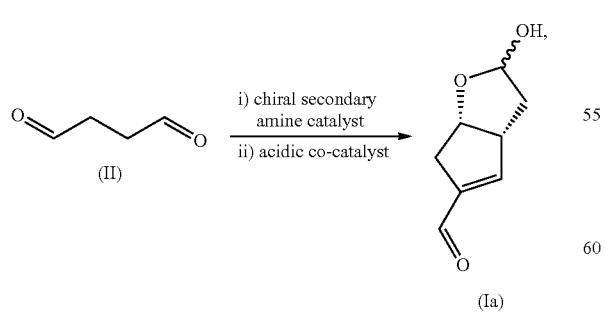

wherein the acidic co-catalyst is added to the reaction mixture after or simultaneously with the chiral secondary amine catalyst;

the chiral secondary amine catalyst has the following structure:

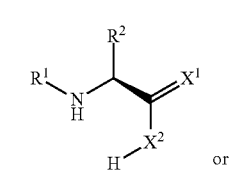

(A)

or

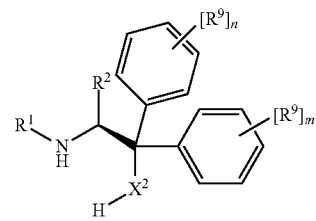

(B)

wherein $R^1$ and $R^2$ are optionally substituted alkyl groups, or $R^1$ and $R^2$ are linked to form part of an optionally substituted 4-, 5- or 6-membered heterocycle;

$X^1$ is O, S or $NR^3$, wherein $R^3$ is an alkyl group, or $R^3$ is linked with $R^4$ to form part of a 5- or 6-membered ring which may contain one or more further N atoms;

$X^2$ is O or $NR^4$, wherein $R^4$ is haloalkyl, aryl substituted with one or more halogens or haloalkyl groups, $SO_2R^5$, or $R^4$ is linked with $R^3$ to form part of a 5- or 6-membered ring which may contain one or more further N atoms, and $R^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;

n is an integer from 1 to 5;

m is an integer from 1 to 5; and each $R^9$ is independently selected from an electron-withdrawing group and an optionally substituted alkyl, and at least one $R^9$ on each phenyl ring is an electron-withdrawing group;

and the acidic co-catalyst is selected from [$Bn_2NH_2$][$OCOCF_3$], [$Bn_2NH_2$][$BF_4$], [$Bn_2NH_2$][$OCOCHCl_2$], [$Bn_2NH_2$][O—$C_6H_3$-2,4-($NO_2$)$_2$], [$Bn_2NH_2$][Cl], 2,6-piperidinedione, morpholinium trifluoroacetate, thiomorpholinium trifluoroacetate, pyridinium trifluoroacetate, benzylammonium trifluoroacetate, quinine trifluoroacetate, 2,2'-bipyridinium monotrifluoroacetate, 2,2':6',2''-terpyridinium monotrifluoroacetate, pyridinium p-toluenesulfonate (PPTS), trifluoroacetic acid (TFA), trifluoromethanesulfonic acid, camphorsulfonic acid (CSA), tartaric acid, 2,4-dinitrophenol, tetrafluoroboric acid, $ZnCl_2$, $Zn(OTf)_2$, $Sc(OTf)_3$, Amberlite 120, Montmorillonite K10, 1,3-bis(3,5-bis(trifluoromethyl)phenyl)thiourea, magnesium sulfate, and combinations thereof;

(b) optionally protecting lactol (Ia) by converting it to an acetal of formula (Ic), in accordance with the following reaction scheme:

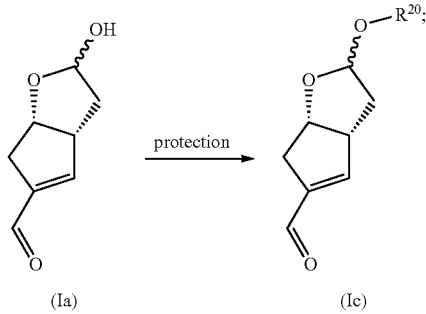

(c) reacting the acetal of formula (Ic) with a soft nucleophile of formula (IV) via a Michael addition, and protecting the resulting enol ether to form a compound of formula (V);

(d) subjecting the compound of formula (V) to oxidative cleavage, followed by reduction to form a compound of formula (VI);

(e) deprotecting the compound of formula (VI) to give a compound of formula (VII); and (f) reacting the compound of formula (VII) with a phosphonium halide of formula (VIII) via a Wittig reaction to form $PGF_{2\alpha}$;

in accordance with the following reaction scheme:

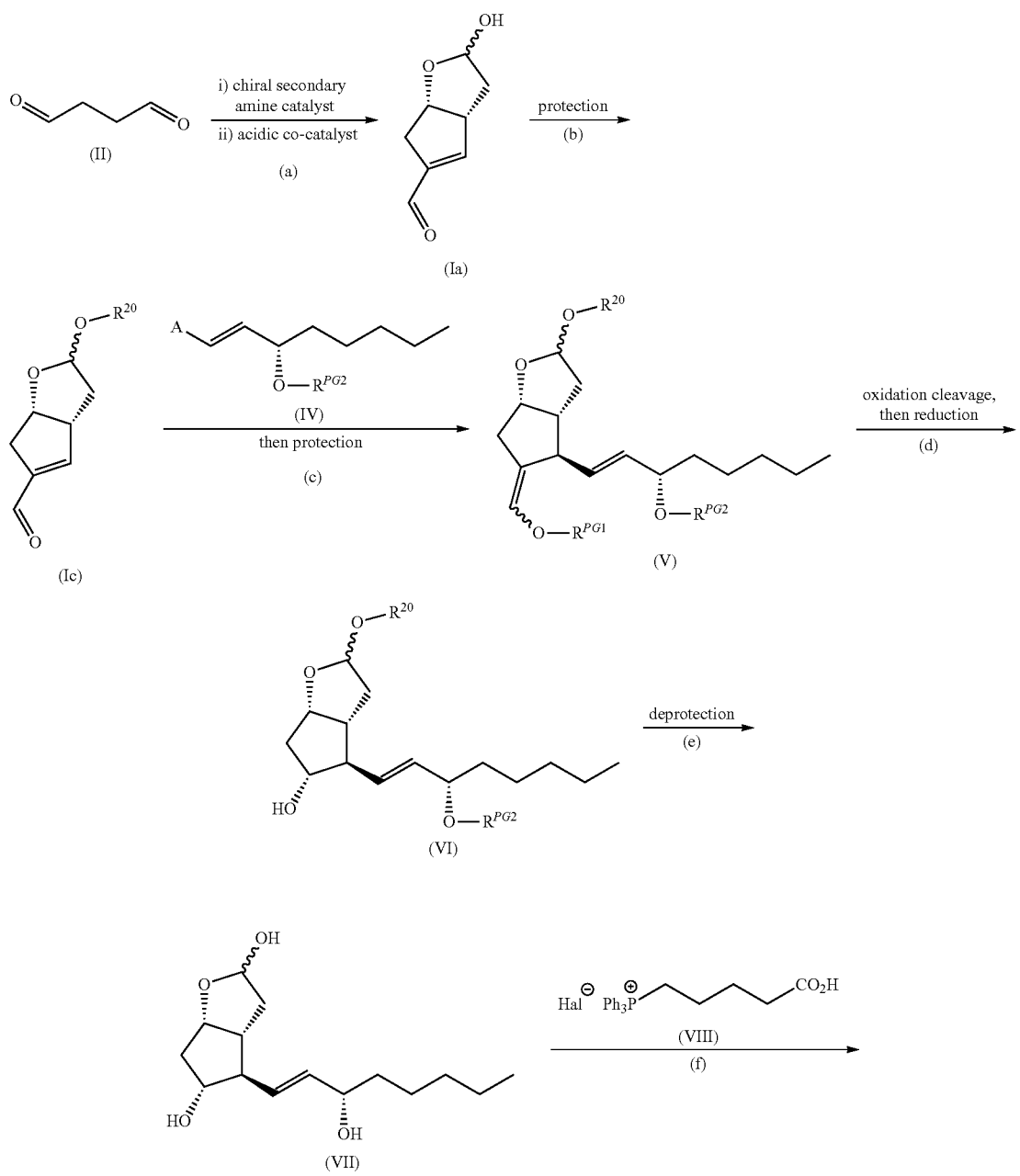

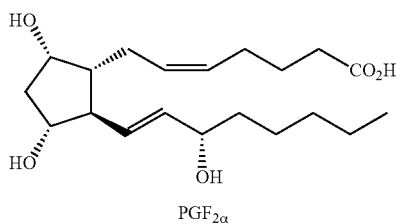

PGF$_{2\alpha}$ wherein
R$^{20}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, CO—R$^{11}$, or a protecting group, and R$^{11}$ is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl;

R$^{PG1}$ and R$^{PG2}$ are protecting groups;

A is a group which allows the compound of formula (IV) to react as a soft nucleophile via a Michael addition; and Hal$^-$ is a halide group selected from iodide, bromide, chloride and fluoride.

14. A process for making latanoprost, which comprises the steps of:

(a) optionally treating succinaldehyde (II) with (i) a chiral secondary amine catalyst and (ii) an acidic co-catalyst, in a solvent system, to form lactol (Ia), in accordance with the following reaction scheme:

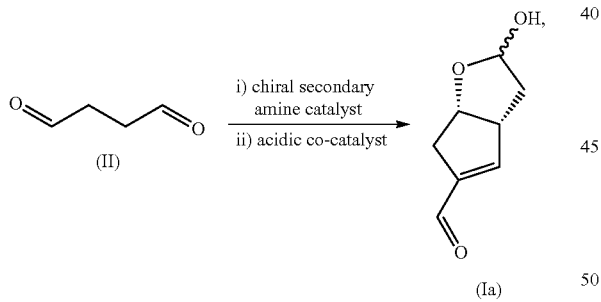

wherein the acidic co-catalyst is added to the reaction mixture after or simultaneously with the chiral secondary amine catalyst;

the chiral secondary amine catalyst has the following structure:

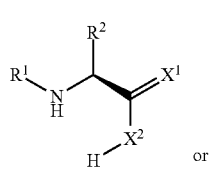
(A)

or

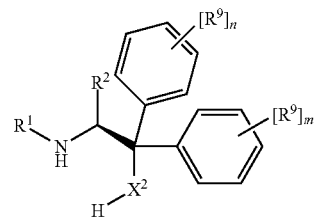
(B)

wherein
R$^1$ and R$^2$ are optionally substituted alkyl groups, or R$^1$ and R$^2$ are linked to form part of an optionally substituted 4-, 5- or 6-membered heterocycle;

X$^1$ is O, S or NR$^3$, wherein R$^3$ is an alkyl group, or R$^3$ is linked with R$^4$ to form part of a 5- or 6-membered ring which may contain one or more further N atoms;

X$^2$ is O or NR$^4$, wherein R$^4$ is haloalkyl, aryl substituted with one or more halogens or haloalkyl groups, SO$_2$R$^5$, or R$^4$ is linked with R$^3$ to form part of a 5- or 6-membered ring which may contain one or more further N atoms, and R$^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;

n is an integer from 1 to 5;
m is an integer from 1 to 5; and
each R$^9$ is independently selected from an electron-withdrawing group and an optionally substituted alkyl, and at least one R$^9$ on each phenyl ring is an electron-withdrawing group;

and
the acidic co-catalyst is selected from [Bn$_2$NH$_2$][OCOCF$_3$], [Bn$_2$NH$_2$][BF$_4$], [Bn$_2$NH$_2$][OCOCHCl$_2$], [Bn$_2$NH$_2$][O—C$_6$H$_3$-2,4-(NO$_2$)$_2$], [Bn$_2$NH$_2$][Cl], 2,6-piperidinedione, morpholinium trifluoroacetate, thiomorpholinium trifluoroacetate, pyridinium trifluoroacetate, benzylammonium trifluoroacetate, quinine trifluoroacetate, 2,2'-bipyridinium monotrifluoroacetate, 2,2':6',2''-terpyridinium monotrifluoroacetate, pyridinium p-toluenesulfonate (PPTS), trifluoroacetic acid (TFA), trifluoromethanesulfonic acid, camphorsulfonic acid (CSA), tartaric acid, 2,4-dinitrophenol, tetrafluoroboric acid, ZnCl$_2$, Zn(OTf)$_2$, Sc(OTf)$_3$, Amberlite 120, Montmorillonite K10, 1,3-bis(3,5-bis(trifluoromethyl)phenyl)thiourea, magnesium sulfate, and combinations thereof;

(b) optionally protecting lactol (Ia) by converting it to an acetal of formula (Ic), in accordance with the following reaction scheme:

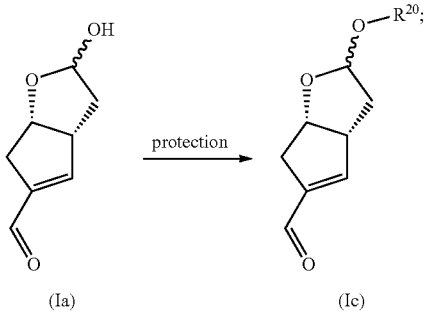

(c) reacting the acetal of formula (Ic) with a soft nucleophile of formula (IV') via a Michael addition, and protecting the resulting enol ether to form a compound of formula (V');

(d) subjecting the compound of formula (V') to oxidative cleavage, followed by reduction to form a compound of formula (VI');

(e) deprotecting the compound of formula (VI') to give a compound of formula (VII');

(f) reacting the compound of formula (VII') with a phosphonium halide of formula (VIII) via a Wittig reaction to form a compound of formula (IX); and (g) alkylating the compound of formula (IX) to form latanoprost;

in accordance with the following reaction scheme:

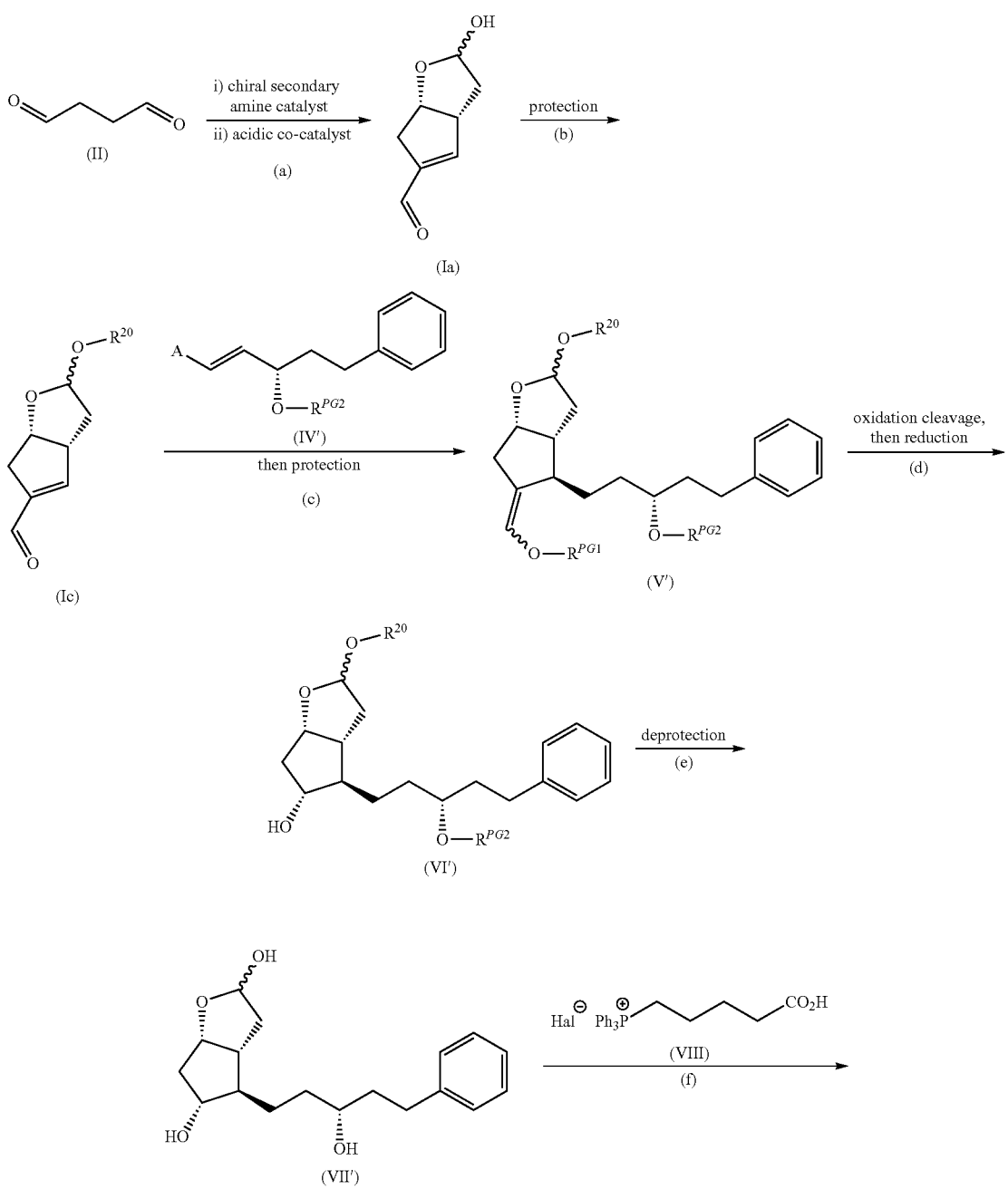

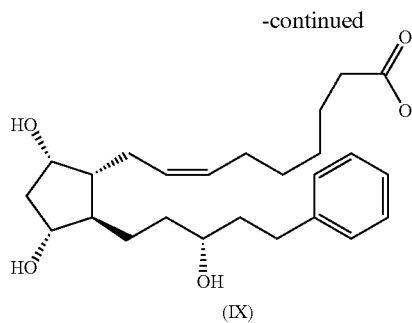

(IX)

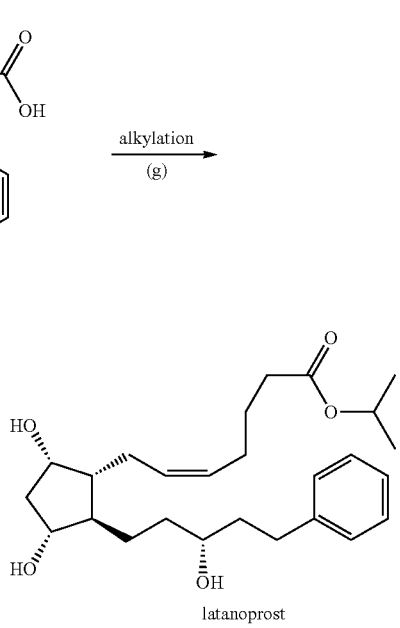

latanoprost wherein
R[20] is optionally substituted alkyl, optionally substituted cycloalkyl, optionally substituted alkenyl, optionally substituted alkynyl, optionally substituted aryl, optionally substituted heteroaryl, optionally substituted heterocyclyl, CO—R[11], or a protecting group, and R[11] is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl;

R[PG1] and R[PG2] are protecting groups;

A is a group which allows the compound of formula (IV') to react as a soft nucleophile via a Michael addition; and Hal[−] is a halide group selected from iodide, bromide, chloride and fluoride.

15. A process for making bimatoprost, which comprises the steps of:
(a) optionally treating succinaldehyde (II) with (i) a chiral secondary amine catalyst and (ii) an acidic co-catalyst, in a solvent system, to form lactol (Ia), in accordance with the following reaction scheme:

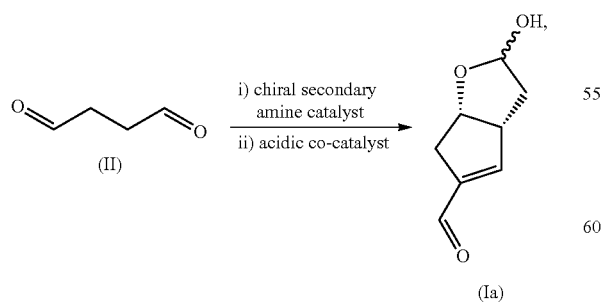

wherein the acidic co-catalyst is added to the reaction mixture after or simultaneously with the chiral secondary amine catalyst;

the chiral secondary amine catalyst has the following structure:

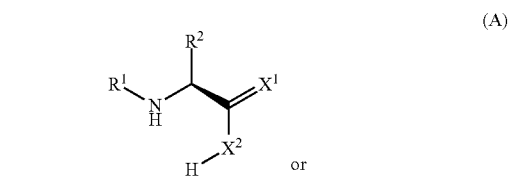

(A)

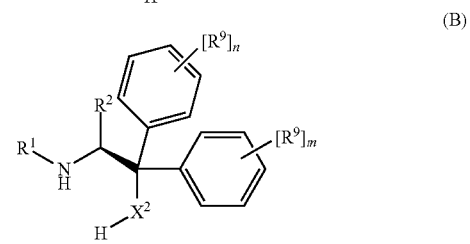

(B)

wherein
$R^1$ and $R^2$ are optionally substituted alkyl groups, or $R^1$ and $R^2$ are linked to form part of an optionally substituted 4-, 5- or 6-membered heterocycle;

$X^1$ is O, S or $NR^3$, wherein $R^3$ is an alkyl group, or $R^3$ is linked with $R^4$ to form part of a 5- or 6-membered ring which may contain one or more further N atoms;

$X^2$ is O or $NR^4$, wherein $R^4$ is haloalkyl, aryl substituted with one or more halogens or haloalkyl groups, $SO_2R^5$, or $R^4$ is linked with $R^3$ to form part of a 5- or 6-membered ring which may contain one or more further N atoms, and $R^5$ is an optionally substituted alkyl group, an optionally substituted cycloalkyl group, an optionally substituted alkenyl group, an optionally substituted alkynyl group, an optionally substituted aryl group, an optionally substituted heteroaryl group, or an optionally substituted heterocyclyl group;

n is an integer from 1 to 5;
m is an integer from 1 to 5; and each $R^9$ is independently selected from an electron-withdrawing group and an optionally substituted alkyl, and at least one $R^9$ on each phenyl ring is an electron-withdrawing group;

and the acidic co-catalyst is selected from $[Bn_2NH_2][OCOCF_3]$, $[Bn_2NH_2][BF_4]$, $[Bn_2NH_2][OCOCHCl_2]$, $[Bn_2NH_2][O-C_6H_3-2,4-(NO_2)_2]$, $[Bn_2NH_2][Cl]$, 2,6-piperidinedione, morpholinium trifluoroacetate, thiomorpholinium trifluoroacetate, pyridinium trifluoroacetate, benzylammonium trifluoroacetate, quinine trifluoroacetate, 2,2'-bipyridinium monotrifluoroacetate, 2,2':6',2''-terpyridinium monotrifluoroacetate, pyridinium p-toluenesulfonate (PPTS), trifluoroacetic acid (TFA), trifluoromethanesulfonic acid, camphorsulfonic acid (CSA), tartaric acid, 2,4-dinitrophenol, tetrafluoroboric acid, $ZnCl_2$, $Zn(OTf)_2$, $Sc(OTf)_3$, Amberlite 120, Montmorillonite K10, 1,3-bis(3,5-bis(trifluoromethyl)phenyl)thiourea, magnesium sulfate, and combinations thereof;

(b) optionally protecting lactol (Ia) by converting it to an acetal of formula (Ic), in accordance with the following reaction scheme:

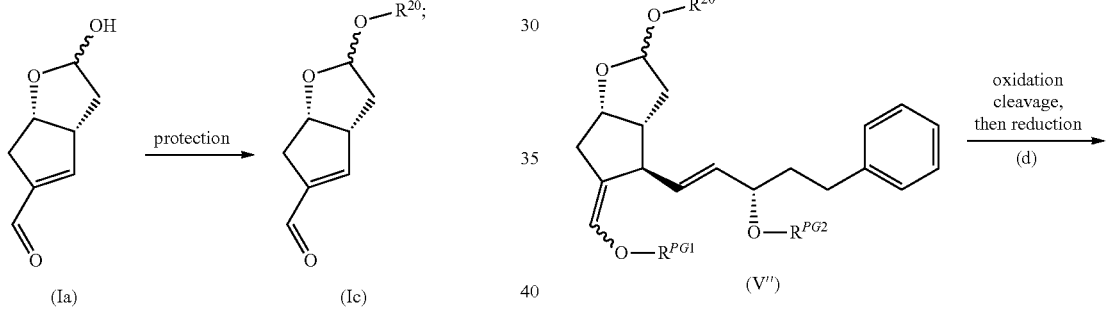

(c) reacting the acetal of formula (Ic) with a soft nucleophile of formula (IV'') via a Michael addition, and protecting the resulting enol ether to form a compound of formula (V'');

(d) subjecting the compound of formula (V'') to oxidative cleavage, followed by reduction to form a compound of formula (VI'');

(e) deprotecting the compound of formula (VI'') to give a compound of formula (VII''); and (f) reacting the compound of formula (VII'') with a phosphonium halide of formula (VIII'') via a Wittig reaction to form bimatoprost;

in accordance with the following reaction scheme:

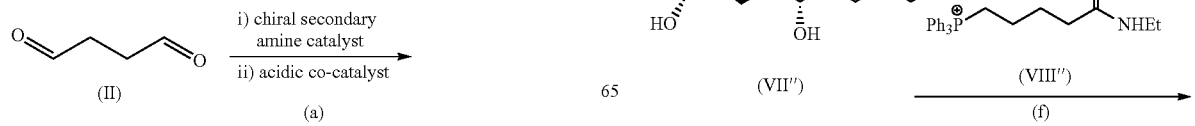

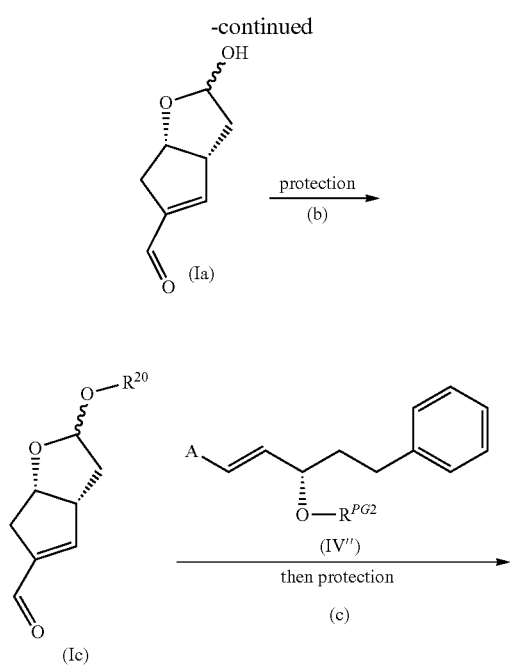

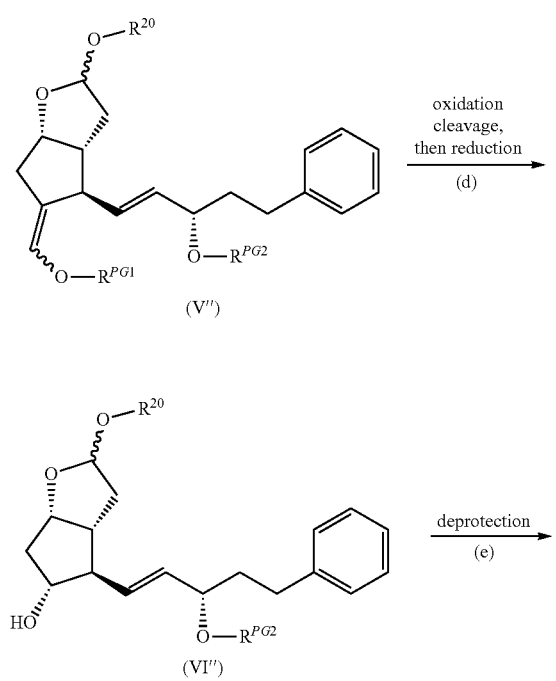

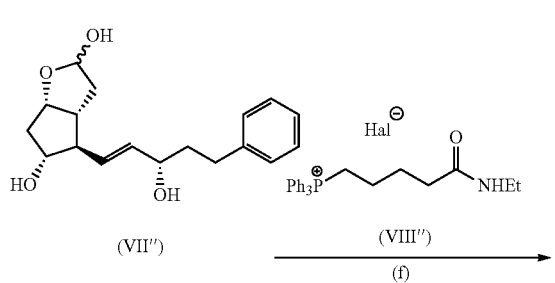

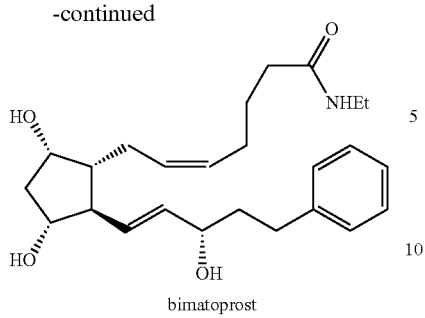

bimatoprost wherein
R[20] is optionally substituted alkyl, optionally substituted cycloalkyl, optionally substituted alkenyl, optionally substituted alkynyl, optionally substituted aryl, optionally substituted heteroaryl, optionally substituted heterocyclyl, CO—R[11], or a protecting group, and R[11] is optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl;

R[PG1] and R[PG2] are protecting groups;

A is a group which allows the compound of formula (IV″) to react as a soft nucleophile via a Michael addition; and Hal[−] is a halide group selected from iodide, bromide, chloride and fluoride.

* * * * *